US010167290B2

(12) United States Patent
Elsner et al.

(10) Patent No.: US 10,167,290 B2
(45) Date of Patent: *Jan. 1, 2019

(54) SUBSTITUTED PYRAZINO[2,3-B]PYRAZINES AS MTOR KINASE INHIBITORS

(71) Applicant: SIGNAL PHARMACEUTICALS, LLC, San Diego, CA (US)

(72) Inventors: Jan Elsner, Solana Beach, CA (US); Roy L. Harris, San Diego, CA (US); Branden Gingsee Lee, San Diego, CA (US); Deborah Mortensen, San Diego, CA (US); Garrick K. Packard, Humbird, WI (US); Patrick Papa, Carlsbad, CA (US); Jason Parnes, San Diego, CA (US); Sophie Perrin-Ninkovic, La Jolla, CA (US); Jennifer Riggs, Cardiff, CA (US); John Sapienza, Chula Vista, CA (US); Graziella I. Shevlin, Lima (PE); Lida Tehrani, San Diego, CA (US); Jingjing Zhao, San Diego, CA (US)

(73) Assignee: Signal Pharmaceuticals, LLC, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/680,688

(22) Filed: Aug. 18, 2017

(65) Prior Publication Data

US 2017/0342080 A1 Nov. 30, 2017

Related U.S. Application Data

(60) Continuation of application No. 14/874,524, filed on Oct. 5, 2015, now Pat. No. 9,771,371, which is a continuation of application No. 14/529,261, filed on Oct. 31, 2014, now Pat. No. 9,193,692, which is a division of application No. 13/927,255, filed on Jun. 26, 2013, now Pat. No. 8,907,087, which is a continuation of application No. 13/295,513, filed on Nov. 14, 2011, now Pat. No. 8,507,492, which is a continuation of application No. 12/605,791, filed on Oct. 26, 2009, now Pat. No. 8,110,578.

(60) Provisional application No. 61/108,627, filed on Oct. 27, 2008.

(51) Int. Cl.

| | |
|---|---|
| ***C07D 487/04*** | (2006.01) |
| ***C07D 498/14*** | (2006.01) |
| ***C07D 241/20*** | (2006.01) |
| ***C07D 471/04*** | (2006.01) |
| ***C07D 471/14*** | (2006.01) |
| ***C07D 487/10*** | (2006.01) |
| ***C07D 487/14*** | (2006.01) |

(52) U.S. Cl.

CPC ......... *C07D 487/04* (2013.01); *C07D 241/20* (2013.01); *C07D 471/04* (2013.01); *C07D 471/14* (2013.01); *C07D 487/10* (2013.01); *C07D 487/14* (2013.01); *C07D 498/14* (2013.01)

(58) Field of Classification Search

CPC .................................................. C07D 487/04

USPC ........................................................ 544/350

See application file for complete search history.

(56) References Cited

U.S. PATENT DOCUMENTS

| | | | |
|---|---|---|---|
| 3,507,866 | A | 4/1970 | Jones et al. |
| 3,567,725 | A | 3/1971 | Grabowski et al. |
| 4,294,836 | A | 10/1981 | Lesher et al. |
| 4,294,837 | A | 10/1981 | Lesher et al. |

(Continued)

FOREIGN PATENT DOCUMENTS

| | | | |
|---|---|---|---|
| CA | 2 458 699 | A1 | 3/2003 |
| DE | 262 026 | | 11/1988 |

(Continued)

OTHER PUBLICATIONS

Barlin 1982, "Purine analogs as amplifiers of phleomycin. VII. Some 1H-inidazo[4,5-b]pyrazines and related compound," Australian Journal of Chemistry, vol. 35:2299-2306.

(Continued)

*Primary Examiner* — Douglas M Willis

(74) *Attorney, Agent, or Firm* — Jones Day

(57) ABSTRACT

Provided herein are methods for the preparation of substituted pyrazino[2,3-b]pyrazines of the formula (II):

(II)

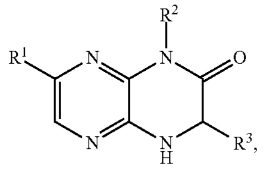

the method comprising contacting a compound of formula (VI):

(VI)

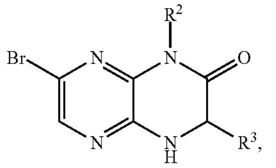

(Continued)

with $R^1$—Y in a solvent, in the presence of a palladium catalyst, wherein said contacting occurs in the presence of a base, wherein $R^1$-$R^3$, Y, the palladium catalyst and the base are as defined herein.

5 Claims, No Drawings

(56) References Cited

U.S. PATENT DOCUMENTS

| | | | |
|---|---|---|---|
| 4,309,537 | A | 1/1982 | Lesher et al. |
| 4,317,909 | A | 3/1982 | Lesher et al. |
| 4,898,872 | A | 2/1990 | Campbell et al. |
| 4,963,561 | A | 10/1990 | Lesher et al. |
| 5,424,311 | A | 6/1995 | Billhardt-Troughton |
| 5,869,659 | A | 2/1999 | Stolle et al. |
| 6,093,728 | A | 7/2000 | McMahon et al. |
| 6,372,740 | B1 | 4/2002 | Murata et al. |
| 6,566,367 | B2 | 5/2003 | Bakthavatchalam et al. |
| 6,825,184 | B2 | 11/2004 | Ciriillo et al. |
| 6,855,723 | B2 | 2/2005 | McMahon et al. |
| 7,608,622 | B2 | 10/2009 | Liu et al. |
| 7,981,893 | B2 | 7/2011 | Mortensen et al. |
| 8,110,578 | B2 | 2/2012 | Perrin-Ninkovic et al. |
| 2006/0004014 | A1 | 1/2006 | Hoffmann et al. |

FOREIGN PATENT DOCUMENTS

| | | |
|---|---|---|
| EP | 0 385 850 | 9/1990 |
| JP | 63275582 | 5/1987 |
| JP | 2001048882 | 2/2001 |
| JP | 2002167387 | 6/2002 |
| WO | WO 99/16438 | 4/1999 |
| WO | WO 99/28320 | 6/1999 |
| WO | WO 00/73306 | 12/2000 |
| WO | WO 02/048152 | 6/2002 |
| WO | WO 03/032989 | 4/2003 |
| WO | WO 2004/042002 | 5/2004 |
| WO | WO 2004/065378 | 8/2004 |
| WO | WO 2004/076454 | 9/2004 |
| WO | WO 2004/085409 | 10/2004 |
| WO | WO 2005/120511 | 12/2005 |
| WO | WO 2006/001266 | 1/2006 |
| WO | WO 2006/020755 | 2/2006 |
| WO | WO 2006/030031 | 3/2006 |
| WO | WO 2006/036883 | 4/2006 |
| WO | WO 2006/045828 | 5/2006 |
| WO | WO 2006/065703 | 6/2006 |
| WO | WO 2006/091737 | 8/2006 |
| WO | WO 2006/108103 | 10/2006 |
| WO | WO 2008/016669 | 2/2008 |
| WO | WO 2008/051493 | 5/2008 |
| WO | WO 2010/062571 | 6/2010 |

OTHER PUBLICATIONS

Beresnev et al., 2000, "Interaction of 5-methoxy-1,2,4-traizines with uras as a new route to 6-azapurines," Medeleev Commu., vol. 2:58-59.
Bergmann et al., 1963, "2-Phenylpurines, their chemical and enzumological reactivity," J. Chem Org. , pp. 3729-3735.
Chupakhin et al., 2001, "A simple one pot synthesis of condensed 1,2,4-triazines by using the tandem $A_N$—$S_N$ipso and $S_N^H$—$S_N$ipso reactions," J. of Heterocyclic Chemistry, vol. 38(4):901-907.
Cohen, P. 2001, "The role of protein phosphorylation in human health and diesease," Eur. J. Biochem, vol. 268:5001-5010.
Cohen, P. 2002, "Protein kinases—the major drug targets of the twenty-first century?" Nature Reviews/Drug Discovery, vol. 1:309-315.
Crofts et al., 1997 "Metabolism of 2-amino-1-methyl-6-phenylimidazo[4,5-b]pyridine (PhIP) by human cytochrome P4501B1," Carcinogenesis, vol. 18(9):1793-1798.
Database CAPLUS Online Chemical Abstracts Service, Columbus, Ohio, Database Accession No. 1951:49974 (XP-002472261) (1951).
Database CAPLUS Online Chemical Abstracts Service, Columbus, Ohio, Database Accession No. 1978:433195 (XP-002472262) (1978).
Database CAPLUS Online Chemical Abstracts Service, Columbus, Ohio, Database Accession No. 1966:26849 (XP-002472263) (1965).
Dornow et al., 1957, "Synthese von2-Oxy-imidazolo-(5',4':2,3)-pyridinen)," Arch Pharm. vol. 290, pp. 20-31 (w/English language abstract).
Dzierba et al., 2004, "Synthesis, structure-activity relationships, and in vivo properties of 3,4-dihydro-1H-pyrido[2,3-b]pyrazin-2-ones as corticotropin-releasing factor-1 receptor antagonists," J of Medicinal Chemistry, vol. 47(23):5783-5790.
Fabbro et al., 2002, "Protein kinases as targets for anticancer agents: from inhibitors touseful drugs," Pharmacology & Therapeutics, vol. 93:79-98.
Farhadi et al., 2006, "The role of protien kinase C isoforms in modulating injuty and repair of the intestinal barrier," J. Pharm. Exp. Ther. vol. 316:1-7.
Frandsen et al., 1992, "Reaction of the N2-acetoxy derivative of 2-amino-1-methyl-6-phenylimidazo[4,5,b]pyridine . . . ," Carcinogenesis, vol. 13(4):629-635.
Georgakis and Younes, 1978, "From rapa nui to rapamycin:targeting PI3K/Akt/mTOR for cancer therapy," Expert Rev. Anticancer Ther, vol. 6:131-140.
Irie et al., 2005, "Toward the development of new medicinal leads with selectivity for protein kinase C isozymes," The Chemical Record, vol. 5:185-195.
Itoh etal., 2004, "A novel practical synthesis of C-2-arylpurines," Advanced Synthesis & Catalysis, vol. 346:1859-1867.
Jones et al., 1973, "6-Substituted-5-chloro-1,3-dihydro-2H-imidazo(4,5-b)pyrazin-2-ones with hypotensive activity," J. Med. Chem., vol. 16(5):537-542.
Kazaoka et al., 2003, "Synthesis of 6-substituted 9-benzyl-8-hydroxypurines with potential interferon-indcuing activity," Chemical & Pharmaceutical Bulletin, vol. 51(5):608-611.
Killday et al., 2001, "Microxine, a new cdc2 kinase inhibitor from the Australian marine sponge *Microxina* species," J. of Natural Products, vol. 64(4):525-526.
Minehan et al., 2000, "Molecular recognition of DNA by Hoechst Benzimidazoles: Exploring beyond theopyrrole-imidazole-hydroxypyrrole polyamide-pairing code," Helvitica Chima Acta, vol. 83(9):2197-2213.
Nagashima et al., 2004, "Solution-Phase parallel synthesis of an N-Alkylated dihydropteridinone library from fluorous amino acids," J of Comb. Chemistry, vol. 6(6):942-949.
Park et al., 2000, "A novel mechanism of TRAF signaling revealed by structural and functional analyses of the TRADD-TRAF2 interaction," Cell, vol. 101:777-787.
Patani et al., 1998, "Bioisosterim: A rational approach in drug design," Chemical Reviews, vol. 96:3147-3176.
Singh et al., 1994, "Novel cAMP PDE III Inhibitors: Imidazo[4,5-b]pyridin-2(3H)-ones and Thiazolo [4,5-b]pyridin-2(3h)-ones and Their Analogs," J. Med. Chem, vol. 37(2):248-254.
Sridhar et al., 2000, "Protein Kinasesas Therapeutic Targets," Pharm. Research, vol. 17(11):1345-353.
Yoneda et al., 1978, "Synthesis of imadazo[4,5-e]-as-triazine (6-Azapurine) Deriviatives," Chem & Pharm Bulletin, vol. 26(10):3154-3160.
Yoneda et al., 1976, "A transformationof 7-azapteridines into 6-azapurines (Imidazo[4,5-e]-as-triazines)," Heterocycles, vol. 4(9):1503-1508.
Jordan, V.C., 2003, Nature Reviews: Drug Discover, vol. 2:205.
Dorwald F. Zaragoza, 2005, "Side Reactions in Organic Synthesis: A Guide to Successful Synthesis Design," Weinheim: Wiley-VCH Verlag GmbH & Co. KgaA, Preface.
Vippagunta et al., 2001, Advanced Drug Delivery Reviews, vol. 48:18.
Wolff, Manfred E., 1996, Ed. Burger's Medicinal Chemistry and Drug Discovery—Fifth Edition, New York: John Wiley & Sons, 1:975-976.
Jordan et al., Nature Reviews: Drug Discovery, 2, 2003, 205.

(56) References Cited

OTHER PUBLICATIONS

Dorwald et al., Side Reactions in Organic Synthesis: A Guide to Successful Synthesis Design, Weinheim: Wiley-VCH Verlag GmbH & Co. KGaA, 2005, Preface.
Vippagunta et al., Advanced Drug Delivery Reviews, 48, 2001, 18.

SUBSTITUTED PYRAZINO[2,3-B]PYRAZINES AS MTOR KINASE INHIBITORS

1. CROSS-REFERENCE TO RELATED APPLICATIONS

This application is a continuation of U.S. application Ser. No. 14/874,524, filed Oct. 5, 2015, currently allowed, which is a continuation of U.S. application Ser. No. 14/529,261, filed Oct. 31, 2014, now U.S. Pat. No. 9,193,692, issued Nov. 24, 2015, which is a divisional of U.S. application Ser. No. 13/927,255, filed Jun. 26, 2013, now U.S. Pat. No. 8,907,087, issued Dec. 9, 2014, which is a continuation of U.S. application Ser. No. 13/295,513, filed Nov. 14, 2011, now U.S. Pat. No. 8,507,492, issued Aug. 13, 2013, which is a continuation of U.S. application Ser. No. 12/605,791, filed Oct. 26, 2009, now U.S. Pat. No. 8,110,578, issued Feb. 7, 2012, which claims the benefit of U.S. Provisional Application No. 61/108,627, filed Oct. 27, 2008, the entire contents of each of which are incorporated herein by reference.

2. BACKGROUND

Provided herein are certain heteroaryl compounds, compositions comprising an effective amount of one or more such compounds and methods for treating or preventing cancer, inflammatory conditions, immunological conditions, metabolic conditions and conditions treatable or preventable by inhibition of a kinase pathway, comprising administering an effective amount of a heteroaryl compound to a patient in need thereof.

The connection between abnormal protein phosphorylation and the cause or consequence of diseases has been known for over 20 years. Accordingly, protein kinases have become a very important group of drug targets. See Cohen, *Nature,* 1:309-315 (2002). Various protein kinase inhibitors have been used clinically in the treatment of a wide variety of diseases, such as cancer and chronic inflammatory diseases, including diabetes and stroke. See Cohen, *Eur. J. Biochem.,* 268:5001-5010 (2001).

The protein kinases are a large and diverse family of enzymes that catalyze protein phosphorylation and play a critical role in cellular signaling. Protein kinases may exert positive or negative regulatory effects, depending upon their target protein. Protein kinases are involved in specific signaling pathways which regulate cell functions such as, but not limited to, metabolism, cell cycle progression, cell adhesion, vascular function, apoptosis, and angiogenesis. Malfunctions of cellular signaling have been associated with many diseases, the most characterized of which include cancer and diabetes. The regulation of signal transduction by cytokines and the association of signal molecules with protooncogenes and tumor suppressor genes have been well documented. Similarly, the connection between diabetes and related conditions, and deregulated levels of protein kinases, has been demonstrated. See e.g., Sridhar et al. *Pharmaceutical Research,* 17(11):1345-1353 (2000). Viral infections and the conditions related thereto have also been associated with the regulation of protein kinases. Park et al. *Cell* 101 (7): 777-787 (2000).

Protein kinases can be divided into broad groups based upon the identity of the amino acid(s) that they target (serine/threonine, tyrosine, lysine, and histidine). For example, tyrosine kinases include receptor tyrosine kinases (RTKs), such as growth factors and non-receptor tyrosine kinases, such as the src kinase family. There are also dual-specific protein kinases that target both tyrosine and serine/threonine, such as cyclin dependent kinases (CDKs) and mitogen-activated protein kinases (MAPKs).

Because protein kinases regulate nearly every cellular process, including metabolism, cell proliferation, cell differentiation, and cell survival, they are attractive targets for therapeutic intervention for various disease states. For example, cell-cycle control and angiogenesis, in which protein kinases play a pivotal role are cellular processes associated with numerous disease conditions such as but not limited to cancer, inflammatory diseases, abnormal angiogenesis and diseases related thereto, atherosclerosis, macular degeneration, diabetes, obesity, and pain.

Protein kinases have become attractive targets for the treatment of cancers. Fabbro et al., *Pharmacology & Therapeutics* 93:79-98 (2002). It has been proposed that the involvement of protein kinases in the development of human malignancies may occur by: (1) genomic rearrangements (e.g., BCR-ABL in chronic myelogenous leukemia), (2) mutations leading to constitutively active kinase activity, such as acute myelogenous leukemia and gastrointestinal tumors, (3) deregulation of kinase activity by activation of oncogenes or loss of tumor suppressor functions, such as in cancers with oncogenic RAS, (4) deregulation of kinase activity by over-expression, as in the case of EGFR and (5) ectopic expression of growth factors that can contribute to the development and maintenance of the neoplastic phenotype. Fabbro et al., *Pharmacology & Therapeutics* 93:79-98 (2002).

The elucidation of the intricacy of protein kinase pathways and the complexity of the relationship and interaction among and between the various protein kinases and kinase pathways highlights the importance of developing pharmaceutical agents capable of acting as protein kinase modulators, regulators or inhibitors that have beneficial activity on multiple kinases or multiple kinase pathways. Accordingly, there remains a need for new kinase modulators.

The protein named mTOR (mammalian target of rapamycin), which is also called FRAP, RAFTI or RAPT1), is a 2549-amino acid Ser/Thr protein kinase, that has been shown to be one of the most critical proteins in the mTOR/PI3K/Akt pathway that regulates cell growth and proliferation. Georgakis and Younes *Expert Rev. Anticancer Ther.* 6(1):131-140 (2006). mTOR exists within two complexes, mTORC1 and mTORC2. mTORC1 is sensitive to rapamycin analogs (such as temsirolimus or everolimus) and mTORC2 is largely rapamycin-insensitive. Several mTOR inhibitors have been or are being evaluated in clinical trials for the treatment of cancer. Temsirolimus was approved for use in renal cell carcinoma in 2007 and everolimus was approved in 2009 for renal cell carcinoma patients that have progressed on vascular endothelial growth factor receptor inhibitors. In addition, sirolimus was approved in 1999 for the prophylaxis of renal transplant rejection. The interesting but limited clinical success of these mTORC1 compounds demonstrates the usefulness of mTOR inhibitors in the treatment of cancer and transplant rejection, and the increased potential for compounds with both mTORC1 and mTORC2 inhibitory activity.

Citation or identification of any reference in Section 2 of this application is not to be construed as an admission that the reference is prior art to the present application.

3. SUMMARY

Provided herein are compounds having the following formula (I):

(I)

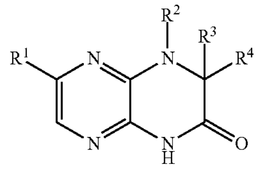

and pharmaceutically acceptable salts, clathrates, solvates, tautomers, stereoisomers and prodrugs thereof, wherein $R^1$-$R^4$ are as defined herein.

Further provided herein are compounds having the following formula (II):

(II)

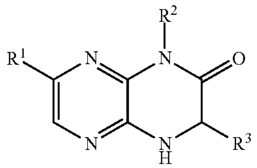

and pharmaceutically acceptable salts, clathrates, solvates, tautomers, stereoisomers and prodrugs thereof, wherein $R^1$, $R^2$ and $R^3$ are as defined herein.

Compounds of formula (I) and (II), or pharmaceutically acceptable salts, clathrates, solvates, hydrates, stereoisomers, tautomers, or prodrugs thereof (each being referred to herein as "Heteroaryl Compounds"), are useful for treating or preventing cancer, inflammatory conditions, immunological conditions, neurodegenerative diseases, diabetes, obesity, neurological disorders, age-related diseases, and cardiovascular conditions, and conditions treatable or preventable by inhibition of a kinase pathway. In one embodiment, the kinase pathway is the mTOR/PI3K/Akt pathway. In another embodiment, the kinase pathway is the PI3Kα, PI3Kβ, PI3Kδ, KDR, GSK3α, GSK3β, ATM, ATX, ATR, cFMS, and/or DNA-PK pathway.

Further provided herein are compositions comprising an effective amount of a Heteroaryl Compound and compositions comprising an effective amount of a Heteroaryl Compound and a pharmaceutically acceptable carrier or vehicle. The compositions are useful for treating or preventing cancer, inflammatory conditions, immunological conditions, neurodegenerative diseases, diabetes, obesity, neurological disorders, age-related diseases, or cardiovascular conditions and conditions treatable or preventable by inhibition of a kinase pathway, in one embodiment, the mTOR/PI3K/Akt pathway.

Further provided herein are methods for treating or preventing cancer, inflammatory conditions, immunological conditions, neurodegenerative diseases, diabetes, obesity, neurological disorders, age-related diseases, or cardiovascular conditions and conditions treatable or preventable by inhibition of a kinase pathway, in one embodiment, the mTOR/PI3K/Akt pathway, comprising administering an effective amount of a Heteroaryl Compound to a patient in need of the treating or preventing.

Also provided herein are methods for inhibiting a kinase in a cell expressing said kinase, comprising contacting the cell with an effective amount of a Heteroaryl Compound as described herein. In one embodiment the kinase is mTOR, DNA-PK, or PI3K or a combination thereof.

The present embodiments can be understood more fully by reference to the detailed description and examples, which are intended to exemplify non-limiting embodiments.

4. DETAILED DESCRIPTION

4.1 Definitions

An "alkyl" group is a saturated, partially saturated, or unsaturated straight chain or branched non-cyclic hydrocarbon having from 1 to 10 carbon atoms, typically from 1 to 8 carbons or, in some embodiments, from 1 to 6, 1 to 4, or 2 to 6 or carbon atoms. Representative alkyl groups include -methyl, -ethyl, -n-propyl, -n-butyl, -n-pentyl and -n-hexyl; while saturated branched alkyls include -isopropyl, -sec-butyl, -isobutyl, -tert-butyl, -isopentyl, 2-methylpentyl, 3-methylpentyl, 4-methylpentyl, 2,3-dimethylbutyl and the like. Examples of unsaturated alkyl groups include, but are not limited to, vinyl, allyl, $-CH{=}CH(CH_3)$, $-CH{=}C(CH_3)_2$, $-C(CH_3){=}CH_2$, $-C(CH_3){=}CH(CH_3)$, $-C(CH_2CH_3){=}CH_2$, $-C{\equiv}CH$, $-C{\equiv}C(CH_3)$, $-C{\equiv}C(CH_2CH_3)$, $-CH_2C{\equiv}CH$, $-CH_2C{\equiv}C(CH_3)$ and $-CH_2C{\equiv}C(CH_7CH_3)$, among others. An alkyl group can be substituted or unsubstituted.

A "cycloalkyl" group is a saturated, partially saturated, or unsaturated cyclic alkyl group of from 3 to 10 carbon atoms having a single cyclic ring or multiple condensed or bridged rings which can be optionally substituted with from 1 to 3 alkyl groups. In some embodiments, the cycloalkyl group has 3 to 8 ring members, whereas in other embodiments the number of ring carbon atoms ranges from 3 to 5, 3 to 6, or 3 to 7. Such cycloalkyl groups include, by way of example, single ring structures such as cyclopropyl, cyclobutyl, cyclopentyl, cyclohexyl, cycloheptyl, cyclooctyl, 1-methylcyclopropyl, 2-methylcyclopentyl, 2-methylcyclooctyl, and the like, or multiple or bridged ring structures such as adamantyl and the like. Examples of unsaturated cycloalkyl groups include cyclohexenyl, cyclopentenyl, cyclohexadienyl, butadienyl, pentadienyl, hexadienyl, among others. A cycloalkyl group can be substituted or unsubstituted. Such substituted cycloalkyl groups include, by way of example, cyclohexanone and the like.

An "aryl" group is an aromatic carbocyclic group of from 6 to 14 carbon atoms having a single ring (e.g., phenyl) or multiple condensed rings (e.g., naphthyl or anthryl). In some embodiments, aryl groups contain 6-14 carbons, and in others from 6 to 12 or even 6 to 10 carbon atoms in the ring portions of the groups. Particular aryls include phenyl, biphenyl, naphthyl and the like. An aryl group can be substituted or unsubstituted. The phrase "aryl groups" also includes groups containing fused rings, such as fused aromatic-aliphatic ring systems (e.g., indanyl, tetrahydronaphthyl, and the like).

A "heteroaryl" group is an aryl ring system having one to four heteroatoms as ring atoms in a heteroaromatic ring system, wherein the remainder of the atoms are carbon atoms. In some embodiments, heteroaryl groups contain 5 to 6 ring atoms, and in others from 6 to 9 or even 6 to 10 atoms in the ring portions of the groups. Suitable heteroatoms include oxygen, sulfur and nitrogen. In certain embodiments, the heteroaryl ring system is monocyclic or bicyclic. Non-limiting examples include but are not limited to, groups such as pyrrolyl, pyrazolyl, imidazolyl, triazolyl, tetrazolyl, oxazolyl, isoxazolyl, thiazolyl, pyrolyl, pyridyl, pyridazinyl, pyrimidinyl, pyrazinyl, thiophenyl, benzothiophenyl, furanyl, benzofuranyl (for example, isobenzofuran-1,3-diimine), indolyl, azaindolyl (for example, pyrrolopyridyl or 1H-pyrrolo[2,3-b]pyridyl), indazolyl, benzimidazolyl (for example, 1H-benzo[d]imidazolyl), imidazopyridyl (for example, azabenzimidazolyl, 3H-imidazo[4,5-b]pyridyl or 1H-imidazo[4,5-b]pyridyl), pyrazolopyridyl, triazolopyridyl, benzotriazolyl, benzoxazolyl, benzothiazolyl, benzothiadiazolyl, isoxazolopyridyl, thianaphthalenyl, purinyl, xanthinyl, adeninyl, guaninyl, quinolinyl, isoquinolinyl, tetrahydroquinolinyl, quinoxalinyl, and quinazolinyl groups.

A "heterocyclyl" is an aromatic (also referred to as heteroaryl) or non-aromatic cycloalkyl in which one to four of the ring carbon atoms are independently replaced with a heteroatom from the group consisting of O, S and N. In some embodiments, heterocyclyl groups include 3 to 10 ring members, whereas other such groups have 3 to 5, 3 to 6, or 3 to 8 ring members. Heterocyclyls can also be bonded to other groups at any ring atom (i.e., at any carbon atom or heteroatom of the heterocyclic ring). A heterocycloalkyl group can be substituted or unsubstituted. Heterocyclyl groups encompass unsaturated, partially saturated and saturated ring systems, such as, for example, imidazolyl, imidazolinyl and imidazolidinyl groups. The phrase heterocyclyl includes fused ring species, including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. Representative examples of a heterocyclyl group include, but are not limited to, aziridinyl, azetidinyl, pyrrolidyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl (for example, tetrahydro-2H-pyranyl), tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithionyl, dihydrodithionyl, homopiperazinyl, quinuclidyl, indolyl, indolinyl, isoindolyl, azaindolyl (pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl; for example, 1H-imidazo[4,5-b]pyridyl, or 1H-imidazo[4,5-b]pyridin-2(3H)-onyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthalenyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed below.

An "cycloalkylalkyl" group is a radical of the formula: -alkyl-cycloalkyl, wherein alkyl and cycloalkyl are defined above. Substituted cycloalkylalkyl groups may be substituted at the alkyl, the cycloalkyl, or both the alkyl and the cycloalkyl portions of the group. Representative cycloalkylalkyl groups include but are not limited to cyclopentylmethyl, cyclopentylethyl, cyclohexylmethyl, cyclohexylethyl, and cyclohexylpropyl. Representative substituted cycloalkylalkyl groups may be mono-substituted or substituted more than once An "aralkyl" group is a radical of the formula: -alkyl-aryl, wherein alkyl and aryl are defined above. Substituted aralkyl groups may be substituted at the alkyl, the aryl, or both the alkyl and the aryl portions of the group. Representative aralkyl groups include but are not limited to benzyl and phenethyl groups and fused (cycloalkylaryl)alkyl groups such as 4-ethyl-indanyl.

An "heterocyclylalkyl" group is a radical of the formula: -alkyl-heterocyclyl, wherein alkyl and heterocyclyl are defined above. Substituted heterocyclylalkyl groups may be substituted at the alkyl, the heterocyclyl, or both the alkyl and the heterocyclyl portions of the group. Representative heterocyclylalkyl groups include but are not limited to 4-ethyl-morpholinyl, 4-propylmorpholinyl, furan-2-yl methyl, furan-3-yl methyl, pyridine-3-yl methyl, (tetrahydro-2H-pyran-4-yl)methyl, (tetrahydro-2H-pyran-4-yl) ethyl, tetrahydrofuran-2-yl methyl, tetrahydrofuran-2-yl ethyl, and indol-2-yl propyl.

A "halogen" is fluorine, chlorine, bromine or iodine.

A "hydroxyalkyl" group is an alkyl group as described above substituted with one or more hydroxy groups.

An "alkoxy" group is —O-(alkyl), wherein alkyl is defined above.

An "alkoxyalkyl" group is -(alkyl)-O-(alkyl), wherein alkyl is defined above.

An "amino" group is a radical of the formula: $—NH_2$.

An "alkylamino" group is a radical of the formula: —NH-alkyl or $—N(alkyl)_2$, wherein each alkyl is independently as defined above.

A "carboxy" group is a radical of the formula: —C(O)OH.

An "aminocarbonyl" group is a radical of the formula: $—C(O)N(R^{\#})_2$, $—C(O)NH(R^{\#})$ or $—C(O)NH_2$, wherein each $R^{\#}$ is independently a substituted or unsubstituted alkyl, cycloalkyl, aryl, aralkyl, heterocyclyl or heterocyclyl group as defined herein.

An "acylamino" group is a radical of the formula: $—NHC(O)(R^{\#})$ or $—N(alkyl)C(O)(R^{\#})$, wherein each alkyl and $R^{\#}$ are independently as defined above.

An "alkylsulfonylamino" group is a radical of the formula: $—NHSO_2(R^{\#})$ or $—N(alkyl)SO_2(R^{\#})$, wherein each alkyl and $R^{\#}$ are defined above.

A "urea" group is a radical of the formula: $—N(alkyl)C(O)N(R^{\#})_2$, $—N(alkyl)C(O)NH(R^{\#})$, $—N(alkyl)C(O)NH_2$, $—NHC(O)N(R^{\#})_2$, $—NHC(O)NH(R^{\#})$, or $—NH(CO)NHR^{\#}$, wherein each alkyl and $R^{\#}$ are independently as defined above.

In one embodiment, when the groups described herein are said to be "substituted," they may be substituted with any appropriate substituent or substituents. Illustrative examples of substituents are those found in the exemplary compounds and embodiments disclosed herein, as well as halogen (chloro, iodo, bromo, or fluoro); alkyl; hydroxyl; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; sulfonyl; sulfone; sulfonamide; ketone; aldehyde; ester; urea; urethane; oxime; hydroxyl amine; alkoxyamine; aralkoxyamine; N-oxide; hydrazine; hydrazide; hydrazone; azide; isocyanate; isothiocyanate; cyanate; thiocyanate; oxygen (=O); $B(OH)_2$, O(alkyl)aminocarbonyl; cycloalkyl, which may be monocyclic or fused or non-fused polycyclic (e.g., cyclopropyl, cyclobutyl, cyclopentyl, or cyclohexyl), or a heterocyclyl, which may be monocyclic or fused or non-fused polycyclic (e.g., pyrrolidyl, piperidyl, piperazinyl, morpholinyl, or thiazinyl); monocyclic or fused or non-fused polycyclic aryl or heteroaryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl) aryloxy; aralkyloxy; heterocyclyloxy; and heterocyclyl alkoxy.

As used herein, the term "pharmaceutically acceptable salt(s)" refers to a salt prepared from a pharmaceutically acceptable non-toxic acid or base including an inorganic acid and base and an organic acid and base. Suitable pharmaceutically acceptable base addition salts of the Heteroaryl Compounds include, but are not limited to metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art, see for example, *Remington's Pharmaceutical Sciences,* $18^{th}$ eds., Mack Publishing, Easton Pa. (1990) or *Remington: The Science and Practice of Pharmacy,* $19^{th}$ eds., Mack Publishing, Easton Pa. (1995).

As used herein and unless otherwise indicated, the term "clathrate" means a Heteroaryl Compound, or a salt thereof, in the form of a crystal lattice that contains spaces (e.g., channels) that have a guest molecule (e.g., a solvent or water) trapped within or a crystal lattice wherein a Heteroaryl Compound is a guest molecule.

As used herein and unless otherwise indicated, the term "solvate" means a Heteroaryl Compound, or a salt thereof, that further includes a stoichiometric or non-stoichiometric amount of a solvent bound by non-covalent intermolecular forces. In one embodiment, the solvate is a hydrate.

As used herein and unless otherwise indicated, the term "hydrate" means a Heteroaryl Compound, or a salt thereof, that further includes a stoichiometric or non-stoichiometric amount of water bound by non-covalent intermolecular forces.

As used herein and unless otherwise indicated, the term "prodrug" means a Heteroaryl Compound derivative that can hydrolyze, oxidize, or otherwise react under biological conditions (in vitro or in vivo) to provide an active compound, particularly a Heteroaryl Compound. Examples of prodrugs include, but are not limited to, derivatives and metabolites of a Heteroaryl Compound that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by *Burger's Medicinal Chemistry and Drug Discovery* $6^{th}$ ed. (Donald J. Abraham ed., 2001, Wiley) and *Design and Application of Prodrugs* (H. Bundgaard ed., 1985, Harwood Academic Publishers Gmfh).

As used herein and unless otherwise indicated, the term "stereoisomer" or "stereomerically pure" means one stereoisomer of a Heteroaryl Compound that is substantially free of other stereoisomers of that compound. For example, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound. The Heteroaryl Compounds can have chiral centers and can occur as racemates, individual enantiomers or diastereomers, and mixtures thereof. All such isomeric forms are included within the embodiments disclosed herein, including mixtures thereof. The use of stereomerically pure forms of such Heteroaryl Compounds, as well as the use of mixtures of those forms are encompassed by the embodiments disclosed herein. For example, mixtures comprising equal or unequal amounts of the enantiomers of a particular Heteroaryl Compound may be used in methods and compositions disclosed herein. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, NY, 1962); and Wilen, S. H., *Tables of Resolving Agents and Optical Resolutions* p. 268 (E. L. Eliel, Ed., Univ. of Notre Dame Press, Notre Dame, Ind., 1972).

It should also be noted the Heteroaryl Compounds can include E and Z isomers, or a mixture thereof, and cis and trans isomers or a mixture thereof. In certain embodiments, the Heteroaryl Compounds are isolated as either the cis or trans isomer. In other embodiments, the Heteroaryl Compounds are a mixture of the cis and trans isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

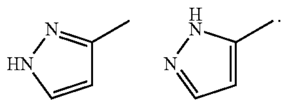

As readily understood by one skilled in the art, a wide variety of functional groups and other structures may exhibit tautomerism and all tautomers of compounds of formula (I) and formula (II) are within the scope of the present invention.

It should also be noted the Heteroaryl Compounds can contain unnatural proportions of atomic isotopes at one or more of the atoms. For example, the compounds may be radiolabeled with radioactive isotopes, such as for example tritium ($^3H$), iodine-125 ($^{125}I$), sulfur-35 ($^{35}S$), or carbon-14 ($^{14}C$), or may be isotopically enriched, such as with deuterium ($^2H$), carbon-13 ($^{13}C$), or nitrogen-15 ($^{15}N$). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the Heteroaryl Compounds as described herein, whether radioactive or not, are intended to be encompassed within the scope of the embodiments provided herein. In some embodiments, there are provided isotopologues of the Heteroaryl Compounds, for example, the isotopologues are deuterium, carbon-13, or nitrogen-15 enriched Heteroaryl Compounds.

"Treating" as used herein, means an alleviation, in whole or in part, of symptoms associated with a disorder or disease, or slowing, or halting of further progression or worsening of those symptoms, or prevention or prophylaxis of the disease or disorder in a patient at risk for developing the disease or disorder.

The term "effective amount" in connection with an Heteroaryl Compound means an amount capable of alleviating, in whole or in part, symptoms associated with a disorder or disease, or slowing or halting further progression or worsening of those symptoms, or preventing or providing prophylaxis for the disease or disorder in a subject at risk for developing the disease or disorder as disclosed herein, such as cancer, inflammatory conditions, immunological conditions, neurodegenerative diseases, diabetes, obesity, neurological disorders, age-related diseases, or cardiovascular conditions, and conditions treatable or preventable by inhibition of a kinase pathway, for example, the mTOR/PI3K/Akt pathway. In one embodiment an effective amount of a Heteroaryl Compound is an amount that inhibits a kinase in a cell, such as, for example, in vitro or in vivo. In one embodiment the kinase is mTOR, DNA-PK, PI3K or a combination thereof. In some embodiments, the effective amount of the Heteroaryl Compound inhibits the kinase in a cell by 10%, 20%, 30%, 40%, 50%, 60%, 70%, 80%, 90% or 99%, compared to the activity of the kinase in an untreated cell. The effective amount of the Heteroaryl Compound, for example in a pharmaceutical composition, may be at a level that will exercise the desired effect; for example, about 0.005 mg/kg of a subject's body weight to about 100 mg/kg of a patient's body weight in unit dosage for both oral and parenteral administration. As will be apparent to those skilled in the art, it is to be expected that the effective amount of an Heteroaryl Compound disclosed herein may vary depending on the indication being treated, e.g., the effective amount of an Heteroaryl Compound would likely be different for treating patients suffering from, or at risk for, inflammatory conditions relative to the effective amount of the Compound for treating patients suffering from, or at risk of, a different disorder, e.g., cancer or a metabolic disorder.

The term "patient" includes an animal, including, but not limited to, an animal such as a cow, monkey, horse, sheep, pig, chicken, turkey, quail, cat, dog, mouse, rat, rabbit or guinea pig, in one embodiment a mammal, in another embodiment a human.

The term "cancer" refers to any of various malignant neoplasms characterized by the proliferation of cells that can invade surrounding tissue and metastasize to new body sites. Both benign and malignant tumors are classified according to the type of tissue in which they are found. For example, fibromas are neoplasms of fibrous connective tissue, and melanomas are abnormal growths of pigment (melanin) cells. Malignant tumors originating from epithelial tissue, e.g., in skin, bronchi, and stomach, are termed carcinomas. Malignancies of epithelial glandular tissue such as are found in the breast, prostate, and colon, are known as adenocarcinomas. Malignant growths of connective tissue, e.g., muscle, cartilage, lymph tissue, and bone, are called sarcomas. Lymphomas and leukemias are malignancies arising among white blood cells. Through the process of metastasis, tumor cell migration to other areas of the body establishes neoplasms in areas away from the site of initial appearance. Bone tissues are one of the most favored sites of metastases of malignant tumors, occurring in about 30% of all cancer cases. Among malignant tumors, cancers of the lung, breast, prostate or the like are particularly known to be likely to metastasize to bone.

In the context of neoplasm, cancer, tumor growth or tumor cell growth, inhibition may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention. In this context, the term "prevention" includes either preventing the onset of clinically evident neoplasia altogether or preventing the onset of a preclinically evident stage of neoplasia in individuals at risk. Also intended to be encompassed by this definition is the prevention of transformation into malignant cells or to arrest or reverse the progression of premalignant cells to malignant cells. This includes prophylactic treatment of those at risk of developing the neoplasia.

4.2 Heteroaryl Compounds

Provided herein are compounds having the following formula (I):

(I)

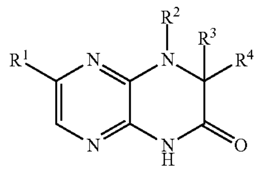

and pharmaceutically acceptable salts, clathrates, solvates, stereoisomers, tautomers, and prodrugs thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ and $R^4$ are each independently H, substituted or unsubstituted $C_{1-8}$ alkyl, substituted or unsubstituted aryl, substituted or unsubstituted cycloalkyl, substituted or unsubstituted heterocyclyl, substituted or unsubstituted heterocyclylalkyl, substituted or unsubstituted aralkyl, substituted or unsubstituted cycloalkylalkyl, or $R^3$ and $R^4$, together with the atoms to which they are attached, form a substituted or unsubstituted cycloalkyl or substituted or unsubstituted heterocyclyl;

or $R^2$ and one of $R^3$ and $R^4$, together with the atoms to which they are attached, form a substituted or unsubstituted heterocyclyl;

provided the compound is not the compounds depicted below, namely:

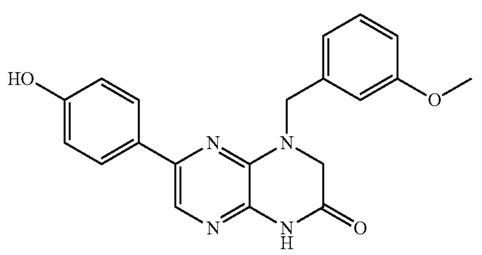 [SMILES: COc1cccc(CN2CC(=O)Nc3ncc(-c4ccc(O)cc4)nc32)c1]

6-(4-hydroxyphenyl)-4-(3-methoxybenzyl)-3,4-dihydropyrazino[2,3-b]pyrazin-2(1H)-one;

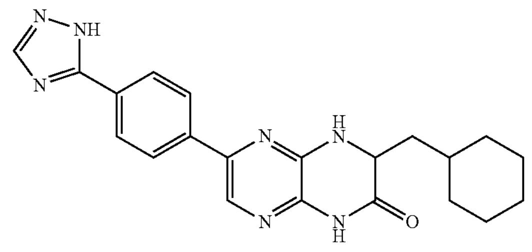 [SMILES: O=C1Nc2ncc(-c3ccc(-c4ncn[nH]4)cc3)nc2NC1CC1CCCCC1]

6-(4-(1H-1,2,4-triazol-5-yl)phenyl)-3-(cyclohexylmethyl)-3,4-dihydropyrazino[2,3-b]pyrazin-2(1H)-one;

or,

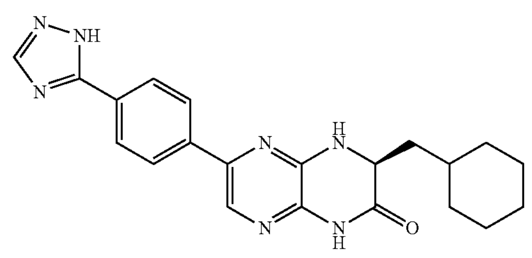 [SMILES: O=C1Nc2ncc(-c3ccc(-c4ncn[nH]4)cc3)nc2N[C@H]1CC1CCCCC1]

(R)-6-(4-(1H-1,2,4-triazol-5-yl)phenyl)-3-(cyclohexylmethyl)-3,4-dihydropyrazino[2,3-b]pyrazin-2(1H)-one.

In some embodiments of compounds of formula (I), $R^1$ is substituted or unsubstituted aryl or substituted or unsubstituted heteroaryl. In one embodiment, $R^1$ is phenyl, pyridyl, pyrimidyl, benzimidazolyl, indolyl, indazolyl, 1H-pyrrolo[2,3-b]pyridyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, substituted or unsubstituted triazolyl or pyrazolyl), halogen (for example, fluorine), aminocarbonyl, cyano, hydroxyalkyl (for example, hydroxypropyl), and hydroxy. In other embodiments, $R^1$ is pyridyl substituted with one or more substituents independently selected from the group consisting of substituted or unsubstituted $C_{1-8}$ alkyl, substituted or unsubstituted heterocyclyl (for example, substituted or unsubstituted triazolyl), halogen, aminocarbonyl, cyano, hydroxyalkyl, —OR, and —$NR_2$, wherein each R is independently H, or a substituted or unsubstituted $C_{1-4}$ alkyl. In yet other embodiments, $R^1$ is 1H-pyrrolo[2,3-b]pyridyl or benzimidazolyl, each optionally substituted with one or more substituents independently selected from the group consisting of substituted or unsubstituted $C_{1-8}$ alkyl, and —$NR_2$, wherein each R is independently H, or a substituted or unsubstituted $C_{1-4}$ alkyl.

In some embodiments of compounds of formula (I), $R^1$ is

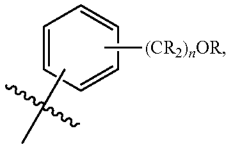
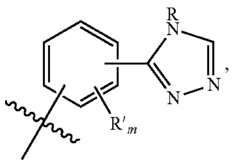
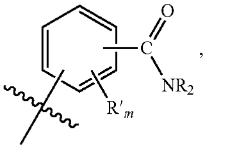
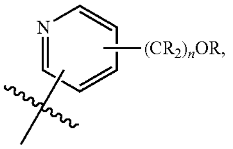
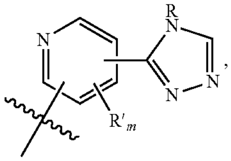
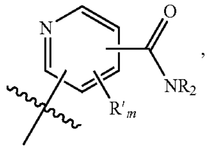
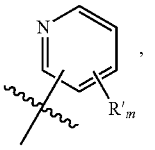
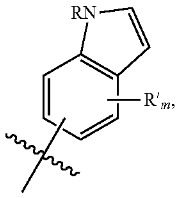
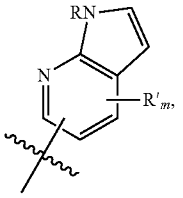
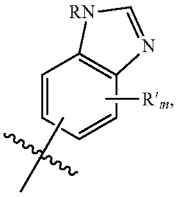
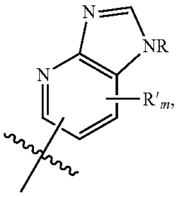

-continued

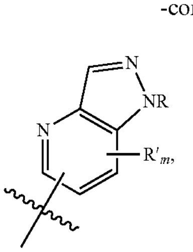 or 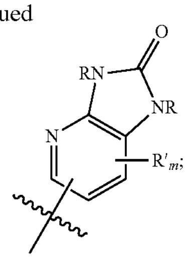

wherein R is at each occurrence independently H, or a substituted or unsubstituted $C_{1-4}$ alkyl (for example, methyl); R' is at each occurrence independently a substituted or unsubstituted $C_{1-4}$ alkyl, halogen (for example, fluorine), cyano, —OR, or —$NR_2$; m is 0-3; and n is 0-3. It will be understood by those skilled in the art that any of the substituents R' may be attached to any suitable atom of any of the rings in the fused ring systems. It will also be understood by those skilled in the art that the connecting bond of $R^1$ (designated by the bisecting wavy line) may be attached to any of the atoms in any of the rings in the fused ring systems.

In some embodiments of compounds of formula (I), $R^1$ is

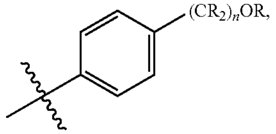 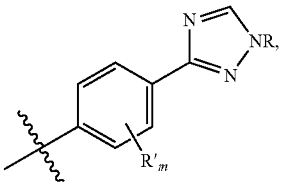

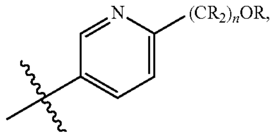 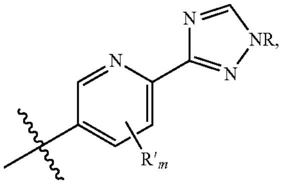

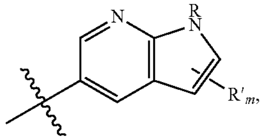 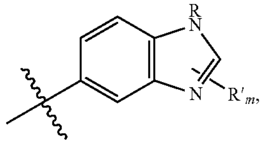

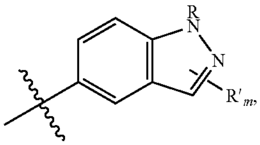 or 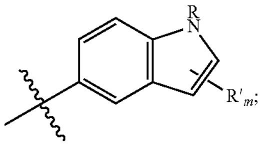

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR, or —$NR_2$; m is 0-3; and n is 0-3.

In some embodiments of compounds of formula (I), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl)(OR),

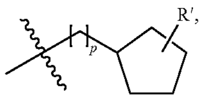 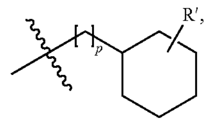

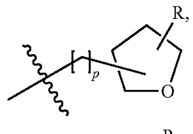 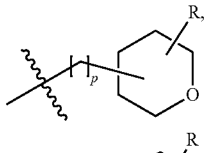

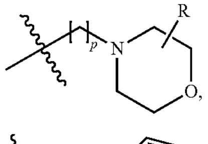 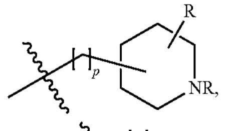

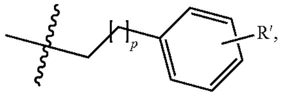 or 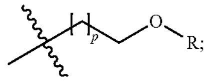

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In some such embodiments, $R^2$ is H, $C_{1-4}$ alkyl, ($C_{1-4}$alkyl)(OR),

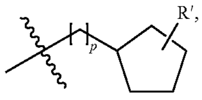 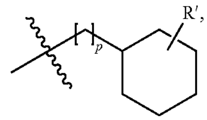

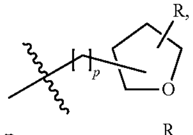 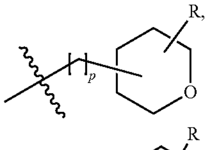

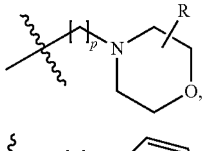 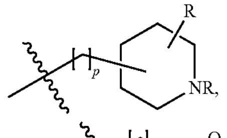

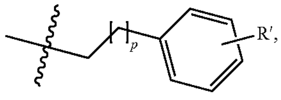 or 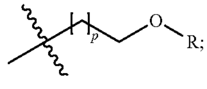

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In some other embodiments of compounds of formula (I), $R^2$ and one of $R^3$ and $R^4$ together with the atoms to which they are attached form a substituted or unsubstituted heterocyclyl. For example, in some embodiments, the compound of formula (I) is

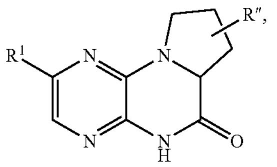 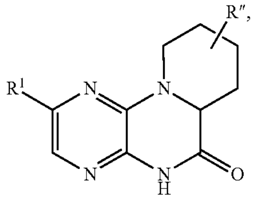

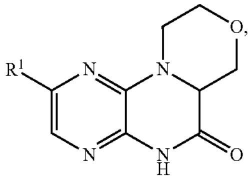 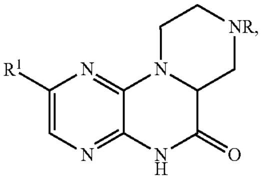 or

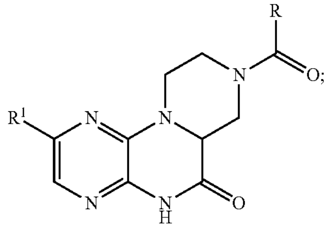

wherein R is at each occurrence independently H, or a substituted or unsubstituted $C_{1-4}$ alkyl; R" is H, OR, or a substituted or unsubstituted $C_{1-4}$ alkyl; and $R^1$ is as defined herein.

In some embodiments of compounds of formula (I), $R^3$ and $R^4$ are both H. In others, one of $R^3$ and $R^4$ is H and the other is other than H. In still others, one of $R^3$ and $R^4$ is $C_{1-4}$ alkyl (for example, methyl) and the other is H. In still others, both of $R^3$ and $R^4$ are $C_{1-4}$ alkyl (for example, methyl).

In some such embodiments described above, $R^1$ is substituted or unsubstituted aryl, or substituted or unsubstituted heteroaryl. For example, $R^1$ is phenyl, pyridyl, pyrimidyl, benzimidazolyl, indolyl, indazolyl, 1H-pyrrolo[2,3-b]pyridyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, halogen, aminocarbonyl, cyano, hydroxyalkyl and hydroxy. In others, $R^1$ is pyridyl substituted with one or more substituents independently selected from the group consisting of cyano, substituted or unsubstituted $C_{1-8}$ alkyl, substituted or unsubstituted heterocyclyl, hydroxyalkyl, halogen, aminocarbonyl, —OR, and $—NR_2$, wherein each R is independently H, or a substituted or unsubstituted $C_{1-4}$ alkyl. In others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and $—NR_2$, wherein R is independently H, or a substituted or unsubstituted $C_{1-4}$ alkyl In certain embodiments, the compounds of formula (I) have an $R^1$ group set forth herein and an $R^2$ group set forth herein.

In some embodiments of compounds of formula (I), the compound at a concentration of 10 μM inhibits mTOR, DNA-PK, or PI3K or a combination thereof, by at least about 50%. Compounds of formula (I) may be shown to be inhibitors of the kinases above in any suitable assay system, such as those described in the Examples herein.

In some embodiments of compounds of formula (I), the compound is 6-(1H-pyrrolo[2,3-b]pyridin-3-yl)-4-(2-(tetrahydro-2H-pyran-4-yl)ethyl)-3,4-dihydropyrazino[2,3-b]pyrazin-2(1H)-one;

6-(4-methyl-6-(1H-1,2,4-triazol-3-yl)pyridin-3-yl)-4-((tetrahydro-2H-pyran-4-yl)methyl)-3,4-dihydropyrazino[2,3-b]pyrazin-2(1H)-one;

6-(5-fluoro-2-methyl-4-(1H-1,2,4-triazol-3-yl)phenyl)-4-((trans-4-methoxycyclohexyl)methyl)-3,4-dihydropyrazino[2,3-b]pyrazin-2(1H)-one;

6-(5-fluoro-2-methyl-4-(1H-1,2,4-triazol-3-yl)phenyl)-4-((cis-4-methoxycyclohexyl)methyl)-3,4-dihydropyrazino[2,3-b]pyrazin-2(1H)-one;

6-(6-(1H-1,2,4-triazol-3-yl)pyridin-3-yl)-4-((trans-4-methoxycyclohexyl)methyl)-3,4-dihydropyrazino[2,3-b]pyrazin-2(1H)-one;

6-(5-fluoro-2-methyl-4-(1H-1,2,4-triazol-3-yl)phenyl)-4-((trans-4-hydroxycyclohexyl)methyl)-3,4-dihydropyrazino[2,3-b]pyrazin-2(1H)-one;

6-(6-(1H-1,2,4-triazol-3-yl)pyridin-3-yl)-4-((cis-4-methoxycyclohexyl)methyl)-3,4-dihydropyrazino[2,3-b]pyrazin-2(1H)-one;

6-(6-(1H-1,2,4-triazol-3-yl)pyridin-3-yl)-4-((trans-4-hydroxycyclohexyl)methyl)-3,4-dihydropyrazino[2,3-b]pyrazin-2(1H)-one;

6-(6-(1H-1,2,4-triazol-3-yl)pyridin-3-yl)-4-(cis-4-hydroxycyclohexyl)-3,4-dihydropyrazino[2,3-b]pyrazin-2(1H)-one;

6-(6-(1H-1,2,4-triazol-3-yl)pyridin-3-yl)-4-((cis-4-hydroxycyclohexyl)methyl)-3,4-dihydropyrazino[2,3-b]pyrazin-2(1H)-one;

6-(5-fluoro-2-methyl-4-(1H-1,2,4-triazol-3-yl)phenyl)-4-(trans-4-methoxycyclohexyl)-3,4-dihydropyrazino[2,3-b]pyrazin-2(1H)-one;

6-(6-(1H-1,2,4-triazol-3-yl)pyridin-3-yl)-4-(trans-4-methoxycyclohexyl)-3,4-dihydropyrazino[2,3-b]pyrazin-2(1H)-one;

6-(6-(1H-1,2,4-triazol-3-yl)pyridin-3-yl)-4-(trans-4-hydroxycyclohexyl)-3,4-dihydropyrazino[2,3-b]pyrazin-2(1H)-one;

6-(5-fluoro-2-methyl-4-(1H-1,2,4-triazol-3-yl)phenyl)-4-((cis-4-hydroxycyclohexyl)methyl)-3,4-dihydropyrazino[2,3-b]pyrazin-2(1H)-one;

6-(6-(1H-1,2,4-triazol-3-yl)pyridin-3-yl)-4-(cis-4-methoxycyclohexyl)-3,4-dihydropyrazino[2,3-b]pyrazin-2(1H)-one;

6-(6-(1H-1,2,4-triazol-3-yl)pyridin-3-yl)-4-(2-methoxyethyl)-3,4-dihydropyrazino[2,3-b]pyrazin-2(1H)-one;

6-(6-(1H-1,2,4-triazol-3-yl)pyridin-3-yl)-4-isopropyl-3,4-dihydropyrazino[2,3-b]pyrazin-2(1H)-one;

6-(5-fluoro-2-methyl-4-(1H-1,2,4-triazol-3-yl)phenyl)-4-(cis-4-hydroxycyclohexyl)-3,4-dihydropyrazino[2,3-b]pyrazin-2(1H)-one;

6-(5-fluoro-2-methyl-4-(1H-1,2,4-triazol-3-yl)phenyl)-4-(cis-4-methoxycyclohexyl)-3,4-dihydropyrazino[2,3-b]pyrazin-2(1H)-one;

6-(5-fluoro-2-methyl-4-(1H-1,2,4-triazol-3-yl)phenyl)-4-(2-methoxyethyl)-3,4-dihydropyrazino[2,3-b]pyrazin-2(1H)-one;

6-(6-(1H-1,2,4-triazol-3-yl)pyridin-3-yl)-4-(tetrahydro-2H-pyran-4-yl)-3,4-dihydropyrazino[2,3-b]pyrazin-2(1H)-one;

6-(6-(1H-1,2,4-triazol-3-yl)pyridin-3-yl)-4-ethyl-3,4-dihydropyrazino[2,3-b]pyrazin-2(1H)-one;

6-(5-fluoro-2-methyl-4-(1H-1,2,4-triazol-3-yl)phenyl)-4-(trans-4-hydroxycyclohexyl)-3,4-dihydropyrazino[2,3-b]pyrazin-2(1H)-one;

6-(5-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one;

6-(5-fluoro-2-methyl-4-(1H-1,2,4-triazol-3-yl)phenyl)-4-isopropyl-3,4-dihydropyrazino[2,3-b]pyrazin-2(1H)-one;

4-ethyl-6-(5-fluoro-2-methyl-4-(1H-1,2,4-triazol-3-yl)phenyl)-3,4-dihydropyrazino[2,3-b]pyrazin-2(1H)-one;

6-(3-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one;

6-(3-fluoro-2-methyl-4-(1H-1,2,4-triazol-3-yl)phenyl)-4-(cis-4-methoxycyclohexyl)-3,4-dihydropyrazino[2,3-b]pyrazin-2(1H)-one;

6-(3-fluoro-2-methyl-4-(1H-1,2,4-triazol-3-yl)phenyl)-4-(trans-4-methoxycyclohexyl)-3,4-dihydropyrazino[2,3-b]pyrazin-2(1H)-one;

4-(2-methoxyethyl)-6-(4-methyl-6-(1H-1,2,4-triazol-3-yl)pyridin-3-yl)-3,4-dihydropyrazino[2,3-b]pyrazin-2(1H)-one;

6-(3-(1H-1,2,4-triazol-5-yl)phenyl)-4-(2-(tetrahydro-2H-pyran-4-yl)ethyl)-3,4-dihydropyrazino[2,3-b]pyrazin-2(1H)-one;

5-(8-(2-methoxyethyl)-6-oxo-5,6,7,8-tetrahydropyrazino[2,3-b]pyrazin-2-yl)-4-methylpicolinamide;

3-(6-oxo-8-(2-(tetrahydro-2H-pyran-4-yl)ethyl)-5,6,7,8-tetrahydropyrazino[2,3-b]pyrazin-2-yl)benzamide;

3-(6-oxo-8-(2-(tetrahydro-2H-pyran-4-yl)ethyl)-5,6,7,8-tetrahydropyrazino[2,3-b]pyrazin-2-yl)benzonitrile;

5-(8-(trans-4-methoxycyclohexyl)-6-oxo-5,6,7,8-tetrahydropyrazino[2,3-b]pyrazin-2-yl)-4-methylpicolinamide;

6-(1H-imidazo[4,5-b]pyridin-6-yl)-4-(2-(tetrahydro-2H-pyran-4-yl)ethyl)-3,4-dihydropyrazino[2,3-b]pyrazin-2(1H)-one;

6-(1H-indazol-6-yl)-4-(2-(tetrahydro-2H-pyran-4-yl)ethyl)-3,4-dihydropyrazino[2,3-b]pyrazin-2(1H)-one;

4-((1R,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;

4-((1S,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;

4-((1R,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;

4-((1S,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one;

4-ethyl-6-(2-methyl-6-(4H-1,2,4-triazol-3-yl)pyridin-3-yl)-3,4-dihydropyrazino[2,3-b]pyrazin-2(1H)-one;

6-(1H-pyrrolo[2,3-b]pyridin-5-yl)-4-(2-(tetrahydro-2H-pyran-4-yl)ethyl)-3,4-dihydropyrazino[2,3-b]pyrazin-2(1H)-one;

6-(1H-indol-6-yl)-4-(2-(tetrahydro-2H-pyran-4-yl)ethyl)-3,4-dihydropyrazino[2,3-b]pyrazin-2(1H)-one;

6-(1H-indol-5-yl)-4-(2-(tetrahydro-2H-pyran-4-yl)ethyl)-3,4-dihydropyrazino[2,3-b]pyrazin-2(1H)-one;

4-(((1R,3S)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one;

4-(((1S,3R)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one;

6-(3-fluoro-2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(3-fluoro-2-methyl-4-(4H-1,2,4-triazol-3-yl)phenyl)-4-(2-methoxyethyl)-3,4-dihydropyrazino[2,3-b]pyrazin-2(1H)-one;

3,3-dimethyl-6-(4-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;

6-(6-(2-hydroxypropan-2-yl)pyridin-3-yl)-4-((1R,3S)-3-methoxycyclopentyl)-3,4-dihydropyrazino[2,3-b]pyrazin-2(1H)-one;

6-(6-(2-hydroxypropan-2-yl)pyridin-3-yl)-4-((1S,3R)-3-methoxycyclopentyl)-3,4-dihydropyrazino[2,3-b]pyrazin-2(1H)-one;

6-(6-(2-hydroxypropan-2-yl)pyridin-3-yl)-4-(((1S,3S)-3-methoxycyclopentyl)methyl)-3,4-dihydropyrazino[2,3-b]pyrazin-2(1H)-one;

6-(6-(2-hydroxypropan-2-yl)pyridin-3-yl)-4-(((1R,3R)-3-methoxycyclopentyl)methyl)-3,4-dihydropyrazino[2,3-b]pyrazin-2(1H)-one;

6-(6-(2-hydroxypropan-2-yl)pyridin-3-yl)-4-((1S,3S)-3-methoxycyclopentyl)-3,4-dihydropyrazino[2,3-b]pyrazin-2(1H)-one;

6-(6-(2-hydroxypropan-2-yl)pyridin-3-yl)-4-((1R,3R)-3-methoxycyclopentyl)-3,4-dihydropyrazino[2,3-b]pyrazin-2(1H)-one;

6-(6-(2-hydroxypropan-2-yl)pyridin-3-yl)-4-(((1R,3S)-3-methoxycyclopentyl)methyl)-3,4-dihydropyrazino[2,3-b]pyrazin-2(1H)-one;

6-(6-(2-hydroxypropan-2-yl)pyridin-3-yl)-4-(((1S,3R)-3-methoxycyclopentyl)methyl)-3,4-dihydropyrazino[2,3-b]pyrazin-2(1H)-one;

6-(3-fluoro-4-(4H-1,2,4-triazol-3-yl)phenyl)-4-(2-methoxyethyl)-3,4-dihydropyrazino[2,3-b]pyrazin-2(1H)-one;

6-(3-fluoro-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

7'-(2-methyl-4-(4H-1,2,4-triazol-3-yl)phenyl)-1'-((tetrahydro-2H-pyran-4-yl)methyl)-1'H-spiro[cyclopentane-1,2'-pyrazino[2,3-b]pyrazin]-3'(4'H)-one;

7'-(2-methyl-4-(4H-1,2,4-triazol-3-yl)phenyl)-1'-((tetrahydro-2H-pyran-4-yl)methyl)-1'H-spiro[cyclobutane-1,2'-pyrazino[2,3-b]pyrazin]-3'(4'H)-one;

4-(cyclopropylmethyl)-6-(6-(2-hydroxypropan-2-yl)pyridin-3-yl)-3,4-dihydropyrazino[2,3-b]pyrazin-2(1H)-one;

7'-(2-methyl-4-(4H-1,2,4-triazol-3-yl)phenyl)-1'H-spiro[cyclopentane-1,2'-pyrazino[2,3-b]pyrazin]-3'(4'H)-one;

7'-(2-methyl-4-(4H-1,2,4-triazol-3-yl)phenyl)-1'H-spiro[cyclobutane-1,2'-pyrazino[2,3-b]pyrazin]-3'(4'H)-one;

7'-(2-methyl-4-(4H-1,2,4-triazol-3-yl)phenyl)-1'H-spiro[cyclopropane-1,2'-pyrazino[2,3-b]pyrazin]-3'(4'H)-one;

(R)-6-(4-(4H-1,2,4-triazol-3-yl)phenyl)-4-((tetrahydrofuran-2-yl)methyl)-3,4-dihydropyrazino[2,3-b]pyrazin-2(1H)-one;

(S)-6-(4-(4H-1,2,4-triazol-3-yl)phenyl)-4-((tetrahydrofuran-2-yl)methyl)-3,4-dihydropyrazino[2,3-b]pyrazin-2(1H)-one;

6-(1H-indazol-5-yl)-4-(2-(tetrahydro-2H-pyran-4-yl)ethyl)-3,4-dihydropyrazino[2,3-b]pyrazin-2(1H)-one;

4-(6-oxo-8-(2-(tetrahydro-2H-pyran-4-yl)ethyl)-5,6,7,8-tetrahydropyrazino[2,3-b]pyrazin-2-yl)benzamide;

4-(2-methoxyethyl)-3,3-dimethyl-6-(2-methyl-4-(4H-1,2,4-triazol-3-yl)phenyl)-3,4-dihydropyrazino[2,3-b]pyrazin-2(1H)-one;

4-ethyl-3,3-dimethyl-6-(2-methyl-4-(4H-1,2,4-triazol-3-yl)phenyl)-3,4-dihydropyrazino[2,3-b]pyrazin-2(1H)-one;

6-(2-methyl-4-(4H-1,2,4-triazol-3-yl)phenyl)-3,4-dihydropyrazino[2,3-b]pyrazin-2(1H)-one;

3,3-dimethyl-6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;

(R)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one;

3,3-dimethyl-6-(2-methyl-4-(4H-1,2,4-triazol-3-yl)phenyl)-4-((tetrahydro-2H-pyran-4-yl)methyl)-3,4-dihydropyrazino[2,3-b]pyrazin-2(1H)-one;

6-(6-(2-hydroxypropan-2-yl)-4-methylpyridin-3-yl)-4-(trans-4-methoxycyclohexyl)-3,4-dihydropyrazino[2,3-b]pyrazin-2(1H)-one;

6-(6-(2-hydroxypropan-2-yl)-4-methylpyridin-3-yl)-4-((tetrahydro-2H-pyran-4-yl)methyl)-3,4-dihydropyrazino[2,3-b]pyrazin-2(1H)-one;

3,3-dimethyl-6-(2-methyl-4-(4H-1,2,4-triazol-3-yl)phenyl)-3,4-dihydropyrazino[2,3-b]pyrazin-2(1H)-one;

3,3-dimethyl-6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;

6-(6-(2-hydroxypropan-2-yl)-2-methylpyridin-3-yl)-4-((tetrahydro-2H-pyran-4-yl)methyl)-3,4-dihydropyrazino[2,3-b]pyrazin-2(1H)-one;

6-(6-(2-hydroxypropan-2-yl)-2-methylpyridin-3-yl)-4-(trans-4-methoxycyclohexyl)-3,4-dihydropyrazino[2,3-b]pyrazin-2(1H)-one;

(S)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one;

3,3-dimethyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(6-(2-hydroxypropan-2-yl)pyridin-3-yl)-3,3-dimethyl-4-(2-(tetrahydro-2H-pyran-4-yl)ethyl)-3,4-dihydropyrazino[2,3-b]pyrazin-2(1H)-one;

6-(4-(2-hydroxypropan-2-yl)phenyl)-4-(trans-4-methoxycyclohexyl)-3,4-dihydropyrazino[2,3-b]pyrazin-2(1H)-one;

6-(4-(2-hydroxypropan-2-yl)phenyl)-4-((trans-4-methoxycyclohexyl)methyl)-3,4-dihydropyrazino[2,3-b]pyrazin-2(1H)-one;

4-(cis-4-methoxycyclohexyl)-6-(2-methyl-6-(4H-1,2,4-triazol-3-yl)pyridin-3-yl)-3,4-dihydropyrazino[2,3-b]pyrazin-2(1H)-one;

4-(trans-4-methoxycyclohexyl)-6-(2-methyl-6-(4H-1,2,4-triazol-3-yl)pyridin-3-yl)-3,4-dihydropyrazino[2,3-b]pyrazin-2(1H)-one;

6-(4-(2-hydroxypropan-2-yl)phenyl)-4-((tetrahydro-2H-pyran-4-yl)methyl)-3,4-dihydropyrazino[2,3-b]pyrazin-2(1H)-one;

4-(2-methoxyethyl)-6-(2-methyl-6-(4H-1,2,4-triazol-3-yl)pyridin-3-yl)-3,4-dihydropyrazino[2,3-b]pyrazin-2(1H)-one;

9-(6-(4H-1,2,4-triazol-3-yl)-3-pyridyl)-6,11,4a-trihydromorpholino[4,3-e]pyrazino[2,3-b]pyrazin-5-one;

6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one;

5-(8-(cis-4-methoxycyclohexyl)-6-oxo-5,6,7,8-tetrahydropyrazino[2,3-b]pyrazin-2-yl)-6-methylpicolinonitrile;

6-(6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;

9-(4-(4H-1,2,4-triazol-3-yl)-2-methylphenyl)-3-(2-methoxyacetyl)-6,11,4a-trihydropiperazino[1,2-e]pyrazino[2,3-b]pyrazin-5-one;

9-(4-(4H-1,2,4-triazol-3-yl)-2-methylphenyl)-6,11,4a-trihydropiperazino[1,2-e]pyrazino[2,3-b]pyrazin-5-one;

9-(4-(4H-1,2,4-triazol-3-yl)-2-methylphenyl)-3-(2-methoxyethyl)-6,11,4a-trihydropiperazino[1,2-e]pyrazino[2,3-b]pyrazin-5-one;

4-(cyclopentylmethyl)-6-(2-methyl-6-(4H-1,2,4-triazol-3-yl)pyridin-3-yl)-3,4-dihydropyrazino[2,3-b]pyrazin-2(1H)-one;

9-(6-(4H-1,2,4-triazol-3-yl)-2-methyl-3-pyridyl)-6,11,4a-trihydromorpholino[4,3-e]pyrazino[2,3-b]pyrazin-5-one;

4-(trans-4-hydroxycyclohexyl)-6-(6-(2-hydroxypropan-2-yl)pyridin-3-yl)-3,4-dihydropyrazino[2,3-b]pyrazin-2(1H)-one;

4-(cis-4-hydroxycyclohexyl)-6-(6-(2-hydroxypropan-2-yl)pyridin-3-yl)-3,4-dihydropyrazino[2,3-b]pyrazin-2(1H)-one;

6-(6-(2-hydroxypropan-2-yl)pyridin-3-yl)-4-((tetrahydrofuran-3-yl)methyl)-3,4-dihydropyrazino[2,3-b]pyrazin-2(1H)-one;

4-(cyclopentylmethyl)-6-(6-(2-hydroxypropan-2-yl)pyridin-3-yl)-3,4-dihydropyrazino[2,3-b]pyrazin-2(1H)-one;

6-(6-(2-hydroxypropan-2-yl)pyridin-3-yl)-4-neopentyl-3,4-dihydropyrazino[2,3-b]pyrazin-2(1H)-one;

6-(6-(2-hydroxypropan-2-yl)pyridin-3-yl)-4-isobutyl-3,4-dihydropyrazino[2,3-b]pyrazin-2(1H)-one;

3-methyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(6-(2-hydroxypropan-2-yl)pyridin-3-yl)-4-(piperidin-4-yl)-3,4-dihydropyrazino[2,3-b]pyrazin-2(1H)-one;

6-(6-(2-hydroxypropan-2-yl)pyridin-3-yl)-4-(2-(tetrahydro-2H-pyran-3-yl)ethyl)-3,4-dihydropyrazino[2,3-b]pyrazin-2(1H)-one;

8-(4-(4H-1,2,4-triazol-3-yl)-2-methylphenyl)(3aS,2R)-2-methoxy-5,10,3a-trihydropyrazino[2,3-b]pyrrolidino[1,2-e]pyrazin-4-one;

8-(4-(4H-1,2,4-triazol-3-yl)-2-methylphenyl)(2R,3aR)-2-methoxy-5,10,3a-trihydropyrazino[2,3-b]pyrrolidino[1,2-e]pyrazin-4-one;

8-(4-(4H-1,2,4-triazol-3-yl)-2-methylphenyl)(2S,3aR)-2-methoxy-5,10,3a-trihydropyrazino[2,3-b]pyrrolidino[1,2-e]pyrazin-4-one;

8-(4-(4H-1,2,4-triazol-3-yl)-2-methylphenyl)(2S,3aS)-2-methoxy-5,10,3a-trihydropyrazino[2,3-b]pyrrolidino[1,2-e]pyrazin-4-one;

6-(6-(2-hydroxypropan-2-yl)pyridin-3-yl)-4-(3-methoxypropyl)-3,4-dihydropyrazino[2,3-b]pyrazin-2(1H)-one;

(S)-6-(6-(2-hydroxypropan-2-yl)pyridin-3-yl)-4-((tetrahydrofuran-2-yl)methyl)-3,4-dihydropyrazino[2,3-b]pyrazin-2(1H)-one;

(R)-6-(6-(2-hydroxypropan-2-yl)pyridin-3-yl)-4-((tetrahydrofuran-2-yl)methyl)-3,4-dihydropyrazino[2,3-b]pyrazin-2(1H)-one;

6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one;

9-(4-(4H-1,2,4-triazol-3-yl)-2-methylphenyl)-3-methyl-6,11,4a-trihydropiperazino[1,2-e]pyrazino[2,3-b]pyrazin-5-one;

9-(4-(4H-1,2,4-triazol-3-yl)phenyl)-6,11,4a-trihydromorpholino[4,3-e]pyrazino[2,3-b]pyrazin-5-one;

9-(4-(4H-1,2,4-triazol-3-yl)-2-methylphenyl)-6,11,4a-trihydropiperidino[1,2-e]pyrazino[2,3-b]pyrazin-5-one;

6-(6-(2-hydroxypropan-2-yl)pyridin-3-yl)-4-(trans-4-methoxycyclohexyl)-3,4-dihydropyrazino[2,3-b]pyrazin-2(1H)-one;

6-(6-(2-hydroxypropan-2-yl)pyridin-3-yl)-4-(cis-4-methoxycyclohexyl)-3,4-dihydropyrazino[2,3-b]pyrazin-2(1H)-one;

6-(6-(2-hydroxypropan-2-yl)pyridin-3-yl)-4-(2-morpholinoethyl)-3,4-dihydropyrazino[2,3-b]pyrazin-2(1H)-one;

6-(6-(2-hydroxypropan-2-yl)pyridin-3-yl)-4-phenethyl-3,4-dihydropyrazino[2,3-b]pyrazin-2(1H)-one;

6-(6-(2-hydroxypropan-2-yl)pyridin-3-yl)-4-(tetrahydro-2H-pyran-4-yl)-3,4-dihydropyrazino[2,3-b]pyrazin-2(1H)-one;

4-(cyclohexylmethyl)-6-(6-(2-hydroxypropan-2-yl)pyridin-3-yl)-3,4-dihydropyrazino[2,3-b]pyrazin-2(1H)-one;

6-(6-(2-hydroxypropan-2-yl)pyridin-3-yl)-4-((trans-4-methoxycyclohexyl)methyl)-3,4-dihydropyrazino[2,3-b]pyrazin-2(1H)-one;

6-(6-(2-hydroxypropan-2-yl)pyridin-3-yl)-4-((cis-4-methoxycyclohexyl)methyl)-3,4-dihydropyrazino[2,3-b]pyrazin-2(1H)-one;

(R)-6-(6-(2-hydroxypropan-2-yl)pyridin-3-yl)-4-(tetrahydrofuran-3-yl)-3,4-dihydropyrazino[2,3-b]pyrazin-2(1H)-one;

(S)-6-(6-(2-hydroxypropan-2-yl)pyridin-3-yl)-4-(tetrahydrofuran-3-yl)-3,4-dihydropyrazino[2,3-b]pyrazin-2(1H)-one;

(S)-6-(6-(2-hydroxypropan-2-yl)pyridin-3-yl)-3-methyl-4-(2-(tetrahydro-2H-pyran-4-yl)ethyl)-3,4-dihydropyrazino[2,3-b]pyrazin-2(1H)-one;

9-[6-(1-hydroxy-isopropyl)-3-pyridyl]-6,11,4a-trihydromorpholino[4,3-e]pyrazino[2,3-b]pyrazin-5-one;

6-(6-(2-hydroxypropan-2-yl)pyridin-3-yl)-4-((tetrahydro-2H-pyran-4-yl)methyl)-3,4-dihydropyrazino[2,3-b]pyrazin-2(1H)-one;

6-(6-(2-hydroxypropan-2-yl)pyridin-3-yl)-4-(2-methoxyethyl)-3,4-dihydropyrazino[2,3-b]pyrazin-2(1H)-one;

6-(2-amino-7-methyl-1H-benzo[d]imidazol-5-yl)-4-(3-(trifluoromethyl)benzyl)-3,4-dihydropyrazino[2,3-b]pyrazin-2(1H)-one;

6-(6-(2-hydroxypropan-2-yl)pyridin-3-yl)-4-(3-(trifluoromethyl)benzyl)-3,4-dihydropyrazino[2,3-b]pyrazin-2(1H)-one;

9-(4-(4H-1,2,4-triazol-3-yl)-2-methylphenyl)-6,11,4a-trihydromorpholino[4,3-e]pyrazino[2,3-b]pyrazin-5-one;

6-(4-methyl-2-(methylamino)-1H-benzo[d]imidazol-6-yl)-4-(2-(tetrahydro-2H-pyran-4-yl)ethyl)-3,4-dihydropyrazino[2,3-b]pyrazin-2(1H)-one;

8-(4-(4H-1,2,4-triazol-3-yl)-2-methylphenyl)-5,10,3a-trihydropyrazino[2,3-b]pyrrolidino[1,2-e]pyrazin-4-one;

6-(4-(4H-1,2,4-triazol-3-yl)phenyl)-4-ethyl-3,4-dihydropyrazino[2,3-b]pyrazin-2(1H)-one;

6-(4-(4H-1,2,4-triazol-3-yl)phenyl)-4-((tetrahydro-2H-pyran-4-yl)methyl)-3,4-dihydropyrazino[2,3-b]pyrazin-2(1H)-one;

6-(6-(2-hydroxypropan-2-yl)pyridin-3-yl)-4-(2-(tetrahydro-2H-pyran-4-yl)ethyl)-3,4-dihydropyrazino[2,3-b]pyrazin-2(1H)-one;

6-(4-(4H-1,2,4-triazol-3-yl)phenyl)-4-(2-methoxyethyl)-3,4-dihydropyrazino[2,3-b]pyrazin-2(1H)-one;

6-(4-(4H-1,2,4-triazol-3-yl)phenyl)-4-(3-(trifluoromethyl)benzyl)-3,4-dihydropyrazino[2,3-b]pyrazin-2(1H)-one;

6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one;

6-(4-methyl-1H-benzo[d]imidazol-6-yl)-4-(2-(tetrahydro-2H-pyran-4-yl)ethyl)-3,4-dihydropyrazino[2,3-b]pyrazin-2(1H)-one;

6-(4-(2-hydroxypropan-2-yl)phenyl)-4-(2-(tetrahydro-2H-pyran-4-yl)ethyl)-3,4-dihydropyrazino[2,3-b]pyrazin-2(1H)-one; or 6-(4-(1H-1,2,4-triazol-5-yl)phenyl)-4-(2-(tetrahydro-2H-pyran-4-yl)ethyl)-3,4-dihydropyrazino[2,3-b]pyrazin-2(1H)-one.

Further provided herein are compounds having the following formula (II):

(II)

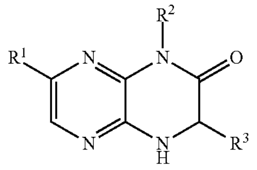

and pharmaceutically acceptable salts, clathrates, solvates, stereoisomers, tautomers, and prodrugs thereof, wherein:

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl;

provided the compound of formula (II) is not 7-(4-hydroxyphenyl)-1-(3-methoxybenzyl)-3,4-dihydropyrazino[2,3-b]pyrazin-2(1H)-one, depicted below:

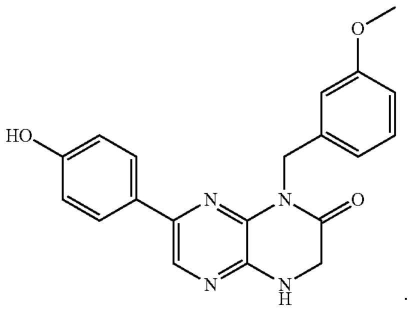

.

In some embodiments of compounds of formula (II), $R^1$ is substituted or unsubstituted aryl or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl or pyrazolyl), aminocarbonyl, halogen (for example, fluorine), cyano, hydroxyalkyl and hydroxy. In other embodiments, $R^1$ is pyridyl substituted with one or more substituents independently selected from the group consisting of substituted or unsubstituted $C_{1-8}$ alkyl (for example, methyl), substituted or unsubstituted heterocyclyl (for example, a substituted or unsubstituted triazolyl), halogen, aminocarbonyl, cyano, hydroxyalkyl (for example, hydroxypropyl), —OR, and —$NR_2$, wherein each R is independently H, or a substituted or unsubstituted $C_{1-4}$ alkyl. In some embodiments, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and —$NR_2$, wherein R is independently H, or a substituted or unsubstituted $C_{1-4}$ alkyl.

In some embodiments, $R^1$ is

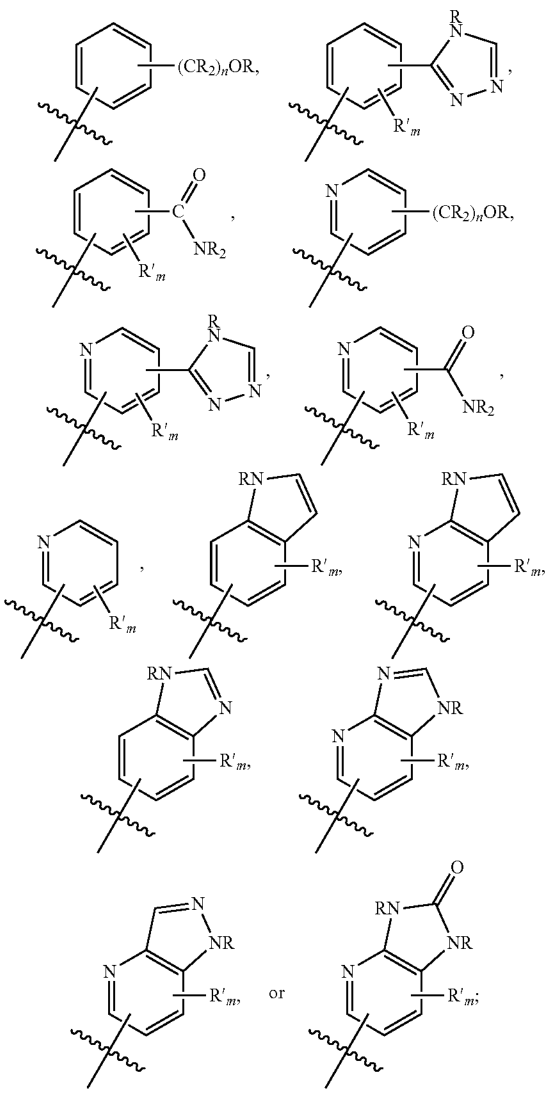

wherein R is at each occurrence independently H, or a substituted or unsubstituted $C_{1-4}$ alkyl (for example, methyl); R' is at each occurrence independently a substituted or unsubstituted $C_{1-4}$ alkyl (for example, methyl), halogen (for example, fluoro), cyano, —OR, or —$NR_2$; m is 0-3; and n is 0-3. It will be understood by those skilled in the art that any of the substituents R' may be attached to any suitable atom of any of the rings in the fused ring systems.

In some embodiments of compounds of formula (II), $R^1$ is

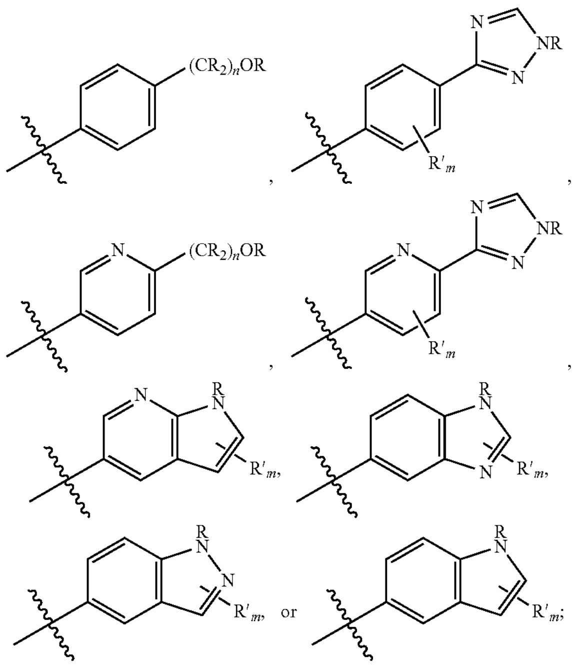

wherein R is at each occurrence independently H, or a substituted or unsubstituted $C_{1-4}$ alkyl; R' is at each occurrence independently a substituted or unsubstituted $C_{1-4}$ alkyl, halogen, cyano, —OR or —$NR_2$; m is 0-3; and n is 0-3.

In some embodiments of compounds of formula (II), $R^2$ is H, substituted or unsubstituted $C_{1-8}$ alkyl, substituted or unsubstituted cycloalkyl, substituted or unsubstituted heterocyclyl, substituted or unsubstituted $C_{1-4}$ alkyl-heterocyclyl, substituted or unsubstituted $C_{1-4}$ alkyl-aryl, or substituted or unsubstituted $C_{1-4}$ alkyl-cycloalkyl. For example, $R^2$ is H, methyl, ethyl, n-propyl, isopropyl, n-butyl, sec-butyl, isobutyl, tert-butyl, n-pentyl, isopentyl, cyclopentyl, cyclohexyl, tetrahydrofuranyl, tetrahydropyranyl, ($C_{1-4}$ alkyl)-phenyl, ($C_{1-4}$ alkyl)-cyclopropyl, ($C_{1-4}$ alkyl)-cyclobutyl, ($C_{1-4}$ alkyl)-cyclopentyl, ($C_{1-4}$ alkyl)-cyclohexyl, ($C_{1-4}$ alkyl)-pyrrolidyl, ($C_{1-4}$ alkyl)-piperidyl, ($C_{1-4}$ alkyl)-piperazinyl, ($C_{1-4}$ alkyl)-morpholinyl, ($C_{1-4}$ alkyl)-tetrahydrofuranyl, or ($C_{1-4}$ alkyl)-tetrahydropyranyl, each optionally substituted.

In other embodiments, $R^2$ is H, $C_{1-4}$ alkyl, ($C_{1-4}$alkyl)(OR),

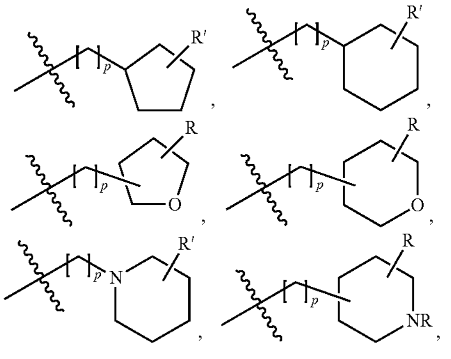

-continued

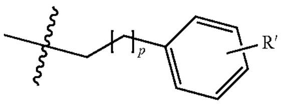, or 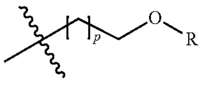;

wherein R is at each occurrence independently H, or a substituted or unsubstituted $C_{1-4}$ alkyl (for example, methyl); R' is at each occurrence independently H, —OR, cyano, or a substituted or unsubstituted $C_{1-4}$ alkyl (for example, methyl); and p is 0-3.

In other embodiments of compounds of formula (II), $R^2$ is H, $C_{1-4}$ alkyl, $(C_{1-4}alkyl)(OR)$,

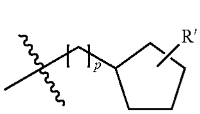, 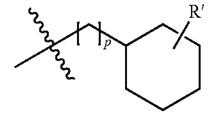,

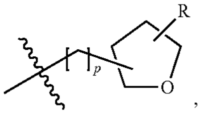, 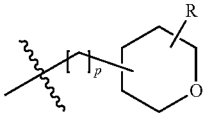,

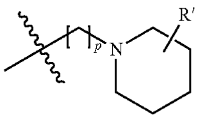, 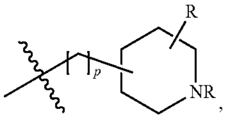,

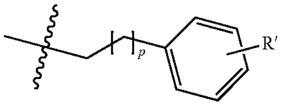, or 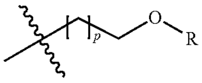;

wherein R is at each occurrence independently H, or a substituted or unsubstituted $C_{1-2}$ alkyl; R' is at each occurrence independently H, —OR, cyano, or a substituted or unsubstituted $C_{1-2}$ alkyl; and p is 0-1.

In other embodiments of compounds of formula (II), $R^3$ is H.

In some such embodiments described herein, $R^1$ is substituted or unsubstituted aryl, or substituted or unsubstituted heteroaryl. For example, $R^1$ is phenyl, pyridyl, pyrimidyl, benzimidazolyl, 1H-pyrrolo[2,3-b]pyridyl, indazolyl, indolyl, 1H-imidazo[4,5-b]pyridine, pyridyl, 1H-imidazo[4,5-b]pyridin-2(3H)-onyl, 3H-imidazo[4,5-b]pyridyl, or pyrazolyl, each optionally substituted. In some embodiments, $R^1$ is phenyl substituted with one or more substituents independently selected from the group consisting of substituted or unsubstituted $C_{1-8}$ alkyl, substituted or unsubstituted heterocyclyl, aminocarbonyl, halogen, cyano, hydroxyalkyl and hydroxy. In others, $R^1$ is pyridyl substituted with one or more substituents independently selected from the group consisting of $C_{1-8}$ alkyl, substituted or unsubstituted heterocyclyl, halogen, aminocarbonyl, cyano, hydroxyalkyl, —OR, and $—NR_2$, wherein each R is independently H, or a substituted or unsubstituted $C_{1-4}$ alkyl. In still others, $R^1$ is 1H-pyrrolo[2,3-b]pyridyl or benzimidazolyl, optionally substituted with one or more substituents independently selected from the group consisting of substituted or unsubstituted $C_{1-8}$ alkyl, and $—NR_2$, wherein R is independently H, or a substituted or unsubstituted $C_{1-4}$ alkyl.

In certain embodiments, the compounds of formula (II) have an $R^1$ group set forth herein and an $R^2$ group set forth herein.

In some embodiments of compounds of formula (II), the compound at a concentration of 10 μM inhibits mTOR, DNA-PK, PI3K, or a combination thereof by at least about 50%. Compounds of formula (II) may be shown to be inhibitors of the kinases above in any suitable assay system, such as those described in the Examples herein.

In some embodiments of compounds of formula (II), the compound is 7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-methoxycyclohexyl)-3,4-dihydropyrazino[2,3-b]pyrazin-2(1H)-one;

7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one;

1-ethyl-7-(1H-pyrrolo[3,2-b]pyridin-5-yl)-3,4-dihydropyrazino[2,3-b]pyrazin-2(1H)-one;

7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one;

7-(1H-benzo[d]imidazol-4-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one;

7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one;

7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(cis-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one;

7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one;

7-(6-(1H-1,2,4-triazol-3-yl)pyridin-3-yl)-1-(2-methoxyethyl)-3,4-dihydropyrazino[2,3-b]pyrazin-2(1H)-one;

7-(6-(1H-1,2,4-triazol-3-yl)pyridin-3-yl)-1-ethyl-3,4-dihydropyrazino[2,3-b]pyrazin-2(1H)-one;

7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one;

7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one;

7-(1H-indol-4-yl)-1-(2-(tetrahydro-2H-pyran-4-yl)ethyl)-3,4-dihydropyrazino[2,3-b]pyrazin-2(1H)-one;

7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one;

7-(6-(1H-1,2,4-triazol-3-yl)pyridin-3-yl)-1-(trans-4-hydroxycyclohexyl)-3,4-dihydropyrazino[2,3-b]pyrazin-2(1H)-one;

7-(6-(1H-1,2,4-triazol-3-yl)pyridin-3-yl)-1-(trans-4-methoxycyclohexyl)-3,4-dihydropyrazino[2,3-b]pyrazin-2(1H)-one;

7-(6-(1H-1,2,4-triazol-3-yl)pyridin-3-yl)-1-isopropyl-3,4-dihydropyrazino[2,3-b]pyrazin-2(1H)-one;

7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one;

7-(5-fluoro-2-methyl-4-(1H-1,2,4-triazol-3-yl)phenyl)-1-(2-methoxyethyl)-3,4-dihydropyrazino[2,3-b]pyrazin-2(1H)-one;

7-(5-fluoro-2-methyl-4-(1H-1,2,4-triazol-3-yl)phenyl)-1-isopropyl-3,4-dihydropyrazino[2,3-b]pyrazin-2(1H)-one;

1-ethyl-7-(5-fluoro-2-methyl-4-(1H-1,2,4-triazol-3-yl)phenyl)-3,4-dihydropyrazino[2,3-b]pyrazin-2(1H)-one;

7-(2-hydroxypyridin-4-yl)-1-(2-(tetrahydro-2H-pyran-4-yl)ethyl)-3,4-dihydropyrazino[2,3-b]pyrazin-2(1H)-one;

1-isopropyl-7-(4-methyl-6-(1H-1,2,4-triazol-3-yl)pyridin-3-yl)-3,4-dihydropyrazino[2,3-b]pyrazin-2(1H)-one;

5-(8-isopropyl-7-oxo-5,6,7,8-tetrahydropyrazino[2,3-b]pyrazin-2-yl)-4-methylpicolinamide;

7-(1H-indazol-4-yl)-1-(2-(tetrahydro-2H-pyran-4-yl)ethyl)-3,4-dihydropyrazino[2,3-b]pyrazin-2(1H)-one;

7-(2-aminopyrimidin-5-yl)-1-(2-(tetrahydro-2H-pyran-4-yl)ethyl)-3,4-dihydropyrazino[2,3-b]pyrazin-2(1H)-one;

7-(2-aminopyridin-4-yl)-1-(2-(tetrahydro-2H-pyran-4-yl)ethyl)-3,4-dihydropyrazino[2,3-b]pyrazin-2(1H)-one;

7-(6-(methylamino)pyridin-3-yl)-1-(2-(tetrahydro-2H-pyran-4-yl)ethyl)-3,4-dihydropyrazino[2,3-b]pyrazin-2(1H)-one;

7-(6-hydroxypyridin-3-yl)-1-(2-(tetrahydro-2H-pyran-4-yl)ethyl)-3,4-dihydropyrazino[2,3-b]pyrazin-2(1H)-one;

7-(4-(1H-pyrazol-3-yl)phenyl)-1-(2-methoxyethyl)-3,4-dihydropyrazino[2,3-b]pyrazin-2(1H)-one;

7-(pyridin-3-yl)-1-(2-(tetrahydro-2H-pyran-4-yl)ethyl)-3,4-dihydropyrazino[2,3-b]pyrazin-2(1H)-one;

7-(1H-indazol-4-yl)-1-(2-methoxyethyl)-3,4-dihydropyrazino[2,3-b]pyrazin-2(1H)-one;

7-(1H-indazol-6-yl)-1-(2-methoxyethyl)-3,4-dihydropyrazino[2,3-b]pyrazin-2(1H)-one;

7-(pyrimidin-5-yl)-1-(2-(tetrahydro-2H-pyran-4-yl)ethyl)-3,4-dihydropyrazino[2,3-b]pyrazin-2(1H)-one;

7-(6-methoxypyridin-3-yl)-1-(2-(tetrahydro-2H-pyran-4-yl)ethyl)-3,4-dihydropyrazino[2,3-b]pyrazin-2(1H)-one;

1-(2-methoxyethyl)-7-(1H-pyrrolo[2,3-b]pyridin-5-yl)-3,4-dihydropyrazino[2,3-b]pyrazin-2(1H)-one;

1-ethyl-7-(1H-pyrrolo[2,3-b]pyridin-5-yl)-3,4-dihydropyrazino[2,3-b]pyrazin-2(1H)-one;

1-ethyl-7-(1H-indazol-4-yl)-3,4-dihydropyrazino[2,3-b]pyrazin-2(1H)-one;

7-(pyridin-4-yl)-1-(2-(tetrahydro-2H-pyran-4-yl)ethyl)-3,4-dihydropyrazino[2,3-b]pyrazin-2(1H)-one;

7-(6-aminopyridin-3-yl)-1-(2-(tetrahydro-2H-pyran-4-yl)ethyl)-3,4-dihydropyrazino[2,3-b]pyrazin-2(1H)-one;

1-methyl-7-(2-methyl-6-(4H-1,2,4-triazol-3-yl)pyridin-3-yl)-3,4-dihydropyrazino[2,3-b]pyrazin-2(1H)-one;

2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide;

4-methyl-5-(7-oxo-8-((tetrahydro-2H-pyran-4-yl)methyl)-5,6,7,8-tetrahydropyrazino[2,3-b]pyrazin-2-yl)picolinamide;

5-(8-((cis-4-methoxycyclohexyl)methyl)-7-oxo-5,6,7,8-tetrahydropyrazino[2,3-b]pyrazin-2-yl)-4-methylpicolinamide;

7-(1H-pyrazol-4-yl)-1-(2-(tetrahydro-2H-pyran-4-yl)ethyl)-3,4-dihydropyrazino[2,3-b]pyrazin-2(1H)-one;

1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one;

3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile;

1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one;

3-(7-oxo-8-(2-(tetrahydro-2H-pyran-4-yl)ethyl)-5,6,7,8-tetrahydropyrazino[2,3-b]pyrazin-2-yl)benzamide;

5-(8-((trans-4-methoxycyclohexyl)methyl)-7-oxo-5,6,7,8-tetrahydropyrazino[2,3-b]pyrazin-2-yl)-4-methylpicolinamide;

3-((7-(6-(2-hydroxypropan-2-yl)pyridin-3-yl)-2-oxo-3,4-dihydropyrazino[2,3-b]pyrazin-1(2H)-yl)methyl)benzonitrile;

7-(6-(2-hydroxypropan-2-yl)pyridin-3-yl)-1-((1R,3R)-3-methoxycyclopentyl)-3,4-dihydropyrazino[2,3-b]pyrazin-2(1H)-one;

7-(6-(2-hydroxypropan-2-yl)pyridin-3-yl)-1-((1S,3R)-3-methoxycyclopentyl)-3,4-dihydropyrazino[2,3-b]pyrazin-2(1H)-one;

7-(6-(2-hydroxypropan-2-yl)pyridin-3-yl)-1-((1 S, 3 S)-3-methoxycyclopentyl)-3,4-dihydropyrazino[2,3-b]pyrazin-2(1H)-one;

7-(6-(2-hydroxypropan-2-yl)pyridin-3-yl)-1-((1R,3 S)-3-methoxycyclopentyl)-3,4-dihydropyrazino[2,3-b]pyrazin-2(1H)-one;

7-(1H-indazol-6-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(2-morpholinoethyl)-3,4-dihydropyrazino[2,3-b]pyrazin-2(1H)-one;

1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(2-morpholinoethyl)-3,4-dihydropyrazino[2,3-b]pyrazin-2(1H)-one;

1-isopropyl-7-(2-methyl-6-(4H-1,2,4-triazol-3-yl)pyridin-3-yl)-3,4-dihydropyrazino[2,3-b]pyrazin-2(1H)-one;

7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one;

1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;

1-(trans-4-hydroxycyclohexyl)-7-(6-(2-hydroxypropan-2-yl)pyridin-3-yl)-3,4-dihydropyrazino[2,3-b]pyrazin-2(1H)-one;

1-(cis-4-hydroxycyclohexyl)-7-(6-(2-hydroxypropan-2-yl)pyridin-3-yl)-3,4-dihydropyrazino[2,3-b]pyrazin-2(1H)-one;

4-(7-oxo-8-(2-(tetrahydro-2H-pyran-4-yl)ethyl)-5,6,7,8-tetrahydropyrazino[2,3-b]pyrazin-2-yl)benzamide;

7-(1H-indazol-5-yl)-1-(2-(tetrahydro-2H-pyran-4-yl)ethyl)-3,4-dihydropyrazino[2,3-b]pyrazin-2(1H)-one;

7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one;

1-((1S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one;

7-(1H-indol-5-yl)-1-(2-(tetrahydro-2H-pyran-4-yl)ethyl)-3,4-dihydropyrazino[2,3-b]pyrazin-2(1H)-one;

1-ethyl-7-(2-methyl-6-(4H-1,2,4-triazol-3-yl)pyridin-3-yl)-3,4-dihydropyrazino[2,3-b]pyrazin-2(1H)-one;

7-(1H-indol-6-yl)-1-(2-(tetrahydro-2H-pyran-4-yl)ethyl)-3,4-dihydropyrazino[2,3-b]pyrazin-2(1H)-one;

7-(4-(2-hydroxypropan-2-yl)phenyl)-1-(trans-4-methoxycyclohexyl)-3,4-dihydropyrazino[2,3-b]pyrazin-2(1H)-one;

7-(6-(2-hydroxypropan-2-yl)pyridin-3-yl)-1-(tetrahydro-2H-pyran-4-yl)-3,4-dihydropyrazino[2,3-b]pyrazin-2(1H)-one;

1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((cis-4-methoxycyclohexyl)methyl)-3,4-dihydropyrazino[2,3-b]pyrazin-2(1H)-one;

1-(2-methoxyethyl)-7-(4-methyl-2-(methylamino)-1H-benzo[d]imidazol-6-yl)-3,4-dihydropyrazino[2,3-b]pyrazin-2(1H)-one;

7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one;

7-(2-methyl-4-(4H-1,2,4-triazol-3-yl)phenyl)-3,4-dihydropyrazino[2,3-b]pyrazin-2(1H)-one;

1-(2-methoxyethyl)-7-(4-methyl-6-(1H-1,2,4-triazol-3-yl)pyridin-3-yl)-3,4-dihydropyrazino[2,3-b]pyrazin-2(1H)-one;

1-benzyl-7-(2-methyl-4-(4H-1,2,4-triazol-3-yl)phenyl)-3,4-dihydropyrazino[2,3-b]pyrazin-2(1H)-one;

7-(3-fluoro-4-(4H-1,2,4-triazol-3-yl)phenyl)-1-(2-methoxyethyl)-3,4-dihydropyrazino[2,3-b]pyrazin-2(1H)-one;

7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-methoxyethyl)-3,4-dihydropyrazino[2,3-b]pyrazin-2(1H)-one;

1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-(trans-4-methoxycyclohexyl)-3,4-dihydropyrazino[2,3-b]pyrazin-2(1H)-one;

7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

1-(2-methoxyethyl)-7-(2-methyl-6-(4H-1,2,4-triazol-3-yl)pyridin-3-yl)-3,4-dihydropyrazino[2,3-b]pyrazin-2(1H)-one;

7-(6-(2-hydroxypropan-2-yl)pyridin-3-yl)-1-((trans-4-methoxycyclohexyl)methyl)-3,4-dihydropyrazino[2,3-b]pyrazin-2(1H)-one;

1-(cyclopentylmethyl)-7-(6-(2-hydroxypropan-2-yl)pyridin-3-yl)-3,4-dihydropyrazino[2,3-b]pyrazin-2(1H)-one;

7-(4-(2-hydroxypropan-2-yl)phenyl)-1-(2-methoxyethyl)-3,4-dihydropyrazino[2,3-b]pyrazin-2(1H)-one;

(S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

(R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one;

7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one;

7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(4-(trifluoromethyl)benzyl)-3,4-dihydropyrazino[2,3-b]pyrazin-2(1H)-one;

7-(6-(2-hydroxypropan-2-yl)pyridin-3-yl)-1-(3-(trifluoromethyl)benzyl)-3,4-dihydropyrazino[2,3-b]pyrazin-2(1H)-one;

7-(6-(2-hydroxypropan-2-yl)pyridin-3-yl)-1-(3-methoxypropyl)-3,4-dihydropyrazino[2,3-b]pyrazin-2(1H)-one;

7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-methoxyethyl)-3,4-dihydropyrazino[2,3-b]pyrazin-2(1H)-one;

7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one;

7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one;

7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one;

7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one;

(R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

(S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one;

7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one;

7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one;

7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one;

7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one;

1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one; or 1-(2-hydroxyethyl)-7-(2-methyl-6-(1H-1,2,4-triazol-3-yl)pyridin-3-yl)-3,4-dihydropyrazino[2,3-b]pyrazin-2(1H)-one.

Representative Heteroaryl Compounds of formula (I) and (II) are set forth in Table 1.

4.3 Methods for Making Heteroaryl Compounds

The Heteroaryl Compounds can be made by one skilled in the art using conventional organic syntheses and commercially available materials. By way of example and not limitation, a Heteroaryl Compound can be prepared as outlined in Schemes 1-9 shown below, as well as in the examples set forth in Section 5.1. It should be noted that one skilled in the art can modify the procedures set forth in the illustrative schemes and examples to arrive at the desired product.

Scheme 1

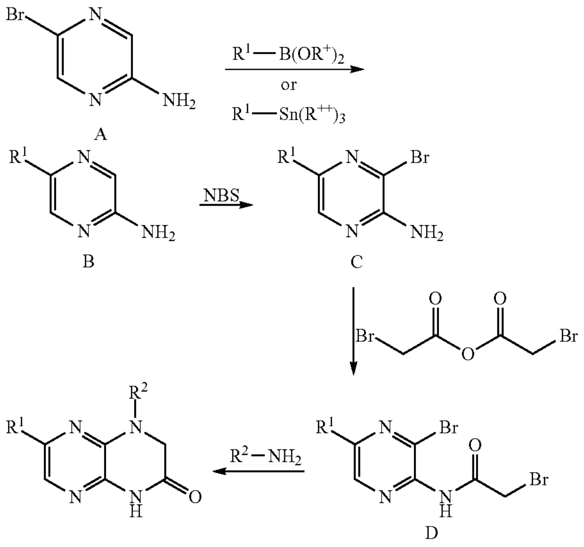

Synthesis of compounds of formula (I) is shown in Scheme 1. Starting from 5-bromopyrazin-2-amine A, the $R^1$ group can be introduced using the appropriate boronic acid or borate ester ($R^+$ is H, or together with the boron atom and the atoms to which they are attached, form a cyclic boronate), palladium catalyst (such as, for example, dichloro[1,1'-bis(diphenylphosphino)ferrocene]palladium(II)dichloromethane), solvent (such as dimethylformamide) and base (such as sodium carbonate) through a Suzuki coupling, or alternately with the appropriate stannane ($R^{++}$ is $C_{1-4}$ alkyl), palladium catalyst (such as dichloro[1,1'-bis(diphenylphosphino)ferrocene]palladium(II)dichloromethane or palladium $(dba)_2$/tri-o-tolylphosphine) and solvent (such as dimethylformamide with or without the addition of a base such as triethylamine) using Stille coupling methodology. Typical reaction conditions and reagents for Suzuki and Stille reactions can be found herein (see also Rossi, et al, *Synthesis* 15:2419-2440 (2004), Buchwald et al. *Accounts of Chemical Research,* 41: 1461-1473 (2008), Fu. *Accounts of Chemical Research,* 41: 1555-1564 (2008), and Echavarren et al. *Angew. Chem. Int. Ed.,* 43: 4704-4734 (2004) and references therein). The resulting $R^1$ amino pyrazine B can be brominated using NBS or other standard brominating conditions to afford the brominated intermediate C, which is then reacted with 2-bromoacetic anhydride to afford the acylated intermediate D. The $R^2$ substituent is introduced through amine addition to D and subsequent ring closure, in the presence of an amine base (such as, for example, triethyl amine) and heating in an appropriate solvent (such as acetonitrile) to afford the desired products.

Scheme 2

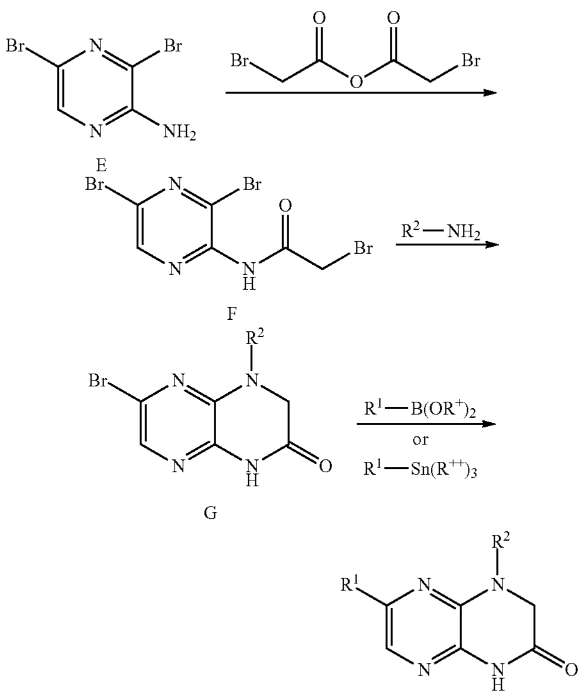

Alternatively as shown in Scheme 2, 3,5-dibromopyrazin-2-amine E, is treated with 2-bromoacetic anhydride as above to provide intermediate F. As described above, the $R^2$ substituent is introduced through amine addition to F and subsequent ring closure to afford intermediate G. The $R^1$ group may then be introduced using the methods described above, namely by reaction with the appropriate boronic acid or borate ester, in the presence of a palladium catalyst and base through a Suzuki coupling, or alternately with the appropriate stannane, in the presence of a palladium catalyst using Stille coupling methodology as described above, to afford the desired products.

Scheme 3

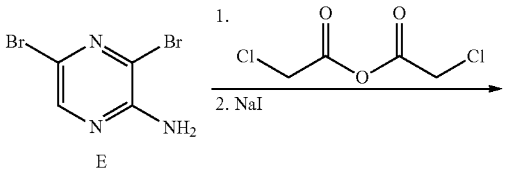

-continued

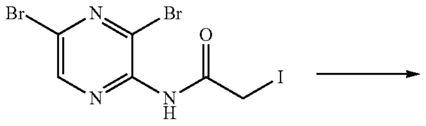

F2

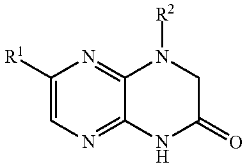

In an another approach (Scheme 3), 3,5-dibromopyrazin-2-amine E, is treated with 2-chloroacetic anhydride followed by sodium iodide to provide the iodo intermediate F2. Intermediate F2 is converted to the desired products following the procedures outlined in Scheme 2 for F.

Scheme 4

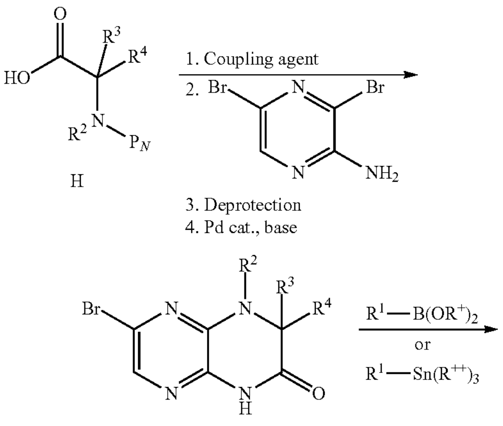

H

I

-continued

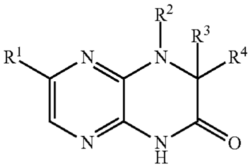

To afford analogs with substitution alpha to the carbonyl (Scheme 4), the appropriately substituted amino-protected amino acid H ($P_N$ is amino protecting group such as Boc), is reacted with 3,5-dibromopyrazin-2-amine in the presence of a coupling agent, such as, for example, 1,1'-carbonyldiimidazole. Deprotection conditions (for example, when $P_N$ is Boc, deprotection is achieved by, for example, treatment with TFA or HCl), followed by palladium catalyzed ring closure (using, for example, sodium bicarbonate, palladium (II) acetate and 4,5-bis(diphenylphosphino)-9,9-dimethylxanthene) to afford intermediate I. As before, the $R^1$ group may be introduced using the appropriate boronic acid or borate ester, palladium catalyst, solvent and base through a Suzuki coupling, or alternately with the appropriate stannane, palladium catalyst and solvent using Stille coupling methodology (described above) to afford the desired products. This method may also be used to afford analogs where $R^2$ is hydrogen. Additionally, this route may be used to afford compounds wherein $R^3$ and $R^4$, together with the atom to which they are both attached, form a spiro-cyclic ring, through the use of appropriate starting amino acids.

Scheme 5

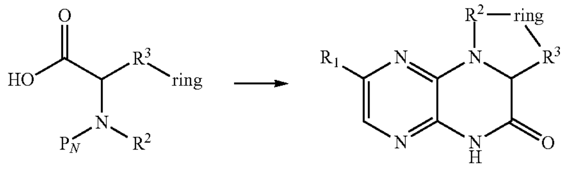

J

Analogs wherein $R^2$ and $R^3$ together with the atoms to which they are attached form a ring (see Scheme 5) may be obtained similarly to the chemistry shown in Scheme 4, beginning with the appropriate cyclic amino acid J.

Scheme 6

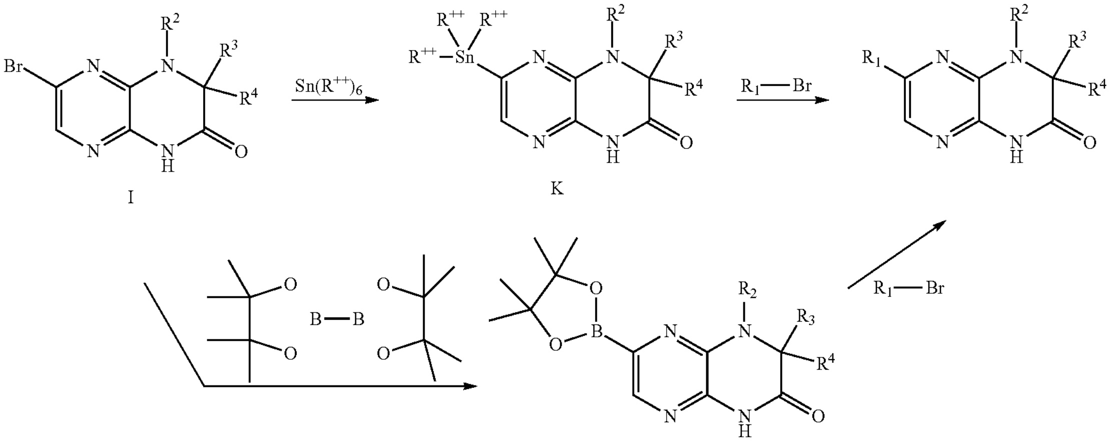

I

K

K2

To obtain the desired products, the reactivity of the coupling partners may be reversed. For example, as shown in Scheme 6, intermediate I may be converted to the corresponding stannane K, through reaction with, for example, hexamethylditin ($R^{++}$ is methyl) in the presence of a palladium catalyst (such as tetrakis(triphenylphosphine)-palladium) and the $R^1$ group may be introduced using the appropriate halogen (such as bromide), and solvent using Stille coupling methodology as described above to afford the desired products. Alternatively, intermediate I may be converted to the corresponding boronate ester K2, by reaction with 4,4,4',4',5,5,5',5'-octamethyl-2,2'-bi(1,3,2-dioxaborolane) in the presence of a palladium catalyst (such as 1,1'-bis(diphenylphosphino)ferrocene]palladium(II)dichloromethane) and a base (such as potassium acetate) in a solvent such as dioxane. The $R^1$ group may be introduced using the appropriate halogen (such as bromide), palladium catalyst and solvent using Suzuki coupling methodology as described above, to afford the desired products.

Scheme 8

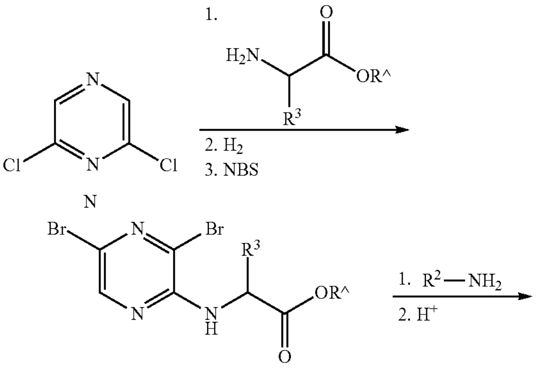

N

O

Scheme 7

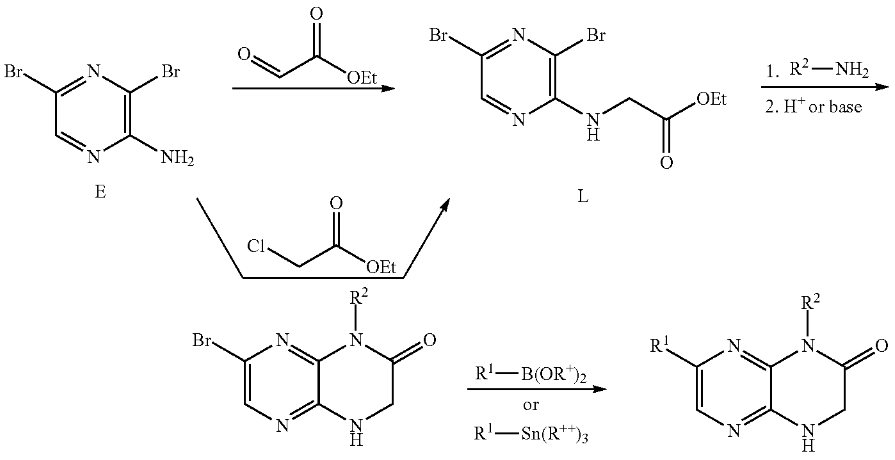

E

L

M

Compounds of formula (II) may be obtained as shown in Scheme 7. Reductive amination of 3,5-dibromopyrazin-2-amine E with ethyl 2-oxoacetate (in the presence of, for example, sodium borohydride as a reducing agent) affords intermediate L. Alternatively, 3,5-dibromopyrazin-2-amine E may be converted to intermediate L by reaction with ethyl 2-chloroacetate under basic conditions (using for example, $Cs_2CO_3$). The $R^2$ substituent is introduced through amine addition to L, in the presence of an amine base, such as diisopropylethylamine, and heating in an appropriate solvent (such as DMSO) and subsequent acid catalyzed ring closure (using, for example, acetic acid) to afford intermediate M. Alternatively, the ring closure of the amine addition product L may proceed under basic catalyzed conditions, such as treatment with potassium t-butoxide in an appropriate solvent. As before, the $R^1$ group may be introduced using the appropriate boronic acid or borate ester, palladium catalyst, solvent and base through a Suzuki coupling, or alternately with the appropriate stannane, palladium catalyst and solvent using Stille coupling methodology (described above) to afford the desired products.

-continued

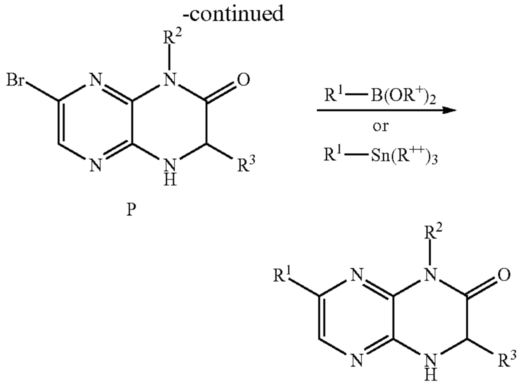

P

An alternative approach (Scheme 8) begins with reaction of 2,6-dichloropyrazine N with the appropriate amino ester ($R^\wedge$ is $C_{1-3}$ alkyl), followed by reductive dehalogenation with hydrogen and a palladium catalyst such as palladium hydroxide, a base such as potassium carbonate, in a solvent such as ethanol, and subsequent bromination by reaction with a brominating agent such as NBS to yield intermediate O. As above, the $R^2$ substituent is introduced through amine addition to O and subsequent acid catalyzed ring closure to afford intermediate P. The $R^1$ group may be introduced using the appropriate boronic acid or borate ester, palladium catalyst, solvent and base through a Suzuki coupling, or alternately with the appropriate stannane, palladium catalyst and solvent using Stille coupling methodology to afford the desired products (described above). This route also allows for the synthesis of analogs with $R^3$ substitution alpha to the carbonyl group.

with $R^1$—Y in a solvent, in the presence of a palladium catalyst, wherein said contacting occurs under conditions suitable to provide a compound of formula (I), wherein R', $R^2$, $R^3$ and $R^4$ are as defined herein, and a) when X is halogen (for example Br, Cl, or I) then Y is $B(OR^+)_2$ or $Sn(R^{++})_3$; or b) when Y is halogen (for example Br, Cl, or I), then X is $B(OR^+)_2$ or $Sn(R^{++})_3$;

Scheme 9

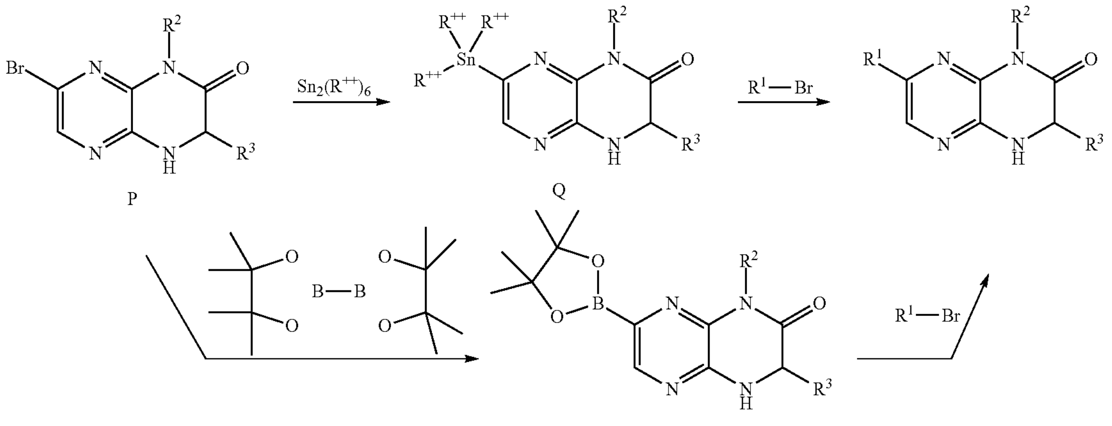

P
Q
Q2

As before, to obtain the desired products, the reactivity of the coupling partners may be reversed (Scheme 9). For example, intermediate P may be converted to the corresponding stannane Q, and the $R^1$ group may be introduced using the appropriate halogen, palladium catalyst and solvent using Stille coupling methodology as described above to afford the desired products. Alternatively, intermediate P may be converted to the corresponding boronate ester Q2, and the $R^1$ group may be introduced using the appropriate halogen, palladium catalyst and solvent using Suzuki coupling methodology as described above to afford the desired products.

Provided herein are methods of preparing a compound of formula (I), (I)

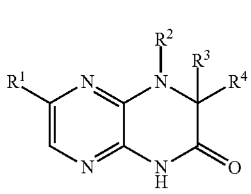

the method comprising contacting a compound of formula (III)

(III)

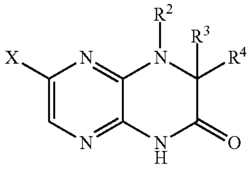

wherein each $R^+$ is independently hydrogen or substituted or unsubstituted $C_{1-3}$ alkyl, or each $R^+$, together with the boron atom and the atoms to which they are attached, form a cyclic boronate; and $R^{++}$ is a $C_{1-4}$ alkyl.

Typically the solvent is dimethylformamide, isopropanol, dioxane, toluene, dimethylacetamide, tetrahydrofuran, acetonitrile, isopropyl acetate, dimethyl sulfoxide, acetone, methanol, methyl t-butyl ether or a combination thereof, with or without the presence of water, and the palladium catalyst is dichloro[1,1'-bis(diphenylphosphino)ferrocene] palladium (II)dichloro-methane), palladium$(dba)_2$/tri-o-tolylphosphine, dichloro[1,1'-bis(ditert-butylphosphino)ferrocene]palladium, dichlorobis(p-dimethylamino phenylditbutylphosphine)palladium(II), tetrakis(triphenylphosphine)palladium(0), or palladium (II) acetate/4,5-bis (diphenylphosphino)-9,9-dimethylxanthene. In some embodiments when X or Y is a halogen, the halogen is Br. In some embodiments when X or Y is $B(OR^+)_2$, the contacting occurs in the presence of a base such as sodium carbonate, triethyl amine, diisopropylethyl amine, piperidine, pyridine, cesium carbonate, potassium carbonate, potassium phosphate, or sodium hydroxide. In some such embodiments, $B(OR^+)_2$ is $B(OH)_2$ or $B(—OC(CH_3)_2C(CH_3)_2O—)$. In other embodiments, when X or Y is $Sn(R^{++})_3$ the contacting optionally occurs in the presence of a base such as triethylamine, sodium carbonate, diisopropylethyl amine, piperidine, pyridine, cesium carbonate, potassium carbonate, potassium phosphate, or sodium hydroxide. In some such embodiments, $R^{++}$ is methyl or n-butyl.

Also provided are methods of preparing a compound of formula (III), (III)

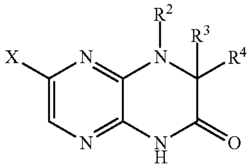

the method comprising contacting a compound of formula (IV)

(IV)

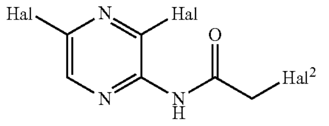

with $R^2$—$NH_2$ in a solvent, such as acetonitrile or tetrahydrofuran, in the presence of a base, such as triethylamine or diisopropylethylamine, wherein said contacting occurs under conditions suitable to provide a compound of formula (III), wherein $R^2$ is as defined herein, $R^3$ and $R^4$ are H, X is a halogen such as Br, Hal is a halogen such as Br, and $Hal^2$ is Br or I.

Also provided are methods of preparing a compound of formula (III), (III)

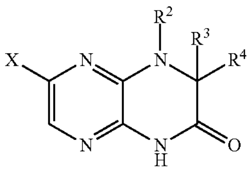

the method comprising cyclizing a compound of formula (V)

(V)

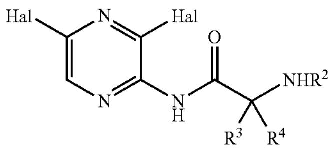

in a solvent, such as acetonitrile, in the presence of a palladium catalyst, such as palladium(II)acetate, a ligand, such as 4,5-bis-(diphenylphosphino)-9,9-dimethylxanthene, and a base, such as sodium bicarbonate, wherein said cyclization occurs under conditions suitable to provide a compound of formula (III), wherein $R^2$ is as defined herein, $R^3$ and $R^4$ are as described herein, X is a halogen such as Br, and Hal is a halogen such as Br.

Also provided are methods of preparing a compound of formula (II), (II)

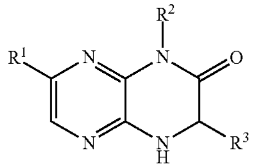

the method comprising contacting a compound of formula (VI)

(VI)

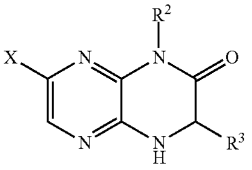

with $R^1$—Y in a solvent, in the presence of a palladium catalyst, wherein said contacting occurs under conditions suitable to provide a compound of formula (I), wherein $R^1$, $R^2$, and $R^3$ are as defined herein, and a) when X is halogen (for example Br, Cl, or I) then Y is $B(OR^+)_2$ or $Sn(R^{++})_3$; or b) when Y is halogen (for example Br, Cl, or I), then X is $B(OR^+)_2$ or $Sn(R^{++})_3$;

wherein each $R^+$ is independently hydrogen or substituted or unsubstituted $C_{1-3}$ alkyl, or each $R^+$, together with the boron atom and the atoms to which they are attached, form a cyclic boronate; and each $R^{++}$ is a $C_{1-3}$ alkyl.

Typically the solvent is dimethylformamide, isopropanol, dioxane, toluene, dimethylacetamide, tetrahydrofuran, acetonitrile, isopropyl acetate, dimethyl sulfoxide, acetone, methanol, methyl t-butyl ether or a combination thereof, with or without the presence of water, and the palladium catalyst is dichloro[1,1'-bis(diphenylphosphino)ferrocene] palladium (II)dichloro-methane), palladium$(dba)_2$/tri-o-tolylphosphine, dichloro[1,1'-bis(ditert-butylphosphino)ferrocene]palladium, dichlorobis(p-dimethylamino phenylditbutylphosphine)palladium(II), tetrakis(triphenylphosphine)palladium(0), or palladium (II) acetate/4,5-bis (diphenylphosphino)-9,9-dimethylxanthene. In some embodiments when X or Y is a halogen, the halogen is Br. In some embodiments when X or Y is $B(OR^+)_2$, the contacting occurs in the presence of a base such as sodium carbonate, triethyl amine, diisopropylethyl amine, piperidine, pyridine, cesium carbonate, potassium carbonate, potassium phosphate, or sodium hydroxide. In some such embodiments, $B(OR^+)_2$ is $B(OH)_2$ or $B(—OC(CH_3)_2C(CH_3)_2O—)$. In other embodiments, when X or Y is $Sn(R^{++})_3$ the contacting optionally occurs in the presence of a base such as triethylamine, sodium carbonate, diisopropylethyl amine, piperidine, pyridine, cesium carbonate, potassium carbonate, potassium phosphate, or sodium hydroxide. In some such embodiments, $R^{++}$ is methyl or n-butyl.

Also provided are methods of preparing a compound of formula (VI), (VI)

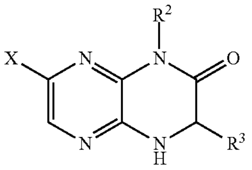

the method comprising cyclizing a compound of formula (VII)

(VII)

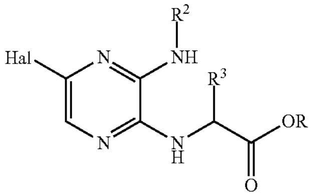

in the presence of a base, such as potassium butoxide, or an acid, such as acetic acid, TFA, HCl, or phosphoric acid, wherein said cyclization occurs under conditions suitable to provide a compound of formula (VI), wherein $R^2$ and $R^3$ are as defined herein, Hal is a halogen such as Br, and R is H or $C_{1-4}$ alkyl. Typically, the cyclization is performed in a solvent, such as, for example, methanol or water.

Also provided are methods of preparing a compound of formula (VII), (VII)

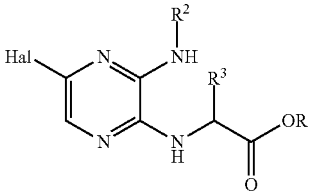

the method comprising contacting a compound of formula (VIII)

(VIII)

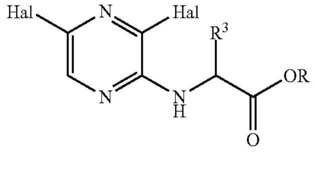

with $R^2$—$NH_2$ in a solvent, such as dimethylsulfoxide or N-methylpyrrolidinone, optionally in the presence of a base, such as triethylamine or diisopropylethylamine, wherein said contacting occurs under conditions suitable to provide a compound of formula (VII), wherein $R^2$ and $R^3$ are as defined herein, and Hal is a halogen such as Br.

Pharmaceutically acceptable salts of the Heteroaryl Compounds can be formed by conventional and known techniques, such as by reacting a Heteroaryl Compound with a suitable acid as disclosed above. Such salts are typically formed in high yields at moderate temperatures, and often are prepared by merely isolating the compound from a suitable acidic wash in the final step of the synthesis. The salt-forming acid may dissolved in an appropriate organic solvent, or aqueous organic solvent, such as an alkanol, ketone or ester. On the other hand, if the Heteroaryl Compound is desired in the free base form, it may be isolated from a basic final wash step, according to known techniques. For example, a typical technique for preparing hydrochloride salt is to dissolve the free base in a suitable solvent, and dry the solution thoroughly, as over molecular sieves, before bubbling hydrogen chloride gas through it.

4.4 Methods of Use

Heteroaryl Compounds described herein have utility as pharmaceuticals to treat or prevent disease in animals or humans. Further, Heteroaryl Compounds described herein are active against kinases (e.g., protein kinases), including those involved in cancer, inflammatory conditions, immunological conditions, neurodegenerative diseases, diabetes, obesity, neurological disorders, age-related diseases, and cardiovascular conditions. Without being limited by theory, it is thought the Heteroaryl Compounds are effective for treating and preventing said diseases and conditions due to their ability to modulate (e.g., inhibit) kinases which are involved in the etiology of these diseases and conditions. Accordingly, provided herein are many uses of the Heteroaryl Compounds, including the treatment or prevention of those diseases set forth below. The methods provided herein comprise the administration of an effective amount of one or more Heteroaryl Compounds to a patient in need thereof. In some embodiments, the methods additionally comprise administration of a second active agent as described herein.

Representative immunological conditions that Heteroaryl Compounds are useful for treating or preventing include, but are not limited to, rheumatoid arthritis, rheumatoid spondylitis, osteoarthritis, multiple sclerosis, lupus, inflammatory bowel disease, ulcerative colitis, Crohn's disease, myasthenia gravis, Graves disease, encephalomyelitis, Type II diabetes, dermatomyositis, and transplant rejection (e.g. in the treatment of recipients of e.g. heart, lung, combined heart-lung, liver, kidney, pancreatic, skin or corneal transplants; or graft-versus-host disease, such as following bone marrow transplantation).

Representative inflammatory conditions that Heteroaryl Compounds are useful for treating or preventing include, but are not limited to, psoriasis, asthma and allergic rhinitis, bronchitis, chronic obstructive pulmonary disease, cystic fibrosis, inflammatory bowel disease, irritable bowel syndrome, Crohn's disease, mucous colitis, ulcerative colitis, and obesity.

Representative cardiovascular diseases that Heteroaryl Compounds are useful for treating or preventing include, but are not limited to, restenosis, Wolf-Parkinson-White Syndrome, stroke, myocardial infarction or ischemic damage to the heart, lung, gut, kidney, liver, pancreas, spleen or brain.

Representative neurodegenerative diseases that Heteroaryl Compounds are useful for treating or preventing include, but are not limited to, Huntington's disease, Alzheimer's disease, Parkinson's disease, dementias caused by tau mutations, spinocerebellar ataxia type 3, motor neuron disease caused by SOD1 mutations, neuronal ceroid lipofucinoses/Batten disease (pediatric neurodegene ration) and HIV-associated encephalitis.

Representative age-related diseases that Heteroaryl Compounds are useful for treating or preventing include but are not limited to cancer, obesity, type II diabetes mellitus, autoimmune disease, cardiovascular diseases and neuronal degeneration.

In another embodiment, provided herein are methods for the treatment or prevention of fibrotic diseases and disorders. In a particular embodiment, provided herein are methods for the treatment or prevention of scleroderma, idiopathic pulmonary fibrosis, renal fibrosis, cystic fibrosis, myelofibrosis, hepatic fibrosis, steatofibrosis and steatohepatitis.

Representative cancers that Heteroaryl Compounds are useful for treating or preventing include, but are not limited to, cancers of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, and brain or central nervous system. Heteroaryl Compounds are also useful for treating or preventing solid tumors and blood-borne tumors.

Particular cancers within the scope of the methods provided herein include those associated with the pathways involving mTOR, PI3K, or Akt kinases and mutants or isoforms thereof. Other cancers within the scope of the methods provided herein include those associated with the pathways of the following kinases: PI3Kα, PI3Kβ, PI3Kδ, KDR, GSK3α, GSK3β, ATM, ATX, ATR, cFMS, and/or DNA-PK kinases and mutants or isoforms thereof. In some embodiments, the cancers associated with mTOR/PI3K/Akt pathways include solid and bloodborne tumors, for example, multiple myeloma, mantle cell lymphoma, diffused large B-cell lymphoma, acute myeloid lymphoma, follicular lymphoma, chronic lymphocytic leukemia; breast, lung, endometrial, ovarian, gastric, cervical, and prostate cancer; glioblastoma; renal carcinoma; hepatocellular carcinoma; colon carcinoma; neuroendocrine tumors; head and neck tumors; and sarcomas.

In a particular embodiment, provided herein are methods for the treatment or prevention of a disease or disorder associated with activation of mTOR signaling, including, but not limited to, tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (Neurofibromin 1), AMPK (AMP-dependent protein kinase STK11, serine/threonine kinase 11), LKB1, VHL (von Hippel-Lindau disease) and PKD1 (polycystin-1). Without being limited by theory, it is thought that genetic defects associated with these proteins results in hyperactivation of the mTOR/PI3K/Akt pathway. Some particular diseases which are treatable or preventable through inhibition of the mTOR/PI3K/Akt pathway include, but are not limited to, Cowden's disease, Cowden syndrome, Cowden-like syndrome, Bannayan-Zonana syndrome, Bannayan-Riley-Ruvalcaba syndrome, Lhermitte-Duclos disease, endometrial carcinoma, tuberous sclerosis complex, lymphangioleiomyomatosis, neurofibromatosis 1, Peutz-Jeghers syndrome, renal cell carcinoma, von Hippel-Lindau disease, Proteus syndrome, and polycystic kidney disease.

In a particular embodiment, provided herein are methods for the treatment or prevention of a disease or disorder associated with mTOR, PI3K, Akt, and/or DNA-PK signaling. Particular diseases which are treatable or preventable by inhibiting mTOR, PI3K, Akt and/or DNA-PK signaling, include, but are not limited to, rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; atherosclerosis; restenosis following angioplasty; left ventricular hypertrophy; myocardial infarction; stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases (including retinitis pigmentosa), solid tumors, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

Also provided herein are methods for inhibiting a kinase in a cell expressing said kinase, comprising contacting the cell with an effective amount of a Heteroaryl Compound as described herein. In one embodiment the kinase is mTOR, DNA-PK, or PI3K or a combination thereof. In some embodiments, the cell is in a patient.

Also provided herein are methods for treating or preventing a condition treatable or preventable by inhibition of a kinase pathway, for example, the mTOR/PI3K/Akt and/or DNA-PK pathway, comprising administering to a patient in need thereof an effective amount of a Heteroaryl Compound as described herein. In some embodiments, the conditions treatable or preventable by inhibition of the mTOR/PI3K/Akt pathway include solid and blood-borne tumors, for example, multiple myeloma, mantle cell lymphoma, diffused large B-cell lymphoma, acute myeloid lymphoma, follicular lymphoma, chronic lymphocytic leukemia; breast, lung, endometrial, ovarian, gastric, cervical, and prostate cancer; glioblastoma; renal carcinoma; hepatocellular carcinoma; colon carcinoma; neuroendocrine tumors; head and neck tumors; sarcomas; tumor syndromes resulting directly or indirectly from genetic defects in PTEN (Phosphatase and tensin homologue deleted on chromosome 10), TSC1 (Tuberous sclerosis 1), TSC2 (Tuberous sclerosis 2), NF1 (Neurofibromin 1), AMPK (AMP-dependent protein kinase STK11, serine/threonine kinase 11), and LKB1, VHL (von Hippel-Lindau disease) and PKD1 (polycystin-1); Cowden's disease, Cowden syndrome, Cowden-like syndrome, Bannayan-Zonana syndrome, Bannayan-Riley-Ruvalcaba syndrome, Lhermitte-Duclos disease, endometrial carcinoma, tuberous sclerosis complex, lymphangioleiomyomatosis, neurofibromatosis 1, Peutz-Jeghers syndrome, renal cell carcinoma, von Hippel-Lindau disease, Proteus syndrome, and polycystic kidney disease; rheumatoid arthritis; rheumatoid spondylitis; osteoarthritis; gout; asthma, bronchitis; allergic rhinitis; chronic obstructive pulmonary disease; cystic fibrosis; inflammatory bowel disease; irritable bowel syndrome; mucous colitis; ulcerative colitis; Crohn's disease; Huntington's disease; gastritis; esophagitis; hepatitis; pancreatitis; nephritis; multiple sclerosis; lupus erythematosus; atherosclerosis; restenosis following angioplasty; left ventricular hypertrophy; myocardial infarction;

stroke; ischemic damages of heart, lung, gut, kidney, liver, pancreas, spleen and brain; acute or chronic organ transplant rejection; preservation of the organ for transplantation; organ failure or loss of limb (e.g., including, but not limited to, that resulting from ischemia-reperfusion injury, trauma, gross bodily injury, car accident, crush injury or transplant failure); graft versus host disease; endotoxin shock; multiple organ failure; psoriasis; burn from exposure to fire, chemicals or radiation; eczema; dermatitis; skin graft; ischemia; ischemic conditions associated with surgery or traumatic injury (e.g., vehicle accident, gunshot wound or limb crush); epilepsy; Alzheimer's disease; Parkinson's disease; immunological response to bacterial or viral infection; cachexia; angiogenic and proliferative diseases, including retinitis pigmentosa, solid tumors, and cancers of a variety of tissues such as colon, rectum, prostate, liver, lung, bronchus, pancreas, brain, head, neck, stomach, skin, kidney, cervix, blood, larynx, esophagus, mouth, pharynx, urinary bladder, ovary or uterine.

More particularly, cancers and related disorders that can be treated or prevented by methods and compositions provided herein include but are not limited to the following: leukemias such as but not limited to, acute leukemia, acute lymphocytic leukemia, acute myelocytic leukemias such as myeloblastic, promyelocytic, myelomonocytic, monocytic, erythroleukemia leukemias and myelodysplastic syndrome (or a symptom thereof such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia and chronic myelomonocytic leukemia (CMML), chronic leukemias such as but not limited to, chronic myelocytic (granulocytic) leukemia (CIVIL), chronic lymphocytic leukemia (CLL), hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, synovial sarcoma; brain tumors such as but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma, gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell cancer, adenocarcinoma, hypernephroma, fibrosarcoma, transitional cell cancer (renal pelvis and/or utero); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine,* 2d Ed., J. B. Lippincott Co., Philadelphia and Murphy et al., 1997, *Informed Decisions: The Complete Book of Cancer Diagnosis, Treatment, and Recovery,* Viking Penguin, Penguin Books U.S.A., Inc., United States of America).

Accordingly, the methods and compositions provided herein are also useful in the treatment or prevention of a variety of cancers or other abnormal proliferative diseases, including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Berketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, glioblastoma multiforme, neuroblastoma, glioma, and schwannomas; solid and bloodborne tumors; tumors of mesenchymal origin, including fibrosarcoma, rhabdomyosarcoma, and osteosarcoma; and other tumors, including melanoma, xenoderma pigmentosum, keratoactanthoma, seminoma, thyroid follicular cancer and teratocarcinoma. It is also contemplated that cancers caused by aberrations in apoptosis would also be treated by the methods and compositions disclosed herein. Such cancers may include but not be limited to follicular lymphomas, carcinomas with p53 mutations, hormone dependent tumors of the breast, prostate and ovary, and precancerous lesions such as familial adenomatous polyposis, juvenile polyposis syndrome, Birt-Hogg-Dubé syndrome (BHD), and myelodysplastic syndromes. In specific embodiments, malignancy or dysproliferative changes (such as metaplasias and dysplasias), or hyperproliferative disorders, are treated or prevented in the ovary, bladder, breast, colon, lung, skin, pancreas, kidney or uterus. In other specific embodiments, sarcoma, melanoma, or leukemia is treated or prevented.

In a particular embodiment, the methods and compositions provided herein are also useful for treating, preventing or managing various types of lymphomas (i.e., a heterogenous group of neoplasms arising in the reticuloendothelial and lymphatic systems), such as Non-Hodgkin's lymphoma (NHL) (i.e., a malignant monoclonal proliferation of lymphoid cells in sites of the immune system, including lymph nodes, bone marrow, spleen, liver and gastrointestinal tract). NHLs that the Heteroaryl Compounds are useful for treating or preventing include, but are not limited to, mantle cell lymphoma, MCL, lymphocytic lymphoma of intermediate differentiation, intermediate lymphocytic lymphoma, ILL, diffuse poorly differentiated lymphocytic lymphoma, PDL, centrocytic lymphoma, diffuse small-cleaved cell lymphoma, DSCCL, follicular lymphoma, and any type of the mantle cell lymphomas that can be seen under the microscope (nodular, diffuse, blastic and mantle zone lymphoma).

In another embodiment, the methods and compositions provided herein are also useful for administration to patients in need of treatment for a malignant disease (e.g., patients suffering from acute lymphocytic leukemia, acute myelogenous leukemia, chronic myelogenous leukemia, chronic lymphocytic leukemia, myelodysplastic syndrome ("preleukemia"), monosomy 7 syndrome, non-Hodgkin's lymphoma, neuroblastoma, brain tumors, multiple myeloma, testicular germ cell tumors, breast cancer, lung cancer, ovarian cancer, melanoma, glioma, sarcoma or other solid tumors), as well as those in need of treatment of a non-malignant disease (e.g., patients suffering from hematologic disorders, congenital immunodeficiencies, mucopolysaccharidoses, lipidoses, osteoporosis, Langerhan's cell histiocytosis, Lesch-Nyhan syndrome or glycogen storage diseases).

In another embodiment, provided herein are methods for the treatment of myeloproliferative disorders or myelodysplastic syndromes, comprising administering to a patient in need thereof an effective amount of a Heteroaryl Compound or a composition thereof. In certain embodiments, the myeloproliferative disorder is polycythemia rubra vera; primary thrombocythemia; chronic myelogenous leukemia; acute or chronic granulocytic leukemia; acute or chronic myelomonocytic leukemia; myelofibro-erythroleukemia; or angiogenic myeloid metaplasia.

In another embodiment, provided herein are methods for the treatment of cancer or tumors resistant to other kinase inhibitors such as imatinib mesylate (STI-571 or Gleevec™) treatment, comprising administering to a patient in need thereof an effective amount of a Heteroaryl Compound or a composition thereof. In a particular embodiment, provided herein are methods for the treatment of leukemias, including, but not limited to, gastrointestinal stromal tumor (GIST), acute lymphocytic leukemia or chronic myelocytic leukemia resistant to imatinib mesylate (STI-571 or Gleevec™) treatment, comprising administering to a patient in need thereof an effective amount of a Heteroaryl Compound or a composition thereof.

In a specific embodiment, provided herein are methods for treating or preventing leukemia (i.e., malignant neoplasms of the blood-forming tissues) including, but not limited to, chronic lymphocytic leukemia, chronic myelocytic leukemia, acute lymphoblastic leukemia, acute myelogenous leukemia and acute myeloblastic leukemia. The leukemia can be relapsed, refractory or resistant to conventional therapy. The term "relapsed" refers to a situation where patients who have had a remission of leukemia after therapy have a return of leukemia cells in the marrow and a decrease in normal blood cells. The term "refractory or resistant" refers to a circumstance where patients, even after intensive treatment, have residual leukemia cells in their marrow.

The various types of the cancers are described in U.S. Patent Application publication no. 2004/0029832, published Feb. 12, 2004, which is incorporated herein in its entirety by reference (see, e.g., Section 2.2. Types of Cancers). Specific cancers include, but are not limited to, leukemias such as chronic lymphocytic leukemia, chronic myelocytic leukemia, acute lymphoblastic leukemia, acute myelogenous leukemia, and acute myeloblastic leukemia; advanced malignancy, amyloidosis, neuroblastoma, meningioma, hemangiopericytoma, multiple brain metastases, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, malignant melanoma, malignant mesothelioma, malignant pleural effusion mesothelioma syndrome, peritoneal carcinoma, papillary serous carcinoma, gynecologic sarcoma, soft tissue sarcoma, cutaneous vasculitis, Langerhans cell histiocytosis, leiomyosarcoma, fibrodysplasia ossificans progressive, hormone refractory prostate cancer, resected high-risk soft tissue sarcoma, unresectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In one embodiment, the cancer is primary or metastatic. In another embodiment, the cancer is relapsed, refractory or resistance to chemotherapy or radiation; in particular, refractory to thalidomide.

Further provided herein are methods for treating patients who have been previously treated for cancer, but are non-responsive to standard therapies, as well as those who have not previously been treated. Also provided herein are methods for treating patients regardless of patient's age, although some cancers are more common in certain age groups. Still further provided herein are methods for treating patients who have undergone surgery in an attempt to treat the cancer at issue, as well as those who have not. Because patients with cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

Further, provide herein are methods for the treatment or prevention of disorders such as pulmonary hypertension, Carney Complex, muscle wasting (atrophy, cachexia), myopathies such as Danon's disease, and bacterial, fungal, and viral infections (including *M. tuberculosis*, group A *streptococcus*, HSV type I, and HIV infection).

A Heteroaryl Compound can be combined with other pharmacologically active compounds ("second active agents") in methods and compositions described herein. It is believed that certain combinations may work in the treatment of particular types of diseases or disorders, and conditions and symptoms associated with such diseases or disorders. A Heteroaryl Compound can also work to alleviate adverse effects associated with certain second active agents, and vice versa.

One or more second active ingredients or agents can be used in the methods and compositions described herein. Second active agents can be large molecules (e.g., proteins) or small molecules (e.g., synthetic inorganic, organometallic, or organic molecules).

Examples of large molecule second active agents include, but are not limited to, hematopoietic growth factors, cytokines, and monoclonal and polyclonal antibodies. Specific examples of the active agents are anti-CD40 monoclonal antibodies (such as, for example, SGN-40); histone deacetlyase inhibitors (such as, for example, MGCD0103, SAHA and LAQ 824); hypomethylating agents (such as Vidaza); IMiDs® brand Immunomodulatory products (such as thalidomide, lenalidomide and pomalidomide); heat-shock protein-90 inhibitors (such as, for example, 17-AAG); insulin-like growth factor-1 receptor kinase inhibitors; vascular endothelial growth factor receptor kinase inhibitors (such as, for example, PTK787); insulin growth factor receptor inhibitors; lysophosphatidic acid acyltransferase inhibitors; IkB kinase inhibitors; p38MAPK inhibitors; Pim kinase inhibitors (such as, for example, SGI-1776, or those disclosed in WO/2008/106692); EGFR inhibitors (such as, for example, gefitinib and erlotinib HCL); HER-2 antibodies (such as, for example, trastuzumab (Herceptin®) and pertuzumab (Omnitarg™), as well as HER-2 kinase inhibitors (such as Lapatinib); VEGFR antibodies (such as, for example, bevacizumab (Avastin™)); VEGFR inhibitors (such as, for example, flk-1 specific kinase inhibitors, SU5416 and ptk787/zk222584); PI3K inhibitors (such as, for example, wortmannin); C-Met inhibitors (such as, for example, PHA-665752); antiestrogens (such as, for example, Letrozole, Fulvestrant, tamoxifen); monoclonal antibodies (such as, for example, rituximab (Rituxan®), tositumomab (Bexxar®), edrecolomab (Panorex®) and G250); and anti-TNF-α antibodies. Examples of small molecule active agents include, but are not limited to, small molecule anti-cancer agents and antibiotics (e.g., clarithromycin).

Specific second active compounds that can be combined with a Heteroaryl Compound vary depending on the specific indication to be treated, prevented or managed.

For instance, for the treatment, prevention or management of cancer, second active agents include, but are not limited to: anti-folates such as Pemetrexed™; semaxanib; cyclosporin; etanercept; doxycycline; bortezomib; acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; celecoxib; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other second agents include, but are not limited to: 20-epi-1,25-dihydroxyvitamin D3; 5-ethynyluracil; abiraterone; aclarubicin; acylfulvene; adecypenol; adozelesin;

aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; compounds targeting metabolism such as resveratol; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clathromycin; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixImab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dihydrotaxol; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (Gleevec®), imiquimod; immunostimulant peptides; insulin-like growth factor-1 receptor inhibitor; interferon agonists; interferons; interleukins; iobenguane; iododoxorubicin; 4-ipomeanol; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, 2-methoxyestradiol, telomestatin, inducers of apoptosis in multiple myeloma cells (such as, for example, TRAIL), bortezomib, statins, semaxanib, cyclosporin, etanercept, doxycycline, bortezomib, oblimersen (Genasense®), remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

Similarly, examples of specific second agents according to the indications to be treated, prevented, or managed can be found in the following references, all of which are incorporated herein in their entireties: U.S. Pat. Nos. 5,635,517, 6,281,230, and 7,189,740; and U.S. patent application publication nos. 2004/0029832, 2004/0087546, 2004/0091455, 2005/0100529, 2005/0214328, 2005/0239842, 2006/0122228, 2006/0143344, 2006/0154880, and 2006/0188475.

Examples of additional second active agents include, but are not limited to, conventional therapeutics used to treat or prevent pain such as antidepressants, anticonvulsants, antihypertensives, anxiolytics, calcium channel blockers, muscle relaxants, non-narcotic analgesics, opioid analgesics, anti-inflammatories, cox-2 inhibitors, immunomodulatory agents, alpha-adrenergic receptor agonists or antagonists, immunosuppressive agents, corticosteroids, hyperbaric oxygen, ketamine, other anesthetic agents, NMDA antagonists, and other therapeutics found, for example, in the *Physician's Desk Reference* 2003. Specific examples include, but are not limited to, salicylic acid acetate (Aspirin®), celecoxib (Celebrex®), Enbrel®, ketamine, gabapentin (Neurontin®), phenytoin (Dilantin®), carbamazepine (Tegretol®), oxcarbazepine (Trileptal®), valproic acid (Depakene®), morphine sulfate, hydromorphone, prednisone, griseofulvin, penthonium, alendronate, dyphenhydramide, guanethidine, ketorolac (Acular®), thyrocalcitonin, dimethylsulfoxide (DMSO), clonidine (Catapress®), bretylium, ketanserin, reserpine, droperidol, atropine, phentolamine, bupivacaine, lidocaine, acetaminophen, nortriptyline (Pamelor®), amitriptyline (Elavil®), imipramine (Tofranil®), doxepin (Sinequan®), clomipramine (Anafranil®), fluoxetine (Prozac®), sertraline (Zoloft®), nefazodone (Serzone®), venlafaxine (Effexor®), trazodone (Desyrel®), bupropion (Wellbutrin®), mexiletine, nifedipine, propranolol, tramadol, lamotrigine, ziconotide, ketamine, dextromethorphan, benzodiazepines, baclofen, tizanidine and phenoxybenzamine.

Examples of additional second active agents include, but are not limited to, a steroid, a light sensitizer, an integrin, an antioxidant, an interferon, a xanthine derivative, a growth hormone, a neutrotrophic factor, a regulator of neovascularization, an anti-VEGF antibody, a prostaglandin, an antibiotic, a phytoestrogen, an anti-inflammatory compound or an antiangiogenesis compound, or a combination thereof. Specific examples include, but are not limited to, verteporfin, purlytin, an angiostatic steroid, rhuFab, interferon-2ÿ, pentoxifylline, tin etiopurpurin, motexafin lutetium, 9-fluoro-11,21-dihydroxy-16, 17-1-methylethylidinebis(oxy)pregna-1,4-diene-3,20-dione, latanoprost (see U.S. Pat. No. 6,225,348), tetracycline and its derivatives, rifamycin and its derivatives, macrolides, metronidazole (U.S. Pat. Nos. 6,218,369 and 6,015,803), genistein, genistin, 6'-O-Mal genistin, 6'-O—Ac genistin, daidzein, daidzin, 6'-O-Mal daidzin, 6'-O—Ac daidzin, glycitein, glycitin, 6'-O-Mal glycitin, biochanin A, formononetin (U.S. Pat. No. 6,001,368), triamcinolone acetomide, dexamethasone (U.S. Pat. No. 5,770,589), thalidomide, glutathione (U.S. Pat. No. 5,632,984), basic fibroblast growth factor (bFGF), transforming growth factor b (TGF-b), brain-derived neurotrophic factor (BDNF), plasminogen activator factor type 2 (PAI-2), EYE101 (Eyetech Pharmaceuticals), LY333531 (Eli Lilly), Miravant, and RETISERT implant (Bausch & Lomb). All of the references cited above are incorporated herein in their entireties by reference.

Examples of additional second active agents include, but are not limited to, keratolytics, retinoids, α-hydroxy acids, antibiotics, collagen, botulinum toxin, interferon, and immunomodulatory agents. Specific examples include, but are not limited to, 5-fluorouracil, masoprocol, trichloroacetic acid, salicylic acid, lactic acid, ammonium lactate, urea, tretinoin, isotretinoin, antibiotics, collagen, botulinum toxin, interferon, corticosteroid, transretinoic acid and collagens such as human placental collagen, animal placental collagen, Dermalogen, AlloDerm, Fascia, Cymetra, Autologen, Zyderm, Zyplast, Resoplast, and Isolagen.

Examples of additional second active agents include, but are not limited to, anticoagulants, diuretics, cardiac glycosides, calcium channel blockers, vasodilators, prostacyclin analogues, endothelin antagonists, phosphodiesterase inhibitors (e.g., PDE V inhibitors), endopeptidase inhibitors, lipid lowering agents, thromboxane inhibitors, and other therapeutics known to reduce pulmonary artery pressure. Specific examples include, but are not limited to, warfarin (Coumadin®), a diuretic, a cardiac glycoside, digoxin-oxygen, diltiazem, nifedipine, a vasodilator such as prostacyclin (e.g., prostaglandin I2 (PGI2), epoprostenol (EPO, Floran®), treprostinil (Remodulin®), nitric oxide (NO), bosentan (Tracleer®), amlodipine, epoprostenol (Floran®), treprostinil (Remodulin®), prostacyclin, tadalafil (Cialis®), simvastatin (Zocor®), omapatrilat (Vanlev®), irbesartan (Avapro®), pravastatin (Pravachol®), digoxin, L-arginine, iloprost, betaprost, and sildenafil (Viagra®).

Examples of additional second active agents include, but are not limited to, anthracycline, platinum, alkylating agent, oblimersen (Genasense®), cisplatinum, cyclophosphamide, temodar, carboplatin, procarbazine, gliadel, tamoxifen, topotecan, methotrexate, taxotere, irinotecan, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, bleomycin, hyaluronidase, mitomycin C, mepacrine, thiotepa, tetracycline and gemcitabine.

Examples of additional second active agents include, but are not limited to, chloroquine, quinine, quinidine, pyrimethamine, sulfadiazine, doxycycline, clindamycin, mefloquine, halofantrine, primaquine, hydroxychloroquine, proguanil, atovaquone, azithromycin, suramin, pentamidine, melarsoprol, nifurtimox, benznidazole, amphotericin B, pentavalent antimony compounds (e.g., sodium stiboglucuronate), interfereon gamma, itraconazole, a combination of dead promastigotes and BCG, leucovorin, corticosteroids, sulfonamide, spiramycin, IgG (serology), trimethoprim, and sulfamethoxazole.

Examples of additional second active agents include, but are not limited to: antibiotics (therapeutic or prophylactic) such as, but not limited to, ampicillin, clarithromycin, tetracycline, penicillin, cephalosporins, streptomycin, kanamycin, and erythromycin; antivirals such as, but not limited to, amantadine, rimantadine, acyclovir, and ribavirin; immunoglobulin; plasma; immunologic enhancing drugs such as, but not limited to, levami sole and isoprinosine; biologics such as, but not limited to, gammaglobulin, transfer factor, interleukins, and interferons; hormones such as, but not limited to, thymic; and other immunologic agents such as, but not limited to, B cell stimulators (e.g., BAFF/BlyS), cytokines (e.g., IL-2, IL-4, and IL-5), growth factors (e.g., TGF-ÿ), antibodies (e.g., anti-CD40 and IgM), oligonucleotides containing unmethylated CpG motifs, and vaccines (e.g., viral and tumor peptide vaccines).

Examples of additional second active agents include, but are not limited to: a dopamine agonist or antagonist, such as, but not limited to, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, and Symmetrel; a MAO inhibitor, such as, but not limited to, iproniazid, clorgyline, phenelzine and isocarboxazid; a COMT inhibitor, such as, but not limited to, tolcapone and entacapone; a cholinesterase inhibitor, such as, but not limited to, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, and demecarium; an anti-inflammatory agent, such as, but not limited to, naproxen sodium, diclofenac sodium, diclofenac potassium, celecoxib, oxaprozin, diflunisal, etodolac, meloxicam, ibuprofen, ketoprofen, nabumetone, refecoxib, methotrexate, leflunomide, sulfasalazine, gold salts, Rho-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone or betamethasone and other glucocorticoids; and an antiemetic agent, such as, but not limited to, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of additional second active agents include, but are not limited to, immunomodulatory agents, immunosuppressive agents, antihypertensives, anticonvulsants, fibrinolytic agents, antiplatelet agents, antipsychotics, antidepressants, benzodiazepines, buspirone, amantadine, and other known or conventional agents used in patients with CNS injury/damage and related syndromes. Specific examples include, but are not limited to: steroids (e.g., glucocorticoids, such as, but not limited to, methylprednisolone, dexamethasone and betamethasone); an anti-inflammatory agent, including, but not limited to, naproxen sodium, diclofenac sodium, diclofenac potassium, celecoxib, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone and benzbromarone; a cAMP analog including, but not limited to, db-cAMP; an agent comprising a methylphenidate drug, which comprises 1-threo-methylphenidate, d-threo-methylphenidate, dl-threo-methylphenidate, 1-erythro-methylphenidate, d-erythro-methylphenidate, dl-erythro-methylphenidate, and a mixture thereof; and a diuretic agent such as, but not limited to, mannitol, furosemide, glycerol, and urea.

Examples of additional second active agents include, but are not limited to, a tricyclic antidepressant agent, a selective serotonin reuptake inhibitor, an antiepileptic agent (gabapentin, pregabalin, carbamazepine, oxcarbazepine, levitiracetam, topiramate), an antiaryhthmic agent, a sodium channel blocking agent, a selective inflammatory mediator inhibitor, an opioid agent, a second immunomodulatory compound, a combination agent, and other known or conventional agents used in sleep therapy. Specific examples include, but are not limited to, Neurontin, oxycontin, morphine, topiramate, amitryptiline, nortryptiline, carbamazepine, Levodopa, L-DOPA, cocaine, α-methyl-tyrosine, reserpine, tetrabenazine, benzotropine, pargyline, fenodolpam mesylate, cabergoline, pramipexole dihydrochloride, ropinorole, amantadine hydrochloride, selegiline hydrochloride, carbidopa, pergolide mesylate, Sinemet CR, Symmetrel, iproniazid, clorgyline, phenelzine, isocarboxazid, tolcapone, entacapone, physostigmine saliclate, physostigmine sulfate, physostigmine bromide, meostigmine bromide, neostigmine methylsulfate, ambenonim chloride, edrophonium chloride, tacrine, pralidoxime chloride, obidoxime chloride, trimedoxime bromide, diacetyl monoxim, endrophonium, pyridostigmine, demecarium, naproxen sodium, diclofenac sodium, diclofenac potassium, celecoxib, sulindac, oxaprozin, diflunisal, etodolac, meloxicam, ibuprofen, ketoprofen, nabumetone, refecoxib, methotrexate, leflunomide, sulfasalazine, gold salts, RHo-D Immune Globulin, mycophenylate mofetil, cyclosporine, azathioprine, tacrolimus, basiliximab, daclizumab, salicylic acid, acetylsalicylic acid, methyl salicylate, diflunisal, salsalate, olsalazine, sulfasalazine, acetaminophen, indomethacin, sulindac, mefenamic acid, meclofenamate sodium, tolmetin, ketorolac, dichlofenac, flurbinprofen, oxaprozin, piroxicam, meloxicam, ampiroxicam, droxicam, pivoxicam, tenoxicam, phenylbutazone, oxyphenbutazone, antipyrine, aminopyrine, apazone, zileuton, aurothioglucose, gold sodium thiomalate, auranofin, methotrexate, colchicine, allopurinol, probenecid, sulfinpyrazone, benzbromarone, betamethasone and other glucocorticoids, metoclopromide, domperidone, prochlorperazine, promethazine, chlorpromazine, trimethobenzamide, ondansetron, granisetron, hydroxyzine, acetylleucine monoethanolamine, alizapride, azasetron, benzquinamide, bietanautine, bromopride, buclizine, clebopride, cyclizine, dimenhydrinate, diphenidol, dolasetron, meclizine, methallatal, metopimazine, nabilone, oxyperndyl, pipamazine, scopolamine, sulpiride, tetrahydrocannabinol, thiethylperazine, thioproperazine, tropisetron, and a mixture thereof.

Examples of additional second active agents include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; and G-CSF; hydroxyurea; butyrates or butyrate derivatives; nitrous oxide; HEMOXIN™ (NIPRISAN™; see U.S. Pat. No. 5,800,819); Gardos channel antagonists such as clotrimazole and triaryl methane derivatives; Deferoxamine; protein C; and transfusions of blood, or of a blood substitute such as Hemospan™ or Hemospan™ PS (Sangart).

Administration of a Heteroaryl Compound and a second active agent to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for Heteroaryl Compounds is oral. Preferred routes of administration for the second active agents or ingredients of the invention are known to those of ordinary skill in the art. See, e.g., *Physicians' Desk Reference,* 1755-1760 (56th ed., 2002).

In one embodiment, the second active agent is administered intravenously or subcutaneously and once or twice daily in an amount of from about 1 to about 1000 mg, from about 5 to about 500 mg, from about 10 to about 350 mg, or from about 50 to about 200 mg. The specific amount of the second active agent will depend on the specific agent used, the type of disease being treated or managed, the severity and stage of disease, and the amount(s) of a Heteroaryl Compound and any optional additional active agents concurrently administered to the patient.

Further provided herein are methods of reducing, treating and/or preventing adverse or undesired effects associated with conventional therapy including, but not limited to, surgery, chemotherapy, radiation therapy, hormonal therapy, biological therapy and immunotherapy. Heteroaryl Compounds and other active ingredients can be administered to a patient prior to, during, or after the occurrence of the adverse effect associated with conventional therapy.

4.5 Pharmaceutical Compositions and Routes of Administration

Provided herein are compositions comprising an effective amount of a Heteroaryl Compound and compositions comprising an effective amount of a Heteroaryl Compound and a pharmaceutically acceptable carrier or vehicle. In some embodiments, the pharmaceutical composition described herein are suitable for oral, parenteral, mucosal, transdermal or topical administration.

The Heteroaryl Compounds can be administered to a patient orally or parenterally in the conventional form of preparations, such as capsules, microcapsules, tablets, granules, powder, troches, pills, suppositories, injections, suspensions and syrups. Suitable formulations can be prepared by methods commonly employed using conventional, organic or inorganic additives, such as an excipient (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrator (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), a diluent (e.g., water), and base wax (e.g., cocoa butter, white petrolatum or polyethylene glycol). The effective amount of the Heteroaryl Compound in the pharmaceutical composition may be at a level that will exercise the desired effect; for example, about 0.005 mg/kg of a patient's body weight to about 10 mg/kg of a patient's body weight in unit dosage for both oral and parenteral administration.

The dose of a Heteroaryl Compound to be administered to a patient is rather widely variable and can be patient to the judgment of a health-care practitioner. In general, the Heteroaryl Compounds can be administered one to four times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight. In one embodiment, one dose is given per day. In any given case, the amount of the Heteroaryl Compound administered will depend on such factors as the solubility of the active component, the formulation used and the route of administration.

In another embodiment, provided herein are methods for the treatment or prevention of a disease or disorder comprising the administration of about 0.375 mg/day to about 750 mg/day, about 0.75 mg/day to about 375 mg/day, about 3.75 mg/day to about 75 mg/day, about 7.5 mg/day to about 55 mg/day or about 18 mg/day to about 37 mg/day of a Heteroaryl Compound to a patient in need thereof.

In another embodiment, provided herein are methods for the treatment or prevention of a disease or disorder comprising the administration of about 1 mg/day to about 1200 mg/day, about 10 mg/day to about 1200 mg/day, about 100 mg/day to about 1200 mg/day, about 400 mg/day to about 1200 mg/day, about 600 mg/day to about 1200 mg/day, about 400 mg/day to about 800 mg/day or about 600 mg/day to about 800 mg/day of a Heteroaryl Compound to a patient in need thereof. In a particular embodiment, the methods disclosed herein comprise the administration of 400 mg/day, 600 mg/day or 800 mg/day of a Heteroaryl Compound to a patient in need thereof.

In another embodiment, provided herein are unit dosage formulations that comprise between about 1 mg and about 2000 mg, about 1 mg and 200 mg, about 35 mg and about 1400 mg, about 125 mg and about 1000 mg, about 250 mg and about 1000 mg, or about 500 mg and about 1000 mg of a Heteroaryl Compound.

In a particular embodiment, provided herein are unit dosage formulation comprising about 100 mg or 400 mg of a Heteroaryl Compound.

In another embodiment, provided herein are unit dosage formulations that comprise 1 mg, 2.5 mg, 5 mg, 10 mg, 15 mg, 20 mg, 30 mg, 35 mg, 50 mg, 70 mg, 100 mg, 125 mg, 140 mg, 175 mg, 200 mg, 250 mg, 280 mg, 350 mg, 500 mg, 560 mg, 700 mg, 750 mg, 1000 mg or 1400 mg of a Heteroaryl Compound.

A Heteroaryl Compound can be administered once, twice, three, four or more times daily.

A Heteroaryl Compound can be administered orally for reasons of convenience. In one embodiment, when administered orally, a Heteroaryl Compound is administered with a meal and water. In another embodiment, the Heteroaryl Compound is dispersed in water or juice (e.g., apple juice or orange juice) and administered orally as a suspension. In another embodiment, when administered orally, a Heteroaryl Compound is administered in a fasted state.

The Heteroaryl Compound can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a Heteroaryl Compound without an additional carrier, excipient or vehicle.

In another embodiment, provided herein are compositions comprising an effective amount of a Heteroaryl Compound and a pharmaceutically acceptable carrier or vehicle, wherein a pharmaceutically acceptable carrier or vehicle can comprise an excipient, diluent, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts, such as the hydrochloride salt. In general, all of the compositions are prepared according to known methods in pharmaceutical chemistry. Capsules can be prepared by mixing a Heteroaryl Compound with a suitable carrier or diluent and filling the proper amount of the mixture in capsules. The usual carriers and diluents include, but are not limited to, inert powdered substances such as starch of many different kinds, powdered cellulose, especially crystalline and microcrystalline cellulose, sugars such as fructose, mannitol and sucrose, grain flours and similar edible powders.

Tablets can be prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. In one embodiment, the pharmaceutical composition is lactose-free. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, stearic acid and hydrogenated vegetable oils. Tablet disintegrators are substances that swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a Heteroaryl Compound as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the Heteroaryl Compound can be delayed or prolonged by proper formulation. For example, a slowly soluble pellet of the Heteroaryl Compound can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the Heteroaryl Compound in oily or emulsified vehicles that allow it to disperse slowly in the serum.

5. EXAMPLES

Chem-4D Draw (ChemInnovation Software, Inc., San Diego, Calif.) or ChemDraw Ultra (Cambridgesoft, Cambridge, Mass.) was used to generate names for chemical structures.

The following abbreviations were used in descriptions and examples:

AmPhos: p-dimethylamino phenylditbutylphosphine

Boc: tert-Butoxycarbonyl dba: dibenzylidene acetone

DMSO: Dimethylsulfoxide

ESI: Electronspray ionization

HPLC: High performance liquid chromatography mp: Melting point

MS: Mass spectrometry

NBS: N-Bromosuccinimide

NMR: Nuclear magnetic resonance

TFA: Trifluoroacetic acid

TLC: Thin layer chromatography

MTBE: methyl tert-butyl ether

The following Examples are presented by way of illustration, not limitation.

5.1 Synthetic Examples

Example 1: 7-(2-Amino-4-methyl-1H-benzo[d]imidazol-6-yl)-1-((tetrahydro-2H-pyran-4-yl)Methyl)-3,4-dihydropyrazino[2,3-b]pyrazin-2(1H)-one

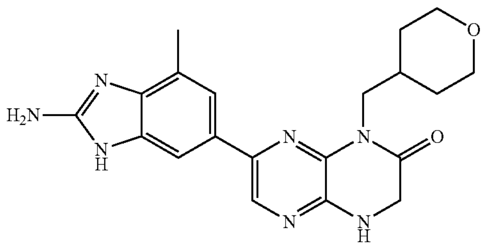 [SMILES: Cc1cc(-c2cnc3c(n2)N(CC2CCOCC2)C(=O)CN3)cc2[nH]c(N)nc12]

A. Ethyl 2-(6-chloropyrazin-2-ylamino)acetate

To 2,6-dichloropyrazine (50 g, 336 mmol) and ethyl 2-aminoacetate (34.6 g, 336 mmol) was added triethylamine (140 mL, 1007 mmol) and acetonitrile (350 mL). The reaction was heated at 80° C. for 3 d. Precipitated triethylamine salts were removed by filtration and washed with ethyl acetate and hexane (1:1) multiple times. The filtrate and wash solvent were combined and concentrated. The resulting white-yellow precipitate was filtered and washed with 20% ethyl acetate in hexane to afford an off-white solid. The filtrate was subjected to the same process to give an additional batch of off-yellow solid. The batches were combined to afford the title compound (35.5 g, 164 mmol, 49% yield). MS (ESI) m/z 216.1 $[M+1]^+$.

B. Ethyl 2-(pyrazin-2-ylamino)acetate

Ethyl 2-(6-chloropyrazin-2-ylamino)acetate (23.6 g, 109 mmol) was dissolved in non-denatured ethanol (250 mL) and potassium carbonate (15.13 g, 109 mmol) was added. The reaction was put under nitrogen and palladium hydroxide (3.84 g, 5.47 mmol) was added. The reaction was stirred under an atmosphere of hydrogen for 18 h. Additional palladium hydroxide (3.84 g, 5.47 mmol) was added and the reaction was charged with additional hydrogen and allowed to stir overnight. The reaction was filtered through Celite and the solvent was removed under reduced pressure to afford the title compound (15.13 g, 84 mmol, 76% yield). MS (ESI) m/z 182.3 $[M+1]^+$.

C. Ethyl 2-(3,5-dibromopyrazin-2-ylamino)acetate

Ethyl 2-(pyrazin-2-ylamino)acetate (7.6 g, 41.9 mmol) was dissolved in dimethylsulfoxide (80 mL) and water (4.00 mL) and cooled to 0° C. N-Bromosuccinimide (18.66 g, 105 mmol) was added slowly over 15 min and the reaction was allowed to warm to rt and stir for 48 h. An additional 1.5 equiv N-bromosuccinimide was added and allowed to stir overnight. The reaction mixture was poured into ice water (200 mL) and extracted with ethyl acetate (150 mL). The aqueous layer was neutralized with sodium carbonate slowly, until pH-7 and extracted with ethyl acetate (3×150 mL). The organic layers were pooled, washed with brine, dried over magnesium sulfate, filtered and concentrated under reduced pressure. The residue was triturated with 25-33% ethyl acetate in hexane and the resulting precipitate was filtered to give a yellow solid. The remaining brown residue was purified using Biotage silica gel chromatography (0-60% ethyl acetate in hexane) to give another batch of off-yellow solid. The two batches were combined to afford 24 g of the title compound (24 g, 71 mmol, 75% yield). MS (ESI) m/z 338.1 $[M]^+$, 340.1 $[M+2]^+$, 342.1 $[M+4]^+$.

D. Ethyl 2-(5-bromo-3-((tetrahydro-2H-pyran-4-yl)methylamino)pyrazin-2-ylamino)acetate Ethyl 2-(3,5-dibromopyrazin-2-ylamino)acetate (2.00 g, 5.90 mmol), (tetrahydro-2H-pyran-4-yl)methanamine (0.713 g, 6.19 mmol), N,N-diisopropylethylamine (3.08 mL, 17.70 mmol) and dimethylsulfoxide (4 mL) were combined in a microwave vial with a stirbar and heated in a Biotage Emrys Optimizer microwave reactor at 150° C. for 1 h. The resulting mixture was transferred to a round bottom flask with methanol. The methanol and N,N-diisopropylethylamine were removed under reduced pressure and the residue purified using Biotage flash chromatography (5-100% ethyl acetate in hexane). Fractions containing the desired product were combined in a separatory funnel and washed twice with water and once with brine. The organics were dried over magnesium sulfate, filtered and concentrated under reduced pressure. The residue was dried under high vacuum at 50° C. to give impure desired product (1.578 g) as an amber waxy solid which was taken on to the next step without further purification. MS (ESI) m/z 373.4 $[M]^+$, 375.4 $[M+2]^+$.

E. 7-Bromo-1-((tetrahydro-2H-pyran-4-yl)methyl)-3,4-dihydropyrazino[2,3-b]pyrazin-2(1H)-one A stirred solution of ethyl 2-(5-bromo-3-((tetrahydro-2H-pyran-4-yl)methylamino)pyrazin-2-ylamino)acetate (1.474 g, 3.95 mmol) in acetic acid (13 mL) in a sealed vessel was heated at 120° C. in an oil bath for 2 h. The acetic acid was removed under reduced pressure. The residue was partitioned between ethyl acetate and saturated aqueous sodium bicarbonate, shaken and the layers separated. The water layer was extracted twice with ethyl acetate. The combined organics were dried over magnesium sulfate, filtered and concentrated under reduced pressure. The residue was taken up in dichloromethane and hexane and the resulting solids collected by vacuum filtration. The solids were washed with hexane and dried under vacuum to give the desired product (0.879 g, 2.688 mmol, 68% yield) as a purple solid. MS (ESI) m/z 327.1 $[M]^+$, 329.0 $[M+2]^+$.

F. 2-Methyl-6-nitro-4-(4,4,5,5-tetramethyl-1,3,2-dioxaborolan-2-yl)aniline

4-Bromo-2-methyl-6-nitroaniline (5 g, 21.64 mmol), bis(pinacolato)diboron (5.50 g, 21.64 mmol), potassium acetate (6.37 g, 64.9 mmol) and N,N-dimethylformamide (100 mL) were combined and degassed under vacuum. Palladium acetate (0.243 g, 1.082 mmol) was added and the system was degassed again. The reaction was heated to 90° C. for 2 h. The reaction was extracted with water and dichloromethane. The organic layer was dried over anhydrous magnesium sulfate, filtered and concentrated. The residue was purified by silica gel column chromatography (0-30% ethyl acetate in hexanes) to give a yellow solid (5.3 g, 19.0 mmol, 88% yield). MS (ESI) m/z 279.0 $[M+1]^+$.

G. 3-Methyl-5-(4,4,5,5-tetramethyl-1,3,2-dioxaborolan-2-yl)benzene-1,2-diamine

A solution of 2-Methyl-6-nitro-4-(4,4,5,5-tetramethyl-1,3,2-dioxaborolan-2-yl)aniline (5.3 g, 19.06 mmol) in methanol (50 mL) was purged with nitrogen gas. Palladium on carbon (10% by wt, 50 mg) was added and the reaction mixture was stirred under a hydrogen balloon for 16 h. The reaction was filtered through Celite and the filter cake was rinsed with methanol. The filtrate was concentrated and the resulting material was purified by silica gel column chromatography (0-100% ethyl acetate in hexanes) to give a dark oil. The oil was triturated with 10% ether in hexanes to give a tan colored solid (4.2 g, 16.9 mmol, 89% yield). MS (ESI) m/z 248.9 $[M+1]^+$.

H. 7-(3,4-Diamino-5-methylphenyl)-1-((tetrahydro-2H-pyran-4-yl)methyl)-3,4-dihydropyrazino[2,3-b]pyrazin-2(1H)-one 3-Methyl-5-(4,4,5,5-tetramethyl-1,3,2-dioxaborolan-2-yl)benzene-1,2-diamine (0.523 g, 2.109 mmol), 7-bromo-1-((tetrahydro-2H-pyran-4-yl)methyl)-3,4-dihydropyrazino[2,3-b]pyrazin-2(1H)-one (0.600 g, 1.834 mmol), [1,1'-bis(diphenylphosphino)-ferrocene]dichloropalladium(II), complex with dichloromethane (1:1) (0.150 g, 0.183 mmol), sodium carbonate (1 M in water, 5.50 mmol), 1,4-dioxane (4.1 mL) and isopropanol (1.4 mL) were combined in a sealable vessel with a stirbar. The system was purged with nitrogen. The resulting mixture was sealed, stirred vigorously and heated at 100° C. for 3.5 h. The resulting mixture was diluted with 20% methanol in dichloromethane and all volatiles removed under reduced pressure. The residue was taken up in 20% methanol in dichloromethane and concentrated under reduced pressure with silica gel. The residue was purified using flash chromatography (1-10% methanol in dichloromethane) to give the desired product (0.669 g, 1.818 mmol, 99% yield) as a brown solid. MS (ESI) m/z 369.1 $[M+1]^+$.

I. 7-(2-Amino-4-methyl-1H-benzo[d]imidazol-6-yl)-1-((tetrahydro-2H-pyran-4-yl)methyl)-3,4-dihydropyrazino[2,3-b]pyrazin-2(1H)-one Cyanogen bromide (0.059 g, 0.556 mmol) in N,N-dimethylformamide (0.5 mL) was added to a stirred solution of 7-(3,4-diamino-5-methylphenyl)-1-((tetrahydro-2H-pyran-4-yl)methyl)-3,4-dihydropyrazino[2,3-b]pyrazin-2(1H)-one (0.195 g, 0.529 mmol) in N,N-dimethylformamide (3 mL) at 0° C. The resulting dark brown mixture was capped and stirred at room temperature for 16 h. The resulting mixture was diluted with methanol, filtered and purified using reverse-phase preparatory HPLC (5-50% acetonitrile+0.1% TFA in water+0.1% TFA, over 30 min). Fractions containing the desired product were combined and most of the solvent removed under reduced pressure. The residue was loaded onto a Strata X-C ion exchange column from Phenomenex. The column was washed successively with water, acetonitrile, methanol and 5% ammonium hydroxide in methanol. The product eluted with the 5% ammonium hydroxide in methanol eluent and was concentrated under reduced pressure and dried under high vacuum at 50° C. to give the desired product (0.130 g, 0.331 mmol, 62% yield) as an orange solid. $^1H$ NMR (400 MHz, $D_2O$ and DMSO-$d_6$) δ (ppm) 8.13 (s, 1H), 7.56 (s, 1H), 7.36 (s, 1H), 4.18 (s, 2H), 4.03 (d, J=6.64 Hz, 2H), 3.84-3.90 (m, 2H), 3.24 (t, J=11.32 Hz, 2H), 2.40 (s, 3H), 2.04-2.19 (m, 1H), 1.59 (d, J=12.10 Hz, 2H), 1.25-1.41 (m, 2H); MS (ESI) m/z 394.2 $[M+1]^+$.

Example 2: 3,3-Dimethyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one

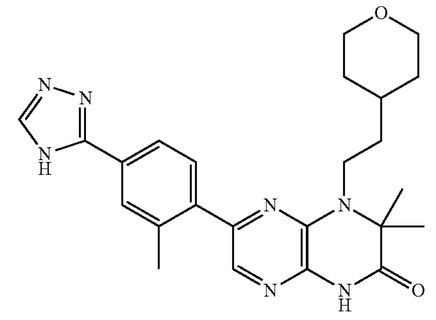 [SMILES: Cc1cc(-c2nnc[nH]2)ccc1-c1cnc2c(n1)N(CCC1CCOCC1)C(C)(C)C(=O)N2]

A. 3-(4-Bromo-3-methylphenyl)-4H-1,2,4-triazole

4-Bromo-3-methylbenzonitrile (10.0 g, 51.0 mmol) was dissolved in ethanol (200 mL) with stirring and cooled to 0° C. under nitrogen. Hydrogen chloride gas was bubbled into the reaction mixture for 20 min. The resulting reaction mixture was capped and stirred while slowly warming to room temperature for 5.5 h. Solvent was removed under reduced pressure and the residue dried under vacuum to give 13.86 g of an off-white solid. The off-white solid, formic hydrazide (4.48 g, 74.6 mmol), triethylamine (28.0 mL, 199 mmol) and ethanol (90 mL) were combined in a sealed tube and heated, with stirring, at 90° C. for 6.5 h. All the solvent was removed under reduced pressure and the resulting residue partitioned between ethyl acetate and water. The layers were separated and the organics washed with brine, dried over magnesium sulfate, filtered and concentrated under reduced pressure. The residue was dissolved in hot ethyl acetate (13 mL), capped and let stand at room temperature overnight. The solvent was decanted away from the solids at the bottom of the flask. The solids were washed with ethyl acetate and diethyl ether and dried under vacuum at 45° C. to give the desired product (7.47 g, 31.4 mmol, 63% yield) as a light yellow solid. MS (ESI) m/z 238.2 $[M]^+$, 240.3 $[M+2]^+$.

B. 3-(4-Bromo-3-methylphenyl)-4-(tetrahydro-2H-pyran-2-yl)-4H-1,2,4-triazole 3-(4-Bromo-3-methylphenyl)-4H-1,2,4-triazole (2.00 g, 8.40 mmol) was dissolved in tetrahydrofuran (10 mL) at room temperature with stirring under nitrogen. 3,4-Dihydro-2H-pyran (3.80 mL, 42.0 mmol) and methanesulfonic acid (0.027 mL, 0.42 mmol) were added and the resulting mixture heated at 50° C. under a reflux condenser under nitrogen for 20 h. The resulting mixture was cooled to room temperature, diluted with ethyl acetate and washed with saturated aqueous sodium bicarbonate and brine. The organics were dried over magnesium sulfate, filtered and concentrated under reduced pressure. Flash chromatography (10-30-50% ethyl acetate in hexanes) gave the desired product (2.64 g, 8.22 mmol, 98% yield) as a yellow oil. MS (ESI) m/z 322 $[M]^+$, 324 $[M+2]^+$.

C. 3-(3-Methyl-4-(4,4,5,5-tetramethyl-1,3,2-dioxaborolan-2-yl)phenyl)-4-(tetrahydro-2H-pyran-2-yl)-4H-1,2,4-triazole 3-(4-Bromo-3-methylphenyl)-4-(tetrahydro-2H-pyran-2-yl)-4H-1,2,4-triazole (2.294 g, 7.12 mmol), bis(pinacolato)

diboron (1.898 g, 7.48 mmol), [1,1'-bis(diphenylphosphino)-ferrocene]dichloropalladium(II), complex with dichloromethane (1:1) (291 mg, 0.36 mmol), potassium acetate (2.096 g, 21.4 mmol) and dimethyl sulfoxide (15 mL) were combined in a round bottom flask and stirred. The atmosphere in the flask was removed under vacuum and replaced with nitrogen three times. The resulting mixture was heated at 90° C. under nitrogen for 4 h. The resulting mixture was diluted with ethyl acetate and filtered through Celite. The filter cake was washed thoroughly with ethyl acetate. The filtrate was washed twice with water, once with brine, dried over magnesium sulfate, filtered and concentrated under reduced pressure. Flash chromatography (30-50% ethyl acetate in hexanes) gave a waxy semi-solid which was triturated with hexane at 45° C. The resulting solids were dried under vacuum to give the desired product (2.10 g, 5.69 mmol, 80% yield) as a pink powder. MS (ESI) m/z 370 $[M+1]^+$.

D. tert-Butyl 1-(3,5-dibromopyrazin-2-ylamino)-2-methyl-1-oxopropan-2-ylcarbamate 1,1'-Carbonyldiimidazole (2.63 g, 16.24 mmol) was added to a stirred solution of 2-(tert-butoxycarbonylamino)-2-methylpropanoic acid (3.00 g, 14.76 mmol) in N,N-dimethylformamide (4 mL) and dichloromethane (8 mL) at room temperature. The resulting clear colorless mixture was stirred at room temperature under nitrogen for 3 h. N,N-Diisopropylethylamine (3.86 mL, 22.14 mmol) was added followed by 3,5-dibromopyrazin-2-amine (5.60 g, 22.14 mmol). The resulting mixture was heated at 50° C. under a reflux condenser under nitrogen for 71 h. Dichloromethane was removed under reduced pressure. The residue was diluted with ethyl acetate and washed with water. The water layer was extracted with ethyl acetate. The combined organics were washed with brine, dried over magnesium sulfate, filtered and concentrated under reduced pressure. The residue was triturated with 30% ethyl acetate in hexane and solids collected by vacuum filtration. The filtrate was concentrated under reduced pressure and purified using flash chromatography (5-50% ethyl acetate in hexane). Fractions containing the desired product were combined with the solids obtained by filtration and concentrated under reduced pressure. The residue was dried under high vacuum to give the desired product (2.38 g, 5.43 mmol, 37% yield) as an off-white solid. MS (ESI) m/z 439.3 $[M+1]^+$, 461.1 $[M+Na]^+$.

E. N-(3,5-Dibromopyrazin-2-yl)-2-methyl-2-(2-(tetrahydro-2H-pyran-4-yl)ethylamino)propanamide trifluoroacetate TFA (3.66 mL, 47.5 mmol) was added to a stirred mixture of tert-butyl 1-(3,5-dibromopyrazin-2-ylamino)-2-methyl-1-oxopropan-2-ylcarbamate (1.04 g, 2.374 mmol) in dichloromethane (20 mL). The resulting clear yellow solution was stirred at room temperature for 3 h. All volatiles were removed under reduced pressure and the residue dried under high vacuum to give a yellow semi-solid. MS (ESI) m/z 339.1 $[M+1]^+$. Sodium sulfate (1.686 g, 11.87 mmol) was added followed by 2-(tetrahydro-2H-pyran-4-yl)acetaldehyde (0.396 g, 3.09 mmol) and 1,2-dichloroethane (20 mL). The resulting mixture was stirred vigorously and heated at 80° C. under a reflux condenser under nitrogen for 2.5 h. More 2-(tetrahydro-2H-pyran-4-yl)acetaldehyde (0.100 g, 0.780 mmol) and sodium sulfate (1.00 g, 7.04 mmol) were added and heating at 80° C. continued for another 2 h. The resulting yellow solution was removed by pipette from the solid sodium sulfate into a dry 250 mL round bottom flask equipped with a stirbar. The resulting mixture was stirred vigorously and cooled to 0° C. under nitrogen. Sodium triacetoxyborohydride (0.553 g, 2.61 mmol) was added slowly. The resulting mixture was stirred vigorously at 0° C. under nitrogen for 30 min. The cold bath was removed and the resulting mixture stirred at room temperature under nitrogen for 2 h. The mixture was cooled to 0° C. and more sodium triacetoxyborohydride (0.250 g, 1.180 mmol) was added. The cold bath was removed and the resulting mixture stirred at room temperature under nitrogen for 1.5 h. More sodium triacetoxyborohydride (0.055 g, 0.260 mmol) was added. The resulting mixture was stirred vigorously at room temperature under nitrogen for 1 h and then stirred overnight at 0° C. The resulting mixture was diluted with methanol and the volatiles removed under reduced pressure. The residue was taken up in methanol, filtered and purified using reverse-phase preparatory HPLC (10-40% acetonitrile+0.1% TFA in water+0.1% TFA, over 30 min). Fractions containing the desired product were combined and the solvent removed under reduced pressure. The residue was dried under vacuum to give the desired product (0.890 g, 1.978 mmol, 67% yield) as a slightly yellow foam-solid. MS (ESI) m/z 451.3 $[M+1]^+$.

F. 6-Bromo-3,3-dimethyl-4-(2-(tetrahydro-2H-pyran-4-yl)ethyl)-3,4-dihydropyrazino[2,3-b]pyrazin-2(1H)-one N-(3,5-Dibromopyrazin-2-yl)-2-methyl-2-(2-(tetrahydro-2H-pyran-4-yl)ethylamino)propanamide trifluoroacetate (0.856 g, 1.517 mmol), N,N-diisopropylethylamine (1.321 mL, 7.59 mmol) and 1,4-dioxane (25 mL) were combined in a sealable vessel with a stirbar. The system was purged with nitrogen and the resulting mixture was sealed, stirred vigorously and heated at 110° C. for 2.5 h. The reaction mixture was concentrated under reduced pressure and purified using flash chromatography (5-50% ethyl acetate in hexane) to give the desired product (0.394 g, 1.068 mmol, 70% yield) as a white solid. MS (ESI) m/z 369.4 $[M]^+$, 371.3 $[M+2]^+$.

G. 3,3-Dimethyl-6-(2-methyl-4-(4-(tetrahydro-2H-pyran-2-yl)-4H-1,2,4-triazol-3-yl)phenyl)-4-(2-(tetrahydro-2H-pyran-4-yl)ethyl)-3,4-dihydropyrazino[2,3-b]pyrazin-2(1H)-one 3-(3-Methyl-4-(4,4,5,5-tetramethyl-1,3,2-dioxaborolan-2-yl)phenyl)-4-(tetrahydro-2H-pyran-2-yl)-4H-1,2,4-triazole (1 equiv), 6-bromo-3,3-dimethyl-4-(2-(tetrahydro-2H-pyran-4-yl)ethyl)-3,4-dihydropyrazino[2,3-b]pyrazin-2(1H)-one (1 equiv), [1,1'-bis(diphenylphosphino)-ferrocene]dichloropalladium(II), complex with dichloromethane (1:1) (0.1 equiv), 1 M sodium carbonate in water (3 equiv), 1,4-dioxane and isopropanol were combined and the system was purged with nitrogen. The resulting mixture was stirred vigorously and heated at 100° C. for 1.5 h. The resulting mixture was cooled to room temperature, diluted with methanol and the volatiles removed under reduced pressure. The residue was partitioned between dichloromethane and water, shaken and the layers separated. The water layer was extracted with dichloromethane. The combined organics were dried over magnesium sulfate, filtered and concentrated under reduced pressure. The residue was purified using flash chromatography (20-100% ethyl acetate in hexane followed by 0-10% methanol in dichloromethane) to give the desired product in 97% yield. MS (ESI) m/z 532.7 $[M+1]^+$.

H. 3,3-Dimethyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one 6 N Hydrochloric acid in water was added to a stirred mixture of 3,3-dimethyl-6-(2-methyl-4-(4-(tetrahydro-2H-pyran-2-yl)-4H-1,2,4-triazol-3-yl)phenyl)-4-(2-(tetrahydro-2H-pyran-4-yl)ethyl)-3,4-dihydropyrazino[2,3-b]pyrazin-2(1H)-one in ethanol at 80° C. The resulting mixture was stirred vigorously and heated at 80° C. under a reflux condenser under nitrogen for 70 min. The resulting mixture was filtered and purified using reverse-phase preparatory HPLC (10-65% acetonitrile+0.1% TFA in water+0.1% TFA, over 30 min). Fractions containing the desired product were combined, neutralized with saturated aqueous sodium bicarbonate and the acetonitrile removed under reduced pressure. Solids were collected by vacuum filtration, washed thoroughly with water and diethyl ether and dried under high vacuum at 50° C. to give the desired product in 48% yield. $^1$H NMR (400 MHz, DMSO-$d_6$) δ (ppm) 11.32 (br. s., 1H), 8.44 (br. s., 1H), 7.96 (s, 1H), 7.90 (d, J=8.59 Hz, 1H), 7.70 (s, 1H), 7.56 (d, J=7.81 Hz, 1H), 3.78 (dd, J=2.93, 11.13 Hz, 2H), 3.52-3.64 (m, 2H), 3.23 (t, J=10.93 Hz, 2H), 2.48 (s, 3H), 1.51-1.66 (m, 5H), 1.49 (s, 6H), 1.11-1.26 (m, 2H); MS (ESI) m/z 448.3 $[M+1]^+$.

Example 3: 7-(2-Methyl-4-(4H-1,2,4-triazol-3-yl)phenyl)-3,4-dihydropyrazino[2,3-b]pyrazin-2(1H)-one hydrochloride

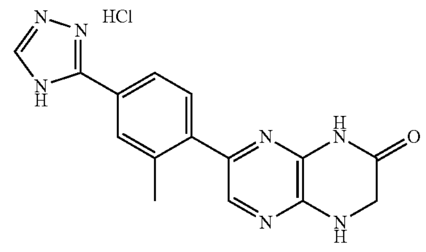 [SMILES: Cl ; Cc1cc(-c2nnc[nH]2)ccc1-c1cnc2c(n1)NC(=O)CN2]

A. Ethyl 2-(5-bromo-3-(2,4-dimethoxybenzylamino)pyrazin-2-ylamino)acetate

Ethyl 2-(3,5-dibromopyrazin-2-ylamino)acetate (See Example 1.C) (1.06 g, 3.13 mmol), (2,4-dimethoxyphenyl)methanamine (0.601 g, 3.60 mmol), N,N-diisopropylethylamine (1.63 mL, 9.38 mmol) and dimethylsulfoxide (1.6 mL) were combined in a microwave vial with a stirbar and heated in a microwave reactor at 150° C. for 2 h. The resulting mixture was purified using flash chromatography (5-60% ethyl acetate in hexane). Fractions containing the desired product were combined and concentrated nearly to dryness under reduced pressure. Ethyl acetate (2 mL) and hexane (18 mL) was added. The resulting solids were collected by vacuum filtration, washed with hexane and dried under high vacuum to give the desired product (0.636 g, 1.495 mmol, 48% yield) as a light pink solid. $^1$H NMR (300 MHz, DMSO-$d_6$) δ (ppm) 7.24 (s, 1H), 7.19 (d, J=8.52 Hz, 1H), 7.11 (t, J=5.63 Hz, 1H), 6.84 (t, J=4.81 Hz, 1H), 6.59 (d, J=2.47 Hz, 1H), 6.50 (dd, J=2.20, 8.24 Hz, 1H), 4.37 (d, J=4.67 Hz, 2H), 3.96-4.15 (m, 4H), 3.81 (s, 3H), 3.75 (s, 3H), 1.17 (t, 3H); MS (ESI) m/z 425.3 $[M]^+$, 426.9 $[M+2]^+$.

B. 7-Bromo-3,4-dihydropyrazino[2,3-b]pyrazin-2(1H)-one trifluoroacetate

Ethyl 2-(5-bromo-3-(2,4-dimethoxybenzylamino)pyrazin-2-ylamino)acetate (0.484 g, 1.138 mmol), methanol (0.461 mL, 11.38 mmol) and TFA (7 mL) were combined in a sealable vessel with a stirbar. The system was purged with nitrogen. The resulting mixture was sealed, stirred vigorously and heated at 75° C. in an oil bath for 25 min. The resulting mixture was diluted with water (14 mL) and stirred at room temperature for 5 min. Solids were collected by vacuum filtration, washed with water and diethyl ether and dried under high vacuum to give the desired product (0.375 g, 1.093 mmol, 96% yield) as a pink solid. MS (ESI) m/z 229.0 $[M]^+$, 231.3 $[M+2]^+$.

C. 7-(2-Methyl-4-(4-(tetrahydro-2H-pyran-2-yl)-4H-1,2,4-triazol-3-yl)phenyl)-3,4-dihydropyrazino[2,3-b]pyrazin-2(1H)-one 3-(3-Methyl-4-(4,4,5,5-tetramethyl-1,3,2-dioxaborolan-2-yl)phenyl)-4-(tetrahydro-2H-pyran-2-yl)-4H-1,2,4-triazole (See Example 2.C) (0.465 g, 1.259 mmol), 7-bromo-3,4-dihydropyrazino[2,3-b]pyrazin-2(1H)-one trifluoroacetate (0.432 g, 1.259 mmol), [1,1'-bis(diphenylphosphino)-ferrocene]dichloropalladium(II), complex with dichloromethane (1:1) (0.103 g, 0.126 mmol), sodium carbonate (1 M in water, 3.78 mL, 3.78 mmol), 1,4-dioxane (2.5 mL) and isopropanol (1 mL) were combined in a sealable vessel with a stirbar. The system was purged with nitrogen. The resulting mixture was sealed, stirred vigorously and heated at 100° C. for 70 min. The resulting mixture was diluted with water and dichloromethane and filtered through a fritted funnel. Solids were washed with 20% methanol in dichloromethane. Filtrate and wash were combined and the solvent was removed under reduced pressure. The residue was triturated with acetonitrile. Water was added. Solids were collected by vacuum filtration and washed thoroughly with water and diethyl ether. Solids were washed with 20% methanol in dichloromethane. Filtrate and wash were combined and the solvent was removed under reduced pressure. The residue was taken up in hot DMSO and methanol, filtered and purified using reverse-phase preparatory HPLC (20-65% acetonitrile+0.1% TFA in water+0.1% TFA, over 30 min). Fractions containing the desired product were combined, neutralized with saturated aqueous sodium bicarbonate and concentrated nearly to dryness under reduced pressure. Solids were collected by vacuum filtration, washed with water and dried under high vacuum to give the desired product (0.072 g, 0.184 mmol, 15% yield) as an off-white solid. MS (ESI) m/z 392.1 $[M+1]^+$.

D. 7-(2-Methyl-4-(4H-1,2,4-triazol-3-yl)phenyl)-3,4-dihydropyrazino[2,3-b]pyrazin-2(1H)-one hydrochloride Hydrochloric acid (6 N in water 0.149 mL, 0.894 mmol) was added to a stirred mixture of 7-(2-methyl-4-(4-(tetrahydro-2H-pyran-2-yl)-4H-1,2,4-triazol-3-yl)phenyl)-3,4-dihydropyrazino[2,3-b]pyrazin-2(1H)-one (0.070 g, 0.179 mmol) in ethanol (3 mL) at 80° C. The system was purged with nitrogen. The resulting mixture was sealed and heated at 80° C. The resulting mixture was heated at 80° C. for 25 min and then cooled to room temperature. Solids were collected by filtration, washed with methanol and dried under high vacuum at 40° C. to give the desired product (0.058 g, 0.169 mmol, 94% yield) as a white solid. $^1H$ NMR (300 MHz, DMSO-$d_6$) δ (ppm) 11.32 (s, 1H), 8.66 (s, 1H), 7.97 (s, 1H), 7.92 (dd, J=1.37, 7.97 Hz, 1H), 7.74 (s, 1H), 7.50 (d, J=7.97 Hz, 1H), 4.14 (s, 2H), 2.44 (s, 3H); MS (ESI) m/z 308.3 $[M+1]^+$.

Example 4: 6-(4-(2-Hydroxypropan-2-yl)phenyl)-4-(2-(tetrahydro-2H-pyran-4-yl)ethyl)-3,4-dihydropyrazino[2,3-b]pyrazin-2(1H)-one

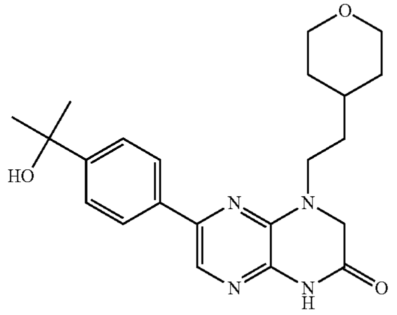 [SMILES: CC(C)(O)c1ccc(-c2cnc3c(n2)N(CCC2CCOCC2)CC(=O)N3)cc1]

A. 2-Bromo-N-(3,5-dibromopyrazin-2-yl)acetamide

A solution of 2-amino-3,5-dibromopyrazine (6.17 g, 23.7 mmol) and bromoacetic anhydride (3.0 g, 11.9 mmol) in acetonitrile (40 mL) was stirred at 70° C. Upon complete consumption of starting material (by TLC), the solution was condensed and partitioned between water and ethyl acetate (3×). The organic layers were combined, dried over magnesium sulfate, filtered and the solvent was removed under reduced pressure. The resulting material was purified using Biotage column chromatography (5-80% ethyl acetate in hexanes) to afford the title compound (3.78 g, 10.1 mmol, 85% yield). MS (ESI) m/z 372.1 $[M-2]^+$, 374.0 $[M]^+$, 376.1 $[M+2]^+$, 378.3 $[M+4]^+$.

B. 6-Bromo-4-(2-(tetrahydro-2H-pyran-4-yl)ethyl)-3,4-dihydropyrazino[2,3-b]pyrazin-2(1H)-one 2-Bromo-N-(3,5-dibromopyrazin-2-yl)acetamide (3.30 g, 8.83 mmol) and 2-(tetrahydro-2H-pyran-4-yl)ethanamine hydrochloride (1.46, 8.83 mmol) and diisopropyl ethylamine (6.67 mL, 35.3 mmol) were combined and heated at 85° C. Upon complete consumption of starting material (by TLC), the reaction solution was condensed and purified via Biotage chromatography (0-100% ethyl acetate in hexanes) to afford the title compound (1.53 g, 4.48 mmol, 50% yield). MS (ESI) m/z 341.4 $[M]^+$, 343.1 $[M+2]^+$.

C. 2-(4-Bromophenyl)propan-2-ol 1-(4-Bromophenyl)ethanone (9.25 g, 46.5 mmol) was dissolved in tetrahydrofuran (200 mL). The solution was cooled in a −50° C. bath. Methylmagnesium bromide (3M in ether, 46.5 mL, 139 mmol) was added over a 15 min period. The reaction was allowed to warm to room temperature and then stirred for 20 h. The reaction was quenched with saturated ammonium chloride and then extracted with ethyl acetate. The organic layer was dried over magnesium sulfate, filtered and concentrated to give an oil. The oil was purified on a silica gel column (0-20% ethyl acetate in hexanes) to give the product a colorless oil (9.1 g, 46.2 mmol, 91% yield). MS (ESI) m/z 197.1 $[M]^+$, 199.1 $[M+2]^+$.

D. 2-(4-(4,4,5,5-Tetramethyl-1,3,2-dioxaborolan-2-yl)phenyl)propan-2-ol 2-(4-Bromophenyl)propan-2-ol (4.7 g, 21.85 mmol), bis(pinacolato)diboron (6.66 g, 26.2 mmol), potassium acetate (6.43 g, 65.6 mmol) and dimethyl sulfoxide (50 mL) were stirred and degassed under vacuum for 10 min. [1,1'-Bis(diphenyl-phosphino)ferrocene]dichloro-palladium(II) complex with dichloromethane (1:1) (0.892 g, 1.093 mmol) was added and the reaction was degassed for another 5 min. The reaction was then heated to 80° C. under nitrogen for 2 h. The reaction was cooled to room temperature and then extracted with 1:1 ether:ethyl acetate and water. The resulting black emulsion was filtered through a pad of celite and the filtrate combined with extraction layers. The organic layer was dried over magnesium sulfate, filtered and then purified on silica gel column (0-25% ethyl acetate in hexanes). The product fractions were concentrated and then triturated in hexanes to give a white solid, (4.0 g, 15.3 mmol, 70% yield). MS (ESI) m/z 263.3 $[M+1]^+$.

E. 6-(4-(2-Hydroxypropan-2-yl)phenyl)-4-(2-(tetrahydro-2H-pyran-4-yl)ethyl)-3,4-dihydropyrazino[2,3-b]pyrazin-2(1H)-one 6-Bromo-4-(2-(tetrahydro-2H-pyran-4-yl)ethyl)-3,4-dihydropyrazino[2,3-b]pyrazin-2(1H)-one (0.250 g, 0.733 mmol), 2-(4-(4,4,5,5-tetramethyl-1,3,2-dioxaborolan-2-yl)phenyl)propan-2-ol (0.192 g, 0.733 mmol) and dichloro[1,1'-bis(diphenylphosphino)ferrocene]palladium (II) dichloromethane (0.030 g, 0.037 mmol) were combined in dimethylformamide (1.0 mL). Sodium carbonate (0.311 g, 2.93 mmol) in water (0.2 mL) was added and the reaction solution was then heated in a Biotage Emrys Optimizer microwave reactor at 120° C. for 15 min. The cooled reaction solution was filtered through Celite and the filter cake was washed with ethyl acetate. Filtrate and ethyl acetate wash were combined and solvent removed under reduced pressure. The resulting material was purified using Biotage column chromatography (0-5% methanol in ethyl acetate) followed by trituration with dimethylformamide and water to afford the title compound (0.074 g, 0.19 mmol, 25%)$^1H$ NMR (400 MHz, DMSO-$d_6$) δ (ppm) □ 12.24 (s, 1H), 7.98 (s, 1H), 7.89 (d, J=8.39 Hz, 2H), 7.53 (d, J=8.39 Hz, 1H), 5.04 (s, 1H), 4.16 (s, 1H), 3.82 (dd, J=11.1, 2.39 Hz, 2H), 3.61 (t, J=7.59 Hz, 2H), 3.25 (t, J=9.59 Hz, 3H), 1.70 (s, 1H), 1.66 (s, 1H), 1.58 (m, 3H), 1.44 (s, 6H), 1.25 (m, 2H); MS (ESI) m/z 397.2 $[M+1]^+$; mp 210-212° C.

Example 5: 6-(6-(2-Hydroxypropan-2-yl)pyridin-3-yl)-4-(2-morpholinoethyl)-3,4-dihydropyrazino[2,3-b]pyrazin-2(1H)-one

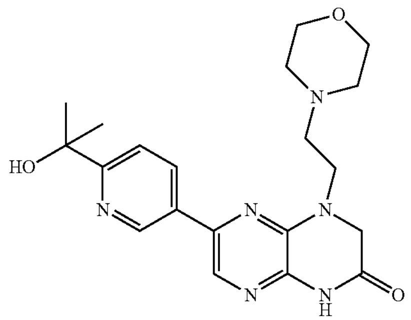 [SMILES: CC(C)(O)c1ccc(-c2cnc3c(n2)N(CCN2CCOCC2)CC(=O)N3)cn1]

A. 2-Chloro-N-(3,5-dibromopyrazin-2-yl)acetamide

A solution of 2-amino-3,5-dibromopyrazine (3.0 g, 11.9 mmol) and chloroacetic anhydride (4.2 g, 8.7 mmol) were reacted in acetonitrile (10 mL) at 70° C. for 16 h. The solution was condensed and diluted with ethyl acetate. The organics were washed with a 1:1 solution of sodium bicarbonate (saturated) and potassium carbonate (1.75 M in water) (4×). The organics were combined, dried over magnesium sulfate, filtered and solvent removed under reduced pressure. The resulting solid was triturated with 10% ethyl acetate in hexanes to afford the title compound (3.12 g, 9.3 mmol, 72% yield). MS (ESI) m/z 328.3 $[M-1]^+$, 330.4 $[M+1]^+$, 332.3 $[M+3]^+$.

B. N-(3,5-Dibromopyrazin-2-yl)-2-iodoacetamide

To a solution of 2-chloro-N-(3,5-dibromopyrazin-2-yl)acetamide (3.0 g, 9.11 mmol) in acetone (40 mL) was added sodium iodide (13.65 g, 91 mmol) dissolved in acetone (20 mL). Solution was allowed to stir at ambient temperature for 16 h. Solution was condensed under reduced pressure and diluted with ethyl acetate (500 mL) and washed consecutively with water (5×) to remove the blue color. Organics were dried over magnesium sulfate, filtered and solvent removed under reduced pressure to afford the crude product. The solid was diluted with 10% ethyl acetate in hexanes (40 mL) and sonicated while scraping the sides of the flask. The solution was then heated under a heat gun for 5 min, then cooled while sonicating at ambient temperature. The resulting solid was filtered and washed with additional hexanes and dried under vacuum to afford the title compound (3.0 g, 7.13 mmol, 78% yield). MS (ESI) m/z 420.3 $[M-1]^+$, 422.0 $[M+1]^+$, 424.0 $[M+3]^+$.

C. 6-Bromo-4-(2-morpholinoethyl)-3,4-dihydropyrazino[2,3-b]pyrazin-2(1H)-one

N-(3,5-Dibromopyrazin-2-yl)-2-iodoacetamide (0.5 g, 1.188 mmol), diisopropylethylamine (0.415 mL, 2.376 mmol) and 2-morpholineethanamine (0.162 g, 1.248 mmol) were combined in acetonitrile (5 mL). The solution was heated to 45° C. for 1 h. Solution was condensed and diluted with 75% ethyl acetate in hexanes. The resulting solid was filtered and the filtrate collected and condensed followed by purification via Biotage chromatography (0-75% ethyl acetate in hexanes then 0-10% methanol in ethyl acetate) to afford the title compound (0.228 g, 0.67 mmol, 56% yield). MS (ESI) m/z 342.4 $[M]^+$, 344.4 $[M+2]^+$.

D. 2-(5-Bromopyridin-2-yl)propan-2-ol 2,5-Dibromopyridine (1.04 g, 4.39 mmol) was dissolved in toluene (22 mL) in a 100 mL round-bottomed flask. The mixture was cooled to −78° C. n-Butyllithium (3.02 mL, 4.83 mmol) was added dropwise. The mixture was stirred 30 min, followed by the addition of acetone (2 mL). The mixture was stirred 40 min and then let warm to rt. The mixture was washed with ammonium chloride (5% aq, 50 mL), water (50 mL) and then brine (50 mL). The organic layer was dried over sodium sulfate, filtered and concentrated. The residue was purified by Biotage (16% ethyl acetate in hexanes). Concentration of the desired fractions afforded the product (0.82 g, 3.78 mmol, 86% yield). MS (ESI) m/z 216.0 $[M]^+$, 218.1 $[M+2]^+$.

E. 2-(5-(Trimethylstannyl)pyridin-2-yl)propan-2-ol 2-(5-Bromopyridin-2-yl)propan-2-ol (0.34 g, 1.574 mmol), 1,1,1,2,2,2-hexamethyldistannane (0.361 mL, 1.652 mmol) and tetrakis(triphenylphosphine)palladium(0) (0.182 g, 0.157 mmol) were combined in toluene (5 mL) in a 50 mL resealable flask. The reaction was stirred at 115° C. for 1.5 h. The mixture was then concentrated to about a 2 mL volume. The residue was purified via Biotage (16% ethyl acetate in hexanes). Concentration of the desired fractions afforded the title compound (0.33 g, 1.10 mmol, 70% yield). MS (ESI) m/z 302.1 $[M+1]^+$.

F. 6-(6-(2-Hydroxypropan-2-yl)pyridin-3-yl)-4-(2-morpholinoethyl)-3,4-dihydropyrazino[2,3-b]pyrazin-2(1H)-one 6-Bromo-4-(2-morpholinoethyl)-3,4-dihydropyrazino[2,3-b]pyrazin-2(1H)-one (0.228 g, 0.666 mmol) and 2-(5-(trimethylstannyl)pyridin-2-yl)propan-2-ol (0.220 g, 0.733 mmol) were combined in dimethylformamide (3 mL). Solution was purged with nitrogen gas followed by the addition of dichloro[1,1'-bis(diphenylphosphino)ferrocene]palladium (II) dichloromethane (0.109 g, 0.133 mmol). Solution was heated to 100° C. for 2 h. Solution was condensed under reduced pressure and the resulting oil purified via reverse-phase-preparative HPLC (5-60% acetonitrile+0.1% TFA in $H_2O$+0.1% TFA, over 30 min) and desired fractions were loaded onto a Strata-XC ion exchange column. The column was washed successively with water, acetonitrile, methanol and 5% ammonium hydroxide in methanol. The product eluted with the 5% ammonium hydroxide in methanol and was concentrated under reduced pressure and dried to afford the title compound (0.070 g, 0.18 mmol, 26% yield). $^1H$ NMR (400 MHz, DMSO-$d_6$) δ (ppm) 11.33 (br. s., 1H), 9.05 (d, J=1.56 Hz, 1H), 8.27 (dd, J=8.59, 2.34 Hz, 1H), 8.06 (s, 1H), 7.72 (d, J=8.59 Hz, 1H), 5.27 (s, 1H), 4.29 (s, 2H), 3.71 (t, J=6.44 Hz, 2H), 3.54 (t, J=4.49 Hz, 4H), 2.62 (t, J=6.44 Hz, 2H), 2.40-2.48 (m, 4H), 1.46 (s, 6H); MS (ESI) m/z 399.2 $[M+1]^+$; mp 239-241° C.

Example 6: 1-(((trans)-4-Methoxycyclohexyl)methyl)-7-(4-methyl-6-(1H-1,2,4-triazol-3-yl)pyridin-3-yl)-3,4-dihydropyrazino[2,3-b]pyrazin-2(1H)-one

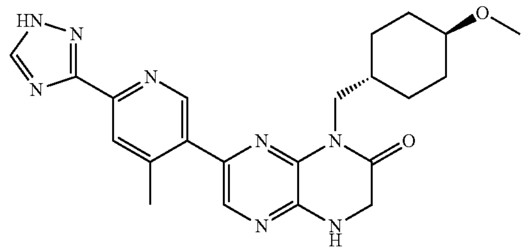 [SMILES: CO[C@H]1CC[C@H](CN2C(=O)CNc3ncc(-c4cnc(-c5nc[nH]n5)cc4C)nc32)CC1]

A. 5-Bromo-4-methylpicolinonitrile 2,5-Dibromo-4-methylpyridine (5.0 g, 19.9 mmol), copper cyanide (1.43 g, 15.9 mmol), sodium cyanide (0.801 g, 16.3 mmol) and dimethylformamide (30 mL) were combined in a sealed reaction vessel and heated at 158° C. for 3 h. The reaction mixture was purified by silica gel column chromatography (0-80% ethyl acetate in hexanes). The resulting material was subjected to a second silica gel column (0-20% methanol in dichloromethane). Clean fractions were combined and concentrated to afford the title compound as a white solid (2.30 g, 11.6 mmol, 58% yield). MS (ESI) m/z 198.0 $[M+1]^+$.

B. Ethyl 2-(3,5-dibromopyrazin-2-ylamino)acetate

A 2000 mL 3-necked round bottomed flask was charged with 2-amino-3,5-dibromopyrazine (172 g, 680 mmol) in dimethylformamide (860 mL) and cooled to 0-5° C. Cesium carbonate (288 g, 884 mmol) was added in one portion followed by the portion-wise addition of ethyl chloroacetate (87 mL, 816 mmol). The solution was allowed to warm to 20-25° C. then heated to 55° C. (exotherm observed, max temperature observed 76° C.). Once the internal reaction temperature subsided to 65° C. the reaction was heated at 65° C. for ~4 h. The reaction was cooled to 20-25° C. and filtered through filter paper to remove inorganic salts and the solid was washed with dimethylformamide (3 vol). The filtrate was added dropwise to 16 vol of ice-water (8 vol ice/8 vol water) and the slurry was allowed to agitate for 12-24 h. The resulting brown solid was isolated following filtration and washed with water (10 vol) and air-dried. Crude product was dissolved in methyl t-butyl ether (3.46 L, 15 vol). Charcoal (C-906 from Ecosorb, 20 wt %, 46.1 g) was added and the mixture was heated at reflux for 1 h. After cooling to rt, the charcoal was removed over a Celite bed and the filtrate was concentrated to dryness. The crude was dissolved in ethyl acetate (576 mL, 2.5 vol) and concentrated to a thick slurry. A solution of 2% ethyl acetate in heptane (1.15 L, 5 vol) was added and the mixture was stirred at rt for 30-60 min. The product was collected by filtration, washed with heptane (2-3 vol) and dried under high vacuum at 35-40° C. for 16 h to afford the desired compound as an off-white solid (109 g, 47% yield). A second crop was isolated from the mother liquor as follows: the filtrate was concentrated to give a crude oil. Ethyl acetate (1 vol.) was added. The resulting solution was seeded with previously isolated product and cooled at 0-5° C. for 1 h. The resulting solid was collected by filtration and washed with cold ethyl acetate:heptane (1:1 mixture, <1 vol). The solid was dried as described previously and combined with the first crop to provide the title compound (132 g, 57% total yield). MS (ESI) m/z 337.8 $[M-1]^+$, 339.8 $[M+1]^+$, 341.8 $[M+3]^+$.

C. 7-Bromo-1-(((trans)-4-methoxycyclohexyl) methyl)-3,4-dihydropyrazino[2,3-b]pyrazin-2(1H)-one A solution of ethyl 2-(3,5-dibromopyrazin-2-ylamino) acetate (500 mg, 1.47 mmol), ((trans)-4-methoxycyclohexyl)methanamine (317 mg, 2.21 mmol) and diisopropylethyl amine (0.77 mL, 4.42 mmol) in anhydrous dimethylsulfoxide (8.0 mL) was placed in a microwave vessel (20 mL). The reaction was heated to 150° C. for 1 h. The reaction was poured into water, extracted with ethyl acetate (2×100 mL), dried over sodium sulfate, filtered and concentrated under reduced pressure. The resulting material was dissolved in acetic acid (30 mL) and placed in a sealed tube. The reaction was heated to 120° C. overnight. The solution was cooled, concentrated under reduced pressure, neutralized with saturated sodium bicarbonate, extracted with ethyl acetate (3×100 mL), dried over sodium sulfate, filtered and adsorbed onto silica gel. Purification by flash chromatography (50% ethyl acetate in hexanes) gave a light orange solid (400 mg, 1.12 mmol, 76% yield). MS (ESI) m/z 355.2 $[M+]^+$, 357.2 $\{M+2]^+$.

D. 1-(((trans)-4-Methoxycyclohexyl)methyl)-7-(trimethylstannyl)-3,4-dihydropyrazino[2,3-b] pyrazin-2(1H)-one 7-Bromo-1-(((trans)-4-methoxycyclohexyl)methyl)-3,4-dihydropyrazino[2,3-b]pyrazin-2(1H)-one (2.71 g, 7.63 mmol), 1,1,1,2,2,2-hexamethyldistannane (3.00 g, 9.15 mmol) and tetrakis(triphenylphosphine)palladium(0) (882 mg, 0.76 mmol) were combined in a sealed tube charged with anhydrous dioxane (40 mL) and purged with nitrogen gas. The reaction was heated to 100° C. for 4 h. The reaction was diluted with ethyl acetate, filtered through celite, washed celite with ethyl acetate and the filtrate concentrated under reduced pressure. The crude material was purified by flash chromatography (0-50% ethyl acetate in hexane) and desired fractions were combined and concentrated to give a light yellow solid (2.32 g, 5.28 mmol, 69% yield). MS (ESI) m/z 441.1 $[M+1]^+$.

E. 5-(8-(((trans)-4-Methoxycyclohexyl)methyl)-7-oxo-5,6,7,8-tetrahydropyrazino[2,3-b]pyrazin-2-yl)-4-methylpicohnonitrile 1-(((trans)-4-Methoxycyclohexyl)methyl)-7-(trimethylstannyl)-3,4-dihydropyrazino[2,3-b]pyrazin-2(1H)-one (0.721 g, 1.64 mmol), 5-bromo-4-methylpicolinonitrile (0.323 g, 1.64 mmol), tris(dibenzylideneacetone)dipalladium(0) (0.150 g, 0.164 mmol), triethylamine (0.687 mL, 4.93 mmol), tri-ortho-tolylphosphine (0.100 g, 0.328 mmol) and dimethylformamide (8 mL) were combined in a sealed reaction vessel. Nitrogen was bubbled through the reaction for 5 min and reaction was heated at 100° C. for 3 h. Reaction is filtered, concentrated and purified by silica gel column chromatography (0-80% ethyl acetate in hexanes). Fractions were combined and concentrated to afford the crude title compound used directly for next step (0.607 g, 1.55 mmol, 94% yield). MS (ESI) m/z 393.5 $[M+1]^+$.

F. 5-(8-(((trans)-4-Methoxycyclohexyl)methyl)-7-oxo-5,6,7,8-tetrahydropyrazino[2,3-b]pyrazin-2-yl)-4-methylpicolinamide 5-(8-(((trans)-4-Methoxycyclohexyl)methyl)-7-oxo-5,6,7,8-tetrahydropyrazino[2,3-b]pyrazin-2-yl)-4-methylpicolinonitrile (0.607 g, 1.55 mmol), trifluroacetic acid (2.0 mL, 26.0 mmol) and sulfuric acid (0.5 mL, 9.38 mmol) were combined and heated at 65° C. for 1 h. Reaction pH was adjusted to 10 with sodium carbonate and the resulting solution was extracted with ethyl acetate (3×15 mL). Organic layers were collected, dried over magnesium sulfate, concentrated and purified using reverse-phase preparatory HPLC (10-100% acetonitrile+0.1% TFA in $H_2O$+0.1% TFA, over 30 min). Clean fractions were combined and condensed under reduced pressure and dried under high vacuum to afford the title compound as a yellow solid (0.425 g, 1.04 mmol, 67% yield). MS (ESI) m/z 411.5 $[M+1]^+$.

G. (Z)—N-((Dimethylamino)methylene)-5-(8-(((trans)-4-methoxycyclohexyl)methyl)-7-oxo-5,6,7,8-tetrahydropyrazino[2,3-b]pyrazin-2-yl)-4-methylpicolinamide 5-(8-(((trans)-4-Methoxycyclohexyl)methyl)-7-oxo-5,6,7,8-tetrahydropyrazino[2,3-b]pyrazin-2-yl)-4-methylpicolinamide (0.412 g, 1.00 mmol), dimethylformamide dineopentylacetal (1.5 mL) and tetrahydrofuran (10 mL) were combined and heated at 85° C. for 3 h. Reaction was concentrated under a stream of nitrogen placed in reaction vessel. Crude product was used directly for next step (0.467 g, 1.00 mmol, 100% yield). MS (ESI) m/z 466.6 [M+1]$^+$ H. 1-(((trans)-4-Methoxycyclohexyl)methyl)-7-(4-methyl-6-(1H-1,2,4-triazol-3-yl)pyridin-3-yl)-3,4-dihydropyrazino[2,3-b]pyrazin-2(1H)-one (Z)—N-((Dimethylamino)methylene)-5-(8-(((trans)-4-methoxycyclohexyl)methyl)-7-oxo-5,6,7,8-tetrahydropyrazino[2,3-b]pyrazin-2-yl)-4-methylpicolinamide (0.467 g, 1.00 mmol) was added to acetic acid (6 mL). The reaction was cooled to 0° C. and hydrazine (1.00 mL, 32 mmol) was added dropwise. The reaction was allowed to stir and warm to 25° C. over 10 min. Reaction was concentrated under a stream of nitrogen placed in reaction vessel. Water (5 mL) was added and the product was collected by filtration and purified using reverse-phase semi-preparatory HPLC (20-70% acetonitrile+0.1% TFA in $H_2O$+0.1% TFA, over 30 min). Clean fractions were combined and condensed under reduced pressure and dried under high vacuum to afford the title compound as a yellow solid (0.046 g, 0.106 mmol, 11% yield). $^1$H NMR (400 MHz, METHANOL-$d_4$) δ (ppm) 8.72 (s, 1H), 8.62 (s, 1H), 8.37 (s, 1H), 7.93 (s, 1H), 4.30 (s, 2H), 3.99 (d, J=7.03 Hz, 2H), 3.32 (s, 3H), 3.08-3.17 (m, 1H), 2.71-2.76 (m, 3H), 2.06 (br. s., 2H), 1.80-1.89 (m, 1H), 1.74 (br. s., 2H), 1.09 (d, J=11.32 Hz, 4H); MS (ESI) m/z 435.5 [M+1]$^+$.

Example 7: 7-(5-Fluoro-2-methyl-4-(1H-1,2,4-triazol-3-yl)phenyl)-1-isopropyl-3,4-dihydropyrazino[2,3-b]pyrazin-2(1H)-one

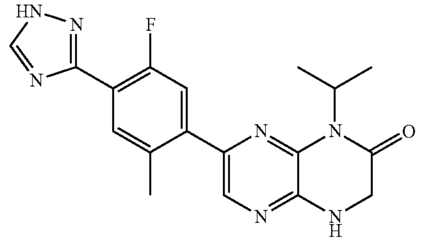 [SMILES: Cc1cc(-c2nc[nH]n2)c(F)cc1-c1cnc2c(n1)N(C(C)C)C(=O)CN2]

A. Ethyl 2-(5-bromo-3-(isopropylamino)pyrazin-2-ylamino)acetate

A mixture of ethyl 2-(3,5-dibromopyrazin-2-ylamino)acetate (See Example 6.B) (1.5 g, 4.43 mmol), isopropylamine (0.17 g, 4.87 mmol), N,N-diisopropylethylamine (1.14 g, 8.84 mmol) and dimethylsulfoxide (10 mL) in a reaction vial was heated in an oil bath at 150° C. for 16 h. After being cooled to room temperature, the resulting mixture was poured into water and extracted with ethyl acetate. The organic layer was dried over sodium sulfate, filtered, evaporated under reduced pressure and purified on silica gel column chromatography (10-20% ethyl acetate in petroleum ether) to give the title compound (780 mg, 55.7% yield). MS (ESI) m/z 316.9 [M+1]$^+$.

B. 7-Bromo-1-isopropyl-3,4-dihydropyrazino[2,3-b]pyrazin-2(1H)-one

A mixture of ethyl 2-(5-bromo-3-(isopropylamino)pyrazin-2-ylamino)acetate (780 mg, 2.26 mmol), methanol (5 mL) and TFA (10 mL) in a sealable vessel was purged with nitrogen, sealed, stirred vigorously and heated at 90° C. with an oil bath for 16 h. The resulting mixture was diluted with methanol and the solvent was removed under reduced pressure. Methanol (10 mL) was added and the solvent was removed under reduced pressure again. Methanol (10 mL) and sodium bicarbonate were added. The resulting mixture was stirred at room temperature until pH=6 (in water), the solvent was removed under reduced pressure. Water (20 mL) was added. The mixture was extracted with methylene chloride (20 mL×3). The organic layer was dried over anhydrous sodium sulfate, concentrated to give the crude product and purified on silica column chromatography (10-20% ethyl acetate in petroleum ether) to give the title compound (360 mg, 39.4% yield).

C. 1-Isopropyl-7-(trimethylstannyl)-3,4-dihydropyrazino[2,3-b]pyrazin-2(1H)-one

7-Bromo-1-isopropyl-3,4-dihydropyrazino[2,3-b]pyrazin-2(1H)-one (0.5 g, 1.844 mmol), hexamethylditin (0.725 g, 2.213 mmol), tetrakis(triphenylphosphine)palladium(0) (0.213 g, 0.184 mmol) and 1,4-dioxane (3 mL) were combined in a sealable vessel with a stirbar. Nitrogen gas was bubbled through the solution. The vessel was sealed, stirred vigorously and heated at 100° C. for 2 h. The resulting cloudy black mixture was diluted with ethyl acetate, filtered and the filter cake washed thoroughly with ethyl acetate. The filtrate was concentrated under reduced pressure and purified using silica gel flash column chromatography (20-80% ethyl acetate in hexanes) to give the desired product (0.49 g, 1.38 mmol, 75% yield) as a yellow-white solid. MS (ESI) m/z 357.4 [M+2]$^+$.

D. 4-Bromo-2-fluoro-5-methylbenzamide

To a solution of 4-bromo-2-fluoro-5-methylbenzonitrile (40 g, 190 mmol) in a mixture of sulfuric acid (98%) and TFA (v/v=4:1, 480 mL) was stirred at 80° C. for 16 h. After the mixture was cooled to room temperature, the resulting mixture was poured into ice-cold water. The resulting precipitate was collected by filtration, washed with water and dried under reduced pressure to give the title compound (41 g, 95% yield) as a white solid. MS (ESI) m/z 232.0 [M+1]$^+$.

E. 4-Bromo-N-((dimethylamino)methylene)-2-fluoro-5-methylbenzamide

A solution of 4-bromo-2-fluoro-5-methylbenzamide (20 g, 86 mmol) in N,N-dimethyl-formamide dimethylacetal (200 mL) was stirred at 100° C. under nitrogen for 3 h. The resulting mixture was concentrated and dried to give the desired product (24.6 g, 95% yield) as a yellow oil, which was used in the next step without further purification. MS (ESI) m/z 287.0 [M+1]$^+$.

F. 3-(4-Bromo-2-fluoro-5-methylphenyl)-1H-1,2,4-triazole

To a solution of 4-bromo-N-((dimethylamino)methylene)-2-fluoro-5-methylbenzamide (24.6 g, 86.2 mmol) in acetic acid (200 mL) was added dropwise hydrazine hydrate (25 mL, 0.70 mol) at 0° C. The reaction mixture was stirred at room temperature overnight. The mixture was filtered washed with water (500 mL×3) and dried under reduced pressure to give the title compound (15 g, 68% yield) as a white solid. MS (ESI) m/z 256.0 $[M+1]^+$.

G. 3-(4-Bromo-2-fluoro-5-methylphenyl)-1-(tetrahydro-2H-pyran-2-yl)-1H-1,2,4-triazole A solution of 3-(4-bromo-2-fluoro-5-methylphenyl)-1H-1,2,4-triazole (15 g, 60 mmol), toluene-4-sulfonic acid (2.0 g, 12 mmol) and 3,4-dihydro-2H-pyran (20 g, 240 mmol) in tetrahydrofuran (200 mL) was stirred at 80° C. under nitrogen for 15 h. The resulting mixture was concentrated and purified on silica gel column (1-25% ethyl acetate in petroleum ether) to give the protected triazole product (15 g, 75% yield) as a white solid. $^1H$ NMR (DMSO-$d_6$, 400 MHz): δ (ppm) 8.83 (s, 1H), 7.96 (d, J=7.6 Hz, 1H), 7.66 (d, J=10.0 Hz, 1H), 5.61 (dd, $J_1$=2.4 Hz, $J_2$=9.6 Hz, 1H), 3.96 (d, J=1.6 Hz, 1H), 3.69 (m, 1H), 2.36 (s, 3H), 2.00 (m, 2H), 1.70 (m, 2H), 1.57 (m, 2H); MS (ESI) m/z 340.0 $[M+1]^+$.

H. 7-(5-Fluoro-2-methyl-4-(1-(tetrahydro-2H-pyran-2-yl)-1H-1,2,4-triazol-3-yl)phenyl)-1-isopropyl-3,4-dihydropyrazino[2,3-b]pyrazin-2(1H)-one 1-Isopropyl-7-(trimethylstannyl)-3,4-dihydropyrazino[2,3-b]pyrazin-2(1H)-one (300 mg, 0.84 mmol), 3-(4-bromo-2-fluoro-5-methylphenyl)-1-(tetrahydro-2H-pyran-2-yl)-1H-1,2,4-triazole (428 mg, 1.26 mmol) and bis(triphenylphosphine)palladium(II) dichloride (56 mg, 0.08 mmol) were combined in N,N-dimethylformamide (5 mL). The mixture was degassed and heated at 140° C. under nitrogen for 3 h. After being cooled to room temperature, the reaction mixture was filtered and the filtrate was partitioned between ethyl acetate (15 mL) and water (15 mL). The organic layer was separated and the aqueous layer was extracted with ethyl acetate (10 mL×2). The combined organic layer was dried over sodium sulfate, filtered, concentrated under reduced pressure and purified by preparative TLC (15% methanol in dichloromethane) to give the title compound (200 mg, yield 52%) as a solid.

I. 7-(5-Fluoro-2-methyl-4-(1H-1,2,4-triazol-3-yl)phenyl)-1-isopropyl-3,4-dihydropyrazino[2,3-b]pyrazin-2(1H)-one A solution of 7-(5-fluoro-2-methyl-4-(1-(tetrahydro-2H-pyran-2-yl)-1H-1,2,4-triazol-3-yl)phenyl)-1-isopropyl-3,4-dihydropyrazino[2,3-b]pyrazin-2(1H)-one (200 mg, 0.44 mmol) in methanolic hydrochloride solution (20 mL, 2 M) was stirred for 5 h at room temperature. The reaction was diluted with saturated aqueous sodium bicarbonate solution (25 mL) and the aqueous mixture was extracted with ethyl acetate (25 mL×2). The organic phase was dried over sodium sulfate, filtered, evaporated under reduced pressure and purified on silica gel column (50-100% ethyl acetate in petroleum ether). The desired fractions were combined and concentrated under reduced pressure to give the title compound (75 mg, 46% yield). $^1H$ NMR (DMSO-$d_6$, 400 MHz): δ (ppm) 14.25 (br. s., 1H), 8.20 (br. s., 1H), 7.90 (m, 2H), 7.58 (s, 1H), 7.35 (s, 1H), 5.24 (m, 1H), 4.10 (s, 2H), 2.43 (s, 3H), 1.44 (d, J=7.2, 6H); MS (ESI) m/z 368.2 $[M+1]^+$.

Example 8: 7'-(2-Methyl-4-(4H-1,2,4-triazol-3-yl)phenyl)-1'H-spiro[cyclopropane-1,2'-pyrazino[2,3-b]pyrazin]-3'(4'H)-one

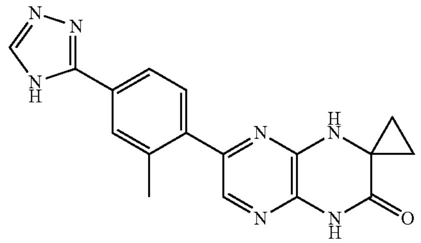 [SMILES: Cc1cc(-c2nnc[nH]2)ccc1-c1cnc2c(n1)NC1(CC1)C(=O)N2]

A. tert-Butyl 1-(3,5-dibromopyrazin-2-ylcarbamoyl)cyclopropyl-carbamate 1,1'-Carbonyldiimidazole (4.37 g, 27.0 mmol) was added to a stirred solution of 1-(tert-butoxycarbonylamino)cyclopropanecarboxylic acid (4.93 g, 24.50 mmol) in N,N-dimethylformamide (6 mL) and dichloromethane (12 mL) at room temperature. The resulting clear yellow mixture was stirred at room temperature under nitrogen for 4 h. N,N-Diisopropylethylamine (8.54 mL, 49.0 mmol) was added followed by 3,5-dibromopyrazin-2-amine (9.29 g, 36.8 mmol). The resulting mixture was heated at 50° C. under a reflux condenser under nitrogen for 60 h. The resulting mixture was diluted with ethyl acetate and washed with water. The layers were separated and the organic layer washed with brine, dried over magnesium sulfate, filtered and concentrated under reduced pressure. The residue was taken up in dichloromethane and purified using flash chromatography (Biotage) (5-60% ethyl acetate in hexane). Fractions containing the desired product were combined and concentrated under reduced pressure. The residue was triturated with 15% ethyl acetate in hexane and dried under high vacuum to give the desired product (5.349 g, 12.27 mmol, 50% yield) as an off-white solid. $^1H$ NMR (400 MHz, DMSO-$d_6$) δ (ppm) 9.92 (br. s., 1H), 8.76 (s, 1H), 7.70 (br. s., 1H), 1.41 (s, 9H), 1.34-1.40 (m, 2H), 1.02-1.09 (m, 2H); MS (ESI) m/z 437.3 $[M+1]^+$, 459.1 $[M+Na]^+$.

B. 1-Amino-N-(3,5-dibromopyrazin-2-yl)cyclopropanecarboxamide bistrifluoracetate TFA (6.02 mL, 78 mmol) was added to a stirred mixture of tert-butyl 1-(3,5-dibromopyrazin-2-ylcarbamoyl)cyclopropylcarbamate (3.410 g, 7.82 mmol) in dichloromethane (20 mL). The resulting clear yellow solution was stirred at room temperature for 4 h. All volatiles were removed under reduced pressure and the residue dried under high vacuum at 40° C. to give the desired product (4.42 g, 7.85 mmol, 100% yield) as a waxy yellow solid. MS (ESI) m/z 337.1 $[M+1]^+$.

C. 7'-Bromo-1'H-spiro[cyclopropane-1,2'-pyrazino[2,3-b]pyrazin]-3'(4'H)-one

1-Amino-N-(3,5-dibromopyrazin-2-yl)cyclopropanecarboxamide bistrifluoracetate (0.394 g, 0.700 mmol), N,N-diisopropylethylamine (0.610 mL, 3.50 mmol) and 1,4-dioxane (6 mL) were combined in a sealable vessel with a stirbar. The system was purged with nitrogen. The resulting mixture was sealed, stirred vigorously and heated at 110° C.

for 2 h. Volatiles were removed under reduced pressure. The residue was dissolved in DMSO and methanol, filtered and purified using reverse-phase preparatory HPLC (10-65% acetonitrile+0.1% TFA in water+0.1% TFA, over 30 min). Fractions containing the desired product were combined, neutralized with saturated aqueous sodium bicarbonate and most of the solvent removed under reduced pressure. Solids were collected by vacuum filtration, washed thoroughly with water and dried under high vacuum to give the desired product (0.141 g, 0.553 mmol, 79% yield) as a light yellow solid. $^1$H NMR (400 MHz, DMSO-$d_6$) δ (ppm) 11.27 (s, 1H), 8.04 (s, 1H), 7.46 (s, 1H), 1.29-1.38 (m, 2H), 0.91-1.01 (m, 2H); MS (ESI) m/z 255.1 $[M]^+$, 257.0 $[M+2]^+$.

D. 7'-(2-Methyl-4-(4-(tetrahydro-2H-pyran-2-yl)-4H-1,2,4-triazol-3-yl)phenyl)-1'H-spiro[cyclopropane-1,2'-pyrazino[2,3-b]pyrazin]-3'(4'H)-one trifluoroacetate 3-(3-Methyl-4-(4,4,5,5-tetramethyl-1,3,2-dioxaborolan-2-yl)phenyl)-4-(tetrahydro-2H-pyran-2-yl)-4H-1,2,4-triazole (See Example 2.C) (0.201 g, 0.545 mmol), 7'-bromo-1'H-spiro[cyclopropane-1,2'-pyrazino[2,3-b]pyrazin]-3'(4'H)-one (0.139 g, 0.545 mmol), [1,1'-bis(diphenylphosphino)-ferrocene]dichloropalladium(II), complex with dichloromethane (1:1) (0.045 g, 0.054 mmol), sodium carbonate (1 M in water, 1.635 mL, 1.635 mmol), 1,4-dioxane (1.2 mL) and isopropanol (0.4 mL) were combined in a sealable vessel with a stirbar. The system was purged with nitrogen. The resulting mixture was sealed, stirred vigorously and heated at 100° C. for 1 h. The resulting mixture was diluted with water and extracted three times with dichloromethane. The combined organics were concentrated under reduced pressure. The residue was taken up in DMSO and methanol, filtered and purified using reverse-phase preparatory HPLC (20-70% acetonitrile+0.1% TFA in water+0.1% TFA, over 30 min). Fractions containing the desired product were combined and the solvent removed under reduced pressure. The residue was dried under high vacuum to give the desired product (0.109 g, 0.205 mmol, 38% yield) as an orange solid. MS (ESI) m/z 418.4 $[M+1]^+$.

E. 7'-(2-Methyl-4-(4H-1,2,4-triazol-3-yl)phenyl)-1'H-spiro[cyclopropane-1,2'-pyrazino[2,3-b]pyrazin]-3'(4'H)-one 6 N Hydrochloric acid in water (0.171 mL, 1.025 mmol) was added to a stirred mixture of 7'-(2-methyl-4-(4-(tetrahydro-2H-pyran-2-yl)-4H-1,2,4-triazol-3-yl)phenyl)-1'H-spiro[cyclopropane-1,2'-pyrazino[2,3-b]pyrazin]-3'(4'H)-one trifluoroacetate (0.109 g, 0.205 mmol) in ethanol (4 mL) at 80° C. The resulting mixture was stirred vigorously and heated at 80° C. under a reflux condenser under nitrogen for 30 min. The resulting mixture was filtered and purified using reverse-phase preparatory HPLC (10-60% acetonitrile+0.1% TFA in water+0.1% TFA, over 30 min). Fractions containing the desired product were combined, neutralized with saturated aqueous sodium bicarbonate and most of the solvent removed under reduced pressure. Solids were collected by vacuum filtration, washed thoroughly with water and dried under high vacuum at 45° C. to give the desired product (0.027 g, 0.079 mmol, 39% yield) as a yellow solid. $^1$H NMR (400 MHz, DMSO-$d_6$) δ (ppm) 11.22 (br. s., 1H), 8.63 (br. s., 1H), 7.93 (s, 1H), 7.89 (d, J=7.81 Hz, 1H), 7.62 (s, 1H), 7.58 (s, 1H), 7.47 (br. s., 1H), 2.43 (s, 3H), 1.29-1.38 (m, 2H), 0.95-1.04 (m, 2H); MS (ESI) m/z 334.2 $[M+1]^+$.

Example 9: 7-(6-(2-Hydroxypropan-2-yl)pyridin-3-yl)-1-((trans)-4-methoxycyclohexyl)-3,4-dihydropyrazino[2,3-b]pyrazin-2(1H)-one

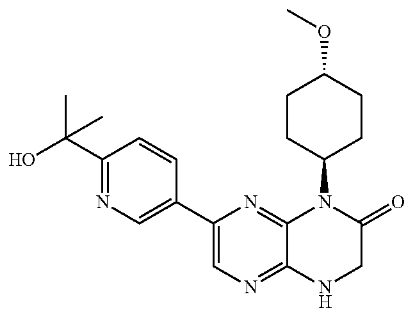 [SMILES: CO[C@H]1CC[C@H](N2C(=O)CNc3ncc(-c4ccc(C(C)(C)O)nc4)nc32)CC1]

A. Ethyl 2-(5-bromo-3-(trans-4-methoxycyclohexylamino)pyrazin-2-ylamino) acetate Ethyl 2-(3,5-dibromopyrazin-2-ylamino)acetate (See Example 6.B) (30.0 g, 88 mmol), trans-4-methoxycyclohexanamine (17.15 g, 133 mmol), N,N-diisopropylethylamine (30.8 mL, 177 mmol) and dimethylsulfoxide (70.8 mL) were combined in a reaction vial with a stirbar and heated in an oil bath at 150° C. for 16 h with stirring. The resulting mixture was diluted with ethyl acetate and the volatiles removed under reduced pressure. The residue was purified using silica gel chromatography on a Biotage SP1 (12% ethyl acetate in hexanes). Fractions containing the desired product were combined and organic volatiles removed under reduced pressure. The residue was triturated with 5% ethyl acetate in hexane. Solids were collected by vacuum filtration, washed with hexane and dried under vacuum to afford ethyl the title compound (15.37 g, 39.7 mmol, 44.8% yield) as an off-white solid. MS (ESI) m/z 387.0 $[M]^+$, 389.0 $[M+2]^+$.

B. 7-Bromo-1-(trans-4-methoxycyclohexyl)-3,4-dihydropyrazino[2,3-b]pyrazin-2(1H)-one The following reaction was split into 3 separate sealed tubes and worked up separately. The material was then combined following purification. Ethyl 2-(5-bromo-3-(trans-4-methoxycyclohexylamino)pyrazin-2-ylamino)acetate (10 g, 25.7 mmol), methanol (10.5 mL, 259 mmol) and TFA (100 mL) were combined in a sealable vessel with a stirbar. The system was purged with nitrogen and the resulting mixture was sealed, stirred vigorously and heated at 90° C. with an oil bath for 18.5 h. The resulting mixture was diluted with methanol and all the solvent was removed under reduced pressure. Methanol (100 mL) was added and all the solvent was removed under reduced pressure again. Methanol (100 mL) and sodium bicarbonate (12.4 g, 147 mmol) were added. The resulting mixture was stirred at room temperature until pH=6 (in water). The mixture was concentrated nearly to dryness. Water (100 mL) was added. The resulting brown solids were collected by vacuum filtration and washed with water. The brown solids were dissolved in hot methanol and acetonitrile and purified using reverse-phase C18 flash column chromatography (20-100% acetonitrile in water). Fractions containing the desired product were combined and concentrated nearly to dryness under reduced pressure. Solids were collected by vacuum filtration, washed with water and dried under high vacuum to give the desired product (4.88 g, 14.3 mmol, 55% yield) as a light tan solid. $^{1}$H NMR (400 MHz, DMSO-$d_6$) δ (ppm) 7.71 (s, 1H), 7.59 (s, 1H), 4.66 (tt, J=3.61, 12.20 Hz, 1H), 4.07 (d, J=1.56 Hz, 2H), 3.25 (s, 3H), 3.06-3.17 (m, 1H), 2.42 (qd, J=3.51, 12.89 Hz, 2H), 2.10 (d, J=10.93 Hz, 2H), 1.61 (d, J=10.93 Hz, 2H), 1.10-1.24 (m, 2H); MS (ESI) m/z 341.3 $[M]^+$, 343.1 $[M+2]^+$.

C. 7-(6-(2-Hydroxypropan-2-yl)pyridin-3-yl)-1-(trans-4-methoxycyclohexyl)-3,4-dihydropyrazino[2,3-b]pyrazin-2(1H)-one 2-(5-(Trimethylstannyl)pyridin-2-yl)propan-2-ol (See Example 5.E) (9.43 g, 31.4 mmol), 7-bromo-1-(trans-4-methoxycyclohexyl)-3,4-dihydropyrazino[2,3-b]pyrazin-2(1H)-one (10.02 g, 29.4 mmol), [1,1'-bis(diphenyl-phosphino)-ferrocene]dichloropalladium(II) dichloromethane adduct (2.398 g, 2.94 mmol) and N,N-dimethylformamide (25 mL) were combined in a round-bottom flask with a stirbar. The atmosphere in the vessel was removed under vacuum and replaced with nitrogen gas three times. The resulting mixture was stirred vigorously and heated at 120° C. under nitrogen for 35 min. The resulting mixture was purified using flash chromatography, split into 4 separate columns, (2-15% methanol in dichloromethane). Fractions containing the desired product were combined and most of the solvent removed under reduced pressure. The resulting mixture was purified using reverse-phase preparatory HPLC (20-40% acetonitrile+0.1% TFA in water+0.1% TFA, over 30 min), split into 6 runs. Fractions containing the desired product were combined and all of the acetonitrile and some of the water were removed under reduced pressure at 25° C. The remaining yellow solution was loaded onto 50 g of Strata X—C ion exchange resin from Phenomenex. The column was washed successively with water, acetonitrile, methanol and then 5% ammonium hydroxide in methanol. The product eluted with the 5% ammonium hydroxide in methanol wash and was concentrated under reduced pressure and dried under high vacuum to give the desired product (4.85 g, 12.20 mmol, 42% yield) as a pink foam-solid. $^{1}$H NMR (400 MHz, DMSO-$d_6$) δ (ppm) 9.03 (d, J=1.56 Hz, 1H), 8.28 (s, 1H), 8.24 (dd, J=2.34, 8.20 Hz, 1H), 7.74 (d, J=7.81 Hz, 1H), 7.61 (s, 1H), 5.26 (s, 1H), 4.90 (tt, J=3.71, 12.10 Hz, 1H), 4.13 (s, 2H), 3.28 (s, 3H), 3.20 (tt, J=4.00, 10.84 Hz, 1H), 2.58 (qd, J=2.93, 12.82 Hz, 2H), 2.14 (d, J=10.15 Hz, 2H), 1.68 (d, J=10.93 Hz, 2H), 1.47 (s, 6H), 1.17-1.35 (m, 2H); MS (ESI) m/z 398.3 $[M+1]^+$; mp 196-198° C. (uncorrected).

D. 7-(6-(2-Hydroxypropan-2-yl)pyridin-3-yl)-1-(trans-4-methoxycyclohexyl)-3,4-dihydropyrazino[2,3-b]pyrazin-2(1H)-one (alternate approach)

Ethyl 2-(3,5-dibromopyrazin-2-ylamino)acetate (1 equiv) and trans-4-methoxycyclohexanamine.hydrochloride (1.5 equiv), NMP and DIEA were combined and heated to 127° C. and maintained at that temperature for 18 h. Upon reaction completion, the mixture was cooled to 35° C. over 4 h. The batch was transferred to a mixture of ethyl acetate and 5% brine. The aqueous layer was removed and the organic layer containing the batch was washed successively with 5% brine and water. The organic layer containing the batch was concentrated by vacuum distillation to a low volume, cooled to ambient temperature and the solids were collected by vacuum filtration. The filter cake was washed with MTBE and the product was dried in a vacuum to give 41% yield of ethyl 2-(5-bromo-3-(trans-4-methoxycyclohexylamino)pyrazin-2-ylamino) acetate. A mixture of ethyl 2-(5-bromo-3-(trans-4-methoxycyclohexylamino)pyrazin-2-ylamino) acetate (1 equiv), water and 85% phosphoric acid (3:1) was heated to 80° C. over 1 h. Heating was maintained for 18 h to effect reaction completion. Upon reaction completion, the mixture was cooled to 25° C. and filtered to give a crude product as tan solid. The resulting solids were washed with water, slurried in water and filtered. The filter cake was washed with water until the pH of the filtrate was between 4 and 8. The resulting material was dried under vacuum to give 89% yield of 7-bromo-1-(trans-4-methoxycyclohexyl)-3,4-dihydropyrazino[2,3-b]pyrazin-2(1H)-one. 7-Bromo-1-(trans-4-methoxycyclohexyl)-3,4-dihydropyrazino[2,3-b]pyrazin-2(1H)-one (1 equiv), 5-(4,4,5,5-tetramethyl-1,3,2-dioxaborolan-2-yl)-2-(2-(trimethylsilyloxy)propan-2-yl)pyridine (1 equiv), sodium carbonate (3 equiv) and $PdCl_2(AmPhos)_2$ (0.003 equiv) were combined in isopropanol and heated at 70° C. for 1.5 h. Standard work-up and purification afforded the protected compound in 93% yield. Deprotection using standard conditions for removal of a trimethylsilyl-group and isolation gave the title compound.

Example 10: 9-(6-(4H-1,2,4-Triazol-3-yl)-2-methyl-3-pyridyl)-6,11,4a-trihydromorpholino[4,3-e]pyrazino[2,3-b]pyrazin-5-one

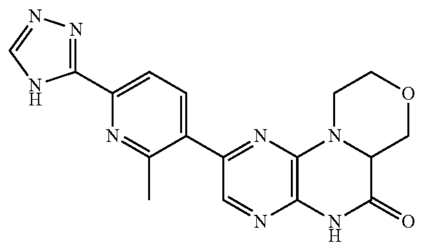 [SMILES: Cc1nc(-c2nnc[nH]2)ccc1-c1cnc2c(n1)N1CCOCC1C(=O)N2]

A. 5-Bromo-6-methylpicolinonitrile 3,6-Dibromo-2-methylpyridine (4.9 g, 19.53 mmol), copper(I)cyanide (1.75 g, 19.53 mmol) and N,N-dimethylformamide (20 mL) were combined in a sealable vessel with a stirbar. The resulting mixture was sealed, stirred vigorously and heated at 110° C. for 4 h. The resulting mixture was diluted with ethyl acetate, poured into a separatory funnel containing water and the layers were separated. The water layer was extracted with ethyl acetate twice. The combined organics were washed with brine, dried over magnesium sulfate, filtered and concentrated under reduced pressure. The resulting solid was purified by silica gel chromatography (10% ethyl acetate in hexanes) to give the title compound as a white solid (1.88 g, 9.54 mmol, 49% yield). MS (ESI) m/z 197.3 $[M]^+$.

B. tert-Butyl 3-(3,5-dibromopyrazin-2-ylcarbamoyl)morpholine-4-carboxylate

A solution of 4-(tert-butoxycarbonyl)morpholine-3-carboxylic acid (1.500 g, 6.49 mmol) and 1,1'-carbonyldiimidazole (1.578 g, 9.73 mmol) in N,N-dimethylformamide (2 mL) and dichloromethane (6 mL) was stirred 4.5 h at room temperature under nitrogen. N,N-Diisopropylethylamine (2.260 mL, 12.97 mmol) was added followed by 3,5-dibromopyrazin-2-amine (3.28 g, 12.97 mmol). The resulting mixture was stirred and heated at 50° C. under a reflux condenser under nitrogen for 2 d. The resulting mixture was concentrated under reduced pressure. The residue was diluted with water and extracted 3 times with ethyl acetate. The combined organics were washed with water and brine, dried over magnesium sulfate, filtered and concentrated under reduced pressure. The residue was purified using flash chromatography (20-30-50% ethyl acetate in hexanes) to give the desired product (2.136 g, 4.58 mmol, 71% yield) as a slightly yellow foam-solid. MS (ESI) m/z 467 $[M+1]^+$.

C. 9-Bromo-6,11,4a-trihydromorpholino[4,3-e]pyrazino[2,3-b]pyrazin-5-one tert-Butyl 3-(3,5-dibromopyrazin-2-ylcarbamoyl)morpholine-4-carboxylate (2.132 g, 4.57 mmol) was dissolved in dichloromethane (45 mL) with stirring at room temperature. TFA (9 mL) was added and the resulting light yellow mixture was capped and stirred at room temperature for 2.5 h. The solvent was removed under reduced pressure and the residue dried under high vacuum at 45° C. to give a viscous yellow oil. The yellow oil was dissolved in isopropanol (wet) (50 mL) with stirring at room temperature. Sodium bicarbonate (3.84 g, 45.7 mmol), palladium(II) acetate (0.103 g, 0.457 mmol) and 4,5-bis(diphenylphosphino)-9,9-dimethylxanthene (0.239 mL, 1.372 mmol) were added. The atmosphere in the flask was removed and replaced with nitrogen. The resulting mixture was stirred vigorously and heated at 80° C. under a reflux condenser under nitrogen for 2 h. The resulting mixture was cooled to room temperature and diluted with water (30 mL). The resulting solids were collected by vacuum filtration, washed thoroughly with water and diethyl ether and dried under high vacuum to give the desired product at ~90% purity (1.441 g, 5.05 mmol, 99% yield) as a yellow solid. MS (ESI) m/z 285 $[M]^+$, 287 $[M+2]^+$.

D. 9-(1,1-Dimethyl-1-stannaethyl)-6,11,4a-trihydromorpholino[4,3-e]pyrazino[2,3-b]pyrazin-5-one 9-Bromo-6,11,4a-trihydromorpholino[4,3-e]pyrazino[2,3-b]pyrazin-5-one (0.30 g, 1.052 mmol), hexamethylditin (0.414 g, 1.263 mmol), tetrakis(triphenylphosphine)palladium (0) (0.122 g, 0.105 mmol) and 1,4-dioxane (5 mL) were combined in a sealable vessel with a stirbar. Nitrogen gas was bubbled through the solution for five min. The vessel was sealed, stirred vigorously and heated at 100° C. for 2 h. The resulting cloudy black mixture was diluted with ethyl acetate, filtered and the filter cake washed thoroughly with ethyl acetate. The filtrate was concentrated under reduced pressure and purified using Biotage flash chromatography (20-80% ethyl acetate in hexanes) to give the desired product (0.350 g, 0.948 mmol, 90% yield) as a yellow-white solid. MS (ESI) m/z 369.5 $[M]^+$.

E. 6-Methyl-5-(5-oxo(6,11,4a-trihydromorphohno[4,3-e]pyrazino[2,3-b]pyrazin-9-yl))pyridine-2-carbonitrile 5-Bromo-6-methylpicolinonitrile (0.080 g, 0.406 mmol), 9-(1,1-dimethyl-1-stannaethyl)-6,11,4a-trihydromorpholino[4,3-e]pyrazino[2,3-b]pyrazin-5-one (0.150 g, 0.406 mmol), tris(dibenzylideneacetone)dipalladium(0) (0.041 g, 0.045 mmol), tri-o-tolylphosphine (0.027 g, 0.089 mmol) and triethylamine (0.170 mL, 1.219 mmol) were placed in a sealed tube and N,N-dimethylformamide (2 mL) was added. Nitrogen gas was bubbled through the reaction mixture for five minutes and the reaction sealed and heated at 100° C. for 1 h. The resulting cloudy black mixture was diluted with methanol, filtered and the filter cake washed thoroughly with methanol. The filtrate was concentrated under reduced pressure and purified using Biotage flash chromatography (50-100% ethyl acetate in hexanes) to give the desired product (0.117 g, 0.363 mmol, 89% yield). MS (ESI) m/z 323.5 $[M+1]^+$ F. 6-Methyl-5-(5-oxo(6,11,4a-trihydromorphohno[4,3-e]pyrazino[2,3-b]pyrazin-9-yl))pyridine-2-carboxamide 6-Methyl-5-(5-oxo(6,11,4a-trihydromorpholino[4,3-e]pyrazino[2,3-b]pyrazin-9-yl))pyridine-2-carbonitrile (0.18 g, 0.558 mmol) was placed in a round bottom flask and while stirring, a mixture of TFA (1.6 mL) and sulfuric acid (0.4 mL) was added. The resulting suspension was allowed to stir for 16 h at room temperature. The mixture was poured over ice and the excess acid was carefully neutralized with solid potassium hydroxide. The solid obtained was filtered, washed with water and dried under high vacuum to yield the title compound (0.153 g, 0.450 mmol, 81% yield) as a red solid. MS (ESI) m/z 341.5 $[M+1]^+$ G. 9-(6-(4H-1,2,4-Triazol-3-yl)-2-methyl-3-pyridyl)-6,11,4a-trihydromorpholino[4,3-e]pyrazino[2,3-b]pyrazin-5-one 6-Methyl-5-(5-oxo(6,11,4a-trihydromorpholino[4,3-e]pyrazino[2,3-b]pyrazin-9-yl))pyridine-2-carboxamide (0.159 g, 0.467 mmol), N,N-dimethylformamide dineopentyl acetal (2 mL, 8.85 mmol) and dimethylsulfoxide (0.5 mL) were placed in a flask and heated to 85° C. for 1 h. The solution was diluted with acetic acid (5 mL, 87 mmol) and hydrazine (0.468 mL, 14.90 mmol) was added dropwise. The reaction was allowed to stir at 25° C. for 30 min. The mixture was concentrated under reduced pressure and the residue was carefully neutralized with a saturated aqueous sodium carbonate solution. This solution then was extracted with ethyl acetate three times, concentrated under reduced pressure and purified using reverse-phase semi-preparatory HPLC (5-50% acetonitrile+0.1% TFA in water+0.1% TFA, over 20 min) to afford the title compound (0.03 g, 0.082 mmol, 17.63% yield). $^1H$ NMR (400 MHz, DMSO-$d_6$) δ (ppm) 7.96-8.04 (m, 2H), 7.88 (s, 1H), 4.33 (dd, J=3.71, 10.74 Hz, 1H), 4.15-4.23 (m, 2H), 3.98 (dd, J=3.51, 11.71 Hz, 1H), 3.51-3.63 (m, 2H), 2.89-2.99 (m, 1H), 2.70 (s, 3H); MS (ESI) m/z 365.5 $[M+1]^+$ Example 11: 6-(6-(1H-1,2,4-Triazol-3-yl)pyridin-3-yl)-4-(tetrahydro-2h-pyran-4-yl)-3,4-dihydropyrazino[2,3-b]pyrazin-2(1H)-one

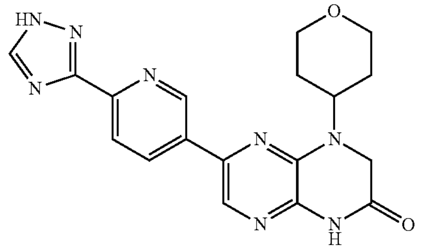 [SMILES: O=C1CN(C2CCOCC2)c2nc(-c3ccc(-c4nc[nH]n4)nc3)cnc2N1]

A. 6-Bromo-4-(tetrahydro-2H-pyran-4-yl)-3,4-dihydropyrazino[2,3-b]pyrazin-2(1H)-one To a solution of N-(3,5-dibromopyrazin-2-yl)-2-iodoacetamide (See Example 5.B) (6.6 g, 15.8 mmol) and diisopropylethylamine (4.0 g, 31.6 mmol) in acetonitrile (50 mL) was added tetrahydro-2H-pyran-4-amine (6.4 g, 63.2 mmol) and the mixture was stirred at ambient temperature for 16 h. The solvent was removed under reduced pressure and the residue which was purified by chromatography on silica gel (5-20% ethyl acetate in petroleum ether) to give the title compound (1.98 g, 40% yield). MS (ESI) m/z 313.1 $[M+1]^+$.

B. 4-(Tetrahydro-2H-pyran-4-yl)-6-(trimethylstannyl)-3,4-dihydropyrazino[2,3-b]pyrazin-2(1H)-one A degassed mixture of 6-bromo-4-(tetrahydro-2H-pyran-4-yl)-3,4-dihydropyrazino[2,3-b]pyrazin-2(1H)-one (1.98 g, 6.35 mmol), tetrakis(triphenylphosphine)palladium (1.45 g, 1.27 mmol) and hexamethylditin (4.0 g, 12.7 mmol) in dioxane (10 mL) was heated at 90° C. for 3 h under nitrogen. The reaction mixture was concentrated under reduced pressure and purified on silica gel column (10-20% ethyl acetate in petroleum ether) to afford the product (1.07 g, 42.3% yield). MS (ESI) m/z 399.1$[M+1]^+$.

C. 6-(6-(1-(Tetrahydro-2H-pyran-2-yl)-1H-1,2,4-triazol-3-yl)pyridin-3-yl)-4-(tetrahydro-2H-pyran-4-yl)-3,4-dihydropyrazino[2,3-b]pyrazin-2(1H)-one A mixture of 4-(tetrahydro-2H-pyran-4-yl)-6-(trimethylstannyl)-3,4-dihydropyrazino[2,3-b]pyrazin-2(1H)-one (1 equiv), 5-bromo-2-(1-(tetrahydro-2H-pyran-2-yl)-1H-1,2,4-triazol-3-yl)pyridine (1.2 equiv), tris(dibenzylideneacetone) dipalladium (0.1 equiv), tri-o-tolylphosphine (0.2 equiv), triethylamine (3 equiv) and N,N-dimethylformamide was heated at 95° C. for 3 h under nitrogen. Concentration and chromatography purification give the desired product in 39% yield. MS (ESI) m/z 463.1 $[M+1]^+$.

D. 6-(6-(1H-1,2,4-Triazol-3-yl)pyridin-3-yl)-4-(tetrahydro-2H-pyran-4-yl)-3,4-dihydro pyrazino[2,3-b]pyrazin-2(1H)-one A mixture of 6-(6-(1-(tetrahydro-2H-pyran-2-yl)-1H-1,2,4-triazol-3-yl)pyridin-3-yl)-4-(tetrahydro-2H-pyran-4-yl)-3,4-dihydropyrazino[2,3-b]pyrazin-2(1H)-one in methanolic hydrochloride solution was stirred at room temperature for 0.5 h. The solvent was evaporated under reduced pressure to give the crude product, which was washed with N,N-dimethylformamide to afford the title compound as a hydrochloride salt in 34% yield. $^1$H NMR (DMSO-$d_6$, 400 MHz) δ (ppm) 11.44 (s, 1H), 9.30 (s, 1H), 8.59 (d, J=8.4 Hz, 1H), 8.46 (s, 1H), 8.22 (m, 2H), 4.70 (t, J=10 Hz, 1H), 4.16 (s, 1H), 3.99 (m, 4H), 3.51 (t, J=11.2 Hz, 2H), 1.86 (m, 2H), 1.69 (d, J=12.8 Hz, 2H); MS (ESI) m/z 379.1 $[M+1]^+$.

Example 12: 1-Ethyl-7-(2-methyl-6-(4H-1,2,4-triazol-3-yl)pyridin-3-yl)-3,4-dihydropyrazino[2,3-b]pyrazin-2(1H)-one

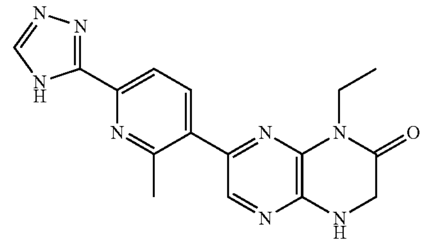 [SMILES: CCN1C(=O)CNc2ncc(-c3ccc(-c4nnc[nH]4)nc3C)nc21]

A. 7-Bromo-1-ethyl-3,4-dihydropyrazino[2,3-b]pyrazin-2(1H)-one

A mixture of ethyl 2-(3,5-dibromopyrazin-2-ylamino)acetate (See Example 6.B) (1 equiv), ethylamine hydrochloride (3.1 equiv), N,N-diisopropylethylamine (4 equiv) in N-methyl pyrrolidinone was heated at 105° C. under nitrogen for 14 h. Standard ethyl acetate/water work up gave the crude product in 77% yield. This material was used without further purification. Crude ethyl 2-(5-bromo-3-(ethylamino)pyrazin-2-ylamino)acetate and acetic acid were combined in methanol. The reaction mixture was refluxed at 60-62° C. under nitrogen for 16 h. The reaction was concentrated under reduced pressure and the resultant residue was diluted with methanol and concentrated. The resultant residue was dissolved in ethyl acetate, treated with sodium carbonate and stirred for 10 min until pH~7. The mixture was filtered and washed with ethyl acetate. The filtrate was concentrated and purification by a silica gel plug purification using (0-40% ethyl acetate in hexanes) gave the product as a tan solid. Additionally the filter-cake was suspended in water to remove potassium carbonate. The remaining solid product was collected by filtration. The process afforded product in a combined yield of 75%.

B. 1-Ethyl-7-(2-methyl-6-(4H-1,2,4-triazol-3-yl)pyridin-3-yl)-3,4-dihydropyrazino[2,3-b]pyrazin-2(1H)-one A mixture of 3-Bromo-2-methyl-6-(1-(tetrahydro-2H-pyran-2-yl)-1H-1,2,4-triazol-3-yl)pyridine (1 equiv), bis(pinacolato)diboron (1.05 equiv), potassium acetate (2 equiv), potassium carbonate (3 equiv), [1,1'-bis(diphenylphosphino)-ferrocene]dichloropalladium(II), complex with dichloromethane (1:1) (0.1 equiv) in anhydrous dioxane was degassed and heated at 90° C. for 2 h. The mixture was cooled to <40° C. and 7-bromo-1-ethyl-3,4-dihydropyrazino[2,3-b]pyrazin-2(1H)-one (1 equiv), water and [1,1'-bis(diphenylphosphino)-ferrocene]dichloropalladium(II), complex with dichloromethane (1:1) (0.05 equiv) were added. The mixture was degassed and heated at 65-70° C. under nitrogen for 1 h. The mixture was cooled to <40° C., diluted with water and ethyl acetate. Standard ethyl acetate/water work up followed by flash column chromatography (0-5% methanol in dichloromethane) gave the title compound in 57% yield. $^1$H NMR (400 MHz, DMSO-$d_6$) δ (ppm) 7.99 (s, 2H), 7.93 (s, 1H), 7.72 (s, 1H), 4.22 (s, 2H), 4.05 (q, J=6.77 Hz, 2H), 2.71 (s, 3H), 1.18 (t, J=7.03 Hz, 3H); MS (ESI) m/z 337.6 $[M+1]^+$.

Example 13: 4-((cis)-4-Methoxycyclohexyl)-6-(2-methyl-6-(4H-1,2,4-triazol-3-yl)pyridin-3-yl)-3,4-dihydropyrazino[2,3-b]pyrazin-2(1H)-one

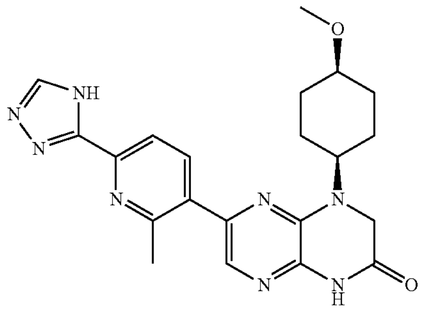 [SMILES: CO[C@H]1CC[C@@H](N2CC(=O)Nc3ncc(-c4ccc(-c5nnc[nH]5)nc4C)nc32)CC1]

A. 5-Bromo-6-methylpicolinamide

A solution of 5-bromo-6-methylpicolinonitrile (1.8 g, 9.14 mmol) in a mixture of TFA and sulfuric acid (30 mL, 4:1, V/V) was stirred at 40° C. for 16 h. The reaction mixture was poured into ice water. The resulting solid was filtered off and washed with water and dried to give the desired product as a white solid (1.0 g, 4.65 mmol, 54% yield). MS (ESI) m/z 217.1 $[M+2]^+$.

B. 3-Bromo-2-methyl-6-(1H-1,2,4-triazol-3-yl)pyridine

5-Bromo-6-methylpicolinamide (1 g, 4.65 mmol) and N,N-dimethylformamide dimethylacetal (20 mL) were combined in a 100 mL round-bottom flask with a stir bar and heated at 85° C. under a reflux condenser under nitrogen for 3 h. The resulting mixture was concentrated under reduced pressure and dried under vacuum to give yellow oil, which was used in the next step without purification. The residue was diluted with acetic acid (10 mL) and hydrazine (2.5 mL, 70.3 mmol) was added drop-wise and allowed to stir at room temperature for 5 h. The reaction mixture was poured into ice water. The resulting solid was filtered, washed with water and dried to give the desired product as a white solid. The aqueous filtrate was extracted with dichloromethane. The organic layer was concentrated under reduced pressure nearly to dryness to yield additional material. Combination of two batches gave the desired product (0.7 g, 2.9 mmol, 63% yield). MS (ESI) m/z 241.1 $[M+2]^+$.

C. 3-Bromo-2-methyl-6-(1-(tetrahydro-2H-pyran-2-yl)-1H-1,2,4-triazol-3-yl)pyridine 3-Bromo-2-methyl-6-(1H-1,2,4-triazol-3-yl)pyridine (0.7 g, 2.93 mmol) and 3,4-dihydro-2H-pyran (0.493 g, 5.86 mmol) were dissolved in tetrahydrofuran (20 mL). TFA (3.34 mg, 0.029 mmol) was added and the resulting solution was heated to 70° C. for 16 h. The reaction mixture was cooled to room temperature, diluted with ethyl acetate, filtered and poured into a separatory funnel containing water and ethyl acetate. The organic layer was concentrated under reduced pressure. Flash chromatography (0-60% ethyl acetate in hexane) gave the desired product as a white solid (0.40 g, 1.23 mmol, 42% yield). MS (ESI) m/z 325.1 $[M+2]^+$.

D. (cis)-4-Methoxycyclohexanamine hydrochloride

To a round bottom flask, under nitrogen atmosphere tert-butyl (cis)-4-hydroxycyclohexylcarbamate (7.8 g, 36.2 mmol) was added and suspended in anhydrous tetrahydrofuran (181.0 mL) and cooled to 0° C. Sodium hydride (2.174 g, 54.3 mmol) was then added and the resulting solution was allowed to stir for 5 min. To a second flask under nitrogen atmosphere methyl iodide (2.265 mL, 36.2 mmol) was added and suspended in anhydrous tetrahydrofuran (10.0 mL). The methyl iodide solution in tetrahydrofuran was slowly added dropwise to first flask over 3 min. The reaction was allowed to stir at rt for 16 h. The organic volatiles were removed under reduced pressure and partitioned between ethyl acetate (3×) and water. Organic fractions were pooled, dried over magnesium sulfate, filtered and condensed under reduced pressure. The resulting material was purified by silica gel column chromatography (25-50% ethyl acetate in hexanes). The desired fractions were combined and organic volatiles removed under reduced pressure followed by the addition of hydrochloric acid (4M in 1,4-dioxane, 23.5 mL). The resulting solution was heated to 40° C. for 1 h and organic volatiles were removed under reduced pressure to afford the title compound (6.0 g, 36.2 mmol, 100% yield). MS (ESI) m/z 130.1 $[M+1]^+$.

E. 6-Bromo-4-((cis)-4-methoxycyclohexyl)-3,4-dihydropyrazino[2,3-b]pyrazin-2(1H)-one To a solution of N-(3,5-dibromopyrazin-2-yl)-2-iodoacetamide (See Example 5.B) (1.0 g, 2.376 mmol) and diisopropylethylamine (1.038 mL, 5.94 mmol) in acetonitrile (10 mL) was added (cis)-4-methoxycyclohexanamine hydrochloride (0.413 g, 2.495 mmol). The solution was stirred at 55° C. for 3 h. The resulting precipitate was filtered and washed with acetonitrile and dried under reduced pressure to afford the title compound (0.442 g, 1.29 mmol, 55% yield). MS (ESI) m/z 341.3 $[M]^+$, 343.3 $[M+2]^+$.

F. 4-((cis)-4-Methoxycyclohexyl)-6-(trimethylstannyl)-3,4-dihydropyrazino[2,3-b]pyrazin-2(1H)-one 6-Bromo-4-((cis)-4-methoxycyclohexyl)-3,4-dihydropyrazino[2,3-b]pyrazin-2(1H)-one (0.442 g, 1.295 mmol), tetrakis(triphenylphosphine)palladium (0.225 g, 0.194 mmol) and hexamethylditin (0.322 mL, 1.554 mmol) were combined in dioxane (5 mL). The solution was purged with nitrogen gas and heated to 90° C. in a screw capped tube for 3 h. The solution was condensed under reduced pressure and purified using Biotage column chromatography (0-50% ethyl acetate in hexanes) to afford the title compound (0.356 g, 0.837 mmol, 65% yield). MS (ESI) m/z 426.5 $[M+1]^+$, 427.5 $[M+1]^+$.

G. 4-((cis)-4-Methoxycyclohexyl)-6-(2-methyl-6-(4-(tetrahydro-2H-pyran-2-yl)-4H-1,2,4-triazol-3-yl)pyridin-3-yl)-3,4-dihydropyrazino[2,3-b]pyrazin-2(1H)-one 4-((cis)-4-Methoxycyclohexyl)-6-(trimethylstannyl)-3,4-dihydropyrazino[2,3-b]pyrazin-2(1H)-one 0.292 g, 0.687 mmol), 3-bromo-2-methyl-6-(1-(tetrahydro-2H-pyran-2-yl)-1H-1,2,4-triazol-3-yl)pyridine (0.244 g, 0.756 mmol), tris(dibenzylideneacetone)dipalladium (0.063 g, 0.069 mmol), tri-o-tolylphosphine (0.042 g, 0.137 mmol), triethylamine (0.287 mL, 2.061 mmol) and dimethylformamide (5.0 mL) were combined in a screw capped flask and heated to 95° C. for 1 h. The solution was condensed under reduced pressure and purified using Biotage chromatography (0-80% ethyl acetate in hexanes followed by 0-10% methanol in ethyl acetate) to afford the title compound (0.279 g, 0.687 mmol, 80% yield). MS (ESI) m/z 505.6 $[M+1]^+$.

H. 4-((cis)-4-Methoxycyclohexyl)-6-(2-methyl-6-(4H-1,2,4-triazol-3-yl)pyridin-3-yl)-3,4-dihydropyrazino[2,3-b]pyrazin-2(1H)-one 4-((cis)-4-Methoxycyclohexyl)-6-(2-methyl-6-(4-(tetrahydro-2H-pyran-2-yl)-4H-1,2,4-triazol-3-yl)pyridin-3-yl)-3,4-dihydropyrazino[2,3-b]pyrazin-2(1H)-one (0.279 g, 0.553 mmol) was diluted with ethanol (15 mL) and hydrogen chloride (4.0 N in dioxanes, 5 mL). The solution was stirred at 75° C. for 1 h and at 80° C. for 2 h. The solution was condensed to a slurry and diluted with ethanol and sonicated. The precipitate was filtered and washed with additional ethanol followed by acetonitrile. The crude solid was purified using reverse-phased semi-preparative HPLC (10-100% acetonitrile+0.1% TFA in water+0.1% TFA, over 30 min) to afford the title compound (0.040 g, 0.095 mmol, 17% yield). $^1$H NMR (400 MHz, METHANOL-$d_4$) δ (ppm) 7.88-8.13 (m, 2H), 7.65 (s, 1H), 4.58 (s, 1H), 4.16 (s, 2H), 3.47 (br. s., 1H), 3.22-3.32 (m, 66H), 2.73 (s, 3H), 2.08 (br. s., 2H), 1.91 (br. s., 2H), 1.56 (br. s., 4H); MS (ESI) m/z 421.2 $[M+1]^+$; mp 192-195° C.

Example 14: 1-Isopropyl-7-(2-methyl-6-(4H-1,2,4-triazol-3-yl)pyridin-3-yl)-3,4-dihydropyrazino[2,3-b]pyrazin-2(1H)-one

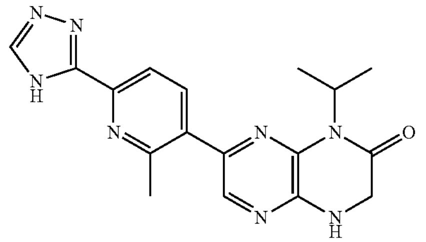 [SMILES: Cc1nc(-c2nnc[nH]2)ccc1-c1cnc2c(n1)N(C(C)C)C(=O)CN2]

A. 1-Isopropyl-7-(trimethylstannyl)-3,4-dihydropyrazino[2,3-b]pyrazin-2(1H)-one

7-Bromo-1-isopropyl-3,4-dihydropyrazino[2,3-b]pyrazin-2(1H)-one (See Example 7.B) (0.5 g, 1.844 mmol), hexamethylditin (0.725 g, 2.213 mmol), tetrakis(triphenylphosphine)palladium(0) (0.213 g, 0.184 mmol) and 1,4-dioxane (3 mL) were combined in a sealable vessel with a stirbar. Nitrogen gas was bubbled through the solution. The vessel was sealed, stirred vigorously and heated at 100° C. for 2 h. The resulting cloudy black mixture was diluted with ethyl acetate, filtered and the filter cake washed thoroughly with ethyl acetate. The filtrate was concentrated under reduced pressure and purified using silica gel flash column chromatography (20-80% ethyl acetate in hexanes) to give the desired product (2.410 g, 77% yield) as a yellow-white solid. MS (ESI) m/z 357.4 $[M+2]^+$ B. 1-Isopropyl-7-(2-methyl-6-(4-(tetrahydro-2H-pyran-2-yl)-4H-1,2,4-triazol-3-yl)pyridin-3-yl)-3,4-dihydropyrazino[2,3-b]pyrazin-2(1H)-one To a flask was added 3-Bromo-2-methyl-6-(1-(tetrahydro-2H-pyran-2-yl)-1H-1,2,4-triazol-3-yl)pyridine (0.446 g, 1.380 mmol), 1-isopropyl-7-(trimethylstannyl)-3,4-dihydropyrazino[2,3-b]pyrazin-2(1H)-one (0.490 g, 1.380 mmol), tris(dibenzylideneacetone)dipalladium(0) (0.139 g, 0.152 mmol), tri-o-tolylphosphine (0.092 g, 0.304 mmol), triethylamine (0.577 mL, 4.14 mmol) and N,N-dimethylformamide (3 mL). Nitrogen gas was bubbled through the reaction mixture for 5 min and the mixture was heated to 100° C. for 1 h. After cooling to rt, the reaction mixture was filtered through Celite, rinsed with methanol and concentrated to dryness. The resulting residue was purified by silica gel flash column chromatography (0-80% ethyl acetate in hexanes, followed by 0-10% methanol in dichloromethane) to yield the desired product (0.40 g, 0.921 mmol, 66.7% yield). MS (ESI) m/z 435.5 $[M+1]^+$.

C. 1-Isopropyl-7-(2-methyl-6-(4H-1,2,4-triazol-3-yl)pyridin-3-yl)-3,4-dihydropyrazino[2,3-b]pyrazin-2(1H)-one To a stirred mixture of 1-isopropyl-7-(2-methyl-6-(4-(tetrahydro-2H-pyran-2-yl)-4H-1,2,4-triazol-3-yl)pyridin-3-yl)-3,4-dihydropyrazino[2,3-b]pyrazin-2(1H)-one (0.400 g, 0.921 mmol) in ethanol (40 mL) at 50° C. was added hydrogen chloride (4 M in dioxane, 1.381 mL, 5.52 mmol). The resulting mixture was heated at 50° C. under nitrogen for 1 h. The suspension was concentrated under reduced pressure and the resulting solid was taken up in dimethylsulfoxide and purified using silica gel chromatography (0-10% ammonia saturated methanol in dichloromethane) to afford the title compound (0.200 g, 0.571 mmol, 62.0% yield) as a brown-red solid. $^1$H NMR (400 MHz, DMSO-$d_6$) δ (ppm) 8.10 (br. s., 1H), 8.01 (br. s., 2H), 7.92 (s, 1H), 5.26 (quin, J=6.93 Hz, 1H), 4.14 (s, 2H), 3.58 (d, J=5.08 Hz, 3H), 1.47 (d, J=6.64 Hz, 6H); MS (ESI) m/z 351.5 $[M+1]^+$.

D. 1-Isopropyl-7-(2-methyl-6-(4H-1,2,4-triazol-3-yl)pyridin-3-yl)-3,4-dihydropyrazino[2,3-b]pyrazin-2(1H)-one (alternate approach)

7-Bromo-1-isopropyl-3,4-dihydropyrazino[2,3-b]pyrazin-2(1H)-one (1 equiv), bis(pinacolato)diboron) (1 equiv), potassium acetate (3 equiv) and bis(1,1'-bis(diphenylphosphino)ferrocene)palladium (0.01 equiv) were combined in dioxane, degassed with nitrogen and heated to 95° C. under nitrogen. Dilution with ethyl acetate, filtration through Celite, concentration, trituration with ethyl acetate and hexanes, filtration and drying gave the boronate ester in 60% yield. tert-Butyl 3-(5-bromo-6-methylpyridin-2-yl)-1H-1,2,4-triazole-1-carboxylate (1 equiv), 1-isopropyl-7-(4,4,5,5-tetramethyl-1,3,2-dioxaborolan-2-yl)-3,4-dihydropyrazino[2,3-b]pyrazin-2(1H)-one (1.2 equiv), tetrakis (triphenylphosphine) palladium(0) (0.05 equiv), sodium carbonate (3 equiv) were combined in (3:1) dimethyl acetamide and water. The mixture was degassed and heated to 100° C. overnight. Standard ethyl acetate/water work up and subsequent trituration in ethyl acetate gave the desired product in 41% yield.

Example 15: 7-(1H-Pyrrolo[2,3-b]pyridin-5-yl)-1-(2-(tetrahydro-2h-pyran-4-yl)ethyl)-3,4-dihydropyrazino[2,3-b]pyrazin-2(1H)-one

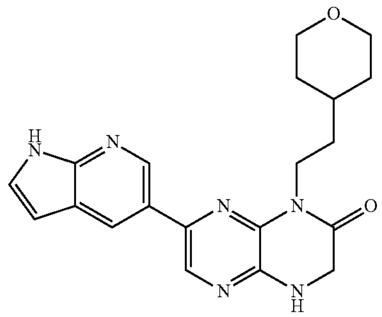 [SMILES: O=C1CNc2ncc(-c3cnc4[nH]ccc4c3)nc2N1CCC1CCOCC1]

A. Ethyl 2-(5-bromo-3-(2-(tetrahydro-2H-pyran-4-yl)ethylamino)pyrazin-2-ylamino)acetate Ethyl 2-(3,5-dibromopyrazin-2-ylamino)acetate (See Example 6.B) (1.0 g, 2.95 mmol) and 2-(tetrahydro-2H-pyran-4-yl)ethanamine (0.381 g, 2.95 mmol) were placed in a microwave vial, dimethylsulfoxide (2 mL) was added and the resulting mixture was heated in a Biotage Emrys Optimizer microwave reactor at 150° C. for 3600 s. The crude reaction mixture was purified using silica gel chromatography (33% ethyl acetate in hexanes) to yield the title compound (0.5 g, 1.3 mmol, 44% yield). MS (ESI) m/z 387.1 $[M]^+$, 389.1 $[M+2]^+$.

B. 7-Bromo-1-(2-(tetrahydro-2H-pyran-4-yl)ethyl)-3,4-dihydropyrazino[2,3-b]pyrazin-2(1H)-one Ethyl 2-(5-bromo-3-(2-(tetrahydro-2H-pyran-4-yl)ethylamino)pyrazin-2-ylamino)acetate (0.5 g, 1.291 mmol) and hydrochloric acid (6 M in water, 0.215 mL, 1.291 mmol) were combined in ethanol (2 mL) and the resulting mixture was heated in a Biotage Emrys Optimizer microwave reactor at 100° C. for 2400 s. The reaction mixture was concentrated and purified using silica gel chromatography (33% ethyl acetate in hexanes) to yield the title compound (quantitative yield). MS (ESI) m/z 341.1 $[M]^+$, 343.1 $[M+2]^+$.

C. 1-(2-(Tetrahydro-2H-pyran-4-yl)ethyl)-7-(trimethylstannyl)-3,4-dihydropyrazino[2,3-b]pyrazin-2(1H)-one 7-Bromo-1-(2-(tetrahydro-2H-pyran-4-yl)ethyl)-3,4-dihydropyrazino[2,3-b]pyrazin-2(1H)-one (0.4 g, 1.29 mmol), hexamethylditin (0.57 g, 1.75 mmol) and tetrakis(triphenylphosphine)palladium(0) (0.2 g, 0.176 mmol) were placed in a sealed tube with 1,4-dioxane (5 mL). The flask was evacuated, flushed with nitrogen, sealed and heated at 110° C. for 1 h. The reaction mixture was cooled to room temperature and filtered through Celite, washing with ethyl acetate. The filtrate was concentrated and sonicated with a small volume of solvent mixture (50% hexane in ethyl acetate) and isolated by filtration to yield the title compound (0.34 g, 0.8 mmol, 54.6% yield). MS (ESI) m/z 427 $[M+2]^+$.

D. 7-(1H-Pyrrolo[2,3-b]pyridin-5-yl)-1-(2-(tetrahydro-2H-pyran-4-yl)ethyl)-3,4-dihydropyrazino[2,3-b]pyrazin-2(1H)-one 1-(2-(Tetrahydro-2H-pyran-4-yl)ethyl)-7-(trimethylstannyl)-3,4-dihydropyrazino[2,3-b]pyrazin-2(1H)-one (1.0 g, 2.352 mmol), 5-bromo-1H-pyrrolo[2,3-b]pyridine (0.556 g, 2.82 mmol), tris(dibenzylideneacetone)palladium(0) (0.237 g, 0.259 mmol), tri-o-tolylphosphine (0.158 g, 0.518 mmol) and triethylamine (0.984 mL, 7.06 mmol) were combined in a sealed tube, dimethylformamide (5 mL) was added. The atmosphere in the vessel was removed under vacuum and replaced with nitrogen gas. The reaction was heated to 100° C. for 1 h. After cooling to room temperature, the reaction mixture was filtered through Celite. The filter cake was washed with ethyl acetate. The wash and filtrate were combined and concentrated nearly to dryness. The resulting solid was dissolved in hot methanol, filtered through Celite and purified by reverse-phase preparative HPLC (5-80% acetonitrile+0.1% TFA in water+0.1% TFA, over 30 min). The clean fractions were collected, neutralized with ammonium hydroxide and concentrated to dryness. The solid obtained was filtered, washed with water and dried under high vacuum to yield the title compound (0.10 g, 0.264 mmol, 11.2% yield). $^1H$ NMR (400 MHz, DMSO-$d_6$) δ (ppm) 11.71 (br. s., 1H), 8.81 (s, 1H), 8.44 (s, 1H), 8.26 (s, 1H), 7.49 (d, J=10.54 Hz, 2H), 6.48 (br. s., 1H), 4.18 (s, 2H), 4.13 (t, J=6.44 Hz, 2H), 3.82 (d, J=12.89 Hz, 2H), 3.27 (t, J=11.13 Hz, 2H), 1.71 (d, J=12.49 Hz, 2H), 1.60 (br. s., 3H), 1.24 (d, 2H); MS (ESI) m/z 379.2 $[M+1]^+$; mp 255-258° C.

Example 16: 6-(6-(2-Hydroxypropan-2-yl)pyridin-3-yl)-4-((tetrahydro-2H-pyran-4-yl)methyl)-3,4-dihydropyrazino[2,3-b]pyrazin-2(1H)-one

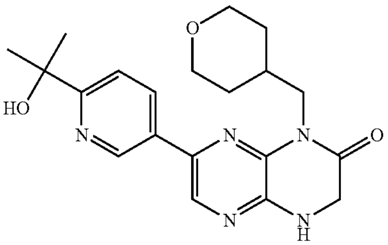 [SMILES: CC(C)(O)c1ccc(-c2cnc3c(n2)N(CC2CCOCC2)C(=O)CN3)cn1]

A. 6-Bromo-4-((tetrahydro-2H-pyran-4-yl)methyl)-3,4-dihydropyrazino[2,3-b]pyrazin-2(1H)-one N-(3,5-Dibromopyrazin-2-yl)-2-iodoacetamide (See Example 5.B) (8.0 g, 19.01 mmol), (tetrahydro-2H-pyran-4-yl)methanamine (2.63 g, 22.81 mmol) and diisopropylethylamine (6.64 mL, 38.0 mmol) were placed in a 250 mL round bottom flask, suspended in acetonitrile (80.0 mL) and heated to 40° C. for 16 h. The resulting white precipitate was filtered, washed with acetonitrile followed by hexanes and dried under vacuum to afford the title compound (4.89 g, 14.95 mmol, 79% yield). MS (ESI) m/z 327.4 $[M]^+$, 329.5 $[M+2]^+$.

B. 6-(6-(2-Hydroxypropan-2-yl)pyridin-3-yl)-4-((tetrahydro-2H-pyran-4-yl)methyl)-3,4-dihydropyrazino[2,3-b]pyrazin-2(1H)-one 6-Bromo-4-((tetrahydro-2H-pyran-4-yl)methyl)-3,4-dihydropyrazino[2,3-b]pyrazin-2(1H)-one (35.98 g, 110 mmol), 2-(5-(trimethylstannyl)pyridin-2-yl)propan-2-ol (See Example 5.E) (33.0 g, 110 mmol) and [1,1'-bis(diphenyl-phosphino)ferrocene]dichloro-palladium(II) complex with dichloromethane (1:1) (8.05 g, 11.00 mmol) were combined in a sealed tube and suspended in N,N-dimethylformamide (288 mL). The reaction was then heated to 125° C. for 2 h. The reaction was cooled slightly and poured while still warm onto a silica gel column and purified using an Biotage SP1 (0-100% (5% methanol in ethyl acetate) in hexanes). The desired fractions were combined and organic volatiles removed under reduced pressure. The residue was triturated with 20% ethyl acetate in hexanes followed by several washes with denatured ethanol. The slightly yellow solid was dried under reduced pressure to afford the desired compound (15.08 g, 39.3 mmol, 35.8% yield). $^1$H NMR (400 MHz, DMSO-$d_6$) δ (ppm) 11.32 (s, 1H), 9.07 (d, J=1.56 Hz, 1H), 8.29 (dd, J=8.59, 2.34 Hz, 1H), 8.05 (s, 1H), 7.72 (d, J=8.20 Hz, 1H), 5.26 (s, 1H), 4.21 (s, 2H), 3.83 (d, J=2.73 Hz, 2H), 3.51 (d, J=7.42 Hz, 2H), 3.27 (t, J=11.32 Hz, 2H), 2.09 (br. s., 1H), 1.61 (d, J=11.3 Hz, 2H), 1.46 (s, 6H), 1.24-1.38 (m, 2H); MS (ESI) m/z 384.2 $[M+1]^+$; mp 268-269° C.

Example 17: 7-(6-(2-Hydroxypropan-2-yl)pyridin-3-yl)-1-(2-methoxyethyl)-3,4-dihydropyrazino[2,3-b]pyrazin-2(1H)-one

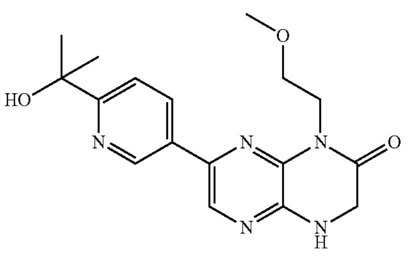 [SMILES: COCCN1C(=O)CNc2ncc(-c3ccc(C(C)(C)O)nc3)nc21]

A. 7-Bromo-1-(2-methoxyethyl)-3,4-dihydropyrazino[2,3-b]pyrazin-2(1H)-one

Ethyl 2-(3,5-dibromopyrazin-2-ylamino)acetate (See Example 1.C) (1 equiv), 2-methoxyethanamine (1 equiv), diisopropylethylamine (3 equiv), were suspended in dimethylsulfoxide and heated in an Emrys Biotage microwave reactor at 150° C. for 1 h. Standard ethyl acetate/water work up gave crude material, which was suspended in 99.7% acetic acid. The reaction was sealed, heated to 120° C. and allowed to stir for 2 h. The reaction was extracted in ethyl acetate. The organic layers were pooled and washed with saturated sodium bicarbonate, followed by brine and dried over magnesium sulfate. Concentration and flash column chromatography (0-100% ethyl acetate in hexanes) gave the desired product in 27% yield over two steps. MS (ESI) m/z 287.4 $[M]^+$, 289.4 $[M+2]^+$.

B. 7-(6-(2-Hydroxypropan-2-yl)pyridin-3-yl)-1-(2-methoxyethyl)-3,4-dihydropyrazino[2,3-b]pyrazin-2(1H)-one 7-Bromo-1-(2-methoxyethyl)-3,4-dihydropyrazino[2,3-b]pyrazin-2(1H)-one (1 equiv), 2-(5-(trimethylstannyl)pyridin-2-yl)propan-2-ol (See Example 5.E) (1 equiv) and dichlorobis(triphenylphosphine)-palladium(II) (0.2 equiv) were suspended in dimethylformamide. The reaction was purged with nitrogen and was heated to 140° C. for 2 h. The reaction was cooled to room temperature, filtered through Celite and washed with ethyl acetate. Volatiles were removed under reduced pressure and the resulting purple slurry was purified using silica gel column chromatography (0-100% (5% methanol in ethyl acetate) in hexanes). The desired fractions were combined and organic volatiles removed under reduced pressure. The solid was triturated in 5% ethyl acetate in hexanes and washed with hexanes to afford the desired product in 38% yield. $^1$H NMR (400 MHz, DMSO-$d_6$) δ (ppm) 9.02 (d, J=1.6 Hz, 1H), 8.27 (s, 1H), 8.24 (dd, J=8.6, 2.3 Hz, 1H), 7.71 (d, J=0.8 Hz, 1H), 7.69 (s, 1H), 5.25 (s, 1H), 4.28 (t, J=6.2 Hz, 2H), 4.20 (d, 2H), 3.60 (t, J=6.2 Hz, 2H), 3.26 (s, 3H), 1.46 (s, 6H); MS (ESI) m/z 344.3 $[M+1]^+$.

Example 18: 7-(1H-Pyrrolo[2,3-b]pyridin-4-yl)-1-[2-(tetrahydro-pyran-4-yl)-ethyl]-3,4-dihydro-1H-pyrazino[2,3-b]pyrazin-2-one

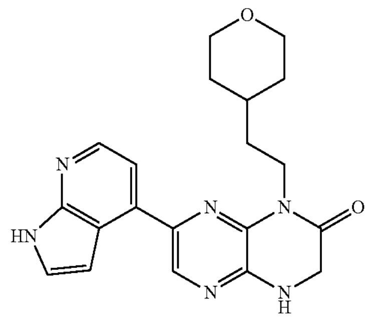 [SMILES: O=C1CNc2ncc(-c3ccnc4[nH]ccc34)nc2N1CCC1CCOCC1]

A. 7-(1H-Pyrrolo[2,3-b]pyridin-4-yl)-1-[2-(tetrahydro-pyran-4-yl)-ethyl]-3,4-dihydro-1H-pyrazino[2,3-b]pyrazin-2-one A mixture of 1-(2-(tetrahydro-2H-pyran-4-yl)ethyl)-7-(trimethylstannyl)-3,4-dihydropyrazino[2,3-b]pyrazin-2(1H)-one (See Example 15.C) (1 equiv), 4-bromo-pyrrolo[2,3-b]pyridine-1-carboxylic acid tert-butyl ester (1 equiv), tris(dibenzylideneacetone) palladium (0.13 equiv), tri-o-tolylphosphine (0.25 equiv) and triethylamine (2.8 equiv) in anhydrous dioxane was purged, degassed for 2 min and stirred at 95° C. under nitrogen for 3-4 h. Upon completion of the reaction as indicated by TLC, the volatiles were removed under reduced pressure and the residue was purified by column chromatography to give the desired product in 35% yield. MS (ESI) m/z 479.7 $[M+1]^+$. tert-Butyl 4-(7-oxo-8-(2-(tetrahydro-2H-pyran-4-yl)ethyl)-5,6,7,8-tetrahydropyrazino[2,3-b]pyrazin-2-yl)-1H-pyrrolo[2,3-b]pyridine-1-carboxylate was stirred in methanolic hydrochloride solution at room temperature. Upon completion of the reaction as indicated by TLC, the solvent was removed under reduced pressure and the residue was purified on silica gel to give the title compound in 63% yield. $^1$H NMR (DMSO-$d_6$, 400 MHz) δ (ppm) 11.72 (s, 1H), 8.38 (s, 1H), 8.25 (d, J=4.8 Hz, 1H), 7.79 (s, 1H), 7.53-7.51 (m, 2H), 6.97 (q, J=1.6 Hz, 1H), 4.23 (s, 2H), 4.14 (t, J=7.6 Hz, 2H), 3.81 (dd, $J_1$=2.4 Hz, $J_2$=11.2 Hz, 2H), 3.25 (d, J=10.8 Hz, 2H), 1.67 (d, J=13.2 Hz, 2H), 1.61 (m, 3H), 1.22 (m, 2H); MS(ESI): m/z 379.2 $[M+1]^+$.

Example 19: 1-(2-Methoxyethyl)-7-(2-methyl-6-(4H-1,2,4-triazol-3-yl)pyridin-3-yl)-3,4-dihydropyrazino[2,3-b]pyrazin-2(1H)-one

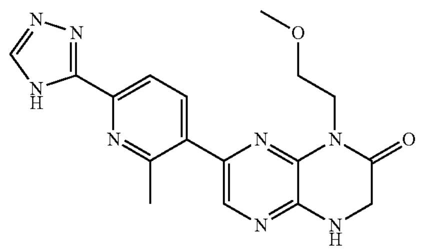 [SMILES: COCCN1C(=O)CNc2ncc(-c3ccc(-c4nnc[nH]4)nc3C)nc21]

A. 1-(2-Methoxyethyl)-7-(trimethylstannyl)-3,4-dihydropyrazino[2,3-b]pyrazin-2(1H)-one 7-Bromo-1-(2-methoxyethyl)-3,4-dihydropyrazino[2,3-b]pyrazin-2(1H)-one (See Example 17.A) (0.5 g, 1.741 mmol), 1,1,1,2,2,2-hexamethyldistannane (0.856 g, 2.61 mmol) and tetrakis(triphenylphosphine) palladium(0) (0.201 g, 0.174 mmol) were combined in 1,4-dioxane (20 mL) and heated at 140° C. for 2 h. The resulting mixture cooled to room temperature, diluted with ethyl acetate and filtered through Celite. The filtrate was concentrated under reduced pressure. Flash chromatography (0-30% ethyl acetate in hexane) gave the desired product as clear oil (0.5 g, 1.34 mmol, 77% yield). MS (ESI) m/z 373.0[M+2]$^+$.

B. 1-(2-Methoxyethyl)-7-(2-methyl-6-(4H-1,2,4-triazol-3-yl)pyridin-3-yl)-3,4-dihydropyrazino[2,3-b]pyrazin-2(1H)-one 1-(2-Methoxyethyl)-7-(trimethylstannyl)-3,4-dihydropyrazino[2,3-b]pyrazin-2(1H)-one (0.5 g, 1.348 mmol), 3-bromo-2-methyl-6-(1-(tetrahydro-2H-pyran-2-yl)-1H-1,2,4-triazol-3-yl)pyridine (0.436 g, 1.348 mmol), tris(dibenzylidineacetone)dipalladium(0) (0.123 g, 0.135 mmol), tri-o-tolylphosphine (0.082 g, 0.270 mmol), triethylamine (0.584 mL, 4.04 mmol) and N,N-dimethylformamide (10 mL) were combined in a 75 mL sealable flask, the atmosphere in the flask was removed and replaced with nitrogen. The mixture was stirred at 130° C. for 3 h. The resulting mixture was cooled to room temperature and filtered. The organic layer was concentrated under reduced pressure. The resulting residue was diluted with methanol and dimethylsulfoxide, filtered and purified using reverse-phase preparatory HPLC (10-30% acetonitrile+0.1% TFA in water+0.1% TFA, over 30 min). Fractions containing clean product were passed through a Phenomenex Strata-X-C solid phase extraction column. The column was washed successively with water, acetonitrile, methanol and 5% ammonium hydroxide in methanol. The product eluted with the 5% ammonium hydroxide in methanol eluent and was concentrated under reduced pressure. The residue was triturated with ethyl ether in hexane to make a fine powder and dried under vacuum at 50° C. to give the desired product (0.05 g, 0.136 mmol, 10% yield) as a white solid. $^1$H NMR (400 MHz, DMSO-$d_6$) δ (ppm) 8.10 (br. s., 1H), 7.98 (br. s., 1H), 7.94 (s, 1H), 7.73 (br. s., 1H), 4.13-4.28 (m, 4H), 3.55 (t, J=6.25 Hz, 2H), 3.24 (s, 3H), 2.70 (br. s., 3H); MS (ESI) m/z 367.2[M+1]$^+$.

Example 20: 6-(4-(4H-1,2,4-Triazol-3-yl)phenyl)-4-ethyl-3,4-dihydropyrazino[2,3-b]pyrazin-2(1H)-one hydrochloride

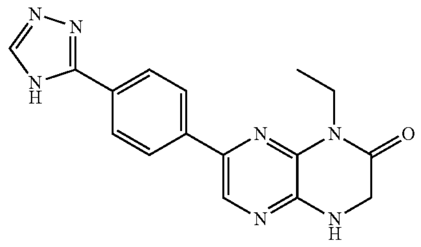 [SMILES: CCN1C(=O)CNc2ncc(-c3ccc(-c4nnc[nH]4)cc3)nc21]

A. 6-Bromo-4-ethyl-3,4-dihydropyrazino[2,3-b]pyrazin-2(1H)-one

To a solution of 2-bromo-N-(3,5-dibromopyrazin-2-yl)acetamide (See Example 4.A) (1 equiv) and diisopropylethylamine (3 equiv) in acetonitrile was added ethanamine hydrochloride (1.05 equiv). The solution was allowed to heat to 70° C. for 30 min. The solution was condensed under reduced pressure and purified using column chromatography (0-75% ethyl acetate in hexanes) to afford the title compound in 36% yield. MS (ESI) m/z 257.5 [M]$^+$, 259.4 [M+2]$^+$.

B. 4-Ethyl-6-(4-(4-(tetrahydro-2H-pyran-2-yl)-4H-1,2,4-triazol-3-yl)phenyl)-3,4-dihydro-pyrazino[2,3-b]pyrazin-2(1H)-one 6-Bromo-4-ethyl-3,4-dihydropyrazino[2,3-b]pyrazin-2(1H)-one (1.1 equiv), 4-(tetrahydro-2H-pyran-2-yl)-3-(4-(4,4,5,5-tetramethyl-1,3,2-dioxaborolan-2-yl)phenyl)-4H-1,2,4-triazole (1 equiv) and dichloro[1,1'-bis(diphenylphosphino)ferrocene]palladium (II) dichloromethane (0.05 equiv) were combined in 1,4-dioxane followed by the addition of sodium carbonate (3 equiv) in water. The solution was heated in a Biotage Emrys Optimizer microwave reactor to 120° C. for 30 min. The solution was condensed under reduced pressure and purified using column chromatography (0-10% methanol in ethyl acetate) to afford the title compound in 45% yield. MS (ESI) m/z 406.6 [M+1]$^+$.

C. 6-(4-(4H-1,2,4-Triazol-3-yl)phenyl)-4-ethyl-3,4-dihydropyrazino[2,3-b]pyrazin-2(1H)-one hydrochloride 4-Ethyl-6-(4-(4-(tetrahydro-2H-pyran-2-yl)-4H-1,2,4-triazol-3-yl)phenyl)-3,4-dihydropyrazino[2,3-b]pyrazin-2(1H)-one in ethanol was treated with 2 N hydrogen chloride in dioxane. The solution was stirred at 75° C. for 1 h. The solution was condensed partially and cooled. Cold ethanol was added to the slurry and the resulting precipitate filtered and washed with additional cold ethanol followed by hexanes to afford the title compound as the hydrochloride salt in 82% yield. $^1$H NMR (400 MHz, METHANOL-$d_4$) δ (ppm) 9.18 (s, 1H), 8.22 (d, J=8.59 Hz, 2H), 8.04-8.09 (m, 3H), 7.66-7.74 (m, 1H), 7.58-7.64 (m, 1H), 4.24 (s, 2H), 3.74 (q, J=7.03 Hz, 2H), 1.29 (t, J=7.03 Hz, 4H), 0.79-0.98 (m, 4H); MS (ESI) m/z 322.2 [M+1]$^+$.

Building Block Synthesis

The following building blocks were prepared and used in the preparations as described herein, or variations known in the art thereof.

tert-Butyl 4-bromo-1H-pyrrolo[2,3-b]pyridine-1-carboxylate

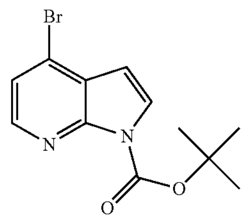 [SMILES: CC(C)(C)OC(=O)n1ccc2c(Br)ccnc21]

A. 4-Bromo-1H-pyrrolo[2,3-b]pyridine

A solution of trifluoromethyl sulfonic anhydride (9.3 g, 33 mmol) was added dropwise to a mixture of 1H-pyrrolo[2,3-b]pyridine 7-oxide (3 g, 22 mmol) and tetrabutyl ammonium bromide (10.8 g, 33 mmol) in N,N-dimethylformamide (30 mL) at 0° C. The resulting mixture was stirred at 0° C. for 4 h and at room temperature overnight. The reaction was quenched with water and neutralized with 1N sodium hydroxide to pH=7. The resulting mixture was extracted twice with a mixture of methylene chloride and i-propanol (30 mL, $V_m$:$V_p$=4:1). The organic layer was combined, dried over anhydrous sodium sulfate, concentrated and purified by a reverse-phase preparatory HPLC (0-30%: acetonitrile+0.1% TFA in water+0.1% TFA, over 15 min.) to give the title compound (1.5 g, 34.3% yield). MS(ESI) m/z 196.8 $[M+1]^+$, 198.8 $[M+3]^+$.

B. tert-Butyl 4-bromo-1H-pyrrolo[2,3-b]pyridine-1-carboxylate

A mixture of 4-bromo-1H-pyrrolo[2,3-b]pyridine (250 mg, 1.26 mmol), di-tert-butyl dicarbonate (302 mg, 1.38 mmol), dimethyl-pyridin-4-yl-amine (7.6 mg, 0.06 mmol) and triethylamine (127 mg, 1.26 mmol) in anhydrous methylene chloride (15 mL) was stirred at room temperature for 3 h. Upon completion of the reaction as indicated by TLC, the volatiles were removed under reduced pressure and the residue was purified by column chromatography on silica gel (9-25% ethyl acetate in petroleum ether) to give the desired product (230 mg, 61% yield) as an oil. MS (ESI) m/z 242.9 $[M-56+1]^+$ 1-(Tetrahydro-2H-pyran-2-yl)-4-(4,4,5,5-tetramethyl-1,3,2-dioxaborolan-2-yl)-1H-indazole

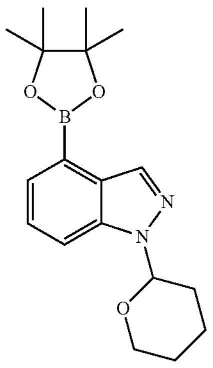 [SMILES: CC1(C)OB(c2cccc3c2cnn3C2CCCCO2)OC1(C)C]

A. 4-Bromo-1H-indazole

To a solution of 3-bromo-2-methylaniline (5 g, 27 mmol) in chloroform (1 mL) was added acetic anhydride (5 g, 27 mmol) at 0° C. and the mixture was stirred at room temperature for 1 h. Potassium acetate (0.75 g, 7.8 mmol) and isoamyl nitrite (0.78 g, 58 mmol) were added and the reaction mixture was refluxed for 18 h. The volatiles were removed under reduced pressure and water (0.65 mL) was added. The mixture was concentrated, diluted with concentrated hydrochloride acid (1 mL) and heated at 50° C. for 2 h. After being cooled to room temperature, aqueous sodium hydroxide solution (50%) was added until pH=10. The aqueous mixture was extracted with ethyl acetate (100 mL×3). The combined organic layer was washed with brine (150 mL), dried over anhydrous sodium sulfate, filtered, evaporated and purified on silica gel column (3% ethyl acetate in petroleum ether) to give the desired product (2.69 g, 34% yield) as a solid. MS (ESI): m/z 197.0 $[M+1]^+$.

B. 4-Bromo-1-(tetrahydro-pyran-2-yl)-1H-indazole

A solution of 4-bromo-1H-indazole (1.82 g, 9.24 mmol), 3,4-dihydro-2H-pyran (1.55 g, 18.48 mmol) and toluene-4-sulfonic acid (0.26 g, 1.39 mmol) in anhydrous tetrahydrofuran (40 mL) was heated at 80° C. overnight under nitrogen. The solvent was removed under reduced pressure and the residue was purified on silica gel column (3% ethyl acetate in petroleum ether) to give the title compound (2.13 g, 81% yield) as a yellow solid. MS (ESI): m/z 280.9 $[M+1]^+$.

C. 1-(Tetrahydro-pyran-2-yl)-4-(4,4,5,5-tetramethyl-[1,3,2]dioxaborolan-2-yl)-1H-Indazole A degassed mixture of 4-bromo-1-(tetrahydro-pyran-2-yl)-1H-indazole (2.13 g, 7.45 mmol), bis(pinacolato)diboron (3.73 g, 14.9 mmol), potassium phosphate (2.70 g, 12.67 mmol), palladium acetate (0.174 g 0.75 mmol) and triphenylphosphine (0.59 g, 2.24 mmol) in 1,2-dimethoxy-ethane (50 mL) was heated at 100° C. under nitrogen overnight. After cooling to room temperature, the reaction mixture was filtered, concentrated under reduced pressure and purified on silica gel column (10-30% ethyl acetate in petroleum ether) to give the product (1.83 g, 74% yield) as a solid. MS (ESI): m/z 329.2 $[M+1]^+$.

3-(4-Bromo-2-fluoro-3-methylphenyl)-4-(tetrahydro-2h-pyran-2-yl)-4H-1,2,4-triazole

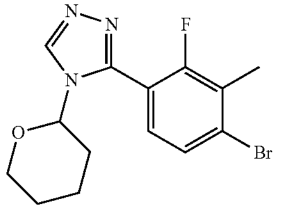 [SMILES: Cc1c(Br)ccc(-c2nncn2C2CCCCO2)c1F]

A. 4-Bromo-3-fluoro-2-methylaniline

To a stirred solution of 3-fluoro-2-methylaniline (25 g, 200 mmol) in acetic acid (140 mL) at 0-5° C. was added hydrogen bromide (100 mL, 200 mmol) then dimethyl sulfoxide (72 mL) was added slowly dropwise (reaction is exothermic and at temperature higher than 5-15° C. produces dibromoisomer). The mixture was stirred at 5-15° C. for 12 h (mixture became clear solution). The resulting solution was cooled to 0° C. and neutralized with sodium hydroxide then with sodium bicarbonate to pH 7. The mixture was extracted with ethyl acetate. The organic layer was concentrated under reduced pressure. Flash chromatography (0-10% ethyl acetate in hexane) gave the desired product as a white solid (23.3 g, 114 mmol, 57% yield). $^1$H NMR (400 MHz, CHLOROFORM-d) δ (ppm) 7.11 (t, J=8.20 Hz, 1H), 6.35 (d, J=8.98 Hz, 1H), 3.72 (br. s., 2H), 2.07 (d, J=1.95 Hz, 3H).

B. 4-Amino-2-fluoro-3-methylbenzonitrile

A mixture of 4-bromo-3-fluoro-2-methylaniline (23 g, 113 mmol) and cyanocopper (20.19 g, 225 mmol) N,N-dimethylformamide (200 mL) was heated to 140° C. for 7 h. After the mixture was cooled to room temperature filtered and poured into a separatory funnel containing water and ethyl acetate (1:1). Layers were separated and the organic layer was concentrated under reduced pressure. Flash chromatography (0-50% ethyl acetate in hexane) gave the desired product (11.4 g, 76 mmol, 67% yield) as a brown solid. $^1$H NMR (400 MHz, CHLOROFORM-d) δ (ppm) 7.22 (t, 1H), 6.45 (d, J=8.59 Hz, 1H), 4.23 (br. s., 2H), 2.07 (s, 3H); MS (ESI) m/z 151.1[M+1]$^+$.

C. 4-Bromo-2-fluoro-3-methylbenzonitrile

A mixture of dimethyl sulfoxide (400 mL) and potassium nitrite (22.67 g, 266 mmol) was stirred to dissolve potassium nitrite and 4-amino-2-fluoro-3-methylbenzonitrile (10 g, 66.6 mmol) and copper(I) bromide (1.911 g, 13.32 mmol) were added. Aqueous 48% hydrogen bromide (33 mL, 266 mmol), diluted with dimethyl sulfoxide (200 mL), was added dropwise and the reaction stirred for 2 h. After complete conversion of starting material, the reaction mixture was poured into iced-cold water and neutralized to pH 7 with cold concentrated sodium hydroxide. The resulting solid was collected by filtration to give the desired product (11.4 g, 53.3 mmol, 80% yield) as white solid. $^1$H NMR (400 MHz, CHLOROFORM-d) δ (ppm) 7.47 (d, J=9.37 Hz, 1H), 7.33 (t, 1H), 2.39 (d, J=2.34 Hz, 3H).

D. 4-Bromo-2-fluoro-3-methylbenzamide

4-Bromo-2-fluoro-3-methylbenzonitrile (11 g, 51.4 mmol) in a 100 mL mixture of TFA-sulfuric acid (4:1, V/V) was stirred at 40° C. for 16 h. After complete conversion of starting material, the reaction mixture was poured into iced-cold water. The resulting solid was filtered off and washed with water and dried to give the desired product (11.24 g, 48.4 mmol, 94% yield) as a white solid. MS (ESI) m/z 234.1 [M+2]$^+$.

E. 3-(4-Bromo-2-fluoro-3-methylphenyl)-1H-1,2,4-triazole

4-Bromo-2-fluoro-3-methylbenzamide (11 g, 47.4 mmol) and N,N-dimethylformamide dimethylacetal (60 mL) were combined in a 100 mL round-bottom flask with a stir bar and heated at 55° C. under a reflux condenser under nitrogen for 3 h. The resulting mixture was concentrated under reduced pressure and dried under vacuum to give yellow oil, which was used in the next step without purification. The residue was diluted with acetic acid (60 mL) at 0° C. and hydrazine monohydrate (20 mL) was added dropwise and allowed to stirred at rt for 5 h. After complete conversion of starting material, the reaction mixture was poured into iced-cold water and neutralized to pH 7 with ice cold concentrated sodium hydroxide. The resulting solids were collected by vacuum filtration. Solid was dissolved in ethyl acetate (400 mL) and stirred for 15 min, filtered the insoluble solid, the filtrate dried over magnesium sulfate, filtered, concentrated under reduced pressure and dried under vacuum to give a brown pure solid (4.3 g, 16.79 mmol, 35% yield) which was used in the next step without purification. $^1$H NMR (400 MHz, CHLOROFORM-d) δ (ppm) 8.12 (s, 1H), 7.97 (t, J=8.00 Hz, 1H), 7.52 (d, J=8.59 Hz, 1H), 2.44 (d, 3H).

F. 3-(4-Bromo-2-fluoro-3-methylphenyl)-4-(tetrahydro-2H-pyran-2-yl)-4H-1,2,4-triazole Methanesulfonic acid (0.090 mL, 1.390 mmol) was added to a stirred solution of 3-(4-bromo-2-fluoro-3-methylphenyl)-1H-1,2,4-triazole (7.0 g, 27.3 mmol) and 3,4-dihydro-2H-pyran (12.68 mL, 139 mmol) in tetrahydrofuran (33 mL). The resulting mixture stirred at 85° C. under a reflux condenser under nitrogen for 20 h. The mixture was diluted with ethyl acetate and washed with saturated aqueous sodium bicarbonate and brine. The organic layer was dried over magnesium sulfate, filtered and concentrated under reduced pressure. The residue was purified using flash chromatography (20-30-50% ethyl acetate in hexane). Product containing fractions were combined and solvent removed under reduced pressure to afford desired product (8.8 g, 95% yield) as a yellow solid. MS (ESI) m/z 340.0 [M]$^+$ 3-(4-Bromo-2-fluorophenyl)-4h-1,2,4-triazole

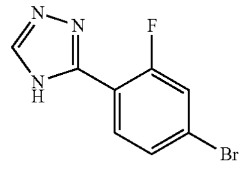 [SMILES: Fc1cc(Br)ccc1-c1nnc[nH]1]

A. 4-Bromo-2-fluorobenzamide

A solution of 4-bromo-2-fluorobenzonitrile (10.0 g, 50.0 mmol) in a 70 mL mixture of TFA (56.0 mL, 727 mmol)-sulfuric acid (14.0 mL, 263 mmol) (4:1 V/V) was stirred at 40° C. for 16 h. The reaction was poured while still warm over ice water. The product precipitated and the solid was filtered and dried to give 4-bromo-2-fluorobenzamide (9.53 g, 43.7 mmol, 87% yield) as a white solid. MS (ESI) m/z 218.1 [M]$^+$, 220.1 [M+2]$^+$.

B. 3-(4-Bromo-2-fluorophenyl)-4H-1,2,4-triazole

4-Bromo-2-fluorobenzamide (9.53 g, 43.7 mmol) and N,N-dimethylformamide dimethylacetal (75.0 mL) were combined in a 500 mL round bottom flask and purged with nitrogen. The reaction was heated to reflux at 85° C. for 2 h. The resulting mixture was concentrated under reduced pressure and dried under vacuum to afford a yellow oil. The oil was suspended in concentrated acetic acid (75.0 mL) and cooled to 0° C. Hydrazine hydrate (21.88 g, 437 mmol) was added dropwise and the mixture was allowed to stir at rt for 5 h. The reaction was poured warm onto cold ice and extracted with dichloromethane (3×200 mL). Organic volatiles were removed under reduced pressure to afford 3-(4-bromo-2-fluorophenyl)-4H-1,2,4-triazole (7.20 g, 29.7 mmol, 68.1% yield) as a white solid. MS (ESI) m/z 241.9 $[M]^+$, 243.9 $[M+2]^+$.

2-(4-Methyl-5-(trimethylstannyl)pyridin-2-yl)propan-2-ol

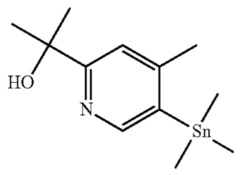

A. 2-(5-Bromo-4-methylpyridin-2-yl)propan-2-ol 2,5-Dibromo-4-methylpyridine (4.0 g, 15.94 mmol) was dissolved in toluene (60.0 mL) and the reaction was cooled to −78° C. Butyllithium (7.01 mL, 17.54 mmol) was added dropwise and the reaction was allowed to stir for 30 min. Acetone (4.69 mL, 63.8 mmol) was then added and the reaction was allowed to warm to rt and stir for 16 h. The reaction was quenched with saturated ammonium chloride, extracted into ethyl acetate (3×200 mL) and washed with water followed by brine. The organics were dried over magnesium sulfate and volatiles removed under reduced pressure. The compound was purified on silica gel chromatography (0-50% ethyl acetate in hexanes) to afford 2-(5-bromo-4-methylpyridin-2-yl)propan-2-ol (2.33 g, 10.13 mmol, 63.5% yield). MS (ESI) m/z 230.3 $[M]^+$, 232.3 $[M+2]^+$.

B. 2-(4-Methyl-5-(trimethylstannyl)pyridin-2-yl)propan-2-ol 2-(5-Bromo-4-methylpyridin-2-yl)propan-2-ol (2.33 g, 10.13 mmol) and tetrakis(triphenylphosphine)palladium(0) (1.045 g, 1.013 mmol) were added to a pressure tube and suspended in 1,4-dioxane (33.8 mL). 1,1,1,2,2,2-Hexamethyldistannane (2.99 mL, 12.15 mmol) was then added and heated to 150° C. for 30 min. The reaction was allowed to cool to rt and was filtered through celite and washed with ethyl acetate. Organic volatiles were removed under reduced pressure followed by an extraction in ethyl acetate (3×200 mL) and water. Organic volatiles were removed under reduced pressure and the compound purified using silica gel column chromatography on an Biotage column (10-50% ethyl acetate in hexanes) to afford 2-(4-methyl-5-(trimethylstannyl)pyridin-2-yl)propan-2-ol (1.75 g, 5.57 mmol, 55.0% yield). $^1H$ NMR (400 MHz, DMSO-$d_6$) δ (ppm) 8.31 (s, 1H), 7.51 (s, 1H), 5.25 (br. s., 1H), 2.37 (s, 3H), 1.41 (s, 6H), 0.65 (br. s., 3H), 0.34 (s, 6H).

Tert-butyl 3-(5-bromo-6-methylpyridin-2-yl)-1H-1,2,4-triazole-1-carboxylate

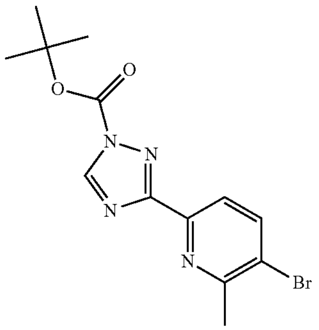 [SMILES: Cc1nc(-c2ncn(C(=O)OC(C)(C)C)n2)ccc1Br]

A. 5-Bromo-6-methylpicolinonitrile

A 1-L, three-neck, round-bottom flask equipped with a mechanical stirrer and a nitrogen inlet was charged with 3,6-dibromo-2-methylpyridine (150 g, 0.59 mol), copper (I) cyanide (42.8 g, 0.47 mol) and sodium cyanide (23 g, 0.47 mol). To the mixture was added N,N-dimethylformamide (300 mL). The mixture was heated to 95° C. and stirred for 48 h. The reaction mixture was cooled to ambient temperature and poured into ethanol (3 L) while stirring. The mixture was filtered through a pad of Celite, the filtrate was concentrated under reduced pressure and partitioned between water (3 L) and ethyl acetate (3 L). The organic layer was separated and washed with brine (2×600 mL), dried over anhydrous sodium sulfate, filtered and concentrated. The crude product was purified by silica gel plug purification (0-5% ethyl acetate in hexanes) to afford the product (61.5 g, 45% yield) as a white solid. In addition, 19.32 g (14%) of the mixture of the starting material and the product was isolated.

B. 5-Bromo-6-methylpicolinohydrazonamide

A 500-mL, three-neck, round-bottom flask was equipped with 5-bromo-6-methylpicolinonitrile (101.5 g, 0.515 mol), ethanol (122 mL) and hydrazine hydrate (50 mL, 1.03 mol). The resulting very thick mixture was allowed to stir at ambient temperature for 24 h. More ethanol (50 mL) was added and the mixture was allowed to stir over the weekend. The mixture was filtered and washed with cold ethanol (100 mL) and cold hexanes (50 mL). The solids were dried in a vacuum oven to afford the product (110 g, 93% yield) as an off-white solid.

C. 3-Bromo-2-methyl-6-(1H-1,2,4-triazol-3-yl)pyridine

A 500-mL, three-neck, round-bottom flask was equipped with a mechanical stirrer, a thermocouple connected to a J-KEM temperature controller and a reflux condenser. The flask was charged with 5-bromo-6-methylpicolinohydrazonamide (100 g, 0.463 mol) and formic acid (250 mL). The resulting solution was heated to 100° C. and stirred for 48 h. Formic acid was removed under reduced pressure and the resulting slurry was treated with water (1.5 L) while vigorously stirring. The mixture was filtered and washed with water (300 mL). The solids were transferred into a round-bottom flask and treated with water (1 L) and 1 M sodium hydroxide solution until pH 7. The mixture was allowed to stir for 30 min, filtered, washed with water (300 mL) and dried in a vacuum oven at 30-35° C. for 48 h to afford the product (96 g, 92% yield) as a white solid.

D. 3-Bromo-2-methyl-6-(1-(tetrahydro-2H-pyran-2-yl)-1H-1,2,4-triazol-3-yl)pyridine To a suspension of 3-bromo-2-methyl-6-(1H-1,2,4-triazol-3-yl)pyridine (96.0 g, 0.4 mol) in tetrahydrofuran (780 mL) was added 3,4-dihydro-2H-pyran (72.5 mL, 0.8 mol) and methanesulfonic acid (3.2 mL). The mixture was heated to 65° C. and the resulting yellow solution was allowed to stir at 65° C. for 6 h. The mixture was cooled to ambient temperature, quenched with triethylamine (23 mL), concentrated under reduced pressure and further dried in a high vacuum for 1 h. The resulting oil was dissolved in acetonitrile (250 mL) and the solution was added into water (750 mL) while stirring vigorously. More acetonitrile (80 mL) was added and the mixture was allowed to stir for 1 h. The resulting solids were filtered, washed with 1:4 acetonitrile/water (800 mL) and dried in a vacuum oven for 48 h to afford the product (110 g, 85% yield) as a white solid. The product was further purified by silica gel plug purification (1:1 hexanes/ethyl acetate) to give 88 g of the pure product as a white solid and 16.2 g of less pure product. MS (ESI) m/z 239.1 $[M]^+$, 241.1 $[M+2]^+$.

E. tert-Butyl 3-(5-bromo-6-methylpyridin-2-yl)-1H-1,2,4-triazole-1-carboxylate

To a mixture of 3-bromo-2-methyl-6-(1H-1,2,4-triazol-3-yl)pyridine (300 g, 1.25 mol) in dioxane (4 L) was added sodium carbonate (398 g, 3.75 mol), followed by water (4 L). di-tert-Butyl dicarbonate (274 g, 1.25 mol) was added and the mixture was stirred of 1 h at room temperature. The mixture was then diluted with cold water (~10 L) and extracted with ethyl acetate (4 L×3). The combined ethyl acetate layer was washed with brine, dried over sodium sulfate, filtered and concentrated to afford the product (254 g, 60% yield) as a slightly yellow solid.

4-(Tetrahydro-2H-pyran-2-yl)-3-(4-(4,4,5,5-tetramethyl-1,3,2-dioxaborolan-2-yl)phenyl)-4h-1,2,4-triazole

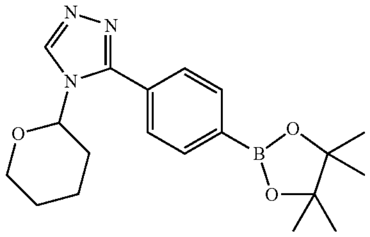 [SMILES: CC1(C)OB(c2ccc(-c3nncn3C3CCCCO3)cc2)OC1(C)C]

A. Ethyl 4-bromobenzimidate hydrochloride

A solution of 4-bromobenzonitrile (17.65 g, 97 mmol) in ethanol (500 mL) was acidified with hydrogen chloride gas at 0° C. for fifteen minutes. The solution was allowed to stir for 16 h. The solution was condensed under reduced pressure to afford the title compound (25.35 g, 99%). MS (ESI) m/z 228.1 $[M]^+$, 230.4 $[M+2]^+$.

B. 3-(4-Bromophenyl)-4H-1,2,4-triazole

Ethyl 4-bromobenzimidate hydrochloride (35.6 g, 135 mmol), formic hydrazide (16.16 g, 269 mmol) and triethylamine (75 mL, 538 mmol) were combined in a screw capped flask and heated to 85° C. for 16 h. The solution was condensed under reduced pressure to afford a solid, which was partitioned between water and ethyl acetate (3×), dried over magnesium sulfate and solvent removed under reduced pressure. The resulting solid was sonicated with 20% ethyl acetate in hexanes, filtered and dried to afford the title compound (14.6 g, 65.2 mmol, 48% yield). MS (ESI) m/z 224.1 $[M]^+$, 226.1 $[M+2]^+$.

C. 3-(4-Bromophenyl)-4-(tetrahydro-2H-pyran-2-yl)-4H-1,2,4-triazole

A solution of 3-(4-Bromophenyl)-4H-1,2,4-triazole (14.1 g, 62.9 mmol), 3,4-dihydro-2H-pyran (10.59 mmol) and methanesulfonic acid (1.19 g, 6.29 mmol) in tetrahydrofuran (150 mL) was heated at 75° C. for 2 h. The solution was condensed and partitioned between sodium bicarbonate solution and ethyl acetate (3×), the organics dried over magnesium sulfate, filtered and solvent removed under reduced pressure. The solid was triturated with 10% ethyl acetate in hexanes to afford the title compound (8.1 g, 26.3 mmol, 70% yield). MS (ESI) m/z 308.4 $[M]^+$, 310.5 $[M+2]^+$.

D. 4-(Tetrahydro-2H-pyran-2-yl)-3-(4-(4,4,5,5-tetramethyl-1,3,2-dioxaborolan-2-yl)phenyl)-4H-1,2,4-triazole 3-(4-Bromophenyl)-4-(tetrahydro-2H-pyran-2-yl)-4H-1,2,4-triazole (8.1 g, 26.3 mmol), bis(pinacolato)diboron (6.67 g, 26.3 mmol) and potassium acetate (10.32 g, 105 mmol) were combined in dimethylformamide (100 mL). The solution was purged with nitrogen gas for 2 minutes. Dichloro [1,1'-bis(diphenylphosphino)ferrocene]palladium (II) dichloromethane (1.07 g, 1.31 mmol) was then added and the solution heated to 100° C. for 16 h. The solution was filtered through celite and the filtrate condensed under reduced pressure to afford a dark oil. The oil was purified via Biotage chromatography (0-70% ethyl acetate in hexanes) to afford a solid upon drying. The solid was diluted with hexanes, sonicated, filtered and dried to afford the title compound (7.1 g, 20.0 mmol, 71% yield). MS (ESI) m/z 356.5 $[M+1]^+$.

5-Bromo-2-(1-(tetrahydro-2H-pyran-2-yl)-1H-1,2,4-triazol-3-yl)pyridine

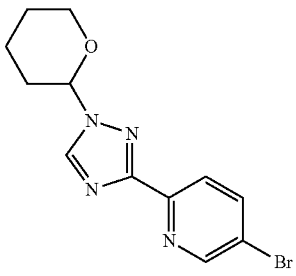 [SMILES: Brc1ccc(-c2ncn(C3CCCCO3)n2)nc1]

A. (E)-5-bromo-N-((dimethylamino)methylene)picolinamide

A solution of 5-bromopicolinamide (0.500 g, 2.49 mmol) and dimethylformamide dimethylacetal (20 mL), were heated to 85° C. for 3 h. The reaction was concentrated and the product was used directly in the next step (0.604 g, 95% yield). MS (ESI) m/z 257.1 $[M+1]^+$.

B. 5-Bromo-2-(1H-1,2,4-triazol-3-yl)pyridine

A solution of (E)-5-bromo-N-((dimethylamino)methylene)picolinamide (0.604 mg, 2.36 mmol) and hydrazine (2.12 g, 66.1 mmol) was stirred at 25° C. for 3 h. The reaction was concentrated and diluted with water. The resulting precipitate was collected by filtration and dried under vacuum to give the title compound (0.442 g, 83% yield). MS (ESI) m/z 226.1 $[M+1]^+$.

C. 5-Bromo-2-(1-(tetrahydro-2H-pyran-2-yl)-1H-1,2,4-triazol-3-yl)pyridine

A solution of 5-bromo-2-(1H-1,2,4-triazol-3-yl)pyridine (0.342 mg, 1.52 mmol), 3,4-dihydro-2H-pyran (0.256 g, 3.04 mmol) and 4-methylbenzenesulfonic acid (0.058 g, 0.30 mmol) in tetrahydrofuran was heated to 75° C. for 6 h. The reaction was concentrated and purified using Biotage column chromatography (0-20% methanol in dichloromethane) to provide semi-clean product as an oil (0.614 g, 1.9 mmol, >100% yield). This material was used without further purification. MS (ESI) m/z 309.4 $[M]^+$, 311.1 $[M+2]^+$.

tert-Butyl 6-bromo-4-methyl-2-(methylamino)-1H-benzo[d]imidazole-1-carboxylate

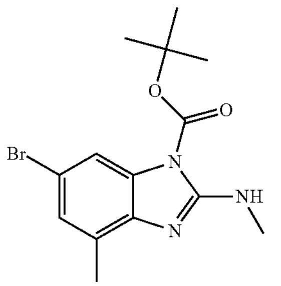 [SMILES: CNc1nc2c(C)cc(Br)cc2n1C(=O)OC(C)(C)C]

A. (6-Bromo-4-methylbenzimidazol-2-yl)-N-methylamine

Isothiocyanatomethane (0.055 g, 0.746 mmol) in N,N-dimethylformamide (1.0 mL) was added dropwise slowly to a stirred solution of 5-bromo-3-methylbenzene-1,2-diamine (0.150 g, 0.746 mmol) in N,N-dimethylformamide (1.5 mL) at 0° C. The cold bath was removed, the reaction mixture was capped and stirred at room temperature for 48 h. N-(3-Dimethylaminopropyl)-N'-ethylcarbodiimide hydrochloride (0.157 g, 0.821 mmol) was added and the reaction mixture capped and heated at 40° C. overnight. The resulting mixture was diluted with methanol, filtered and purified using reverse-phase preparatory HPLC (10-50% acetonitrile+0.1% TFA in $H_2O$+0.1% TFA, over 30 min). Fractions containing the desired product were combined and most of the solvent removed under reduced pressure. Acetonitrile was added and the resulting mixture loaded on a Strata ion exchange column. The column was washed successively with water, acetonitrile, methanol and 5% ammonium hydroxide in methanol. The product eluted with the 5% ammonium hydroxide in methanol and was concentrated under reduced pressure and dried under high vacuum to give the desired product (0.128 g, 0.53 mmol, 72% yield) as a slightly yellow waxy solid. MS (ESI) m/z 240 $[M]^+$, 242 $[M+2]^+$.

B. tert-Butyl 6-bromo-4-methyl-2-(methylamino)-1H-benzo[d]imidazole-1-carboxylate (6-Bromo-4-methylbenzimidazol-2-yl)-N-methylamine (0.128 g, 0.533 mmol), diisopropylethylamine (0.464 mL, 2.67 mmol), di-tert-butyl dicarbonate (0.349 g, 1.599 mmol) and N,N-dimethylformamide (5 mL) were combined in a 100 mL round bottom flask, capped and stirred at room temperature for 21 h. The resulting mixture was partitioned between water and ethyl acetate. The layers were separated and the organics were washed with water and brine. The organics were dried over magnesium sulfate, filtered, concentrated under reduced pressure and purified using flash chromatography (10-30% ethyl acetate in hexanes) to give the desired product (0.092 g, 0.27 mmol, 51% yield) as a yellow waxy solid. MS (ESI) m/z 340 $[M]^+$, 342 $[M+2]^+$.

Tert-butyl 6-bromo-4-methyl-2-(methylamino)-1H-benzo[d]imidazole-1-carboxylate

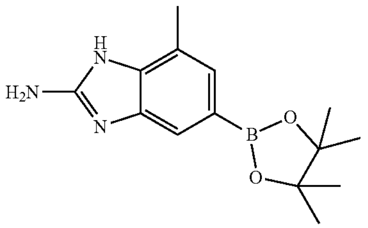 [SMILES: Cc1cc(B2OC(C)(C)C(C)(C)O2)cc2nc(N)[nH]c12]

A. 7-Methyl-5-(4,4,5,5-tetramethyl-1,3,2-dioxaborolan-2-yl)-1H-benzo[d]imidazol-2-amine 3-Methyl-5-(4,4,5,5-tetramethyl-1,3,2-dioxaborolan-2-yl)benzene-1,2-diamine (See Example 1.G) (500 mg, 2.015 mmol) and cyanic bromide (0.484 mL, 2.418 mmol) were added to a round bottom flask at room temperature, suspended in methanol (10.0 mL) and allowed to stir for 1.5 h. Volatiles were removed under reduced pressure followed by the addition of saturated sodium bicarbonate. The precipitate was collected via filtration, washed with ethyl acetate and dried under reduced pressure to afford the title compound (557 mg, 2.039 mmol, quant. yield). Compound was carried forward without further purification or characterization. MS (ESI) m/z 273.8 $[M+1]^+$.

tert-Butyl 6-bromo-4-methyl-2-(methylamino)-1H-benzo[d]imidazole-1-carboxylate

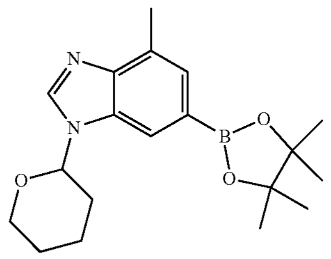 [SMILES: Cc1cc(B2OC(C)(C)C(C)(C)O2)cc2c1ncn2C1CCCCO1]

A. 6-Bromo-4-methyl-1-(tetrahydro-2H-pyran-2-yl)-1H-benzo[d]imidazole

6-Bromo-4-methyl-1H-benzo[d]imidazole (1.02 g, 4.83 mmol) was dissolved in tetrahydrofuran (10 mL) at room temperature with stirring under nitrogen. 3,4-Dihydro-2H-pyran (3.5 mL, 38.4 mmol) and methanesulfonic acid (0.032 mL, 0.48 mmol) were added and the resulting mixture heated at 75° C. for 49 h. The resulting mixture was cooled to room temperature, diluted with ethyl acetate and washed with saturated aqueous sodium bicarbonate and brine. The organics were dried over magnesium sulfate, filtered and concentrated under reduced pressure. Flash chromatography (50-100% ethyl acetate in hexanes) gave the desired product (1.32 g, 4.47 mmol, 93% yield) as a light yellow solid. MS (ESI) m/z 295.1 $[M]^+$, 297.3 $[M+2]^+$.

B. 4-Methyl-1-(tetrahydro-2H-pyran-2-yl)-6-(4,4,5,5-tetramethyl-1,3,2-dioxaborolan-2-yl)-1H-benzo[d]imidazole 6-Bromo-4-methyl-1-(tetrahydro-2H-pyran-2-yl)-1H-benzo[d]imidazole (1.320 g, 4.47 mmol), bis(pinacolato)diboron (1.192 g, 4.70 mmol), [1,1'-bis(diphenylphosphino)ferrocene]dichloropalladium(II), complex with dichloromethane (1:1) (183 mg, 0.22 mmol), potassium acetate (1.317 g, 13.4 mmol) and dimethyl sulfoxide (9 mL) were combined in a round bottom flask and stirred. The atmosphere in the flask was removed under vacuum and replaced with nitrogen three times. The resulting mixture was heated at 90° C. under nitrogen for 1.5 h. The resulting mixture was diluted with ethyl acetate and filtered through Celite. The filter cake was washed thoroughly with ethyl acetate. The filtrate was washed twice with water, once with brine, dried over magnesium sulfate, filtered and concentrated on a under reduced pressure. Flash chromatography (50-100% ethyl acetate in hexanes) gave the desired product at ~90% purity (1.31 g, 3.83 mmol, 77% yield) as a yellow tan foam-solid. MS (ESI) m/z 343.2 $[M+1]^+$.

5.2 Biological Examples

5.2.1 Biochemical Assays mTOR HTR-FRET Assay.

The following is an example of an assay that can be used to determine the mTOR inhibitory activity of a test compound. Heteroaryl Compounds were dissolved in DMSO and prepared as 10 mM stocks and diluted appropriately for the experiments. Reagents were prepared as follows:

"Simple TOR buffer" (used to dilute high glycerol TOR fraction): 10 mM Tris pH 7.4, 100 mM NaCl, 0.1% Tween-20, 1 mM DTT. Invitrogen mTOR (cat#PR8683A) was diluted in this buffer to an assay concentration of 0.200 μg/mL.

ATP/Substrate solution: 0.075 mM ATP, 12.5 mM $MnCl_2$, 50 mM Hepes, pH 7.4, 50 mM β-GOP, 250 nM Microcystin LR, 0.25 mM EDTA, 5 mM DTT, and 3.5 μg/mL GST-p70S6.

Detection reagent solution: 50 mM HEPES, pH 7.4, 0.01% Triton X-100, 0.01% BSA, 0.1 mM EDTA, 12.7 μg/mL Cy5-αGST Amersham (Cat#PA92002V), 9 ng/mL α-phospho p70S6 (Thr389) (Cell Signaling Mouse Monoclonal #9206L), 627 ng/mL α-mouse Lance Eu (Perkin Elmer Cat#AD0077).

To 20 μL of the Simple mTor buffer is added 0.5 μL of test compound in DMSO. To initiate the reaction 5 μL of ATP/Substrate solution was added to 20 μL of the Simple TOR buffer solution (control) and to the compound solution prepared above. The assay was stopped after 60 min by adding 5 μL of a 60 mM EDTA solution; 10 μL of detection reagent solution was then added and the mixture was allowed to sit for at least 2 hours before reading on a Perkin-Elmer Envision Microplate Reader set to detect LANCE Eu TR-FRET (excitation at 320 nm and emission at 495/520 nm).

PI3K Alpha and Gamma Assays.

PI3K alpha and gamma assays were run using the procedures described in the Millipore PI3K assay kit (cat#33-017). PI3K alpha and gamma enzyme were obtained from Invitrogen (Cat# PV4788 and PV4786).

Selected Heteroaryl Compounds have, or are expected to have, an $IC_{50}$ below 10 μM in this assay, with some compounds having an $IC_{50}$ below 1 μM, and others having an $IC_{50}$ below 0.10 μM.

DNA-PK Assay.

DNA-PK assays were performed using the procedures supplied in the Promega DNA-PK assay kit (catalog # V7870). DNA-PK enzyme was purchased from Promega (Promega cat#V5811).

Selected Heteroaryl Compounds have, or are expected to have, an $IC_{50}$ below 10 μM in this assay, with some compounds having an $IC_{50}$ below 1 μM, and others having an $IC_{50}$ below 0.10 μM.

5.2.2 Cell-Based Assays

PC-3 p-S6 and p-Akt MesoScale Assay.

The following is an example of an assay that can be used to determine the anticancer activity of a test compound. PC-3, a prostate adenocarcinoma cell line (#CRL-1435) was used in the pS6 Mesoscale Assay. The cells were grown in F-12 Kaighns' supplemented with 10% Fetal Bovine Serum and 1% Penicillin/Streptomycin. The following buffers were used: Complete Tris Lysis Buffer (for 10 mL use: 100 μL phosphatase inhibitor I (100× stock), 100 μL phosphatase inhibitor II (100× stock), 1 tablet Complete Mini (EDTA-free), 40 μL PMSF, all mixed thoroughly for 5 minutes at room temperature); 1× Tris wash Buffer (for 250 mL use: 25 mL 10× Tris wash buffer, 225 mL deionized water, store at room temperature); MSD blocking solution-A (for 20 mL use: 20 mL 1× tris wash buffer and 600 mg MSD blocker A, store on ice); Antibody dilution buffer (for 3 mL use: 1 mL blocking solution-A, 1.82 mL 1× tris wash buffer, 150 μL 2% MSD blocker D-M, 30 μL 10% MSD blocker D-R, store on ice).

On day one in the afternoon, cells were plated in 96-well flat bottom cell culture plates at 20,000 cells/well in 180 μL of volume. On day 2 in the morning, test compounds were diluted to the desired concentration and added to the cells. Cells were treated with compound for 1 hour at 37° C., 5% $CO_2$. The media was removed carefully and 50 μL 1× Tris Lysis Buffer was added to each well and the plate placed on a shaker at 4° C. for 1 hour to lyse the cells. 35 μL of lysate from each well was used to assay for p-S6 levels using the protocol described in the manual for MA6000 Phospho-S6RP (Ser235/236) Whole Cell Lysate Kit #K110DFD-3. The lysate was assayed for p-Akt levels using the protocol described in the manual for MA6000 Phospho-Akt (Ser4730 whole cell lysate Kit (#K111CAD-3). The plate was read on Sector Imager plate reader. $IC_{50}$ values were calculated from dose response curves.

Heteroaryl Compounds have, or are expected to have, an $IC_{50}$ below 10 μM in this assay, with some compounds having an $IC_{50}$ below 1 μM, and others having an $IC_{50}$ below 0.10 μM.

Btk-PH, Akt-PH and FoxO-EGFP Translocation Assays.

The following is an example of an assay that can be used to determine the anticancer activity of a test compound. BTK-PH_CHO cells (Bioimage C007A) were grown in Nut.MixF-12-Ham supplemented with 10% Fetal Bovine Serum, 1% Penicillin/Streptomycin, 0.5 mg/mL Geneticin and 0.25% DMSO. The cells were plated at 12,000 cells per well in a black wall clear bottom 96-well plate. Following 24 hour incubation, the cells were washed with cell wash buffer and incubated for 1 hour with cell wash buffer. Cells were then treated with control/test compounds and IGF-1 (insulin-like growth factor-1) for 4 minutes at room temperature. The cells were then fixed, washed and stained with Hoescht in PBS containing 0.5% Triton X-100. Plates were sealed and then read on Cellomics after 30 minutes. Akt-PH_CHO cells (Bioimage C006A) were grown in the same media as the BTK-PH_CHO cells. The cells were plated at 10,000 cells per well in a black clear bottom 96-well plate. The rest of the protocol was identical to the Btk-PH assay (as above). U-2 OS cell lines stably transfected with FoxO-EGFP construct was a gift from Gary Chiang, Burnham Institute, La Jolla. The cells were grown in DMEM supplemented with 10% Fetal Calf Serum and 1% Penicillin/Streptomycin. The cells were plated at 20,000 cells per well in a black clear bottom 96-well plate. Following overnight incubation, the cells were treated with control/test compounds and incubated for 2 hours. The cells were fixed, washed and stained with Hoescht. The plates were then washed with PBS three times and then 100 μL PBS was added to each well. The plate was then covered with a transparent cover slip. The plate was read on Cellomics and the $IC_{50}$ values were calculated compared to Wortmannin.

Selected Heteroaryl Compounds have, or are expected to have, an $IC_{50}$ below 30 μM in this assay, with some compounds having an $IC_{50}$ below 1 μM, and others having an $IC_{50}$ below 0.10 μM.

Cell Proliferation Assay.

The following is an example of an assay that can be used to determine the anticancer activity of a test compound. The assay was used to quantify cell proliferation based on measurement of metabolic activity via the reduction of tetrazolium salts to formazon salts. WST-1 (Roche Cat#11 644 807 001) was used to measure the proliferation of PC-3 cells. PC-3 cells were plated in 180 μL of growth media (F-12 Kaighns' supplemented with 10% Fetal Bovine Serum and 1% Penicillin/Streptomycin) at 3000 cells per well. The plated cells were incubated overnight in 5% $CO_2$ at 37° C. Compounds were diluted in DMSO from 10 mM stock solution and then into F-12 Kaighns medium. 20 μL of compound dilutions including the DMSO control in triplicate were added to the cells in the 96-well plate. The cells were incubated with compound for 3 days in 5% $CO_2$ at 37° C. 20 μL of WST-1 was added to each well. The plates were incubated for two hours in 5% $CO_2$ at 37° C. The plates were read on a Victor 2 multilabel plate reader (Perkin Elmer) at 450 nm. $IC_{50}$ values were calculated compared to the DMSO control.

Heteroaryl Compounds have, or are expected to have, an $IC_{50}$ below 30 μM in this assay, with some compounds having an $IC_{50}$ below 1 μM, and others having an $IC_{50}$ below 0.10 μM.

IL-2 Inflammation Assay.

The following is an example of an assay that can be used to determine the anti-inflammatory activity of a test compound. IL-2 production from stimulated primary T cells was assayed using the IL-2 kit from Mesoscale (MA6000#L41AHB-1). Human primary T cells were pre-treated with compound for 30 minutes and then stimulated with anti-human CD3 beads and anti CD28 beads for 24 hours. After cell treatment, the media was harvested. 25 μL of sample or calibration standard was added to human IL-2 cytokine Mesoscale Assay plate. The media was incubated for 1-2 hours with shaking at room temperature. The plates were washed three times with 1×PBS. 150 μL of 2×MSD Read buffer T was added per well and the plate was analyzed on Mesoscale Discovery Sector Imager plate reader.

Heteroaryl Compounds have, or are expected to have, an $IC_{50}$ below 30 μM in this assay, with some compounds having an $IC_{50}$ below 1 μM, and others having an $IC_{50}$ below 0.10 μM.

5.2.3 In Vivo Models

Delayed-Type Hypersensitivity (DTH) Model.

On day 0, CD-1 mice were sensitized using 3% oxazolone, painted on the shaved abdomen (sensitization). On day 5 the right ear was painted with 1% oxazolone and the left ear was painted with vehicle (acetone:olive oil) (elicitation). Compound treatment was started one day prior to the 1% oxazolone elicitation step. Compounds were administered either orally, intraperitoneally, or intravenously, using once or twice daily dosing for the duration of the study. On day 6 (24 hr post elicitation) the right ear of untreated animals showed redness (erythema) and swelling (edema). The ears of compound-treated animals were measured 24, 48 and 72 hr post elicitation. Differences between right and left ear thickness, indicating DTH development was determined by microcaliper measurements.

In this model, Heteroaryl Compounds have, or are expected to have, an $ED_{50}$ value of <100 mg/kg, with some compounds having an $ED_{50}$ of <10 mg/kg and others an $ED_{50}$ of <1 mg/kg.

Xenograft Cancer Model.

Human cancer cell lines were injected into SCID (severe combined immunodeficiency) mice. For cells maintained in vitro, tumors were generated by injecting precisely determined numbers of cells into mice. For tumors which were best propagated in vivo, tumor fragments from donor mice were implanted into small numbers of mice for maintenance, or larger numbers of mice for study initiation. A typical efficacy study design involved administering one or more compounds to tumor-bearing mice. Additionally, reference chemotherapeutic agents (positive control) and negative controls were similarly administered and maintained. Routes of administration can include subcutaneous (SC), intraperitoneal (IP), intravenous (IV), intramuscular (IM) and oral (PO). Tumor measurements and body weights were taken over the course of the study and morbidity and mortality were recorded. Necropsy, histopathology, bacteriology, parasitology, serology and PCR can also be performed to enhance understanding of disease and drug action.

Some of the typical human cancer cell lines that were or can be used in the above xenograft models are: the MDA MB-231, MCF7, MDA-MB-435, and T-47D cell lines for breast cancer; the KM 12, HCT-15, COLO 205, HCT 116 and HT29 cell lines for colon cancer; the NCI-H460 and A549 cell lines for lung cancer; the CRW22, LNCAP, PC-3, and DU-145 cell lines for prostate cancer; the LOX-IMVI and A375 cell lines for melanoma; the SK-O V-3 and A2780 cell lines for ovarian cancer; and the CAKI-I, A498, and SN12C cell lines for renal cancer; and U-87MG cell line for glioma cancer.

In short, SCID mice were dosed with compounds ranging from, for example, 100 mg/kg to 0.1 mg/kg with different dose scheduling, including, but not limited to, qd, q2d, q3d, q5d and bid. The compounds were formulated in, for example 0.5% CMC/0.25% Tween and delivered orally. The mice were dosed for 21 days and tumor volume measurements were taken every three days. Example Xenograft models tested included PC-3, HCT-116, A549, MDA MB-231 and U-87MG models.

In this model, Heteroaryl Compounds have, or are expected to have, an $ED_{50}$ value of <100 mg/kg, with some compounds having an $ED_{50}$ of <10 mg/kg and others an $ED_{50}$ of <1 mg/kg.

5.3 Heteroaryl Compound Activity

Each of the compounds in Table 1 was tested in the mTor HTR-FRET assay and was found to have activity therein, with all of the compounds having an $IC_{50}$ below 10 μM in the assay, with some compounds having an $IC_{50}$ between and 0.005 nM and 250 nM (Activity level D), others having an $IC_{50}$ between and 250 nM and 500 nM (Activity level C), others having an $IC_{50}$ between 500 nM and 1 μM (Activity level B), and others having an $IC_{50}$ between 1 μM and 10 μM (Activity level A).

TABLE 1

| Cmpd No. | Cmpd Structure | Cmpd Name | MS (ESI) m/z | Act. Level |
|---|---|---|---|---|
| 1 | 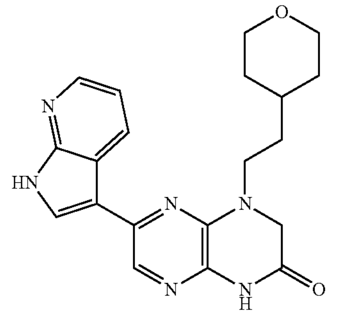 [SMILES: O=C1CN(CCC2CCOCC2)c2nc(-c3c[nH]c4ncccc34)cnc2N1] | 6-(1H-pyrrolo[2,3-b]pyridin-3-yl)-4-(2-(tetrahydro-2H-pyran-4-yl)ethyl)-3,4-dihydropyrazino[2,3-b]pyrazin-2(1H)-one | 379.3 $[M + 1]^+$ | D |
| 2 | 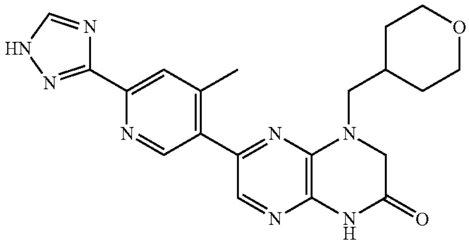 [SMILES: Cc1cc(-c2nc[nH]n2)ncc1-c1cnc2c(n1)N(CC1CCOCC1)CC(=O)N2] | 6-(4-methyl-6-(1H-1,2,4-triazol-3-yl)pyridin-3-yl)-4-((tetrahydro-2H-pyran-4-yl)methyl)-3,4-dihydropyrazino[2,3-b]pyrazin-2(1H)-one | 407.1 $[M + 1]^+$ | D |
| 3 | 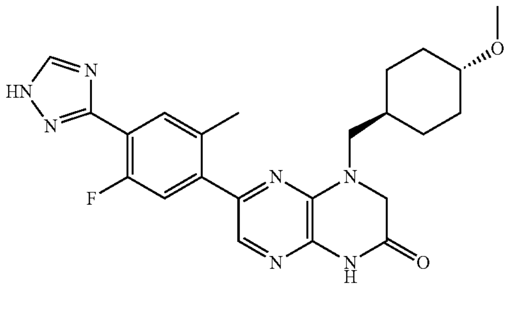 [SMILES: CO[C@H]1CC[C@H](CN2CC(=O)Nc3ncc(-c4cc(F)c(-c5nc[nH]n5)cc4C)nc32)CC1] | 6-(5-fluoro-2-metyl-4-(1H-1,2,4-triazol-3-yl)phenyl)-4-((trans-4-methoxycyclohexyl)methyl)-3,4-dihydropyrazino[2,3-b]pyrazin-2(1H)-one | 452.2 $[M + 1]^+$ | D |

TABLE 1-continued

| Cmpd No. | Cmpd Structure | Cmpd Name | MS (ESI) m/z | Act. Level |
|---|---|---|---|---|
| 4 | 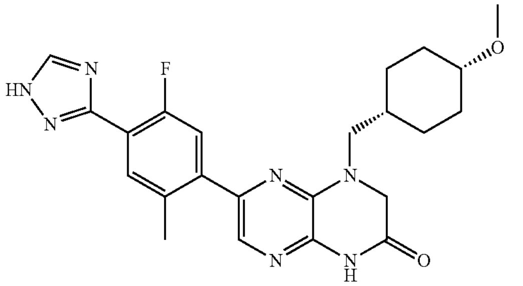 [SMILES: CO[C@H]1CC[C@@H](CN2CC(=O)Nc3ncc(-c4cc(F)c(-c5nc[nH]n5)cc4C)nc32)CC1] | 6-(5-fluoro-2-methyl-4-(1H-1,2,4-triazol-3-yl)phenyl)-4-((cis-4-methoxycyclohexyl)methyl)-3,4-dihydropyrazino[2,3-b]pyrazin-2(1H)-one | 452.2 $[M + 1]^+$ | D |
| 5 | 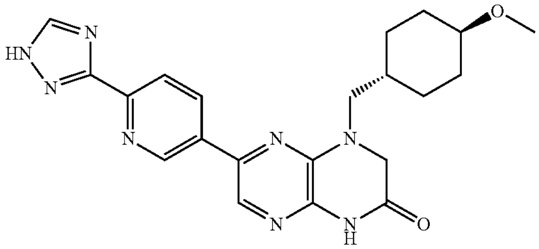 [SMILES: CO[C@H]1CC[C@H](CN2CC(=O)Nc3ncc(-c4ccc(-c5nc[nH]n5)nc4)nc32)CC1] | 6-(6-(1H-1,2,4-triazol-3-yl)pyridin-3-yl)-4-((trans-4-methoxycyclohexyl)methyl)-3,4-dihydropyrazino[2,3-b]pyrazin-2(1H)-one | 421.3 $[M + 1]^+$ | D |
| 6 | 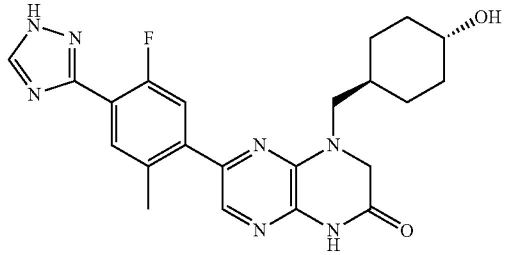 [SMILES: Cc1cc(-c2nc[nH]n2)c(F)cc1-c1cnc2c(n1)N(C[C@H]1CC[C@H](O)CC1)CC(=O)N2] | 6-(5-fluoro-2-methyl-4-(1H-1,2,4-triazol-3-yl)phenyl)-4-((trans-4-hydroxycyclohexyl)methyl)-3,4-dihydropyrazino[2,3-b]pyrazin-2(1H)-one | 438.1 $[M + 1]^+$ | D |
| 7 | 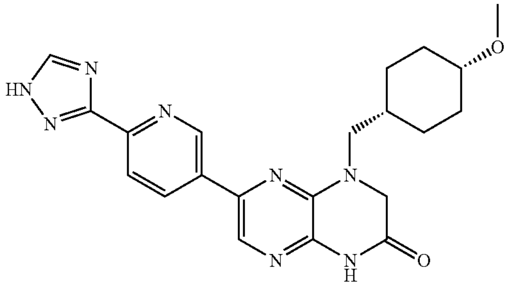 [SMILES: CO[C@H]1CC[C@@H](CN2CC(=O)Nc3ncc(-c4ccc(-c5nc[nH]n5)nc4)nc32)CC1] | 6-(6-(1H-1,2,4-triazol-3-yl)pyridin-3-yl)-4-((cis-4-methoxycyclohexyl)methyl)-3,4-dihydropyrazino[2,3-b]pyrazin-2(1H)-one | 421.2 $[M + 1]^+$ | D |
| 8 | 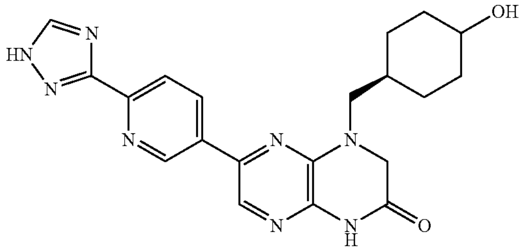 | 6-(6-(1H-1,2,4-triazol-3-yl)pyridin-3-yl)-4-((trans-4-hydroxycyclohexyl)methyl)-3,4-dihydropyrazino[2,3-b]pyrazin-2(1H)-one | 407.1 $[M + 1]^+$ | D |

TABLE 1-continued

| Cmpd No. | Cmpd Structure | Cmpd Name | MS (ESI) m/z | Act. Level |
|---|---|---|---|---|
| 9 | 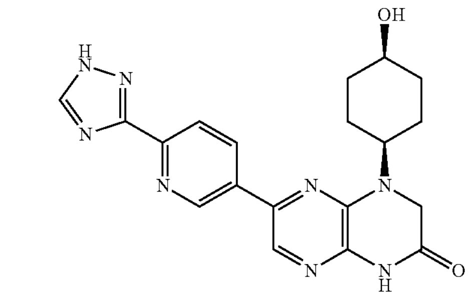 [SMILES: O=C1CN([C@H]2CC[C@@H](O)CC2)c2nc(-c3ccc(-c4nc[nH]n4)nc3)cnc2N1] | 6-(6-(1H-1,2,4-triazol-3-yl)pyridin-3-yl)-4-(cis-4-hydroxycyclohexyl)-3,4-dihydropyrazino[2,3-b]pyrazin-2(1H)-one | 393.2 $[M + 1]^+$ | D |
| 10 | 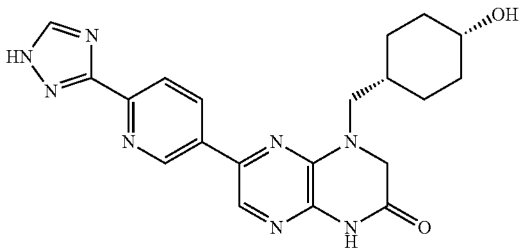 [SMILES: O=C1CN(C[C@H]2CC[C@@H](O)CC2)c2nc(-c3ccc(-c4nc[nH]n4)nc3)cnc2N1] | 6-(6-(1H-1,2,4-triazol-3-yl)pyridin-3-yl)-4-((cis-4-hydroxycyclohexyl)methyl)-3,4-dihydropyrazino[2,3-b]pyrazin-2(1H)-one | 407.3 $[M + 1]^+$ | D |
| 11 | 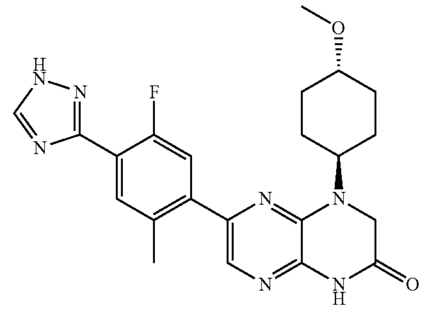 [SMILES: CO[C@H]1CC[C@H](N2CC(=O)Nc3ncc(-c4cc(F)c(-c5nc[nH]n5)cc4C)nc32)CC1] | 6-(5-fluoro-2-methyl-4-(1H-1,2,4-triazol-3-yl)phenyl)-4-(trans-4-methoxycyclohexyl)-3,4-dihydropyrazino[2,3-b]pyrazin-2(1H)-one | 438.2 $[M + 1]^+$ | D |
| 12 | 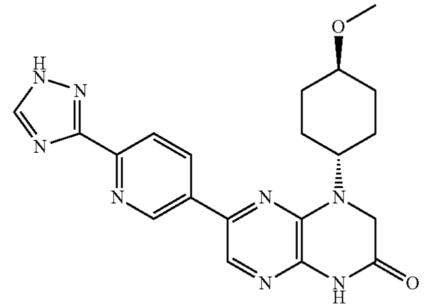 [SMILES: CO[C@H]1CC[C@H](N2CC(=O)Nc3ncc(-c4ccc(-c5nc[nH]n5)nc4)nc32)CC1] | 6-(6-(1H-1,2,4-triazol-3-yl)pyridin-3-yl)-4-(trans-4-methoxycyclohexyl)-3,4-dihydropyrazino[2,3-b]pyrazin-2(1H)-one | 407.2 $[M + 1]^+$ | D |
| 13 | 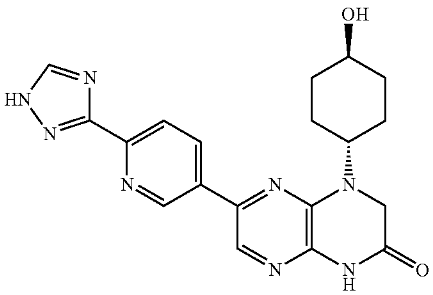 [SMILES: O=C1CN([C@H]2CC[C@H](O)CC2)c2nc(-c3ccc(-c4nc[nH]n4)nc3)cnc2N1] | 6-(6-(1H-1,2,4-triazol-3-yl)pyridin-3-yl)-4-(trans-4-hydroxycyclohexyl)-3,4-dihydropyrazino[2,3-b]pyrazin-2(1H)-one | 393.2 $[M + 1]^+$ | D |

TABLE 1-continued

| Cmpd No. | Cmpd Structure | Cmpd Name | MS (ESI) m/z | Act. Level |
|---|---|---|---|---|
| 14 | 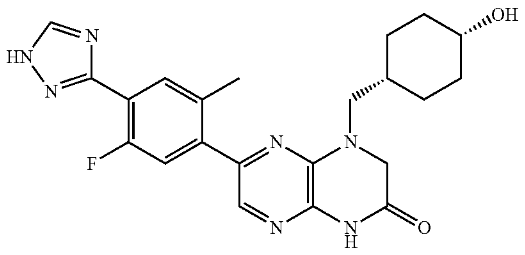 [SMILES: Cc1cc(-c2nc[nH]n2)c(F)cc1-c1cnc2c(n1)N(C[C@H]1CC[C@@H](O)CC1)CC(=O)N2] | 6-(5-fluoro-2-methyl-4-(1H-1,2,4-triazol-3-yl)phenyl)-4-((cis-4-hydroxycyclohexyl)methyl)-3,4-dihydropyrazino[2,3-b]pyrazin-2(1H)-one | 438.2 $[M + 1]^+$ | D |
| 15 | 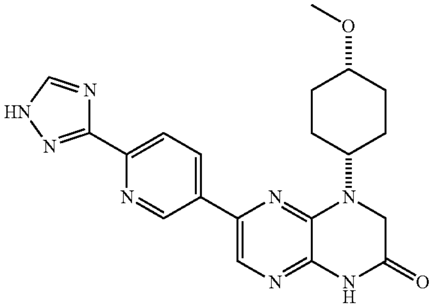 [SMILES: CO[C@H]1CC[C@@H](N2CC(=O)Nc3ncc(-c4ccc(-c5nc[nH]n5)nc4)nc32)CC1] | 6-(6-(1H-,1,2,4-triazol-3-yl)pyridin-3-yl)-4-(cis-4-methoxycyclohexyl)-3,4-dihydropyrazino[2,3-b]pyrazin-2(1H)-one | 407.3 $[M + 1]^+$ | D |
| 16 | 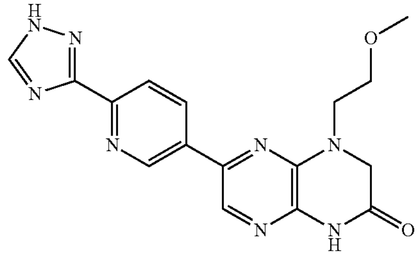 [SMILES: COCCN1CC(=O)Nc2ncc(-c3ccc(-c4nc[nH]n4)nc3)nc21] | 6-(6-(1H,1,2,4-triazol-3-yl)pyridin-3-yl)-4-(2-methoxyethyl)-3,4-dihydropyrazino[2,3-b]pyrazin-2(1H)-one | 353.2 $[M + 1]^+$ | D |
| 17 | 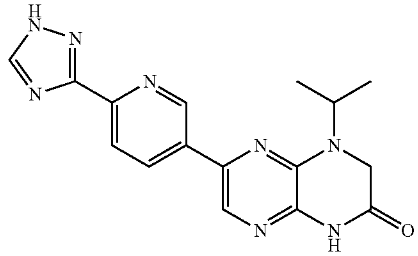 [SMILES: CC(C)N1CC(=O)Nc2ncc(-c3ccc(-c4nc[nH]n4)nc3)nc21] | 6-(6-(1H-1,2,4-triazol-3-yl)pyridin-3-yl)-4-isopropyl-3,4-dihydropyrazino[2,3-b]pyrazin-2(1H)-one | 337.1 $[M + 1]^+$ | D |
| 18 | 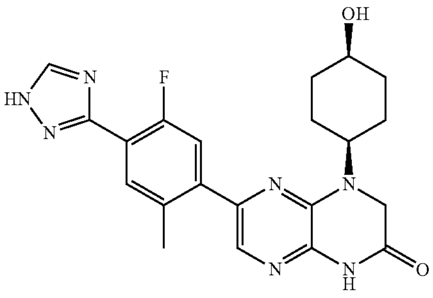 [SMILES: Cc1cc(-c2nc[nH]n2)c(F)cc1-c1cnc2c(n1)N([C@H]1CC[C@@H](O)CC1)CC(=O)N2] | 6-(5-fluoro-2-methyl-4-(1H-1,2,4-triazol-3-yl)phenyl)-4-(cis-4-hydroxycyclohexyl)-3,4-dihydropyrazino[2,3-b]pyrazin-2(1H)-one | 424.2 $[M + 1]^+$ | D |

TABLE 1-continued

| Cmpd No. | Cmpd Structure | Cmpd Name | MS (ESI) m/z | Act. Level |
|---|---|---|---|---|
| 19 | 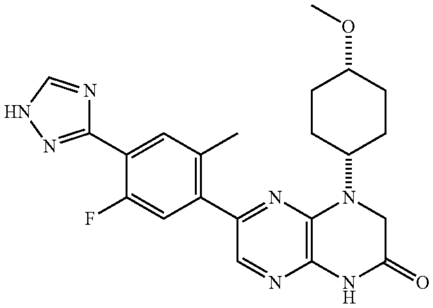 [SMILES: CO[C@H]1CC[C@@H](N2CC(=O)Nc3ncc(-c4cc(F)c(-c5nc[nH]n5)cc4C)nc32)CC1] | 6-(5-fluoro-2-methyl-4-(1H-1,2,4-triazol-3-yl)phenyl)-4-(cis-4-methoxycyclohexyl)-3,4-dihydropyrazino[2,3-b]pyrazin-2(1H)-one | 438.3 $[M + 1]^+$ | D |
| 20 | 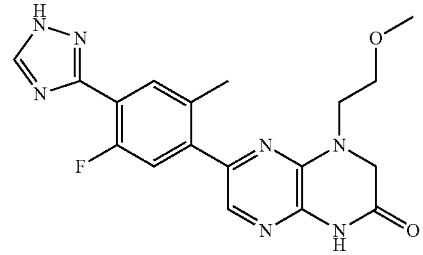 [SMILES: COCCN1CC(=O)Nc2ncc(-c3cc(F)c(-c4nc[nH]n4)cc3C)nc21] | 6-(5-fluoro-2-methyl-4-(1H-1,2,4-triazol-3-yl)phenyl)-4-(2-methoxyethyl)-3,4-dihydropyrazino[2,3-b]pyrazin-2(1H)-one | 384.2 $[M + 1]^+$ | D |
| 21 | 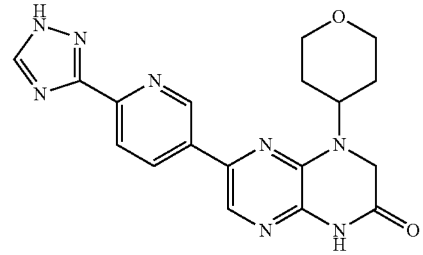 [SMILES: O=C1CN(C2CCOCC2)c2nc(-c3ccc(-c4nc[nH]n4)nc3)cnc2N1] | 6-(6-(1H-1,2,4-triazol-3-yl)pyridin-3-yl)-4-(tetrahydro-2H-pyran-4-yl)-3,4-dihydropyrazino[2,3-b]pyrazin-2(1H)-one | 379.1 $[M + 1]^+$ | D |
| 22 | 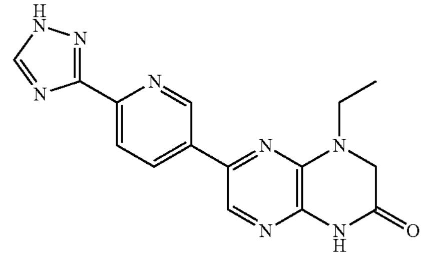 [SMILES: CCN1CC(=O)Nc2ncc(-c3ccc(-c4nc[nH]n4)nc3)nc21] | 6-(6-(1H-1,2,4-triazol-3-yl)pyridin-3-yl)-4-ethyl-3,4-dihydropyrazino[2,3-b]pyrazin-2(1H)-one | 323.1 $[M + 1]^+$ | D |
| 23 | 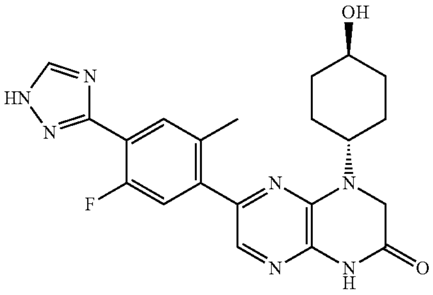 [SMILES: Cc1cc(-c2nc[nH]n2)c(F)cc1-c1cnc2c(n1)N([C@H]1CC[C@H](O)CC1)CC(=O)N2] | 6-(5-fluoro-2-methyl-4-(1H-1,2,4-triazol-3-yl)phenyl)-4-(trans-4-hydroxycyclohexyl)-3,4-dihydropyrazino[2,3-b]pyrazin-2(1H)-one | 424.2 $[M + 1]^+$ | D |

TABLE 1-continued

| Cmpd No. | Cmpd Structure | Cmpd Name | MS (ESI) m/z | Act. Level |
|---|---|---|---|---|
| 24 | 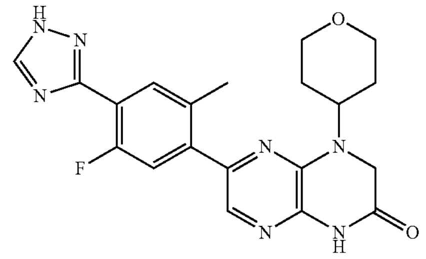 [SMILES: Cc1cc(-c2nc[nH]n2)c(F)cc1-c1cnc2c(n1)N(C1CCOCC1)CC(=O)N2] | 6-(5-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one | 410.1 [M + 1]+ | D |
| 25 | 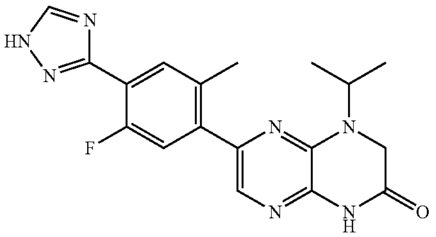 [SMILES: Cc1cc(-c2nc[nH]n2)c(F)cc1-c1cnc2c(n1)N(C(C)C)CC(=O)N2] | 6-(5-fluoro-2-methyl-4-(1H-1,2,4-triazol-3-yl)phenyl)-4-isopropyl-3,4-dihydropyrazino[2,3-b]pyrazin-2(1H)-one | 368.1 [M + 1]+ | D |
| 26 | 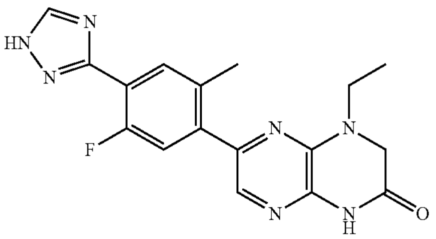 [SMILES: CCN1CC(=O)Nc2ncc(-c3cc(F)c(-c4nc[nH]n4)cc3C)nc21] | 4-ethyl-6-(5-fluoro-2-methyl-4-(1H-1,2,4-triazol-3-yl)phenyl)-3,4-dihydropyrazino[2,3-b]pyrazin-2(1H)-one | 354.2 [M + 1]+ | D |
| 27 | 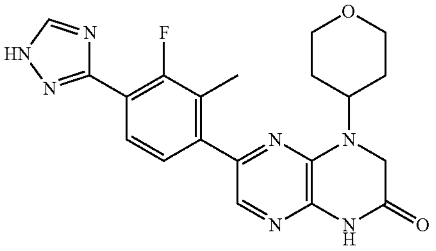 [SMILES: Cc1c(-c2cnc3c(n2)N(C2CCOCC2)CC(=O)N3)ccc(-c2nc[nH]n2)c1F] | 6-(3-fluoro-2-methyl-4-(1H-1,2,4-triazol-3-yl)phenyl)-4-(tetrahydro-2H-pyran-4-yl)-3,4-dihydropyrazino[2,3-b]pyrazin-2(1H)-one | 409.7 [M + 1]+ | D |
| 28 | 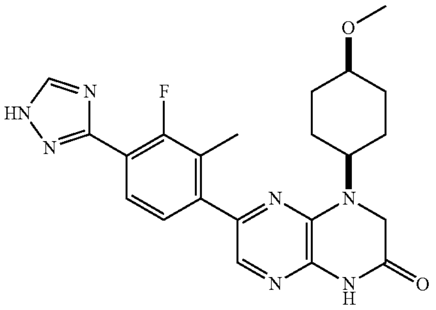 [SMILES: CO[C@H]1CC[C@@H](N2CC(=O)Nc3ncc(-c4ccc(-c5nc[nH]n5)c(F)c4C)nc32)CC1] | 6-(3-fluoro-2-methyl-4-(1H-1,2,4-triazol-3-yl)phenyl)-4-(cis-4-methoxycyclohexyl)-3,4-dihydropyrazino[2,3-b]pyrazin-2(1H)-one | 437.7 [M + 1]+ | D |

TABLE 1-continued

| Cmpd No. | Cmpd Structure | Cmpd Name | MS (ESI) m/z | Act. Level |
|---|---|---|---|---|
| 29 | 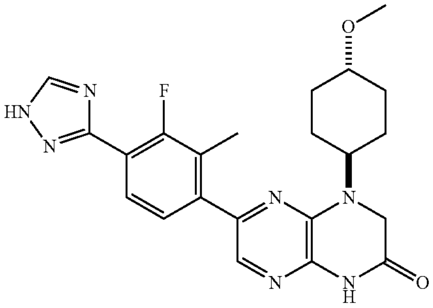 | 6-(3-fluoro-2-methyl-4-(1H-1,2,4-triazol-3-yl)phenyl)-4-(trans-4-methoxycyclohexyl)-3,4-dihydropyrazino[2,3-b]pyrazin-2(1H)-one | 438.0 $[M + 1]^+$ | D |
| 30 | 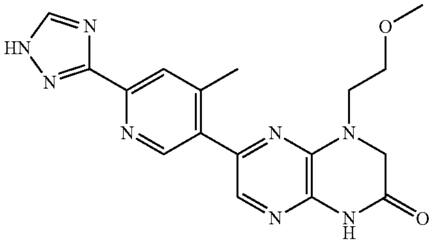 [SMILES: COCCN1CC(=O)Nc2ncc(-c3cnc(-c4nc[nH]n4)cc3C)nc21] | 4-(2-methoxyethyl)-6-(4-methyl-6-(1H-1,2,4-triazol-3-yl)pyridin-3-yl)-3,4-dihydropyrazino[2,3-b]pyrazin-2(1H)-one | 367.4 $[M + 1]^+$ | D |
| 31 | 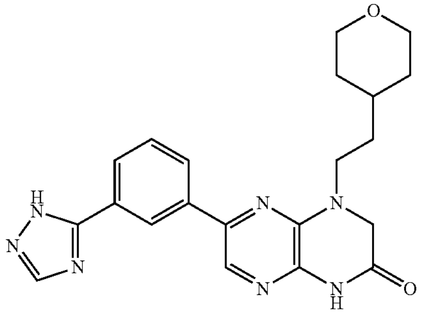 [SMILES: O=C1CN(CCC2CCOCC2)c2nc(-c3cccc(-c4ncn[nH]4)c3)cnc2N1] | 6-(3-(1H-1,2,4-triazol-5-yl)phenyl)-4-(2-(tetrahydro-2H-pyran-4-yl)ethyl)-3,4-dihydropyrazino[2,3-b]pyrazin-2(1H)-one | 406.2 $[M + 1]^+$ | A |
| 32 | 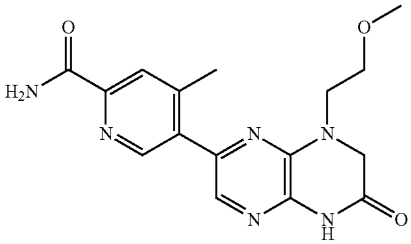 | 5-(8-(2-methoxyethyl)-6-oxo-5,6,7,8-tetrahydropyrazino[2,3-b]pyrazin-2-yl)-4-methylpicolinamide | 397.4 $[M + 1]^+$ | D |
| 33 | 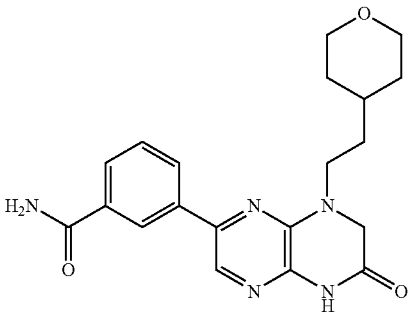 [SMILES: NC(=O)c1cccc(-c2cnc3c(n2)N(CCC2CCOCC2)CC(=O)N3)c1] | 3-(6-oxo-8-(2-(tetrahydro-2H-pyran-4-yl)ethyl)-5,6,7,8-tetrahydropyrazino[2,3-b]pyrazin-2-yl)benzamide | 382.1 $[M + 1]^+$ | B |

TABLE 1-continued

| Cmpd No. | Cmpd Structure | Cmpd Name | MS (ESI) m/z | Act. Level |
|---|---|---|---|---|
| 34 | 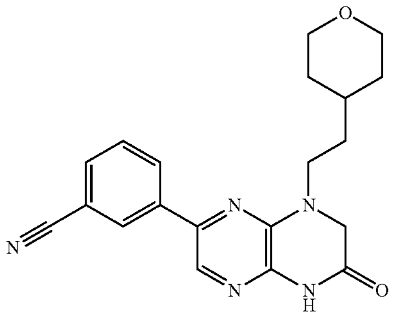 [SMILES: N#Cc1cccc(-c2cnc3c(n2)N(CCC2CCOCC2)CC(=O)N3)c1] | 3-(6-oxo-8-(2-(tetrahydro-2H-pyran-4-yl)ethyl)-5,6,7,8-tetrahydropyrazino[2,3-b]pyrazin-2-yl)benzonitrile | 364.8 $[M + 1]^+$ | B |
| 35 | 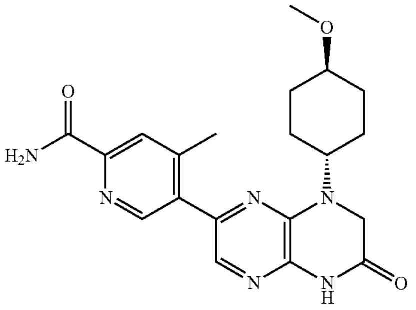 [SMILES: CO[C@H]1CC[C@H](N2CC(=O)Nc3ncc(-c4cnc(C(N)=O)cc4C)nc32)CC1] | 5-(8-(trans-4-methoxycyclohexyl)-6-oxo-5,6,7,8-tetrahydropyrazino[2,3-b]pyrazin-2-yl)-4-methylpicolinamide | 397.4 $[M + 1]^+$ | D |
| 36 | 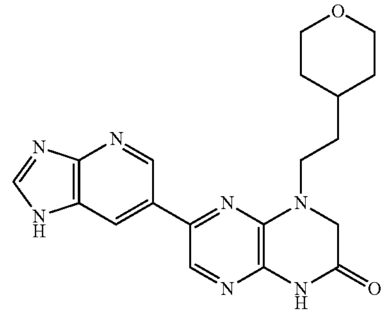 [SMILES: O=C1CN(CCC2CCOCC2)c2nc(-c3cnc4nc[nH]c4c3)cnc2N1] | 6-(1H-imidazo[4,5-b]pyridin-6-yl)-4-(2-(tetrahydro-2H-pyran-4-yl)ethyl)-3,4-dihydropyrazino[2,3-b]pyrazin-2(1H)-one | 380.2 $[M + 1]^+$ | B |
| 37 | 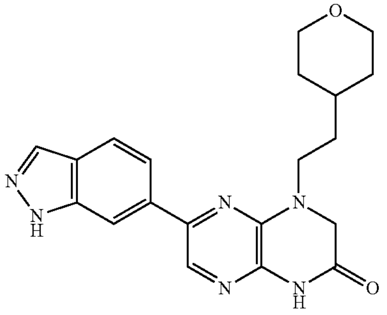 [SMILES: O=C1CN(CCC2CCOCC2)c2nc(-c3ccc4cn[nH]c4c3)cnc2N1] | 6-(1H-indazol-6-yl)-4-(2-(tetrahydro-2H-pyran-4-yl)ethyl)-3,4-dihydropyrazino[2,3-b]pyrazin-2(1H)-one | 379.5 $[M + 1]^+$ | A |
| 38 | 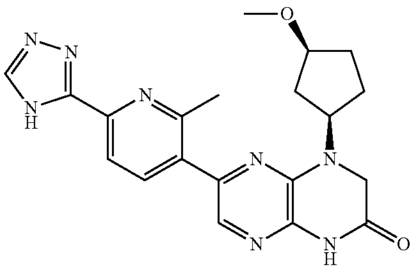 [SMILES: CO[C@H]1CC[C@@H](N2CC(=O)Nc3ncc(-c4ccc(-c5nnc[nH]5)nc4C)nc32)C1] | 4-((1R,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one | 407.3 $[M + 1]^+$ | D |

TABLE 1-continued

| Cmpd No. | Cmpd Structure | Cmpd Name | MS (ESI) m/z | Act. Level |
|---|---|---|---|---|
| 39 | 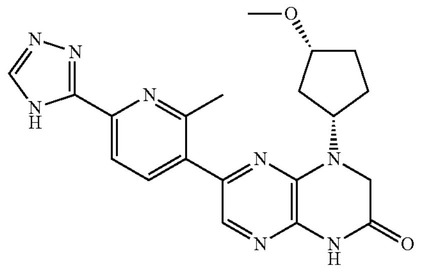 [SMILES: CO[C@@H]1CC[C@H](N2CC(=O)Nc3ncc(-c4ccc(-c5nnc[nH]5)nc4C)nc32)C1] | 4-((1S,3R)-3-methoxycyclopentyl)-6-(2-methyl-6-(4H-1,2,4-triazol-3-yl)pyridin-3-yl)-3,4-dihydropyrazino[2,3-b]pyrazin-2(1H)-one | 407.3 $[M + 1]^+$ | D |
| 40 | 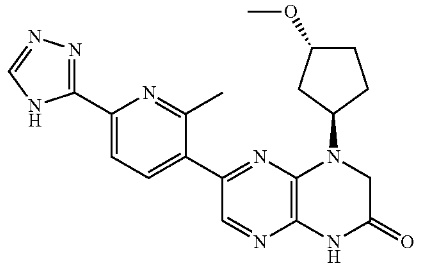 [SMILES: CO[C@@H]1CC[C@@H](N2CC(=O)Nc3ncc(-c4ccc(-c5nnc[nH]5)nc4C)nc32)C1] | 4-((1R,3R)-3-methoxycylopentyl)-6-(2-methyl-6-(4H-1,2,4-triazol-3-yl)pyridin-3-yl)-3,4-dihydropyrazino[2,3-b]pyrazin-2(1H)-one | 407.3 $[M + 1]^+$ | D |
| 41 | 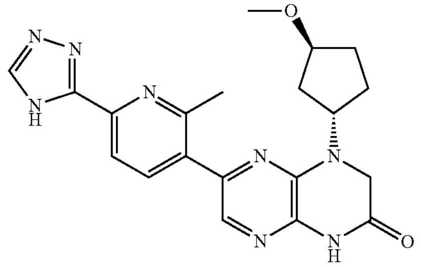 [SMILES: CO[C@H]1CC[C@H](N2CC(=O)Nc3ncc(-c4ccc(-c5nnc[nH]5)nc4C)nc32)C1] | 4-((1S,3S)-3-methoxycyclopentyl)-6-(2-methyl-6-(4H-1,2,4-triazol-3-yl)pyridin-3-yl)-3,4-dihydropyrazino[2,3-b]pyrazin-2(1H)-one | 407.3 $[M + 1]^+$ | D |
| 42 | 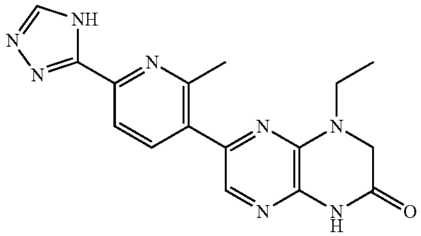 [SMILES: CCN1CC(=O)Nc2ncc(-c3ccc(-c4nnc[nH]4)nc3C)nc21] | 4-ethyl-6-(2-methyl-6-(4H-1,2,4-triazol-3-yl)pyridin-3-yl)-3,4-dihydropyrazino[2,3-b]pyrazin-2(1H)-one | 337.7 $[M + 1]^+$ | D |
| 43 | 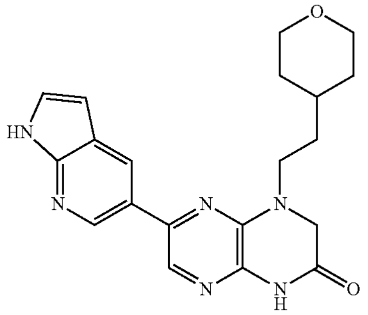 [SMILES: O=C1CN(CCC2CCOCC2)c2nc(-c3cnc4[nH]ccc4c3)cnc2N1] | 6-(1H-pyrrolo[2,3-b]pyridin-5-yl)-4-(2-(tetrahydro-2H-pyran-4-yl)ethyl)-3,4-dihydropyrazino[2,3-b]pyrazin-2(1H)-one | 379.2 $[M + 1]^+$ | D |

TABLE 1-continued

| Cmpd No. | Cmpd Structure | Cmpd Name | MS (ESI) m/z | Act. Level |
|---|---|---|---|---|
| 44 | 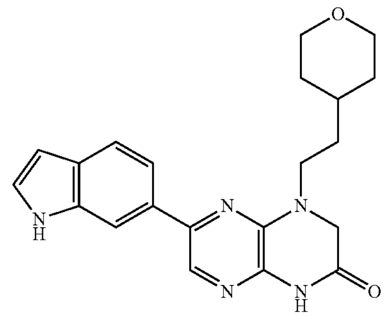 [SMILES: O=C1CN(CCC2CCOCC2)c2nc(-c3ccc4cc[nH]c4c3)cnc2N1] | 6-(1H-indol-6-yl)-4-(2-(tetrahydro-2H-pyran-4-yl)ethyl)-3,4-dihydropyrazino[2,3-b]pyrazin-2(1H)-one | 378.1 [M + 1]+ | C |
| 45 | 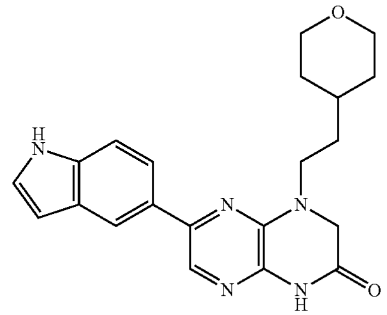 [SMILES: O=C1CN(CCC2CCOCC2)c2nc(-c3ccc4[nH]ccc4c3)cnc2N1] | 6-(1H-indol-5-yl)-4-(2-(tetrahydro-2H-pyran-4-yl)ethyl)-3,4-dihydropyrazino[2,3-b]pyrazin-2(1H)-one | 378.1 [M + 1]+ | D |
| 46 | 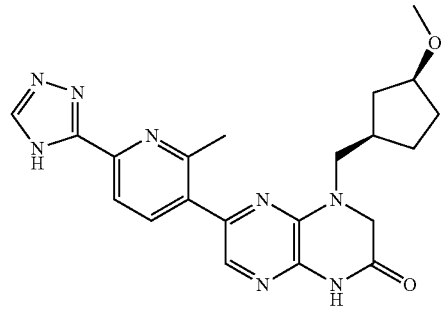 [SMILES: CO[C@H]1CC[C@@H](CN2CC(=O)Nc3ncc(-c4ccc(-c5nnc[nH]5)nc4C)nc32)C1] | 4-(((1R,3S)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one | 421.2 [M + 1]+ | D |
| 47 | 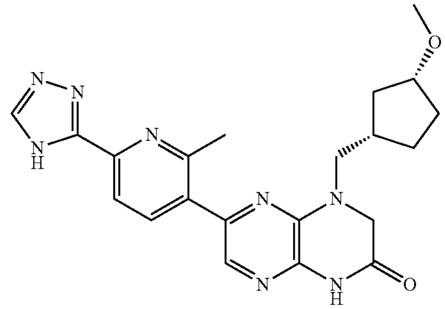 [SMILES: CO[C@@H]1CC[C@H](CN2CC(=O)Nc3ncc(-c4ccc(-c5nnc[nH]5)nc4C)nc32)C1] | 4-(((1S,3R)-3-methoxycyclopentyl)methyl)-6-(2-methyl-6-(4H-1,2,4-triazol-3-yl)pyridin-3-yl)-3,4-dihydropyrazino[2,3-b]pyrazin-2(1H)-one | 421.2 [M + 1]+ | D |
| 48 | 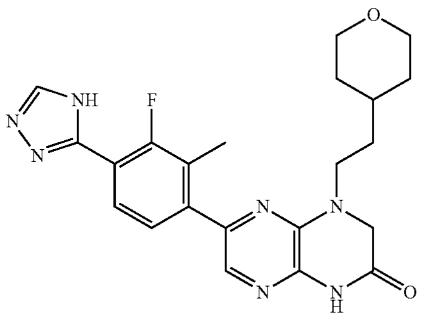 [SMILES: Cc1c(-c2cnc3c(n2)N(CCC2CCOCC2)CC(=O)N3)ccc(-c2nnc[nH]2)c1F] | 6-(3-fluoro-2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one | 438.3 [M + 1]+ | D |

TABLE 1-continued

| Cmpd No. | Cmpd Structure | Cmpd Name | MS (ESI) m/z | Act. Level |
|---|---|---|---|---|
| 49 | 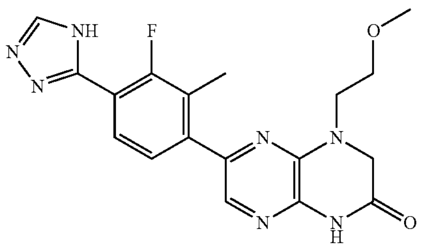 [SMILES: COCCN1CC(=O)Nc2ncc(-c3ccc(-c4nnc[nH]4)c(F)c3C)nc21] | 6-(3-fluoro-2-methyl-4-(4H-1,2,4-triazol-3-yl)phenyl)-4-(2-methoxyethyl)-3,4-dihydropyrazino[2,3-b]pyrazin-2(1H)-one | 384.3 $[M + 1]^+$ | D |
| 50 | 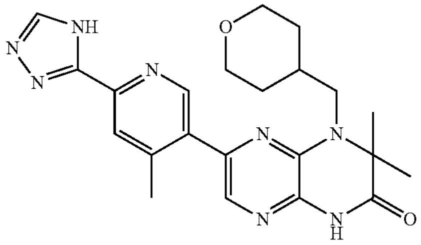 [SMILES: Cc1cc(-c2nnc[nH]2)ncc1-c1cnc2c(n1)N(CC1CCOCC1)C(C)(C)C(=O)N2] | 3,3-dimethyl-6-(4-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one | 435.3 $[M + 1]^+$ | D |
| 51 | 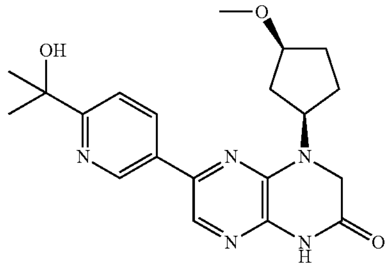 [SMILES: CO[C@H]1CC[C@@H](N2CC(=O)Nc3ncc(-c4ccc(C(C)(C)O)nc4)nc32)C1] | 6-(6-(2-hydroxypropan-2-yl)pyridin-3-yl)-4-((1R,3S)-3-methoxycyclopentyl)-3,4-dihydropyrazino[2,3-b]pyrazin-2(1H)-one | 384.3 $[M + 1]^+$ | D |
| 52 | 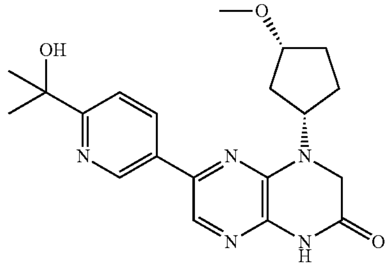 [SMILES: CO[C@@H]1CC[C@H](N2CC(=O)Nc3ncc(-c4ccc(C(C)(C)O)nc4)nc32)C1] | 6-(6-(2-hydroxypropan-2-yl)pyridin-3-yl)-4-((1S,3R)-3-methoxycyclopentyl)-3,4-dihydropyrazino[2,3-b]pyrazin-2(1H)-one | 384.3 $[M + 1]^+$ | D |
| 53 | 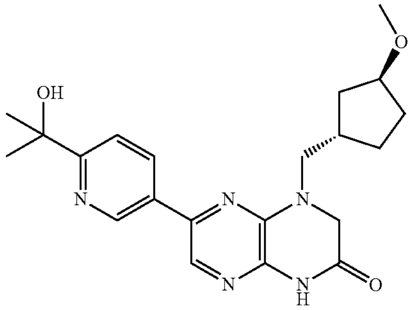 [SMILES: CO[C@H]1CC[C@H](CN2CC(=O)Nc3ncc(-c4ccc(C(C)(C)O)nc4)nc32)C1] | 6-(6-(2-hydroxypropan-2-yl)pyridin-3-yl)-4-(((1S,3S)-3-methoxycyclopentyl)methyl)-3,4-dihydropyrazino[2,3-b]pyrazin-2(1H)-one | 398.3 $[M + 1]^+$ | D |

TABLE 1-continued

| Cmpd No. | Cmpd Structure | Cmpd Name | MS (ESI) m/z | Act. Level |
|---|---|---|---|---|
| 54 | 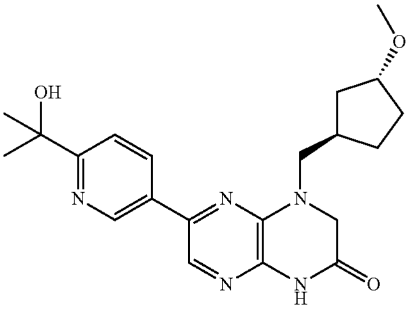 [SMILES: CO[C@@H]1CC[C@@H](CN2CC(=O)Nc3ncc(-c4ccc(C(C)(C)O)nc4)nc32)C1] | 6-(6-(2-hydroxypropan-2-yl)pyridin-3-yl)-4-(((1R,3R)-3-methoxycyclopentyl)methyl)-3,4-dihydropyrazino[2,3-b]pyrazin-2(1H)-one | 398.3 $[M + 1]^+$ | D |
| 55 | 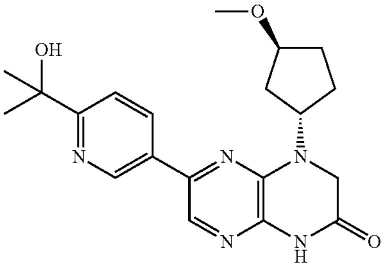 [SMILES: CO[C@H]1CC[C@H](N2CC(=O)Nc3ncc(-c4ccc(C(C)(C)O)nc4)nc32)C1] | 6-(6-(2-hydroxypropan-2-yl)pyridin-3-yl)-4-((1S,3S)-3-methoxycyclopentyl)-3,4-dihydropyrazino[2,3-b]pyrazin-2(1H)-one | 384.3 $[M + 1]^+$ | A |
| 56 | 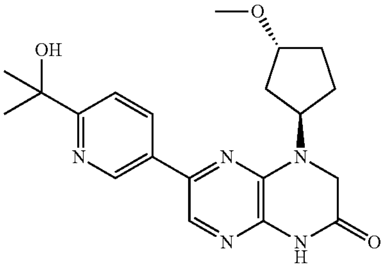 [SMILES: CO[C@@H]1CC[C@@H](N2CC(=O)Nc3ncc(-c4ccc(C(C)(C)O)nc4)nc32)C1] | 6-(6-(2-hydroxypropan-2-yl)pyridin-3-yl)-4-((1R,3R)-3-methoxycyclopentyl)-3,4-dihydropyrazino[2,3-b]pyrazin-2(1H)-one | 384.3 $[M + 1]^+$ | D |
| 57 | 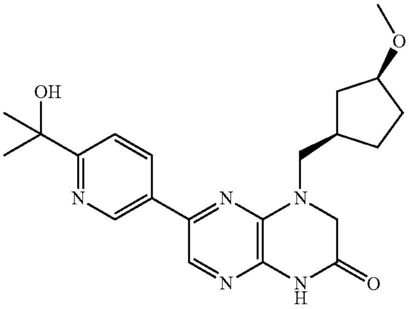 [SMILES: CO[C@H]1CC[C@@H](CN2CC(=O)Nc3ncc(-c4ccc(C(C)(C)O)nc4)nc32)C1] | 6-(6-(2-hydroxypropan-2-yl)pyridin-3-yl)-4-(((1R,3S)-3-methoxycyclopentyl)methyl)-3,4-dihydropyrazino[2,3-b]pyrazin-2(1H)-one | 398.3 $[M + 1]^+$ | D |
| 58 | 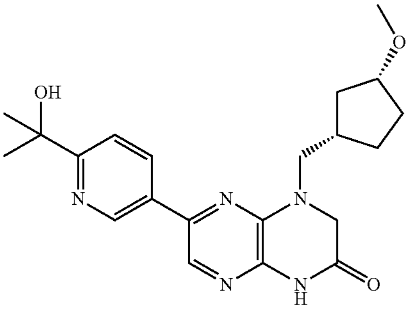 [SMILES: CO[C@@H]1CC[C@H](CN2CC(=O)Nc3ncc(-c4ccc(C(C)(C)O)nc4)nc32)C1] | 6-(6-(2-hydroxypropan-2-yl)pyridin-3-yl)-4-(((1S,3R)-3-methoxycyclopentyl)methyl)-3,4-dihydropyrazino[2,3-b]pyrazin-2(1H)-one | 398.3 $[M + 1]^+$ | D |

TABLE 1-continued

| Cmpd No. | Cmpd Structure | Cmpd Name | MS (ESI) m/z | Act. Level |
|---|---|---|---|---|
| 59 | 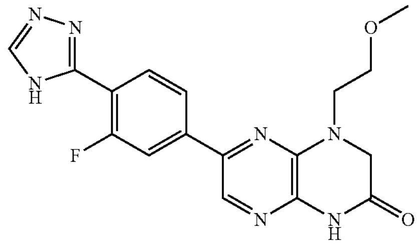 [SMILES: COCCN1CC(=O)Nc2ncc(-c3ccc(-c4nnc[nH]4)c(F)c3)nc21] | 6-(3-fluoro-4-(4H-1,2,4-triazol-3-yl)phenyl)-4-(2-methoxyethyl)-3,4-dihydropyrazino[2,3-b]pyrazin-2(1H)-one | 370.2 $[M + 1]^+$ | D |
| 60 | 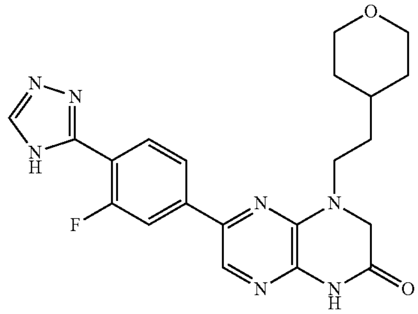 [SMILES: O=C1CN(CCC2CCOCC2)c2nc(-c3ccc(-c4nnc[nH]4)c(F)c3)cnc2N1] | 6-(3-fluoro-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one | 424.3 $[M + 1]^+$ | D |
| 61 | 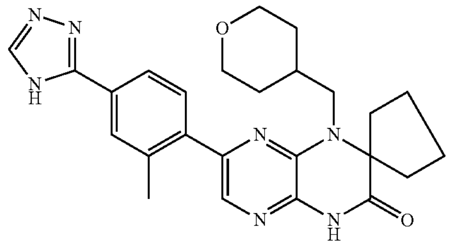 [SMILES: Cc1cc(-c2nnc[nH]2)ccc1-c1cnc2c(n1)N(CC1CCOCC1)C1(CCCC1)C(=O)N2] | 7'-(2-methyl-4-(4H-1,2,4-triazol-3-yl)phenyl)-1'-((tetrahydro-2H-pyran-4-yl)methyl)-1'H-spiro[cyclopentane-1,2'-pyrazino[2,3-b]pyrazin]-3'(4'H)-one | 460.4 $[M + 1]^+$ | D |
| 62 | 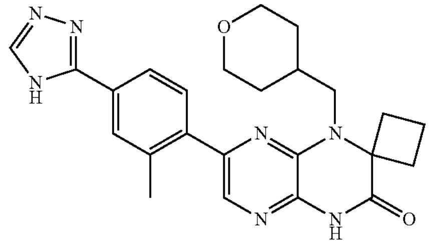 [SMILES: Cc1cc(-c2nnc[nH]2)ccc1-c1cnc2c(n1)N(CC1CCOCC1)C1(CCC1)C(=O)N2] | 7'-(2-methyl-4-(4H-1,2,4-triazol-3-yl)phenyl)-1'-((tetrahydro-2H-pyran-4-yl)methyl)-1'H-spiro[cyclobutane-1,2'-pyrazino[2,3-b]pyrazin]-3'(4'H)-one | 446.4 $[M + 1]^+$ | D |
| 63 | 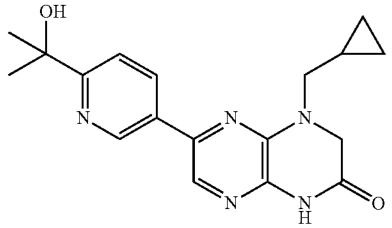 [SMILES: CC(C)(O)c1ccc(-c2cnc3c(n2)N(CC2CC2)CC(=O)N3)cn1] | 4-(cyclopropylmethyl)-6-(6-(2-hydroxypropan-2-yl)pyridin-3-yl)-3,4-dihydropyrazino[2,3-b]pyrazin-2(1H)-one | 340.2 $[M + 1]^+$ | C |
| 64 | 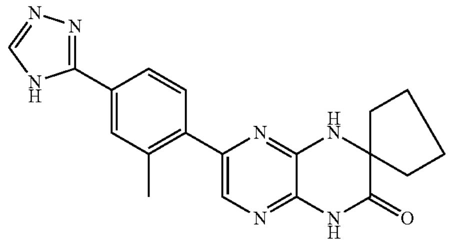 [SMILES: Cc1cc(-c2nnc[nH]2)ccc1-c1cnc2c(n1)NC1(CCCC1)C(=O)N2] | 7'-(2-methyl-4-(4H-1,2,4-triazol-3-yl)phenyl)-1'H-spiro[cyclopentane-1,2'-pyrazino[2,3-b]pyrazin]-3'(4'H)-one | 362.3 $[M + 1]^+$ | C |

TABLE 1-continued

| Cmpd No. | Cmpd Structure | Cmpd Name | MS (ESI) m/z | Act. Level |
|---|---|---|---|---|
| 65 | 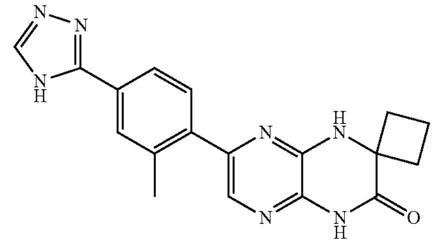 [SMILES: Cc1cc(-c2nnc[nH]2)ccc1-c1cnc2c(n1)NC1(CCC1)C(=O)N2] | 7'-(2-methyl-4-(4H-1,2,4-triazol-3-yl)phenyl)-1'H-spiro[cyclobutane-1,2'-pyrazino[2,3-b]pyrazin]-3'(4'H)-one | 348.2 [M + 1]+ | C |
| 66 | 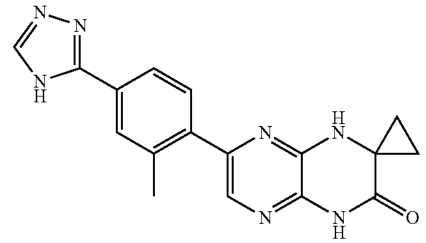 [SMILES: Cc1cc(-c2nnc[nH]2)ccc1-c1cnc2c(n1)NC1(CC1)C(=O)N2] | 7'-(2-methyl-4-(4H-1,2,4-triazol-3-yl)phenyl)-1'H-spiro[cyclopropane-1,2'-pyrazino[2,3-b]pyrazin]-3'(4'H)-one | 334.2 [M + 1]+ | D |
| 67 | 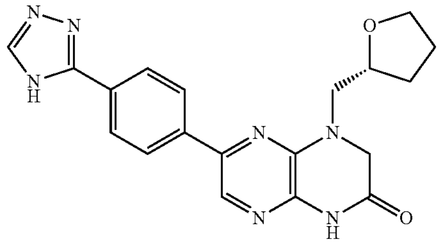 [SMILES: O=C1CN(C[C@H]2CCCO2)c2nc(-c3ccc(-c4nnc[nH]4)cc3)cnc2N1] | (R)-6-(4-(4H-1,2,4-triazol-3-yl)phenyl)-4-((tetrahydrofuran-2-yl)methyl)-3,4-dihydropyrazino[2,3-b]pyrazin-2(1H)-one | 378.1 [M + 1]+ | D |
| 68 | 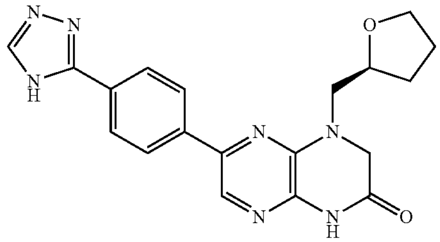 [SMILES: O=C1CN(C[C@@H]2CCCO2)c2nc(-c3ccc(-c4nnc[nH]4)cc3)cnc2N1] | (S)-6-(4-(4H-1,2,4-triazol-3-yl)phenyl)-4-((tetrahydrofuran-2-yl)methyl)-3,4-dihydropyrazino[2,3-b]pyrazin-2(1H)-one | 378.1 [M + 1]+ | D |
| 69 | 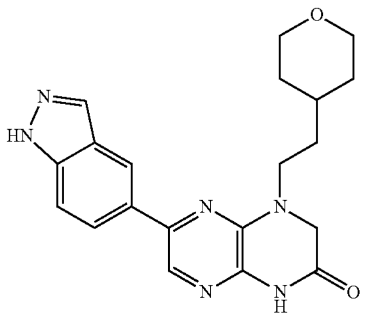 [SMILES: O=C1CN(CCC2CCOCC2)c2nc(-c3ccc4[nH]ncc4c3)cnc2N1] | 6-(1H-indazol-5-yl)-4-(2-(tetrahydro-2H-pyran-4-yl)ethyl)-3,4-dihydropyrazino[2,3-b]pyrazin-2(1H)-one | 379.0 [M + 1]+ | C |

TABLE 1-continued

| Cmpd No. | Cmpd Structure | Cmpd Name | MS (ESI) m/z | Act. Level |
|---|---|---|---|---|
| 70 | 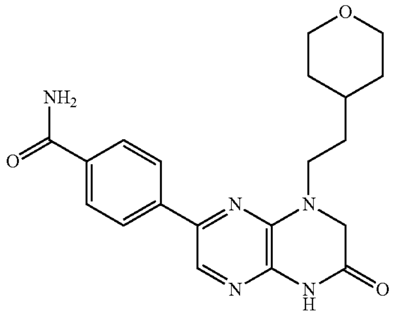 [SMILES: NC(=O)c1ccc(-c2cnc3c(n2)N(CCC2CCOCC2)CC(=O)N3)cc1] | 4-(6-oxo-8-(2-(tetrahydro-2H-pyran-4-yl)ethyl)-5,6,7,8-tetrahydropyrazino[2,3-b]pyrazin-2-yl)benzamide | 382.5 $[M + 1]^+$ | A |
| 71 | 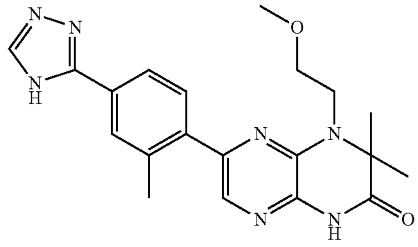 [SMILES: COCCN1c2nc(-c3ccc(-c4nnc[nH]4)cc3C)cnc2NC(=O)C1(C)C] | 4-(2-methoxyethyl)-3,3-dimethyl-6-(2-methyl-4-(4H-1,2,4-triazol-3-yl)phenyl)-3,4-dihydropyrazino[2,3-b]pyrazin-2(1H)-one | 394.2 $[M + 1]^+$ | D |
| 72 | 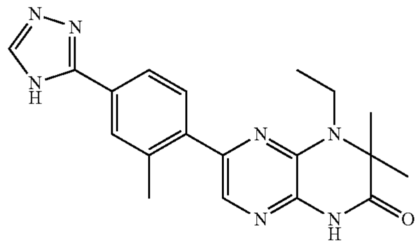 [SMILES: CCN1c2nc(-c3ccc(-c4nnc[nH]4)cc3C)cnc2NC(=O)C1(C)C] | 4-ethyl-3,3-dimethyl-6-(2-methyl-4-(4H-1,2,4-triazol-3-yl)phenyl)-3,4-dihydropyrazino[2,3-b]pyrazin-2(1H)-one | 364.2 $[M + 1]^+$ | D |
| 73 | 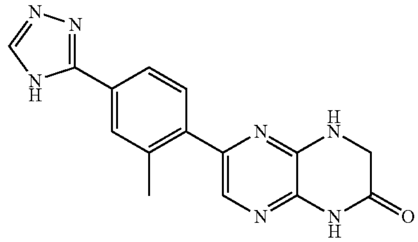 [SMILES: Cc1cc(-c2nnc[nH]2)ccc1-c1cnc2c(n1)NCC(=O)N2] | 6-(2-methyl-4-(4H-1,2,4-triazol-3-yl)phenyl)-3,4-dihydropyrazino[2,3-b]pyrazin-2(1H)-one | 308.1 $[M + 1]^+$ | C |
| 74 | 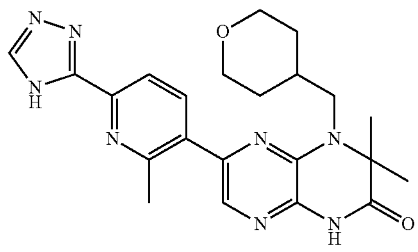 | 3,3-dimethyl-6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one | 435.3 $[M + 1]^+$ | D |

TABLE 1-continued

| Cmpd No. | Cmpd Structure | Cmpd Name | MS (ESI) m/z | Act. Level |
|---|---|---|---|---|
| 75 | 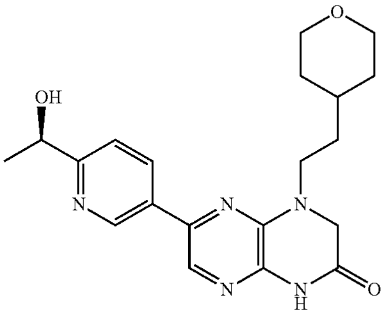 [SMILES: C[C@@H](O)c1ccc(-c2cnc3c(n2)N(CCC2CCOCC2)CC(=O)N3)cn1] | (R)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one | 384.3 $[M + 1]^+$ | D |
| 76 | 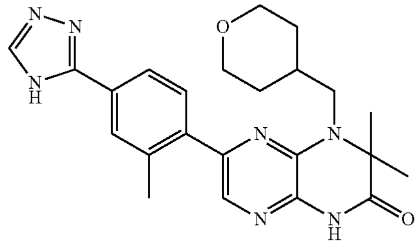 [SMILES: Cc1cc(-c2nnc[nH]2)ccc1-c1cnc2c(n1)N(CC1CCOCC1)C(C)(C)C(=O)N2] | 3,3-dimethyl-6-(2-methyl-4-(4H-1,2,4-triazol-3-yl)phenyl)-4-((tetrahydro-2H-pyran-4-yl)methyl)-3,4-dihydropyrazino[2,3-b]pyrazin-2(1H)-one | 434.2 $[M + 1]^+$ | D |
| 77 | 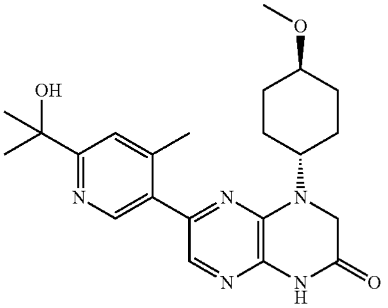 [SMILES: CO[C@H]1CC[C@H](N2CC(=O)Nc3ncc(-c4cnc(C(C)(C)O)cc4C)nc32)CC1] | 6-(6-(2-hydroxypropan-2-yl)-4-methylpyridin-3-yl)-4-(trans-4-methoxycyclohexyl)-3,4-dihydropyrazino[2,3-b]pyrazin-2(1H)-one | 412.4 $[M + 1]^+$ | D |
| 78 | 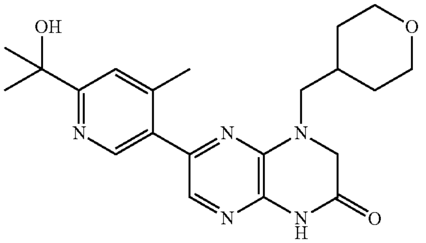 [SMILES: Cc1cc(C(C)(C)O)ncc1-c1cnc2c(n1)N(CC1CCOCC1)CC(=O)N2] | 6-(6-(2-hydroxypropan-2-yl)-4-methylpyridin-3-yl)-4-((tetrahydro-2H-pyran-4-yl)methyl)-3,4-dihydropyrazino[2,3-b]pyrazin-2(1H)-one | 398.3 $[M + 1]^+$ | D |
| 79 | 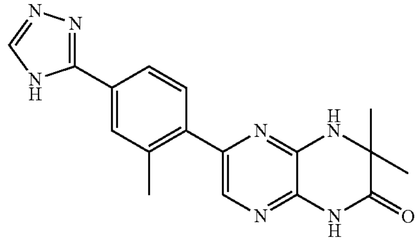 [SMILES: Cc1cc(-c2nnc[nH]2)ccc1-c1cnc2c(n1)NC(C)(C)C(=O)N2] | 3,3-dimethyl-6-(2-methyl-4-(4H-1,2,4-triazol-3-yl)phenyl)-3,4-dihydropyrazino[2,3-b]pyrazin-2(1H)-one | 336.2 $[M + 1]^+$ | C |

TABLE 1-continued

| Cmpd No. | Cmpd Structure | Cmpd Name | MS (ESI) m/z | Act. Level |
|---|---|---|---|---|
| 80 | 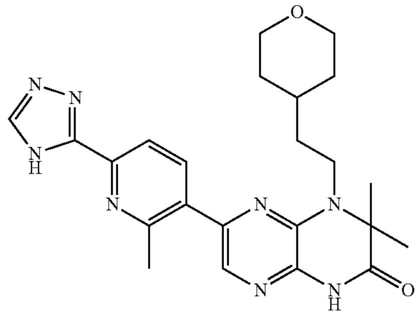 | 3,3-dimethyl-6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one | 449.2 [M + 1]$^+$ | D |
| 81 | 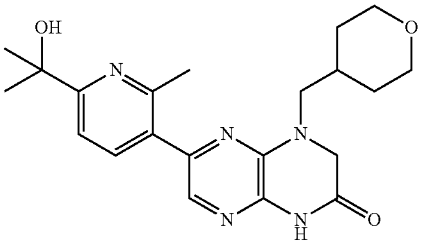 [SMILES: Cc1nc(C(C)(C)O)ccc1-c1cnc2c(n1)N(CC1CCOCC1)CC(=O)N2] | 6-(6-(2-hydroxypropan-2-yl)-2-methylpyridin-3-yl)-4-((tetrahydro-2H-pyran-4-yl)methyl)-3,4-dihydropyrazino[2,3-b]pyrazin-2(1H)-one | 398.5 [M + 1]$^+$ | D |
| 82 | 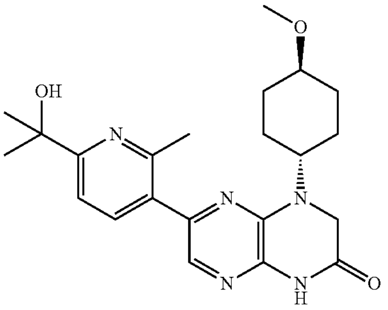 [SMILES: CO[C@H]1CC[C@H](N2CC(=O)Nc3ncc(-c4ccc(C(C)(C)O)nc4C)nc32)CC1] | 6-(6-(2-hydroxypropan-2-yl)-2-methylpyridin-3-yl)-4-(trans-4-methoxycyclohexyl)-3,4-dihydropyrazino[2,3-b]pyrazin-2(1H)-one | 412.5 [M + 1]$^+$ | C |
| 83 | 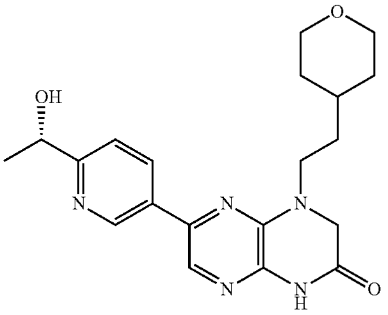 [SMILES: C[C@H](O)c1ccc(-c2cnc3c(n2)N(CCC2CCOCC2)CC(=O)N3)cn1] | (S)-6-(6-(1-hydroxyethyl)pyridin-3-yl)-4-(2-(tetrahydro-2H-pyran-4-yl)ethyl)-3,4-dihydropyrazino[2,3-b]pyrazin-2(1H)-one | 384.3 [M + 1]$^+$ | C |
| 84 | 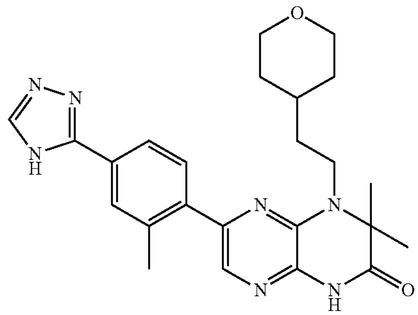 [SMILES: Cc1cc(-c2nnc[nH]2)ccc1-c1cnc2c(n1)N(CCC1CCOCC1)C(C)(C)C(=O)N2] | 3,3-dimethyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one | 448.3 [M + 1]$^+$ | D |

TABLE 1-continued

| Cmpd No. | Cmpd Structure | Cmpd Name | MS (ESI) m/z | Act. Level |
|---|---|---|---|---|
| 85 | 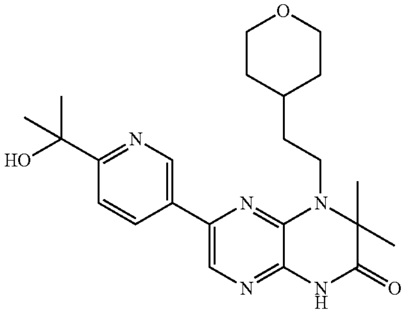 [SMILES: CC(C)(O)c1ccc(-c2cnc3c(n2)N(CCC2CCOCC2)C(C)(C)C(=O)N3)cn1] | 6-(6-(2-hydroxypropan-2-yl)pyridin-3-yl)-3,3-dimethyl-4-(2-(tetrahydro-2H-pyran-4-yl)ethyl)-3,4-dihydropyrazino[2,3-b]pyrazin-2(1H)-one | 426.3 $[M + 1]^+$ | B |
| 86 | 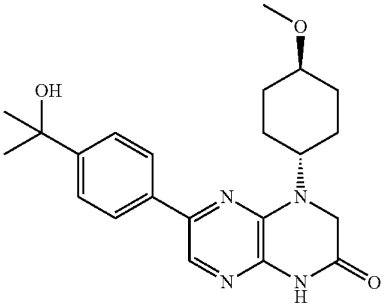 | 6-(4-(2-hydroxypropan-2-yl)phenyl)-4-(trans-4-methoxycyclohexyl)-3,4-dihydropyrazino[2,3-b]pyrazin-2(1H)-one | 397.2 $[M + 1]^+$ | D |
| 87 | 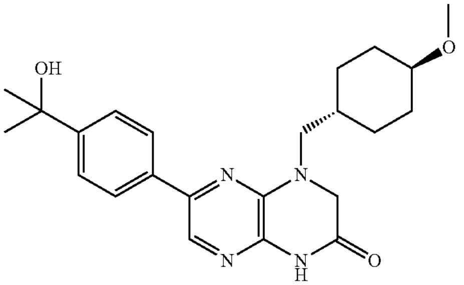 [SMILES: CO[C@H]1CC[C@H](CN2CC(=O)Nc3ncc(-c4ccc(C(C)(C)O)cc4)nc32)CC1] | 6-(4-(2-hydrdoxypropan-2-yl)phenyl)-4-((trans-4-methoxycyclohexyl)methyl)-3,4-dihydropyrazino[2,3-b]pyrazin-2(1H)-one | 411.3 $[M + 1]^+$ | C |
| 88 | 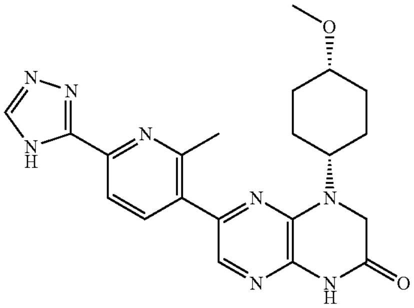 [SMILES: CO[C@H]1CC[C@@H](N2CC(=O)Nc3ncc(-c4ccc(-c5nnc[nH]5)nc4C)nc32)CC1] | 4-(cis-4-methoxycyclohexyl)-6-(2-methyl-6-(4H-1,2,4-triazol-3-yl)pyridin-3-yl)-3,4-dihydropyrazino[2,3-b]pyrazin-2(1H)-one | 421.2 $[M + 1]^+$ | D |
| 89 | 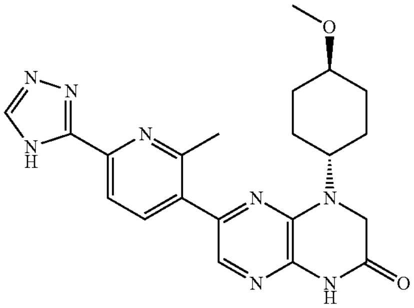 [SMILES: CO[C@H]1CC[C@H](N2CC(=O)Nc3ncc(-c4ccc(-c5nnc[nH]5)nc4C)nc32)CC1] | 4-(trans-4-methoxycyclohexyl)-6-(2-methyl-6-(4H-1,2,4-triazol-3-yl)pyridin-3-yl)-3,4-dihydropyrazino[2,3-b]pyrazin-2(1H)-one | 421.0 $[M + 1]^+$ | D |

TABLE 1-continued

| Cmpd No. | Cmpd Structure | Cmpd Name | MS (ESI) m/z | Act. Level |
| --- | --- | --- | --- | --- |
| 90 | 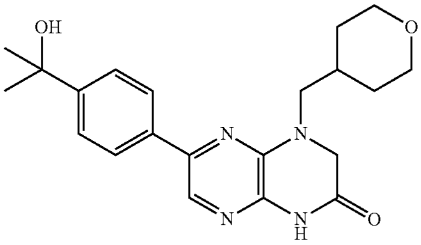 | 6-(4-(2-hydroxypropan-2-yl)phenyl)-4-((tetrahydro-2H-pyran-4-yl)methyl)-3,4-dihydropyrazino[2,3-b]pyrazin-2(1H)-one | 383.3 [M + 1]+ | D |
| 91 | 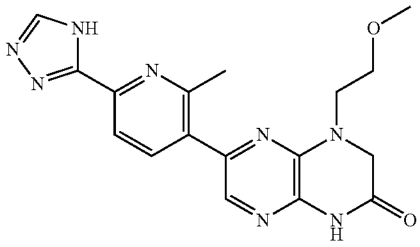 [SMILES: COCCN1CC(=O)Nc2ncc(-c3ccc(-c4nnc[nH]4)nc3C)nc21] | 4-(2-methoxyethyl)-6-(2-methyl-6-(4H-1,2,4-triazol-3-yl)pyridin-3-yl)-3,4-dihydropyrazino[2,3-b]pyrazin-2(1H)-one | 367.5 [M + 1]+ | D |
| 92 | 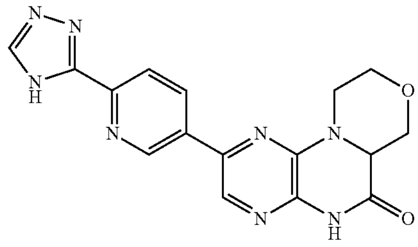 [SMILES: O=C1Nc2ncc(-c3ccc(-c4nnc[nH]4)nc3)nc2N2CCOCC12] | 9-(6-(4H-1,2,4-triazol-3-yl)-3-pyridyl)-6,11,4a-trihydromorpholino[4,3-e]pyrazino[2,3-b]pyrazin-5-one | 351.5 [M + 1]+ | B |
| 93 | 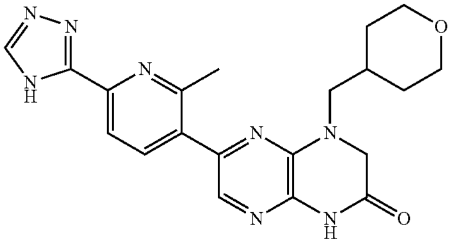 [SMILES: Cc1nc(-c2nnc[nH]2)ccc1-c1cnc2c(n1)N(CC1CCOCC1)CC(=O)N2] | 6-(2-methyl-6-(4H-1,2,4-triazol-3-yl)pyridin-3-yl)-4-((tetrahydro-2H-pyran-4-yl)methyl)-3,4-dihydropyrazino[2,3-b]pyrazin-2(1H)-one | 407.8 [M + 1]+ | C |
| 94 | 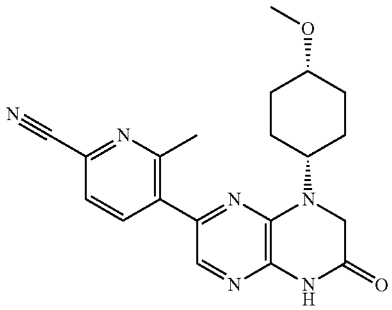 [SMILES: CO[C@H]1CC[C@@H](N2CC(=O)Nc3ncc(-c4ccc(C#N)nc4C)nc32)CC1] | 5-(8-(cis-4-methoxycyclohexyl)-6-oxo-5,6,7,8-tetrahydropyrazino[2,3-b]pyrazin-2-yl)-6-methylpicolinonitrile | 379.2 [M + 1]+ | A |

TABLE 1-continued

| Cmpd No. | Cmpd Structure | Cmpd Name | MS (ESI) m/z | Act. Level |
|---|---|---|---|---|
| 95 | 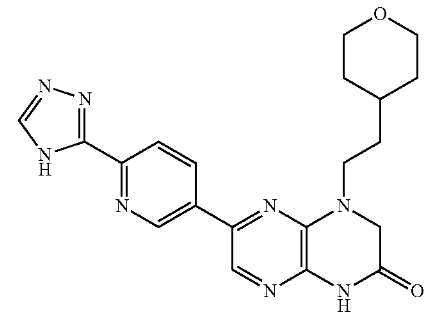 [SMILES: O=C1CN(CCC2CCOCC2)c2nc(-c3ccc(-c4nnc[nH]4)nc3)cnc2N1] | 6-(6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one | 407.3 $[M + 1]^+$ | D |
| 96 | 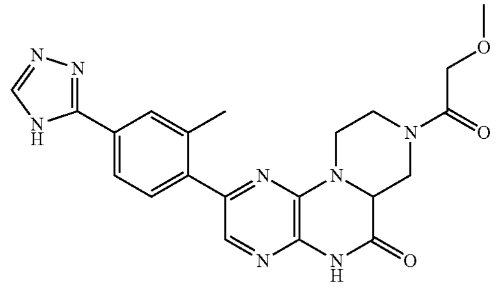 [SMILES: COCC(=O)N1CCN2c3nc(-c4ccc(-c5nnc[nH]5)cc4C)cnc3NC(=O)C2C1] | 9-(4-(4H-1,2,4-triazol-3-yl)-2-methylphenyl)-3-(2-methoxyacetyl)-6,11,4a-trihydropiperazino[1,2-e]pyrazino[2,3-b]pyrazin-5-one | 435.3 $[M + 1]^+$ | D |
| 97 | 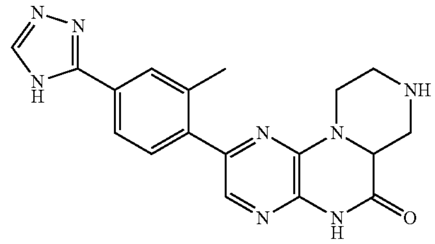 [SMILES: Cc1cc(-c2nnc[nH]2)ccc1-c1cnc2c(n1)N1CCNCC1C(=O)N2] | 9-(4-(4H-1,2,4-triazol-3-yl)-2-methylphenyl)-6,11,4a-trihydropiperazino[1,2-e]pyrazino[2,3-b]pyrazin-5-one | 363.2 $[M + 1]^+$ | D |
| 98 | 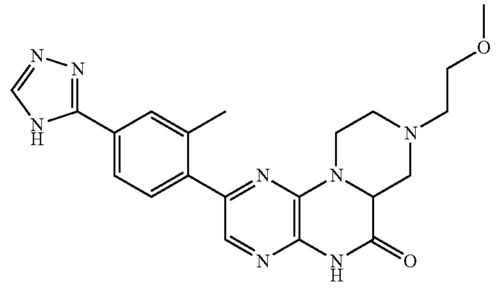 [SMILES: COCCN1CCN2c3nc(-c4ccc(-c5nnc[nH]5)cc4C)cnc3NC(=O)C2C1] | 9-(4-(4H-1,2,4-triazol-3-yl)-2-methylphenyl)-3-(2-methoxyethyl)-6,11,4a-trihydropiperazino[1,2-e]pyrazino[2,3-b]pyrazin-5-one | 421.4 $[M + 1]^+$ | C |
| 99 | 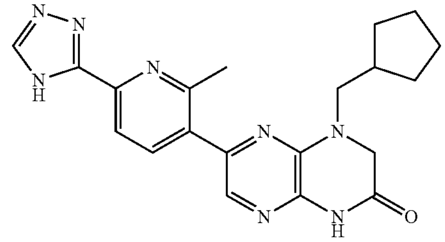 [SMILES: Cc1nc(-c2nnc[nH]2)ccc1-c1cnc2c(n1)N(CC1CCCC1)CC(=O)N2] | 4-(cyclopentylmethyl)-6-(2-methyl-6-(4H-1,2,4-triazol-3-yl)pyridin-3-yl)-3,4-dihydropyrazino[2,3-b]pyrazin-2(1H)-one | 391.8 $[M + 1]^+$ | D |

TABLE 1-continued

| Cmpd No. | Cmpd Structure | Cmpd Name | MS (ESI) m/z | Act. Level |
|---|---|---|---|---|
| 100 | 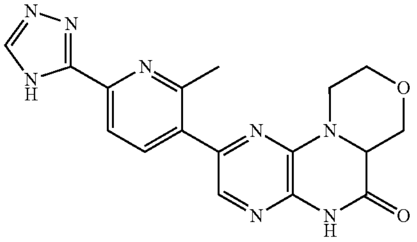 [SMILES: Cc1nc(-c2nnc[nH]2)ccc1-c1cnc2c(n1)N1CCOCC1C(=O)N2] | 9-(6-(4H-1,2,4-triazol-3-yl)-2-methyl-3-pyridyl)-6,11,4a-trihydromorpholino[4,3-e]pyrazino[2,3-b]pyrazin-5-one | 365.5 [M + 1]+ | C |
| 101 | 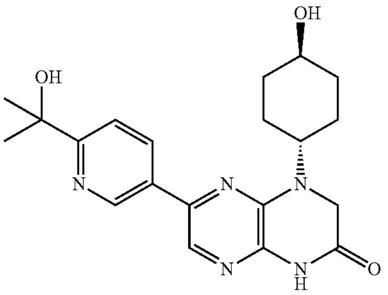 [SMILES: CC(C)(O)c1ccc(-c2cnc3c(n2)N([C@H]2CC[C@H](O)CC2)CC(=O)N3)cn1] | 4-(trans-4-hydroxycyclohexyl)-6-(6-(2-hydroxypropan-2-yl)pyridin-3-yl)-3,4-dihydropyrazino[2,3-b]pyrazin-2(1H)-one | 384.2 [M + 1]+ | D |
| 102 | 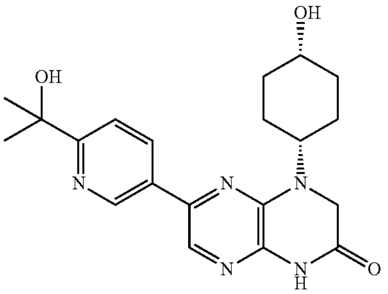 [SMILES: CC(C)(O)c1ccc(-c2cnc3c(n2)N([C@H]2CC[C@@H](O)CC2)CC(=O)N3)cn1] | 4-(cis-4-hydroxycyclohexyl)-6-(6-(2-hydroxypropan-2-yl)pyridin-3-yl)-3,4-dihydropyrazino[2,3-b]pyrazin-2(1H)-one | 384.2 [M + 1]+ | C |
| 103 | 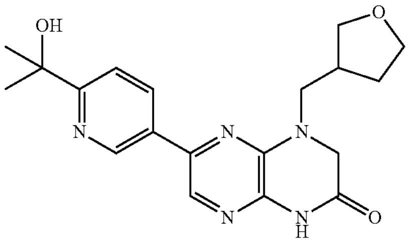 [SMILES: CC(C)(O)c1ccc(-c2cnc3c(n2)N(CC2CCOC2)CC(=O)N3)cn1] | 6-(6-(2-hydroxypropan-2-yl)pyridin-3-yl)-4-((tetrahydrofuran-3-yl)methyl)-3,4-dihydropyrazino[2,3-b]pyrazin-2(1H)-one | 370.3 [M + 1]+ | B |
| 104 | 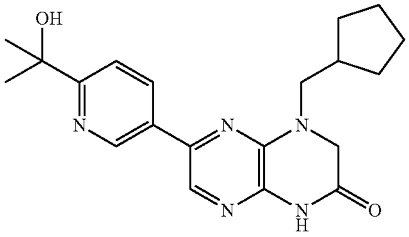 [SMILES: CC(C)(O)c1ccc(-c2cnc3c(n2)N(CC2CCCC2)CC(=O)N3)cn1] | 4-(cyclopentylmethyl)-6-(6-(2-hydroxypropan-2-yl)pyridin-3-yl)-3,4-dihydropyrazino[2,3-b]pyrazin-2(1H)-one | 368.1 [M + 1]+ | D |
| 105 | 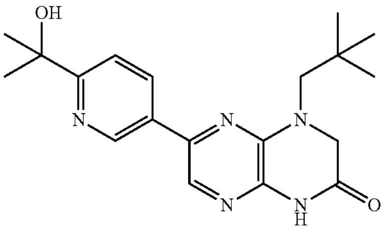 [SMILES: CC(C)(C)CN1CC(=O)Nc2ncc(-c3ccc(C(C)(C)O)nc3)nc21] | 6-(6-(2-hydroxypropan-2-yl)pyridin-3-yl)-4-neopentyl-3,4-dihydropyrazino[2,3-b]pyrazin-2(1H)-one | 356.1 [M + 1]+ | C |

TABLE 1-continued

| Cmpd No. | Cmpd Structure | Cmpd Name | MS (ESI) m/z | Act. Level |
|---|---|---|---|---|
| 106 | 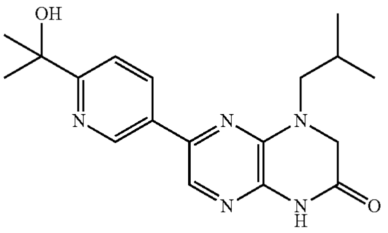 [SMILES: CC(C)CN1CC(=O)Nc2ncc(-c3ccc(C(C)(C)O)nc3)nc21] | 6-(6-(2-hydroxypropan-2-yl)pyridin-3-yl)-4-isobutyl-3,4-dihydropyrazino[2,3-b]pyrazin-2(1H)-one | 342.2 [M + 1]+ | B |
| 107 | 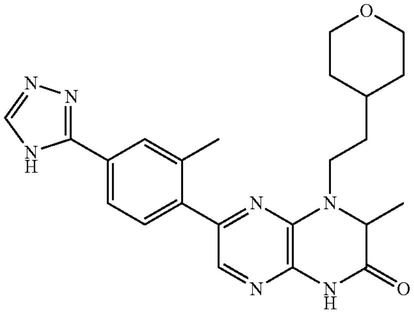 [SMILES: Cc1cc(-c2nnc[nH]2)ccc1-c1cnc2c(n1)N(CCC1CCOCC1)C(C)C(=O)N2] | 3-methyl-6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one | 434.1 [M + 1]+ | D |
| 108 | 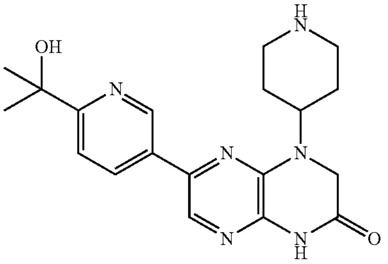 [SMILES: CC(C)(O)c1ccc(-c2cnc3c(n2)N(C2CCNCC2)CC(=O)N3)cn1] | 6-(6-(2-hydroxypropan-2-yl)pyridin-3-yl)-4-(piperidin-4-yl)-3,4-dihydropyrazino[2,3-b]pyrazin-2(1H)-one | 369.3 [M + 1]+ | A |
| 109 | 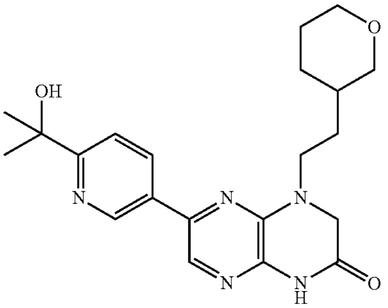 [SMILES: CC(C)(O)c1ccc(-c2cnc3c(n2)N(CCC2CCCOC2)CC(=O)N3)cn1] | 6-(6-(2-hydroxypropan-2-yl)pyridin-3-yl)-4-(2-(tetrahydro-2H-pyran-3-yl)ethyl)-3,4-dihydropyrazino[2,3-b]pyrazin-2(1H)-one | 398.1 [M + 1]+ | D |
| 110 | 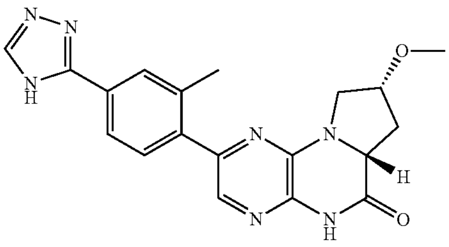 [SMILES: CO[C@@H]1C[C@@H]2C(=O)Nc3ncc(-c4ccc(-c5nnc[nH]5)cc4C)nc3N2C1] | 8-(4-(4H-1,2,4-triazol-3-yl)-2-methylphenyl)(3aS,2R)-2-methoxy-5,10,3a-trihydropyrazino[2,3-b]pyrrolidino[1,2-e]pyrazin-4-one | 378.2 [M + 1]+ | N/A |

TABLE 1-continued

| Cmpd No. | Cmpd Structure | Cmpd Name | MS (ESI) m/z | Act. Level |
|---|---|---|---|---|
| 111 | 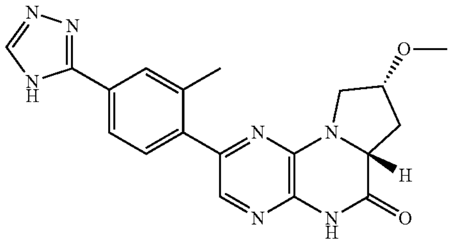 [SMILES: CO[C@@H]1C[C@@H]2C(=O)Nc3ncc(-c4ccc(-c5nnc[nH]5)cc4C)nc3N2C1] | 8-(4-(4H-1,2,4-triazol-3-yl)-2-methylphenyl)(2R,3aR)-2-methoxy-5,10,3a-trihydropyrazino[2,3-b]pyrrolidino[1,2-e]pyrazin-4-one | 378.2 $[M + 1]^+$ | N/A |
| 112 | 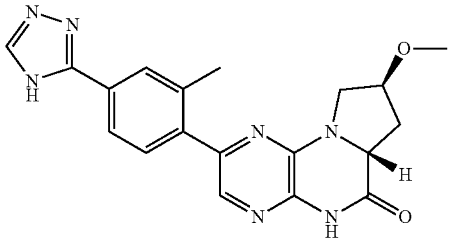 [SMILES: CO[C@H]1C[C@@H]2C(=O)Nc3ncc(-c4ccc(-c5nnc[nH]5)cc4C)nc3N2C1] | 8-(4-(4H-1,2,4-triazol-3-yl)-2-methylphenyl)(2S,3aR)-2-methoxy-5,10,3a-trihydropyrazino[2,3-b]pyrrolidino[1,2-e]pyrazin-4-one | 378.2 $[M + 1]^+$ | D |
| 113 | 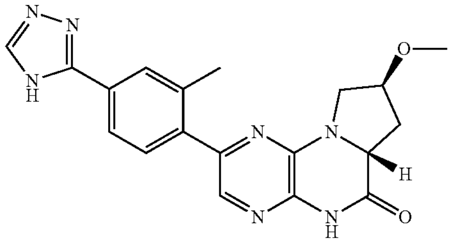 [SMILES: CO[C@H]1C[C@@H]2C(=O)Nc3ncc(-c4ccc(-c5nnc[nH]5)cc4C)nc3N2C1] | 8-(4-(4H-1,2,4-triazol-3-yl)-2-methylphenyl)(2S,3aS)-2-methoxy-5,10,3a-trihydropyrazino[2,3-b]pyrrolidino[1,2-e]pyrazin-4-one | 378.2 $[M + 1]^+$ | C |
| 114 | 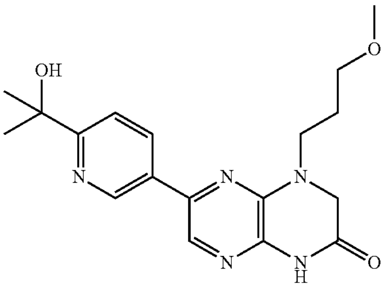 [SMILES: COCCCN1CC(=O)Nc2ncc(-c3ccc(C(C)(C)O)nc3)nc21] | 6-(6-(2-hydroxypropan-2-yl)pyridin-3-yl)-4-(3-methoxypropyl)-3,4-dihydropyrazino[2,3-b]pyrazin-2(1H)-one | 358.4 $[M + 1]^+$ | A |
| 115 | 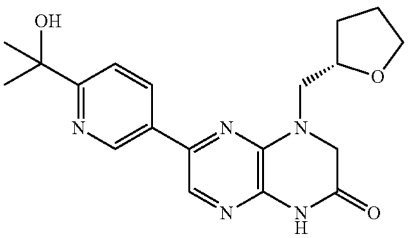 [SMILES: CC(C)(O)c1ccc(-c2cnc3c(n2)N(C[C@@H]2CCCO2)CC(=O)N3)cn1] | (S)-6-(6-(2-hydroxypropan-2-yl)pyridin-3-yl)-4-((tetrahydrofuran-2-yl)methyl)-3,4-dihydropyrazino[2,3-b]pyrazin-2(1H)-one | 370.3 $[M + 1]^+$ | A |
| 116 | 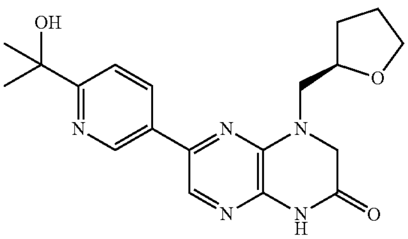 [SMILES: CC(C)(O)c1ccc(-c2cnc3c(n2)N(C[C@H]2CCCO2)CC(=O)N3)cn1] | (R)-6-(6-(2-hydroxypropan-2-yl)pyridin-3-yl)-4-((tetrahydrofuran-2-yl)methyl)-3,4-dihydropyrazino[2,3-b]pyrazin-2(1H)-one | 370.3 $[M + 1]^+$ | B |

TABLE 1-continued

| Cmpd No. | Cmpd Structure | Cmpd Name | MS (ESI) m/z | Act. Level |
|---|---|---|---|---|
| 117 | 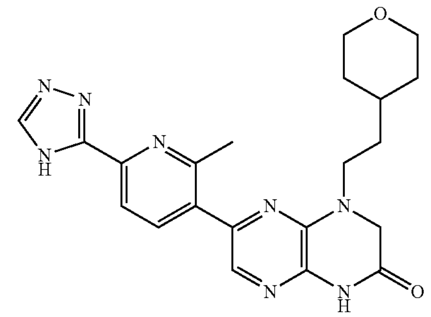 [SMILES: Cc1nc(-c2nnc[nH]2)ccc1-c1cnc2c(n1)N(CCC1CCOCC1)CC(=O)N2] | 6-(2-methyl-6-(4H-1,2,4-triazol-3-yl)pyridin-3-yl)-4-(2-(tetrahydro-2H-pyran-4-yl)ethyl)-3,4-dihydropyrazino[2,3-b]pyrazin-2(1H)-one | 421.1 [M + 1]+ | D |
| 118 | 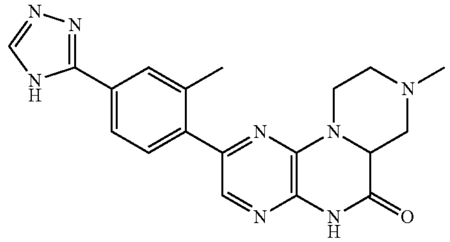 [SMILES: Cc1cc(-c2nnc[nH]2)ccc1-c1cnc2c(n1)N1CCN(C)CC1C(=O)N2] | 9-(4-(4H-1,2,4-triazol-3-yl)-2-methylphenyl)-3-methyl-6,11,4a-trihydropiperazino[1,2-e]pyrazino[2,3-b]pyrazin-5-one | 377.4 [M + 1]+ | B |
| 119 | 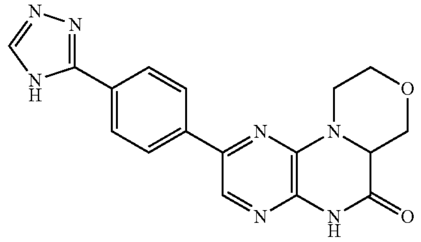 | 9-(4-(4H-1,2,4-triazol-3-yl)phenyl)-6,11,4a-trihydromorpholino[4,3-e]pyrazino[2,3-b]pyrazin-5-one | 350.5 [M + 1]+ | D |
| 120 | 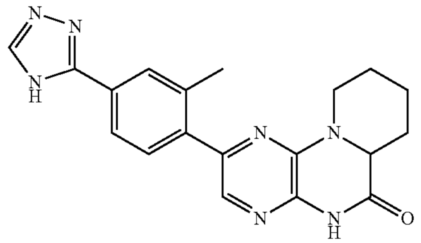 | 9-(4-(4H-1,2,4-triazol-3-yl)-2-methylphenyl)-6,11,4a-trihydropiperidino[1,2-e]pyrazino[2,3-b]pyrazin-5-one | 362.1 [M + 1]+ | D |
| 121 | 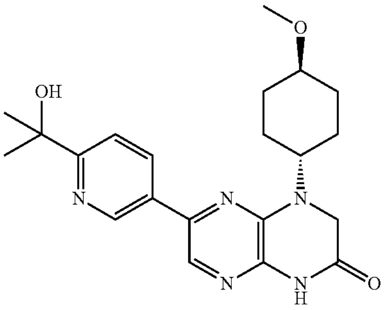 [SMILES: CO[C@H]1CC[C@H](N2CC(=O)Nc3ncc(-c4ccc(C(C)(C)O)nc4)nc32)CC1] | 6-(6-(2-hydroxypropan-2-yl)pyridin-3-yl)-4-(trans-4-methoxycyclohexyl)-3,4-dihydropyrazino[2,3-b]pyrazin-2(1H)-one | 398.3 [M + 1]+ | D |

TABLE 1-continued

| Cmpd No. | Cmpd Structure | Cmpd Name | MS (ESI) m/z | Act. Level |
|---|---|---|---|---|
| 122 | 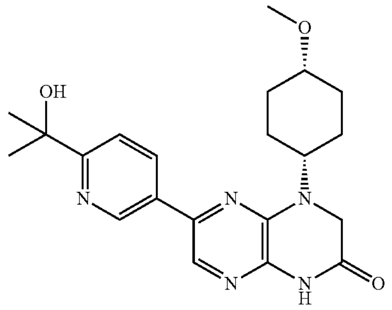 [SMILES: CO[C@H]1CC[C@@H](N2CC(=O)Nc3ncc(-c4ccc(C(C)(C)O)nc4)nc32)CC1] | 6-(6-(2-hydroxypropan-2-yl)pyridin-3-yl)-4-(cis-4-methoxycyclohexyl)-3,4-dihydropyrazino[2,3-b]pyrazin-2(1H)-one | 398.2 [M + 1]+ | C |
| 123 | 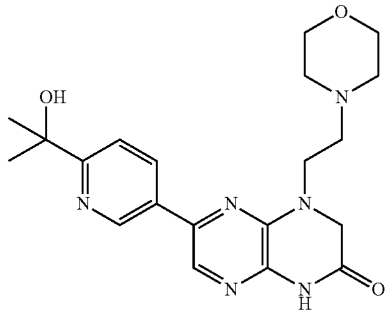 | 6-(6-(2-hydroxypropan-2-yl)pyridin-3-yl)-4-(2-morpholinoethyl)-3,4-dihydropyrazino[2,3-b]pyrazin-2(1H)-one | 399.2 [M + 1]+ | A |
| 124 | 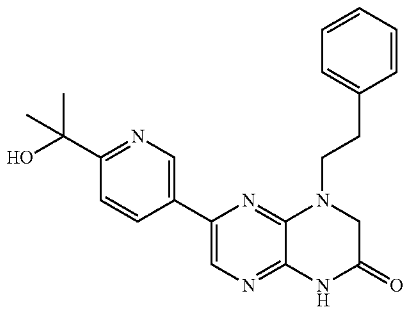 [SMILES: CC(C)(O)c1ccc(-c2cnc3c(n2)N(CCc2ccccc2)CC(=O)N3)cn1] | 6-(6-(2-hydroxypropan-2-yl)pyridin-3-yl)-4-phenethyl-3,4-dihydropyrazino[2,3-b]pyrazin-2(1H)-one | 390.2 [M + 1]+ | C |
| 125 | 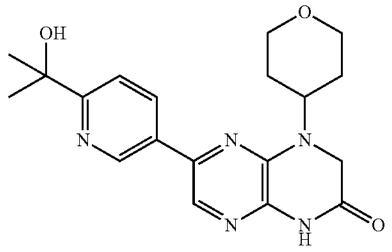 [SMILES: CC(C)(O)c1ccc(-c2cnc3c(n2)N(C2CCOCC2)CC(=O)N3)cn1] | 6-(6-(2-hydroxypropan-2-yl)pyridin-3-yl)-4-(tetrahydro-2H-pyran-4-yl)-3,4-dihydropyrazino[2,3-b]pyrazin-2(1H)-one | 370.3 [M + 1]+ | B |
| 126 | 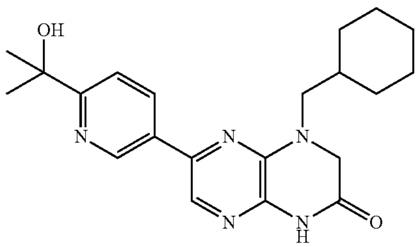 [SMILES: CC(C)(O)c1ccc(-c2cnc3c(n2)N(CC2CCCCC2)CC(=O)N3)cn1] | 4-(cyclohexylmethyl)-6-(6-(2-hydroxypropan-2-yl)pyridin-3-yl)-3,4-dihydropyrazino[2,3-b]pyrazin-2(1H)-one | 382.3 [M + 1]+ | D |

TABLE 1-continued

| Cmpd No. | Cmpd Structure | Cmpd Name | MS (ESI) m/z | Act. Level |
|---|---|---|---|---|
| 127 | 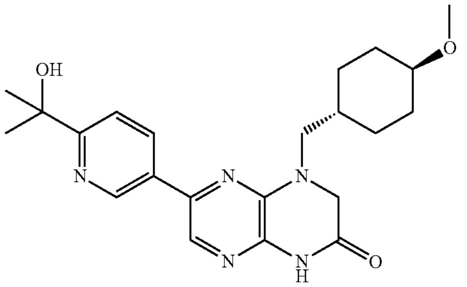 | 6-(6-(2-hydroxypropan-2-yl)pyridin-3-yl)-4-((trans-4-methoxycyclohexyl)methyl)-3,4-dihydropyrazino[2,3-b]pyrazin-2(1H)-one | 412.2 $[M + 1]^+$ | D |
| 128 | 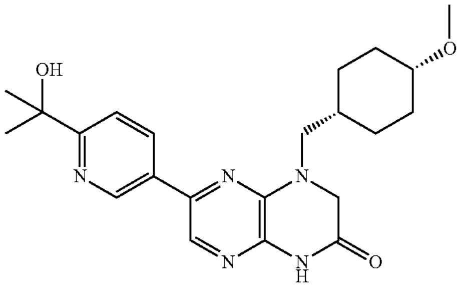 [SMILES: CO[C@H]1CC[C@@H](CN2CC(=O)Nc3ncc(-c4ccc(C(C)(C)O)nc4)nc32)CC1] | 6-(6-(2-hydroxypropan-2-yl)pyridin-3-yl)-4-((cis-4-methoxycyclohexyl)methyl)-3,4-dihydropyrazino[2,3-b]pyrazin-2(1H)-one | 412.2 $[M + 1]^+$ | D |
| 129 | 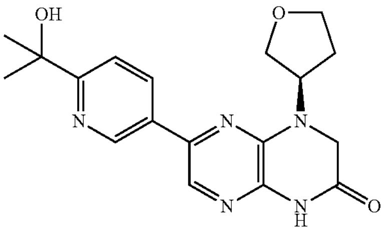 [SMILES: CC(C)(O)c1ccc(-c2cnc3c(n2)N([C@@H]2CCOC2)CC(=O)N3)cn1] | (R)-6-(6-(2-hydroxypropan-2-yl)pyridin-3-yl)-4-(tetrahydrofuran-3-yl)-3,4-dihydropyrazino[2,3-b]pyrazin-2(1H)-one | 356.2 $[M + 1]^+$ | B |
| 130 | 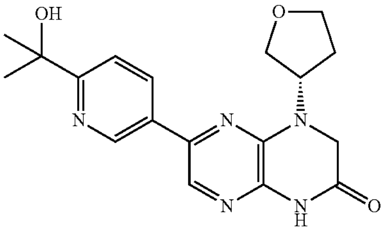 [SMILES: CC(C)(O)c1ccc(-c2cnc3c(n2)N([C@H]2CCOC2)CC(=O)N3)cn1] | (S)-6-(6-(2-hydroxypropan-2-yl)pyridin-3-yl)-4-(tetrahydrofuran-3-yl)-3,4-dihydropyrazino[2,3-b]pyrazin-2(1H)-one | 356.1 $[M + 1]^+$ | B |
| 132 | 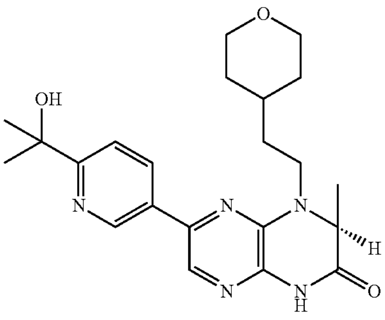 [SMILES: C[C@H]1C(=O)Nc2ncc(-c3ccc(C(C)(C)O)nc3)nc2N1CCC1CCOCC1] | (S)-6-(6-(2-hydroxypropan-2-yl)pyridin-3-yl)-3-methyl-4-(2-(tetrahydro-2H-pyran-4-yl)ethyl)-3,4-dihydropyrazino[2,3-b]pyrazin-2(1H)-one | 412.3 $[M + 1]^+$ | D |

TABLE 1-continued

| Cmpd No. | Cmpd Structure | Cmpd Name | MS (ESI) m/z | Act. Level |
|---|---|---|---|---|
| 133 | 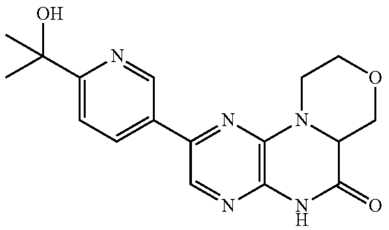 [SMILES: CC(C)(O)c1ccc(-c2cnc3c(n2)N2CCOCC2C(=O)N3)cn1] | 9-[6-(1-hydroxy-isopropyl)-3-pyridyl]-6,11,4a-trihydromorpholino[4,3-e]pyrazino[2,3-b]pyrazin-5-one | 342.0 [M + 1]$^+$ | B |
| 134 | 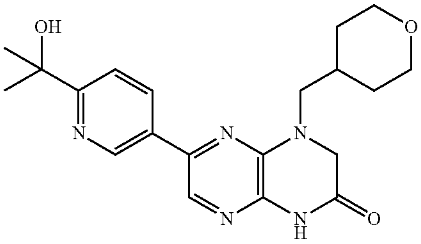 [SMILES: CC(C)(O)c1ccc(-c2cnc3c(n2)N(CC2CCOCC2)CC(=O)N3)cn1] | 6-(6-(2-hydroxypropan-2-yl)pyridin-3-yl)-4-((tetrahydro-2H-pyran-4-yl)methyl)-3,4-dihydropyrazino[2,3-b]pyrazin-2(1H)-one | 384.2 [M + 1]$^+$ | C |
| 135 | 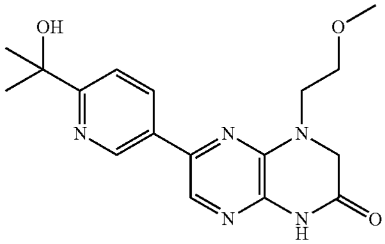 [SMILES: COCCN1CC(=O)Nc2ncc(-c3ccc(C(C)(C)O)nc3)nc21] | 6-(6-(2-hydroxypropan-2-yl)pyridin-3-yl)-4-(2-methoxyethyl)-3,4-dihydropyrazino[2,3-b]pyrazin-2(1H)-one | 344.1 [M + 1]$^+$ | A |
| 136 | 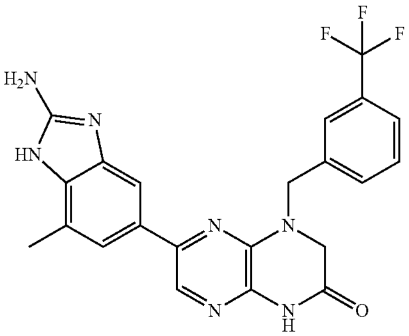 [SMILES: Cc1cc(-c2cnc3c(n2)N(Cc2cccc(C(F)(F)F)c2)CC(=O)N3)cc2nc(N)[nH]c12] | 6-(2-amino-7-methyl-1H-benzo[d]imidazol-5-yl)-4-(3-(trifluoromethyl)benzyl)-3,4-dihydropyrazino[2,3-b]pyrazin-2(1H)-one | 454.4 [M + 1]$^+$ | B |
| 137 | 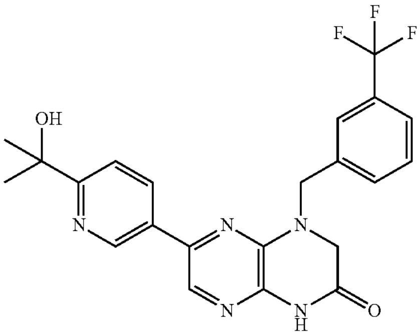 [SMILES: CC(C)(O)c1ccc(-c2cnc3c(n2)N(Cc2cccc(C(F)(F)F)c2)CC(=O)N3)cn1] | 6-(6-(2-hydroxypropan-2-yl)pyridin-3-yl)-4-(3-(trifluoromethyl)benzyl)-3,4-dihydropyrazino[2,3-b]pyrazin-2(1H)-one | 444.4 [M + 1]$^+$ | D |

TABLE 1-continued

| Cmpd No. | Cmpd Structure | Cmpd Name | MS (ESI) m/z | Act. Level |
|---|---|---|---|---|
| 138 | 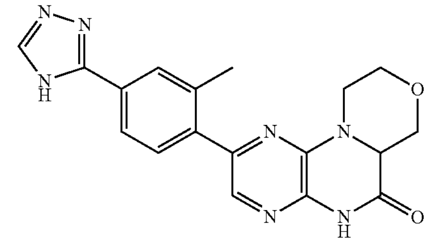 [SMILES: Cc1cc(-c2nnc[nH]2)ccc1-c1cnc2c(n1)N1CCOCC1C(=O)N2] | 9-(4-(4H-1,2,4-triazol-3-yl)-2-methylphenyl)-6,11,4a-trihydromorpholino[4,3-e]pyrazino[2,3-b]pyrazin-5-one | 364 [M + 1]$^+$ | D |
| 139 | 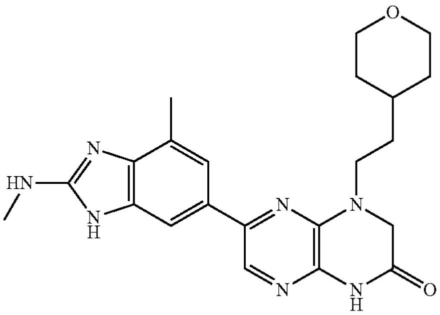 [SMILES: CNc1nc2c(C)cc(-c3cnc4c(n3)N(CCC3CCOCC3)CC(=O)N4)cc2[nH]1] | 6-(4-methyl-2-(methylamino)-1H-benzo[d]imidazol-6-yl)-4-(2-(tetrahydro-2H-pyran-4-yl)ethyl)-3,4-dihydropyrazino[2,3-b]pyrazin-2(1H)-one | 422.2 [M + 1]$^+$ | D |
| 140 | 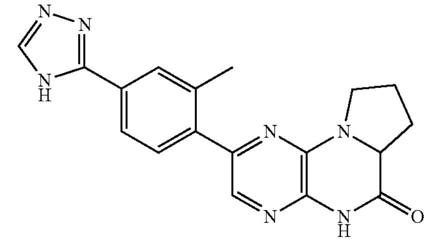 [SMILES: Cc1cc(-c2nnc[nH]2)ccc1-c1cnc2c(n1)N1CCCC1C(=O)N2] | 8-(4-(4H-1,2,4-triazol-3-yl)-2-methylphenyl)-5,10,3a-trihydropyrazino[2,3-b]pyrrolidino[1,2-e]pyrazin-4-one | 348.3 [M + 1]$^+$ | D |
| 141 | 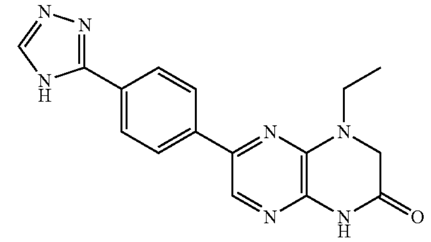 [SMILES: CCN1CC(=O)Nc2ncc(-c3ccc(-c4nnc[nH]4)cc3)nc21] | 6-(4-(4H-1,2,4-triazol-3-yl)phenyl)-4-ethyl-3,4-dihydropyrazino[2,3-b]pyrazin-2(1H)-one | 322.2 [M + 1]$^+$ | C |
| 142 | 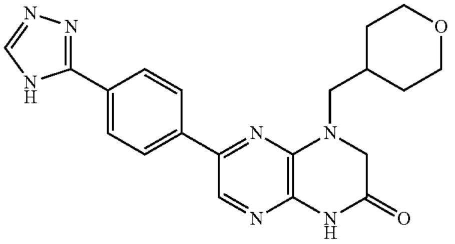 [SMILES: O=C1CN(CC2CCOCC2)c2nc(-c3ccc(-c4nnc[nH]4)cc3)cnc2N1] | 6-(4-(4H-1,2,4-triazol-3-yl)phenyl)-4-((tetrahydro-2H-pyran-4-yl)methyl)-3,4-dihydropyrazino[2,3-b]pyrazin-2(1H)-one | 392.3 [M + 1]$^+$ | D |

TABLE 1-continued

| Cmpd No. | Cmpd Structure | Cmpd Name | MS (ESI) m/z | Act. Level |
|---|---|---|---|---|
| 143 | 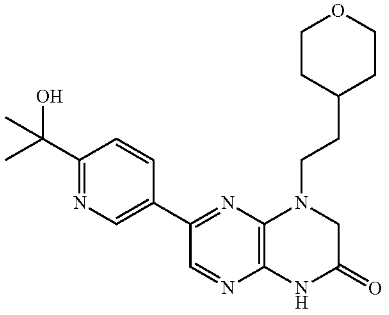 [SMILES: CC(C)(O)c1ccc(-c2cnc3c(n2)N(CCC2CCOCC2)CC(=O)N3)cn1] | 6-(6-(2-hydroxypropan-2-yl)pyridin-3-yl)-4-(2-(tetrahydro-2H-pyran-4-yl)ethyl)-3,4-dihydropyrazino[2,3-b]pyrazin-2(1H)-one | 398.3 $[M + 1]^+$ | D |
| 144 | 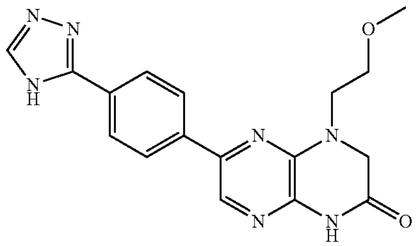 [SMILES: COCCN1CC(=O)Nc2ncc(-c3ccc(-c4nnc[nH]4)cc3)nc21] | 6-(4-(4H-1,2,4-triazol-3-yl)phenyl)-4-(2-methoxyethyl)-3,4-dihydropyrazino[2,3-b]pyrazin-2(1H)-one | 352.2 $[M + 1]^+$ | D |
| 145 | 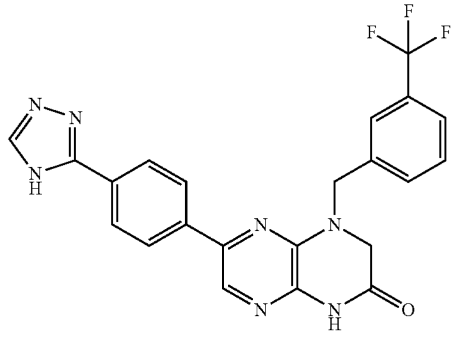 [SMILES: O=C1CN(Cc2cccc(C(F)(F)F)c2)c2nc(-c3ccc(-c4nnc[nH]4)cc3)cnc2N1] | 6-(4-(4H-1,2,4-triazol-3-yl)phenyl)-4-(3-(trifluoromethyl)benzyl)-3,4-dihydropyrazino[2,3-b]pyrazin-2(1H)-one | 420.3 $[M + 1]^+$ | D |
| 146 | 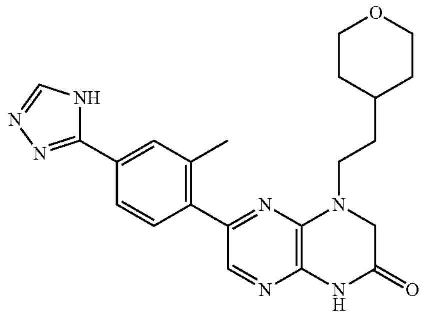 [SMILES: Cc1cc(-c2nnc[nH]2)ccc1-c1cnc2c(n1)N(CCC1CCOCC1)CC(=O)N2] | 6-(2-methyl-4-(4H-1,2,4-triazol-3-yl)phenyl)-4-(2-(tetrahydro-2H-pyran-4-yl)ethyl)-3,4-dihydropyrazino[2,3-b]pyrazin-2(1H)-one | 420.3 $[M + 1]^+$ | D |
| 147 | 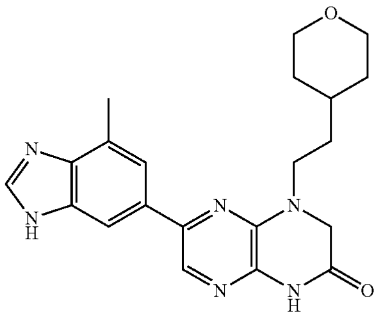 [SMILES: Cc1cc(-c2cnc3c(n2)N(CCC2CCOCC2)CC(=O)N3)cc2[nH]cnc12] | 6-(4-methyl-1H-benzo[d]imidazol-6-yl)-4-(2-(tetrahydro-2H-pyran-4-yl)ethyl)-3,4-dihydropyrazino[2,3-b]pyrazin-2(1H)-one | 393.3 $[M + 1]^+$ | B |

TABLE 1-continued

| Cmpd No. | Cmpd Structure | Cmpd Name | MS (ESI) m/z | Act. Level |
|---|---|---|---|---|
| 148 | 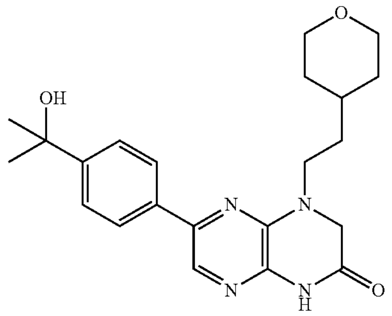 [SMILES: CC(C)(O)c1ccc(-c2cnc3c(n2)N(CCC2CCOCC2)CC(=O)N3)cc1] | 6-(4-(2-hydroxypropan-2-yl)phenyl)-4-(2-(tetrahydro-2H-pyran-4-yl)ethyl)-3,4-dihydropyrazino[2,3-b]pyrazin-2(1H)-one | 397.2 [M + 1]$^+$ | D |
| 149 | 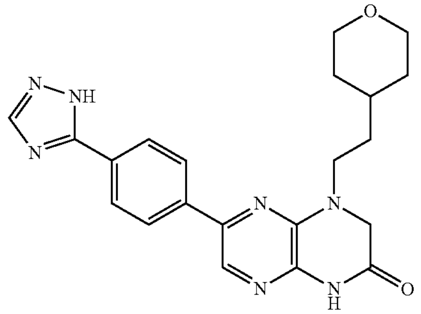 [SMILES: O=C1CN(CCC2CCOCC2)c2nc(-c3ccc(-c4ncn[nH]4)cc3)cnc2N1] | 6-(4-(1H-1,2,4-triazol-5-yl)phenyl)-4-(2-(tetrahydro-2H-pyran-4-yl)ethyl)-3,4-dihydropyrazino[2,3-b]pyrazin-2(1H)-one | 406.2 [M + 1]$^+$ | D |
| 150 | 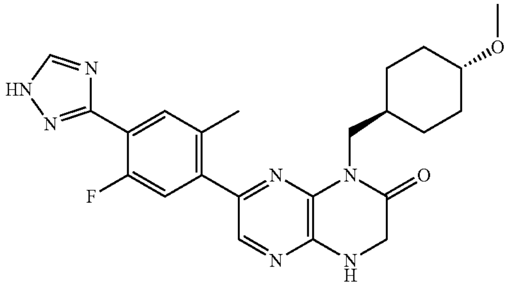 [SMILES: CO[C@H]1CC[C@H](CN2C(=O)CNc3ncc(-c4cc(F)c(-c5nc[nH]n5)cc4C)nc32)CC1] | 7-(5-fluoro-2-methyl-4-(1H-1,2,4-triazol-3-yl)phenyl)-1-((trans-4-methoxycyclohexyl)methyl)-3,4-dihydropyrazino[2,3-b]pyrazin-2(1H)-one | 452.3 [M + 1]$^+$ | D |
| 151 | 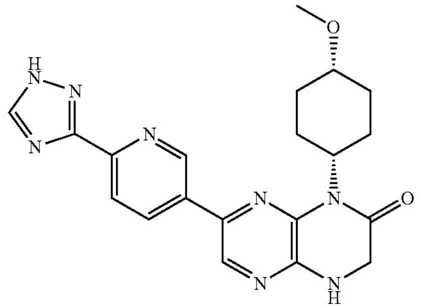 [SMILES: CO[C@H]1CC[C@@H](N2C(=O)CNc3ncc(-c4ccc(-c5nc[nH]n5)nc4)nc32)CC1] | 7-(6-(1H-1,2,4-triazol-3-yl)pyridin-3-yl)-1-(cis-4-methoxycyclohexyl)-3,4-dihydropyrazino[2,3-b]pyrazin-2(1H)-one | 407.3 [M + 1]$^+$ | D |
| 152 | 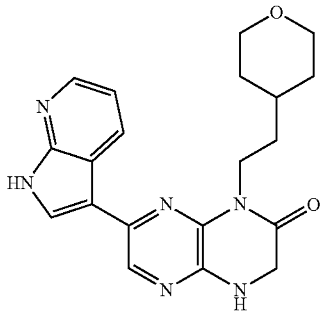 [SMILES: O=C1CNc2ncc(-c3c[nH]c4ncccc34)nc2N1CCC1CCOCC1] | 7-(1H-pyrrolo[2,3-b]pyridin-3-yl)-1-(2-(tetrahydro-2H-pyran-4-yl)ethyl)-3,4-dihydropyrazino[2,3-b]pyrazin-2(1H)-one | 379.1 [M + 1]$^+$ | D |

TABLE 1-continued

| Cmpd No. | Cmpd Structure | Cmpd Name | MS (ESI) m/z | Act. Level |
|---|---|---|---|---|
| 153 | 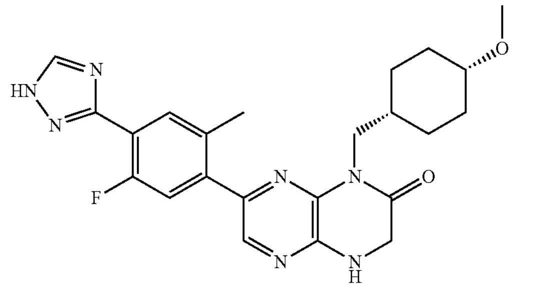 [SMILES: CO[C@H]1CC[C@@H](CN2C(=O)CNc3ncc(-c4cc(F)c(-c5nc[nH]n5)cc4C)nc32)CC1] | 7-(5-fluoro-2-methyl-4-(1H-1,2,4-triazol-3-yl)phenyl)-1-((cis-4-methoxycyclohexyl)methyl)-3,4-dihydropyrazino[2,3-b]pyrazin-2(1H)-one | 452.3 $[M + 1]^+$ | D |
| 154 | 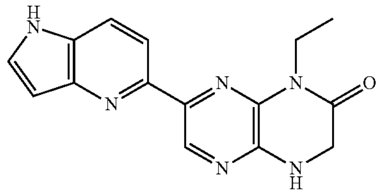 [SMILES: CCN1C(=O)CNc2ncc(-c3ccc4[nH]ccc4n3)nc21] | 1-ethyl-7-(1H-pyrrolo[3,2-b]pyridin-5-yl)-3,4-dihydropyrazino[2,3-b]pyrazin-2(1H)-one | 295.1 $[M + 1]^+$ | A |
| 155 | 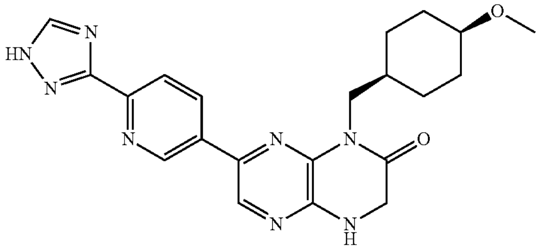 [SMILES: CO[C@H]1CC[C@@H](CN2C(=O)CNc3ncc(-c4ccc(-c5nc[nH]n5)nc4)nc32)CC1] | 7-(6-(1H-1,2,4-triazol-3-yl)pyridin-3-yl)-1-((cis-4-methoxycyclohexyl)methyl)-3,4-dihydropyrazino[2,3-b]pyrazin-2(1H)-one | 421.4 $[M + 1]^+$ | D |
| 156 | 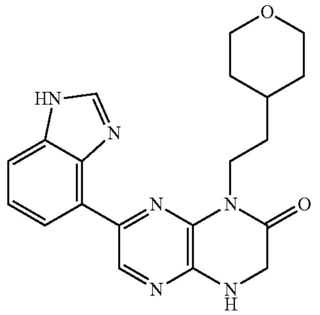 [SMILES: O=C1CNc2ncc(-c3cccc4[nH]cnc34)nc2N1CCC1CCOCC1] | 7-(1H-benzo[d]imidazol-4-yl)-1-(2-(tetrahydro-2H-pyran-4-yl)ethyl)-3,4-dihydropyrazino[2,3-b]pyrazin-2(1H)-one | 379.2 $[M + 1]^+$ | B |
| 157 | 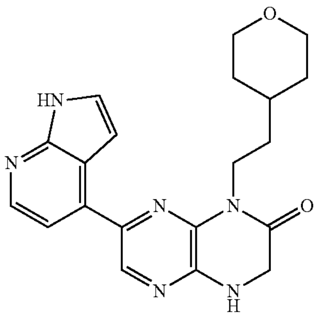 [SMILES: O=C1CNc2ncc(-c3ccnc4[nH]ccc34)nc2N1CCC1CCOCC1] | 7-(1H-pyrrolo[2,3-b]pyridin-4-yl)-1-(2-(tetrahydro-2H-pyran-4-yl)ethyl)-3,4-dihydropyrazino[2,3-b]pyrazin-2(1H)-one | 379.2 $[M + 1]^+$ | D |

TABLE 1-continued

| Cmpd No. | Cmpd Structure | Cmpd Name | MS (ESI) m/z | Act. Level |
|---|---|---|---|---|
| 158 | 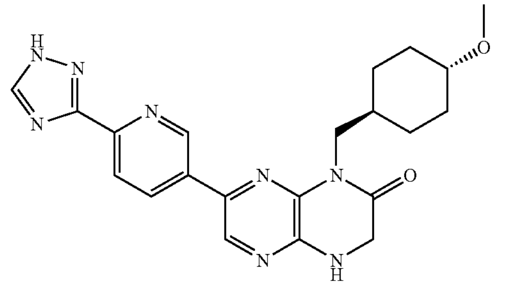 [SMILES: CO[C@H]1CC[C@H](CN2C(=O)CNc3ncc(-c4ccc(-c5nc[nH]n5)nc4)nc32)CC1] | 7-(6-(1H-1,2,4-triazol-3-yl)pyridin-3-yl)-1-((trans-4-methoxycyclohexyl)methyl)-3,4-dihydropyrazino[2,3-b]pyrazin-2(1H)-one | 421.3 $[M + 1]^+$ | D |
| 159 | 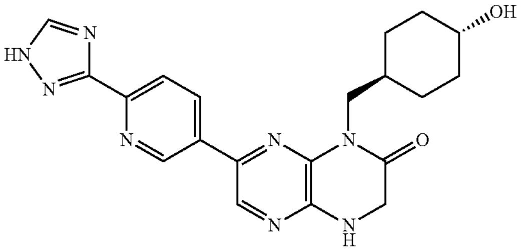 [SMILES: O=C1CNc2ncc(-c3ccc(-c4nc[nH]n4)nc3)nc2N1C[C@H]1CC[C@H](O)CC1] | 7-(6-(1H-1,2,4-triazol-3-yl)pyridin-3-yl)-1-((trans-4-hydroxycyclohexyl)methyl)-3,4-dihydropyrazino[2,3-b]pyrazin-2(1H)-one | 407.2 $[M + 1]^+$ | D |
| 160 | 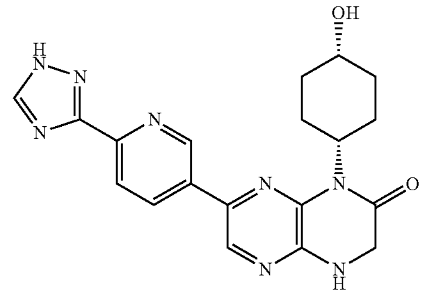 [SMILES: O=C1CNc2ncc(-c3ccc(-c4nc[nH]n4)nc3)nc2N1[C@H]1CC[C@@H](O)CC1] | 7-(6-(1H-1,2,4-triazol-3-yl)pyridin-3-yl)-1-(cis-4-hydroxycyclohexyl)-3,4-dihydropyrazino[2,3-b]pyrazin-2(1H)-one | 393.3 $[M + 1]^+$ | D |
| 161 | 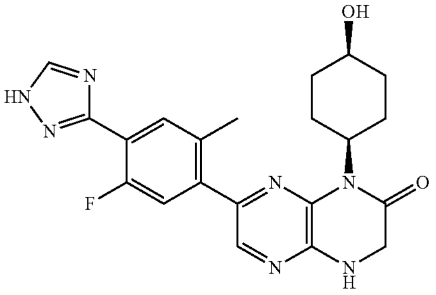 [SMILES: Cc1cc(-c2nc[nH]n2)c(F)cc1-c1cnc2c(n1)N([C@H]1CC[C@@H](O)CC1)C(=O)CN2] | 7-(5-fluoro-2-methyl-4-(1H-1,2,4-triazol-3-yl)phenyl)-1-(cis-4-hydroxycyclohexyl)-3,4-dihydropyrazino[2,3-b]pyrazin-2(1H)-one | 424.2 $[M + 1]^+$ | D |
| 162 | 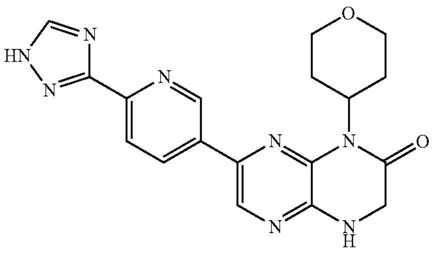 [SMILES: O=C1CNc2ncc(-c3ccc(-c4nc[nH]n4)nc3)nc2N1C1CCOCC1] | 7-(6-(1H-1,2,4-triazol-3-yl)pyridin-3-yl)-1-(tetrahydro-2H-pyran-4-yl)-3,4-dihydropyrazino[2,3-b]pyrazin-2(1H)-one | 379.2 $[M + 1]^+$ | D |

TABLE 1-continued

| Cmpd No. | Cmpd Structure | Cmpd Name | MS (ESI) m/z | Act. Level |
|---|---|---|---|---|
| 163 | 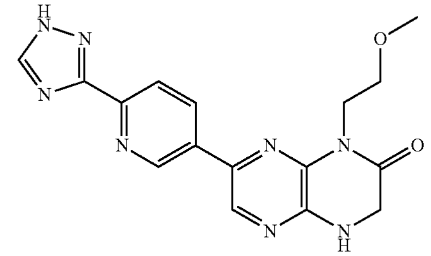 [SMILES: COCCN1C(=O)CNc2ncc(-c3ccc(-c4nc[nH]n4)nc3)nc21] | 7-(6-(1H-1,2,4-triazol-3-yl)pyridin-3-yl)-1-(2-methoxyethyl)-3,4-dihydropyrazino[2,3-b]pyrazin-2(1H)-one | 353.2 $[M + 1]^+$ | D |
| 164 | 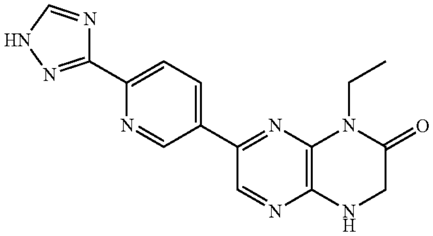 [SMILES: CCN1C(=O)CNc2ncc(-c3ccc(-c4nc[nH]n4)nc3)nc21] | 7-(6-(1H-1,2,4-triazol-3-yl)pyridin-3-yl)-1-ethyl-3,4-dihydropyrazino[2,3-b]pyrazin-2(1H)-one | 323.2 $[M + 1]^+$ | D |
| 165 | 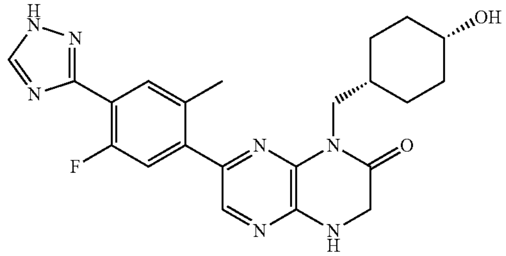 [SMILES: Cc1cc(-c2nc[nH]n2)c(F)cc1-c1cnc2c(n1)N(C[C@H]1CC[C@@H](O)CC1)C(=O)CN2] | 7-(5-fluoro-2-methyl-4-(1H-1,2,4-triazol-3-yl)phenyl)-1-((cis-4-hydroxycyclohexyl)methyl)-3,4-dihydropyrazino[2,3-b]pyrazin-2(1H)-one | 438.1 $[M + 1]^+$ | D |
| 166 | 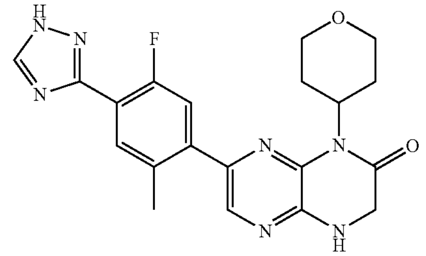 [SMILES: Cc1cc(-c2nc[nH]n2)c(F)cc1-c1cnc2c(n1)N(C1CCOCC1)C(=O)CN2] | 7-(5-fluoro-2-methyl-4-(1H-1,2,4-triazol-3-yl)phenyl)-1-(tetrahydro-2H-pyran-4-yl)-3,4-dihydropyrazino[2,3-b]pyrazin-2(1H)-one | 410.3 $[M + 1]^+$ | D |
| 167 | 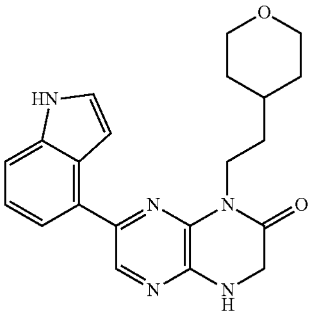 [SMILES: O=C1CNc2ncc(-c3cccc4[nH]ccc34)nc2N1CCC1CCOCC1] | 7-(1H-indol-4-yl)-1-(2-(tetrahydro-2H-pyran-4-yl)ethyl)-3,4-dihydropyrazino[2,3-b]pyrazin-2(1H)-one | 378.2 $[M + 1]^+$ | C |

TABLE 1-continued

| Cmpd No. | Cmpd Structure | Cmpd Name | MS (ESI) m/z | Act. Level |
|---|---|---|---|---|
| 168 | 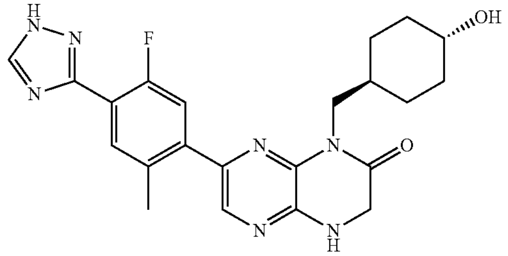 [SMILES: Cc1cc(-c2nc[nH]n2)c(F)cc1-c1cnc2c(n1)N(C[C@H]1CC[C@H](O)CC1)C(=O)CN2] | 7-(5-fluoro-2-methyl-4-(1H-1,2,4-triazol-3-yl)phenyl)-1-((trans-4-hydroxycyclohexyl)methyl)-3,4-dihydropyrazino[2,3-b]pyrazin-2(1H)-one | 438.2 [M + 1]+ | D |
| 169 | 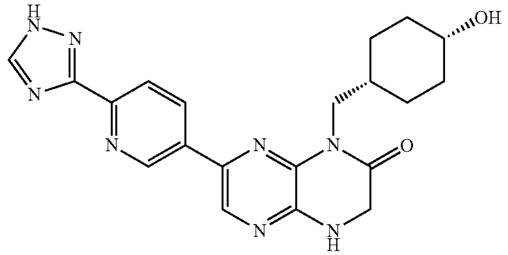 [SMILES: O=C1CNc2ncc(-c3ccc(-c4nc[nH]n4)nc3)nc2N1C[C@H]1CC[C@@H](O)CC1] | 7-(6-(1H-1,2,4-triazol-3-yl)pyridin-3-yl)-1-((cis-4-hydroxycyclohexyl)methyl)-3,4-dihydropyrazino[2,3-b]pyrazin-2(1H)-one | 407.1 [M + 1]+ | D |
| 170 | 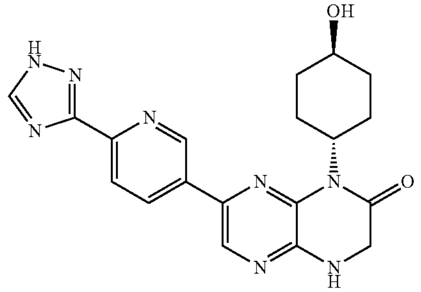 [SMILES: O=C1CNc2ncc(-c3ccc(-c4nc[nH]n4)nc3)nc2N1[C@H]1CC[C@H](O)CC1] | 7-(6-(1H-1,2,4-triazol-3-yl)pyridin-3-yl)-1-(trans-4-hydroxycyclohexyl)-3,4-dihydropyrazino[2,3-b]pyrazin-2(1H)-one | 393.2 [M + 1]+ | D |
| 171 | 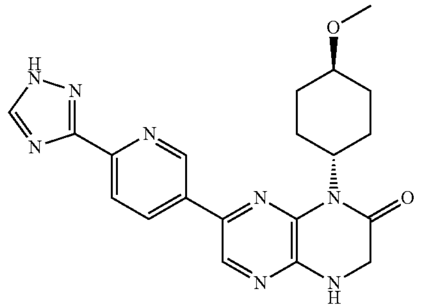 [SMILES: CO[C@H]1CC[C@H](N2C(=O)CNc3ncc(-c4ccc(-c5nc[nH]n5)nc4)nc32)CC1] | 7-(6-(1H-1,2,4-triazol-3-yl)pyridin-3-yl)-1-(trans-4-methoxycyclohexyl)-3,4-dihydropyrazino[2,3-b]pyrazin-2(1H)-one | 407.3 [M + 1]+ | D |
| 172 | 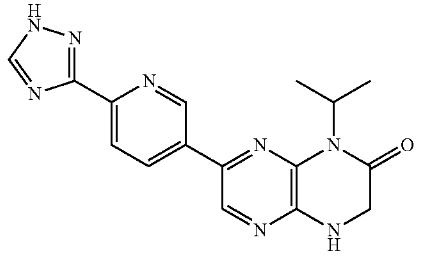 [SMILES: CC(C)N1C(=O)CNc2ncc(-c3ccc(-c4nc[nH]n4)nc3)nc21] | 7-(6-(1H-1,2,4-triazol-3-yl)pyridin-3-yl)-1-isopropyl-3,4-dihydropyrazino[2,3-b]pyrazin-2(1H)-one | 337.1 [M + 1]+ | D |

TABLE 1-continued

| Cmpd No. | Cmpd Structure | Cmpd Name | MS (ESI) m/z | Act. Level |
|---|---|---|---|---|
| 173 | 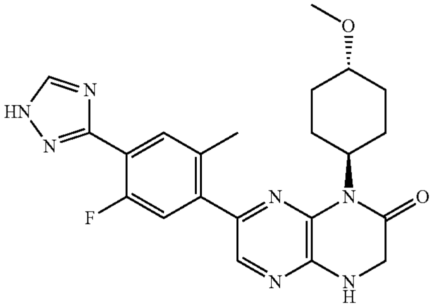 [SMILES: CO[C@H]1CC[C@H](N2C(=O)CNc3ncc(-c4cc(F)c(-c5nc[nH]n5)cc4C)nc32)CC1] | 7-(5-fluoro-2-methyl-4-(1H-1,2,4-triazol-3-yl)phenyl)-1-(trans-4-methoxycyclohexyl)-3,4-dihydropyrazino[2,3-b]pyrazin-2(1H)-one | 438.3 $[M + 1]^+$ | D |
| 174 | 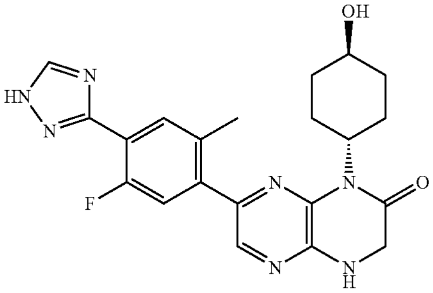 [SMILES: Cc1cc(-c2nc[nH]n2)c(F)cc1-c1cnc2c(n1)N([C@H]1CC[C@H](O)CC1)C(=O)CN2] | 7-(5-fluoro-2-methyl-4-(1H-1,2,4-triazol-3-yl)phenyl)-1-(trans-4-hydroxycyclohexyl)-3,4-dihydropyrazino[2,3-b]pyrazin-2(1H)-one | 424.3 $[M + 1]^+$ | D |
| 175 | 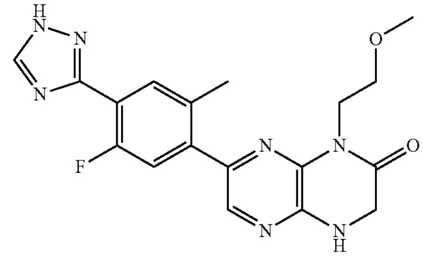 | 7-(5-fluoro-2-methyl-4-(1H-1,2,4-triazol-3-yl)phenyl)-1-(2-methoxyethyl)-3,4-dihydropyrazino[2,3-b]pyrazin-2(1H)-one | 368.2 $[M + 1]^+$ | D |
| 176 | 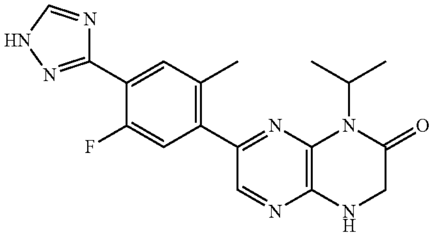 | 7-(5-fluoro-2-methyl-4-(1H-1,2,4-triazol-3-yl)phenyl)-1-isopropyl-3,4-dihydropyrazino[2,3-b]pyrazin-2(1H)-one | 323.2 $[M + 1]^+$ | D |
| 177 | 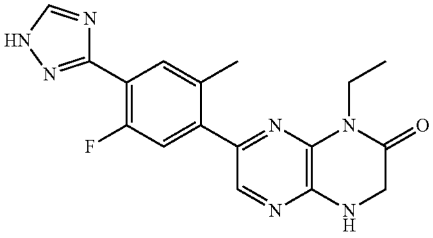 [SMILES: CCN1C(=O)CNc2ncc(-c3cc(F)c(-c4nc[nH]n4)cc3C)nc21] | 1-ethyl-7-(5-fluoro-2-methyl-4-(1H-1,2,4-triazol-3-yl)phenyl)-3,4-dihydropyrazino[2,3-b]pyrazin-2(1H)-one | 354.2 $[M + 1]^+$ | D |

TABLE 1-continued

| Cmpd No. | Cmpd Structure | Cmpd Name | MS (ESI) m/z | Act. Level |
|---|---|---|---|---|
| 178 | 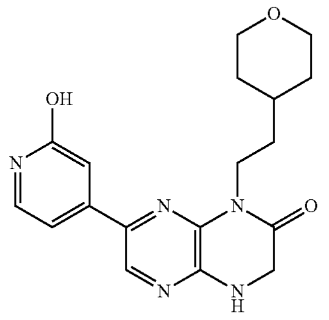 [SMILES: O=C1CNc2ncc(-c3ccnc(O)c3)nc2N1CCC1CCOCC1] | 7-(2-hydroxypyridin-4-yl)-1-(2-(tetrahydro-2H-pyran-4-yl)ethyl)-3,4-dihydropyrazino[2,3-b]pyrazin-2(1H)-one | 356.1 $[M + 1]^+$ | B |
| 179 | 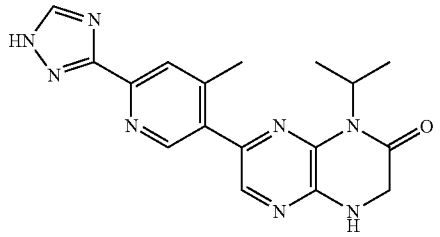 [SMILES: Cc1cc(-c2nc[nH]n2)ncc1-c1cnc2c(n1)N(C(C)C)C(=O)CN2] | 1-isopropyl-7-(4-methyl-6-(1H-1,2,4-triazol-3-yl)pyridin-3-yl)-3,4-dihydropyrazino[2,3-b]pyrazin-2(1H)-one | 351.4 $[M + 1]^+$ | D |
| 180 | 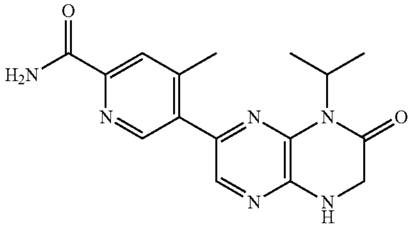 [SMILES: Cc1cc(C(N)=O)ncc1-c1cnc2c(n1)N(C(C)C)C(=O)CN2] | 5-(8-isopropyl-7-oxo-5,6,7,8-tetrahydropyrazino[2,3-b]pyrazin-2-yl)-4-methylpicolinamide | 327.4 $[M + 1]^+$ | D |
| 181 | 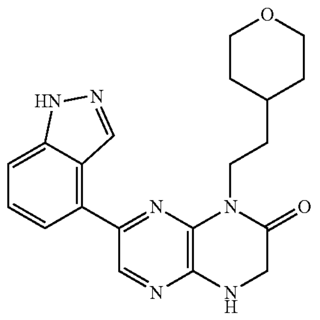 [SMILES: O=C1CNc2ncc(-c3cccc4[nH]ncc34)nc2N1CCC1CCOCC1] | 7-(1H-indazol-4-yl)-1-(2-(tetrahydro-2H-pyran-4-yl)ethyl)-3,4-dihydropyrazino[2,3-b]pyrazin-2(1H)-one | 379.2 $[M + 1]^+$ | D |
| 182 | 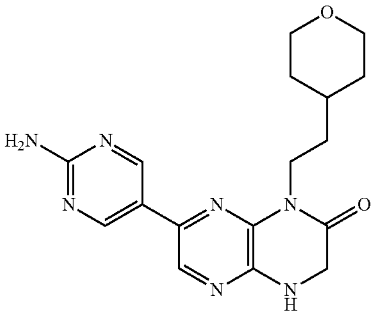 [SMILES: Nc1ncc(-c2cnc3c(n2)N(CCC2CCOCC2)C(=O)CN3)cn1] | 7-(2-aminopyrimidin-5-yl)-1-(2-(tetrahydro-2H-pyran-4-yl)ethyl)-3,4-dihydropyrazino[2,3-b]pyrazin-2(1H)-one | 355.1 $[M + 1]^+$ | C |

TABLE 1-continued

| Cmpd No. | Cmpd Structure | Cmpd Name | MS (ESI) m/z | Act. Level |
|---|---|---|---|---|
| 183 | 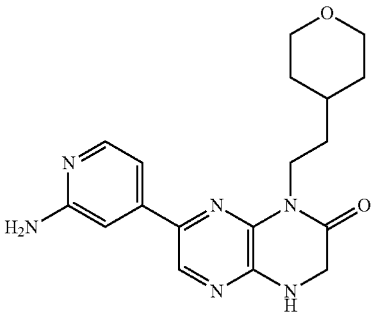 [SMILES: Nc1cc(-c2cnc3c(n2)N(CCC2CCOCC2)C(=O)CN3)ccn1] | 7-(2-aminopyridin-4-yl)-1-(2-(tetrahydro-2H-pyran-4-yl)ethyl)-3,4-dihydropyrazino[2,3-b]pyrazin-2(1H)-one | 355.2 $[M + 1]^+$ | B |
| 184 | 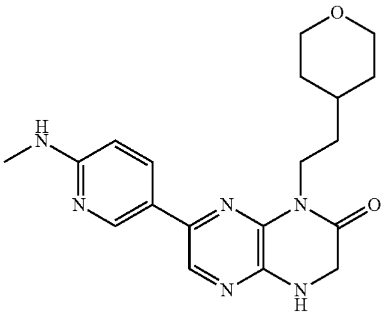 [SMILES: CNc1ccc(-c2cnc3c(n2)N(CCC2CCOCC2)C(=O)CN3)cn1] | 7-(6-(methylamino)pyridin-3-yl)-1-(2-(tetrahydro-2H-pyran-4-yl)ethyl)-3,4-dihydropyrazino[2,3-b]pyrazin-2(1H)-one | 369.3 $[M + 1]^+$ | D |
| 185 | 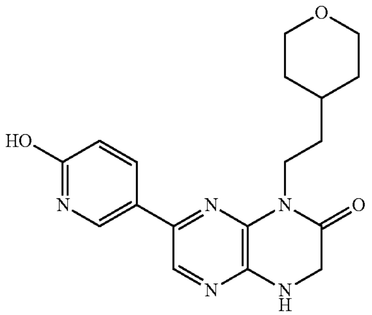 [SMILES: O=C1CNc2ncc(-c3ccc(O)nc3)nc2N1CCC1CCOCC1] | 7-(6-hydroxypyridin-3-yl)-1-(2-(tetrahydro-2H-pyran-4-yl)ethyl)-3,4-dihydropyrazino[2,3-b]pyrazin-2(1H)-one | 356.2 $[M + 1]^+$ | A |
| 186 | 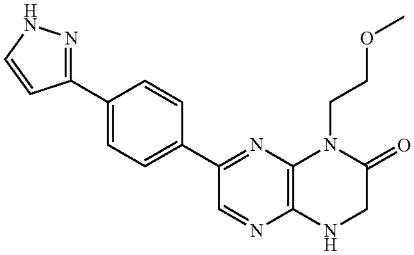 [SMILES: COCCN1C(=O)CNc2ncc(-c3ccc(-c4cc[nH]n4)cc3)nc21] | 7-(4-(1H-pyrazol-3-yl)phenyl)-1-(2-methoxyethyl)-3,4-dihydropyrazino[2,3-b]pyrazin-2(1H)-one | 351.3 $[M + 1]^+$ | D |
| 187 | 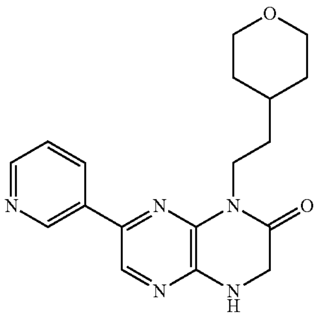 [SMILES: O=C1CNc2ncc(-c3cccnc3)nc2N1CCC1CCOCC1] | 7-(pyridin-3-yl)-1-(2-(tetrahydro-2H-pyran-4-yl)ethyl)-3,4-dihydropyrazino[2,3-b]pyrazin-2(1H)-one | 340.1 $[M + 1]^+$ | B |

TABLE 1-continued

| Cmpd No. | Cmpd Structure | Cmpd Name | MS (ESI) m/z | Act. Level |
|---|---|---|---|---|
| 188 | 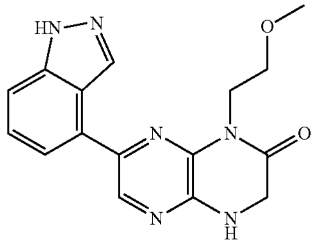 [SMILES: COCCN1C(=O)CNc2ncc(-c3cccc4[nH]ncc34)nc21] | 7-(1H-indazol-4-yl)-1-(2-methoxyethyl)-3,4-dihydropyrazino[2,3-b]pyrazin-2(1H)-one | 325.0 $[M + 1]^+$ | A |
| 189 | 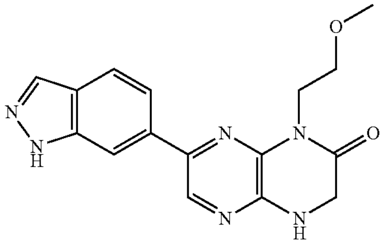 [SMILES: COCCN1C(=O)CNc2ncc(-c3ccc4cn[nH]c4c3)nc21] | 7-(1H-indazol-6-yl)-1-(2-methoxyethyl)-3,4-dihydropyrazino[2,3-b]pyrazin-2(1H)-one | 324.7 $[M + 1]^+$ | A |
| 190 | 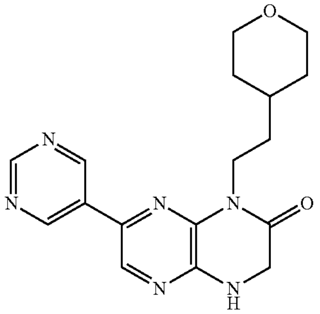 [SMILES: O=C1CNc2ncc(-c3cncnc3)nc2N1CCC1CCOCC1] | 7-(pyrimidin-5-yl)-1-(2-(tetrahydro-2H-pyran-4-yl)ethyl)-3,4-dihydropyrazino[2,3-b]pyrazin-2(1H)-one | 341.2 $[M + 1]^+$ | A |
| 191 | 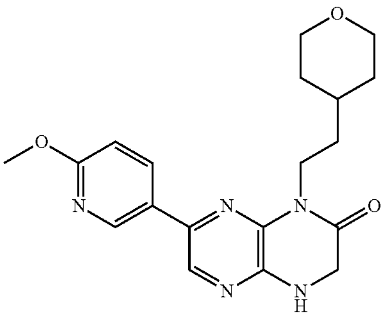 [SMILES: COc1ccc(-c2cnc3c(n2)N(CCC2CCOCC2)C(=O)CN3)cn1] | 7-(6-methoxypyridin-3-yl)-1-(2-(tetrahydro-2H-pyran-4-yl)ethyl)-3,4-dihydropyrazino[2,3-b]pyrazin-2(1H)-one | 370.2 $[M + 1]^+$ | B |
| 192 | 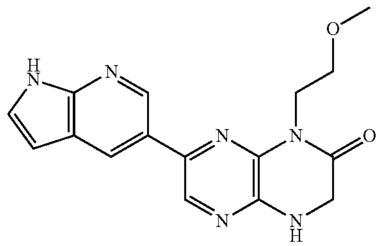 [SMILES: COCCN1C(=O)CNc2ncc(-c3cnc4[nH]ccc4c3)nc21] | 1-(2-methoxyethyl)-7-(1H-pyrrolo[2,3-b]pyridin-5-yl)-3,4-dihydropyrazino[2,3-b]pyrazin-2(1H)-one | 325.0 $[M + 1]^+$ | D |

TABLE 1-continued

| Cmpd No. | Cmpd Structure | Cmpd Name | MS (ESI) m/z | Act. Level |
|---|---|---|---|---|
| 193 | 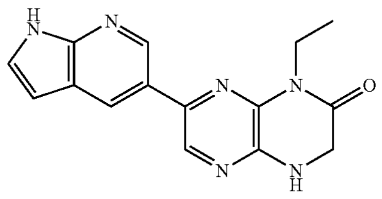 [SMILES: CCN1C(=O)CNc2ncc(-c3cnc4[nH]ccc4c3)nc21] | 1-ethyl-7-(1H-pyrrolo[2,3-b]pyridin-5-yl)-3,4-dihydropyrazino[2,3-b]pyrazin-2(1H)-one | 295.2 $[M + 1]^+$ | C |
| 194 | 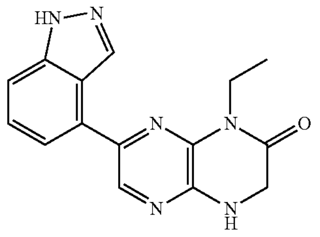 [SMILES: CCN1C(=O)CNc2ncc(-c3cccc4[nH]ncc34)nc21] | 1-ethyl-7-(1H-indazol-4-yl)-3,4-dihydropyrazino[2,3-b]pyrazin-2(1H)-one | 295.2 $[M + 1]^+$ | A |
| 195 | 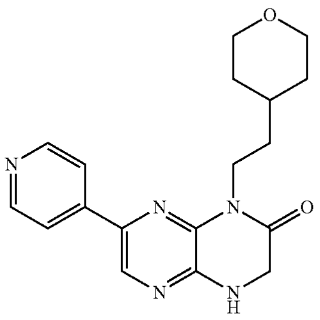 [SMILES: O=C1CNc2ncc(-c3ccncc3)nc2N1CCC1CCOCC1] | 7-(pyridin-4-yl)-1-(2-(tetrahydro-2H-pyran-4-yl)ethyl)-3,4-dihydropyrazino[2,3-b]pyrazin-2(1H)-one | 340.2 $[M + 1]^+$ | A |
| 196 | 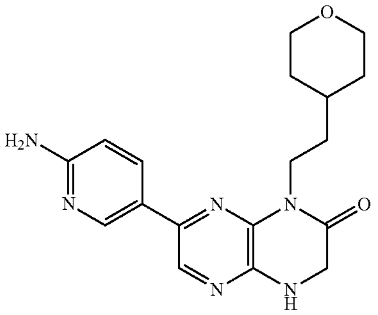 [SMILES: Nc1ccc(-c2cnc3c(n2)N(CCC2CCOCC2)C(=O)CN3)cn1] | 7-(6-aminopyridin-3-yl)-1-(2-(tetrahydro-2H-pyran-4-yl)ethyl)-3,4-dihydropyrazino[2,3-b]pyrazin-2(1H)-one | 355.1 $[M + 1]^+$ | D |
| 197 | 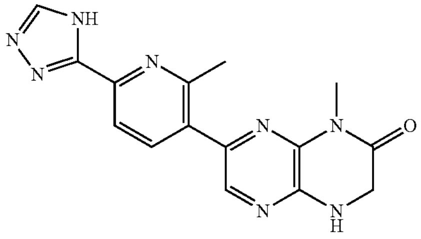 [SMILES: Cc1nc(-c2nnc[nH]2)ccc1-c1cnc2c(n1)N(C)C(=O)CN2] | 1-methyl-7-(2-methyl-6-(4H-1,2,4-triazol-3-yl)pyridin-3-yl)-3,4-dihydropyrazino[2,3-b]pyrazin-2(1H)-one | 323.3 $[M + 1]^+$ | D |

TABLE 1-continued

| Cmpd No. | Cmpd Structure | Cmpd Name | MS (ESI) m/z | Act. Level |
|---|---|---|---|---|
| 198 | 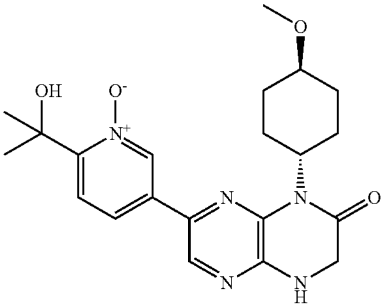 [SMILES: CO[C@H]1CC[C@H](N2C(=O)CNc3ncc(-c4ccc(C(C)(C)O)[n+]([O-])c4)nc32)CC1] | 2-(2-hydroxypropan-2-yl)-5-(8-(trans-4-methoxycyclohexyl)-7-oxo-5,6,7,8-tetrahydropyrazino[2,3-b]pyrazin-2-yl)pyridine 1-oxide | 414.2 [M + 1]$^+$ | A |
| 199 | 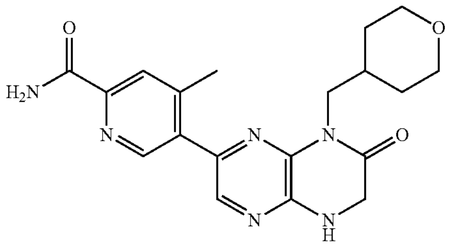 [SMILES: Cc1cc(C(N)=O)ncc1-c1cnc2c(n1)N(CC1CCOCC1)C(=O)CN2] | 4-methyl-5-(7-oxo-8-((tetrahydro-2H-pyran-4-yl)methyl)-5,6,7,8-tetrahydropyrazino[2,3-b]pyrazin-2-yl)picolinamide | 383.4 [M + 1]$^+$ | A |
| 200 | 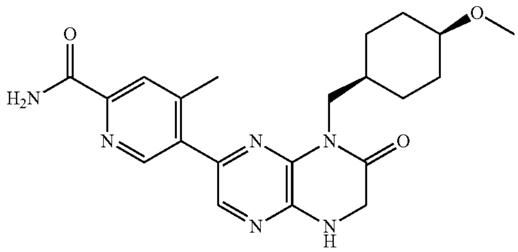 [SMILES: CO[C@H]1CC[C@@H](CN2C(=O)CNc3ncc(-c4cnc(C(N)=O)cc4C)nc32)CC1] | 5-(8-((cis-4-methoxycyclohexyl)methyl)-7-oxo-5,6,7,8-tetrahydropyrazino[2,3-b]pyrazin-2-yl)-4-methylpicolinamide | 411.5 [M + 1]$^+$ | A |
| 201 | 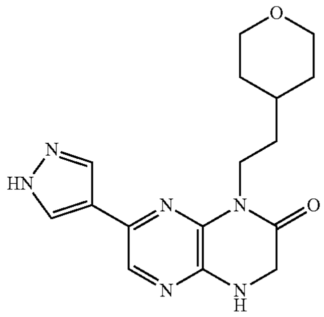 [SMILES: O=C1CNc2ncc(-c3cn[nH]c3)nc2N1CCC1CCOCC1] | 7-(1H-pyrazol-4-yl)-1-(2-(tetrahydro-2H-pyran-4-yl)ethyl)-3,4-dihydropyrazino[2,3-b]pyrazin-2(1H)-one | 329.4 [M + 1]$^+$ | A |
| 202 | 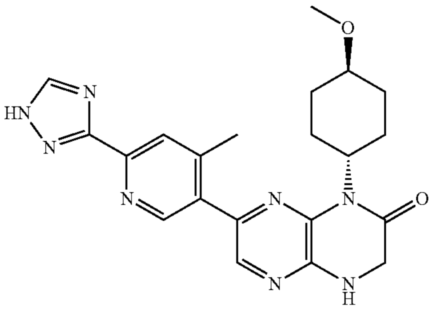 [SMILES: CO[C@H]1CC[C@H](N2C(=O)CNc3ncc(-c4cnc(-c5nc[nH]n5)cc4C)nc32)CC1] | 1-(trans-4-methoxycyclohexyl)-7-(4-methyl-6-(1H-1,2,4-triazol-3-yl)pyridin-3-yl)-3,4-dihydropyrazino[2,3-b]pyrazin-2(1H)-one | 421.5 [M + 1]$^+$ | D |

TABLE 1-continued

| Cmpd No. | Cmpd Structure | Cmpd Name | MS (ESI) m/z | Act. Level |
| --- | --- | --- | --- | --- |
| 203 | 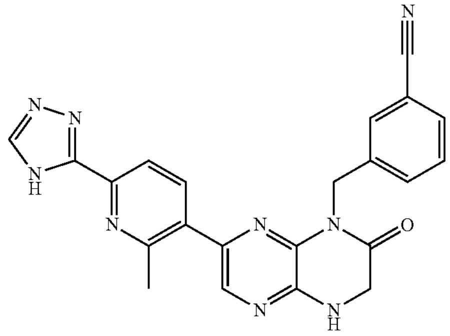 [SMILES: Cc1nc(-c2nnc[nH]2)ccc1-c1cnc2c(n1)N(Cc1cccc(C#N)c1)C(=O)CN2] | 3-((7-(2-methyl-6-(4H-1,2,4-triazol-3-yl)pyridin-3-yl)-2-oxo-3,4-dihydropyrazino[2,3-b]pyrazin-1(2H)-yl)methyl)benzonitrile | 424.0 $[M + 1]^+$ | D |
| 204 | 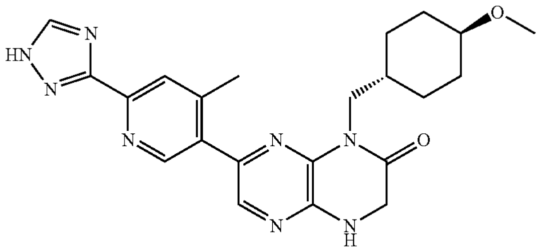 [SMILES: CO[C@H]1CC[C@H](CN2C(=O)CNc3ncc(-c4cnc(-c5nc[nH]n5)cc4C)nc32)CC1] | 1-((trans-4-methoxycyclohexyl)methyl)-7-(4-methyl-6-(1H-1,2,4-triazol-3-yl)pyridin-3-yl)-3,4-dihydropyrazino[2,3-b]pyrazin-2(1H)-one | 435.5 $[M + 1]^+$ | D |
| 205 | 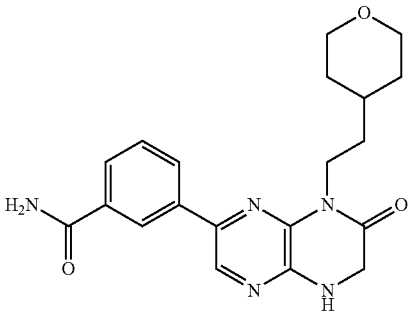 [SMILES: NC(=O)c1cccc(-c2cnc3c(n2)N(CCC2CCOCC2)C(=O)CN3)c1] | 3-(7-oxo-8-(2-(tetrahydro-2H-pyran-4-yl)ethyl)-5,6,7,8-tetrahydropyrazino[2,3-b]pyrazin-2-yl)benzamide | 382.1 $[M + 1]^+$ | A |
| 206 | 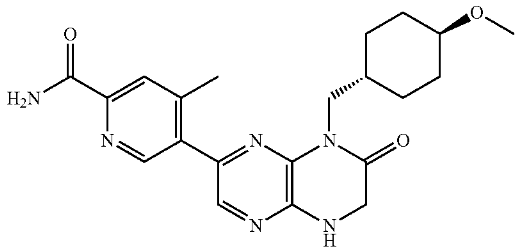 [SMILES: CO[C@H]1CC[C@H](CN2C(=O)CNc3ncc(-c4cnc(C(N)=O)cc4C)nc32)CC1] | 5-(8-((trans-4-methoxycyclohexyl)methyl)-7-oxo-5,6,7,8-tetrahydropyrazino[2,3-b]pyrazin-2-yl)-4-methylpicolinamide | 411.5 $[M + 1]^+$ | A |
| 207 | 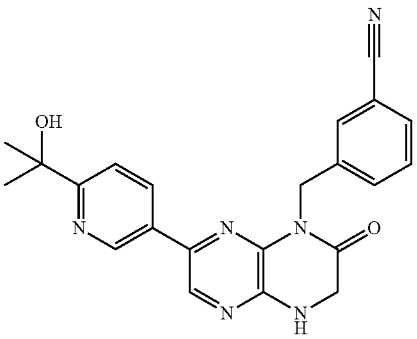 [SMILES: CC(C)(O)c1ccc(-c2cnc3c(n2)N(Cc2cccc(C#N)c2)C(=O)CN3)cn1] | 3-((7-(6-(2-hydroxypropan-2-yl)pyridin-3-yl)-2-oxo-3,4-dihydropyrazino[2,3-b]pyrazin-1(2H)-yl)methyl)benzonitrile | 401.2 $[M + 1]^+$ | D |

TABLE 1-continued

| Cmpd No. | Cmpd Structure | Cmpd Name | MS (ESI) m/z | Act. Level |
|---|---|---|---|---|
| 208 | 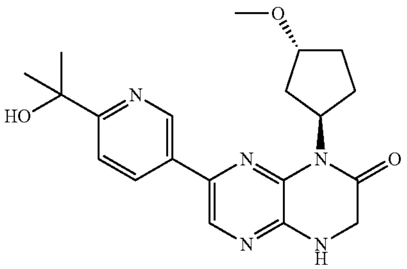 [SMILES: CO[C@@H]1CC[C@@H](N2C(=O)CNc3ncc(-c4ccc(C(C)(C)O)nc4)nc32)C1] | 7-(6-(2-hydroxypropan-2-yl)pyridin-3-yl)-1-((1R,3R)-3-methoxycyclopentyl)-3,4-dihydropyrazino[2,3-b]pyrazin-2(1H)-one | 384.2 $[M + 1]^+$ | D |
| 209 | 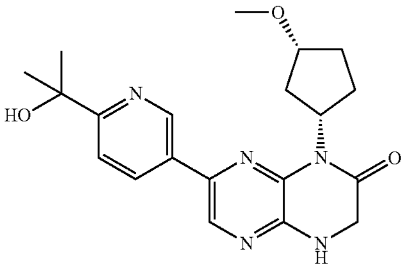 [SMILES: CO[C@@H]1CC[C@H](N2C(=O)CNc3ncc(-c4ccc(C(C)(C)O)nc4)nc32)C1] | 7-(6-(2-hydroxypropan-2-yl)pyridin-3-yl)-1-((1S,3R)-3-methoxycyclopentyl)-3,4-dihydropyrazino[2,3-b]pyrazin-2(1H)-one | 384.1 $[M + 1]^+$ | D |
| 210 | 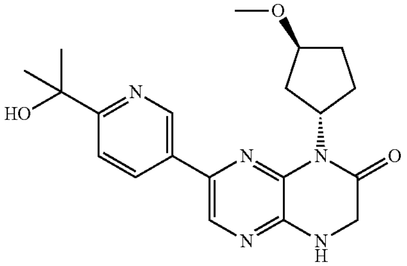 [SMILES: CO[C@H]1CC[C@H](N2C(=O)CNc3ncc(-c4ccc(C(C)(C)O)nc4)nc32)C1] | 7-(6-(2-hydroxypropan-2-yl)pyridin-3-yl)-1-((1S,3S)-3-methoxycyclopentyl)-3,4-dihydropyrazino[2,3-b]pyrazin-2(1H)-one | 384.1 $[M + 1]^+$ | D |
| 211 | 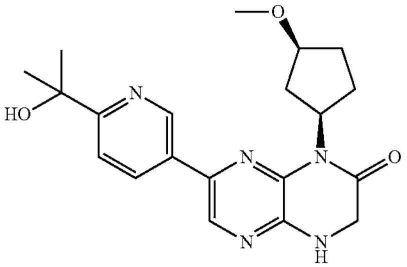 [SMILES: CO[C@H]1CC[C@@H](N2C(=O)CNc3ncc(-c4ccc(C(C)(C)O)nc4)nc32)C1] | 7-(6-(2-hydroxypropan-2-yl)pyridin-3-yl)-1-((1R,3S)-3-methoxycyclopentyl)-3,4-dihydropyrazino[2,3-b]pyrazin-2(1H)-one | 384.1 $[M + 1]^+$ | D |
| 212 | 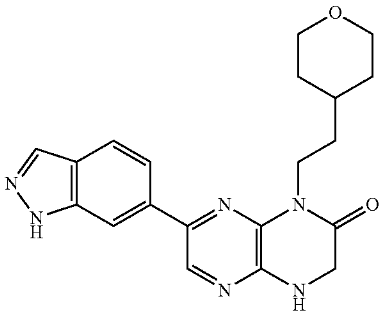 [SMILES: O=C1CNc2ncc(-c3ccc4cn[nH]c4c3)nc2N1CCC1CCOCC1] | 7-(1H-indazol-6-yl)-1-(2-(tetrahydro-2H-pyran-4-yl)ethyl)-3,4-dihydropyrazino[2,3-b]pyrazin-2(1H)-one | 379.2 $[M + 1]^+$ | D |

TABLE 1-continued

| Cmpd No. | Cmpd Structure | Cmpd Name | MS (ESI) m/z | Act. Level |
|---|---|---|---|---|
| 213 | 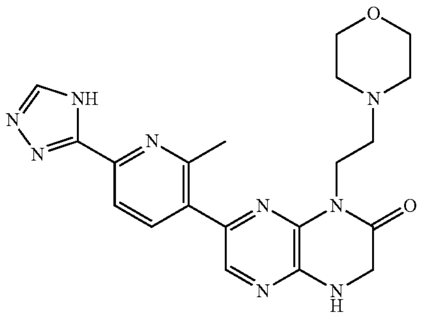 [SMILES: Cc1nc(-c2nnc[nH]2)ccc1-c1cnc2c(n1)N(CCN1CCOCC1)C(=O)CN2] | 7-(2-methyl-6-(4H-1,2,4-triazol-3-yl)pyridin-3-yl)-1-(2-morpholinoethyl)-3,4-dihydropyrazino[2,3-b]pyrazin-2(1H)-one | 422.2 [M + 1]+ | D |
| 214 | 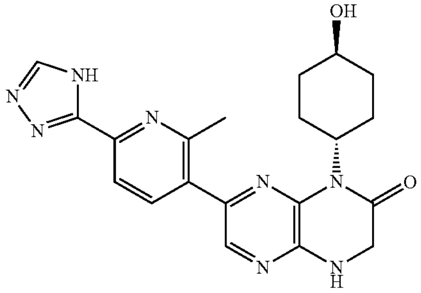 [SMILES: Cc1nc(-c2nnc[nH]2)ccc1-c1cnc2c(n1)N([C@H]1CC[C@H](O)CC1)C(=O)CN2] | 1-(trans-4-hydroxycyclohexyl)-7-(2-methyl-6-(4H-1,2,4-triazol-3-yl)pyridin-3-yl)-3,4-dihydropyrazino[2,3-b]pyrazin-2(1H)-one | 407.3 [M + 1]+ | D |
| 215 | 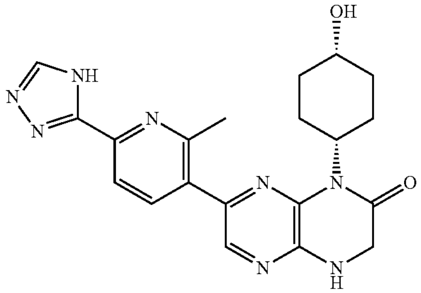 [SMILES: Cc1nc(-c2nnc[nH]2)ccc1-c1cnc2c(n1)N([C@H]1CC[C@@H](O)CC1)C(=O)CN2] | 1-(cis-4-hydroxycyclohexyl)-7-(2-methyl-6-(4H-1,2,4-triazol-3-yl)pyridin-3-yl)-3,4-dihydropyrazino[2,3-b]pyrazin-2(1H)-one | 407.3 [M + 1]+ | D |
| 216 | 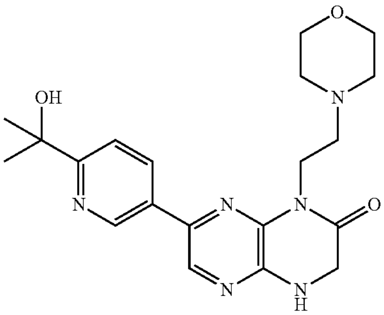 [SMILES: CC(C)(O)c1ccc(-c2cnc3c(n2)N(CCN2CCOCC2)C(=O)CN3)cn1] | 7-(6-(2-hydroxypropan-2-yl)pyridin-3-yl)-1-(2-morpholinoethyl)-3,4-dihydropyrazino[2,3-b]pyrazin-2(1H)-one | 399.2 [M + 1]+ | D |
| 217 | 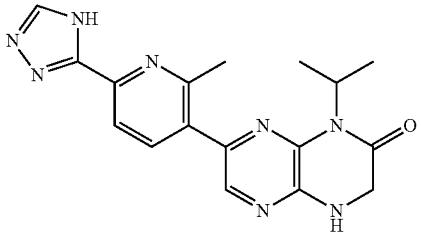 [SMILES: Cc1nc(-c2nnc[nH]2)ccc1-c1cnc2c(n1)N(C(C)C)C(=O)CN2] | 1-isopropyl-7-(2-methyl-6-(4H-1,2,4-triazol-3-yl)pyridin-3-yl)-3,4-dihydropyrazino[2,3-b]pyrazin-2(1H)-one | 351.5 [M + 1]+ | D |

TABLE 1-continued

| Cmpd No. | Cmpd Structure | Cmpd Name | MS (ESI) m/z | Act. Level |
|---|---|---|---|---|
| 218 | 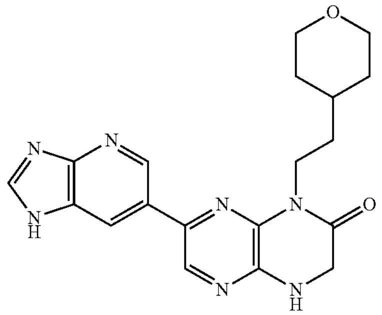 [SMILES: O=C1CNc2ncc(-c3cnc4nc[nH]c4c3)nc2N1CCC1CCOCC1] | 7-(1H-imidazo[4,5-b]pyridin-6-yl)-1-(2-(tetrahydro-2H-pyran-4-yl)ethyl)-3,4-dihydropyrazino[2,3-b]pyrazin-2(1H)-one | 380.2 $[M + 1]^+$ | A |
| 219 | 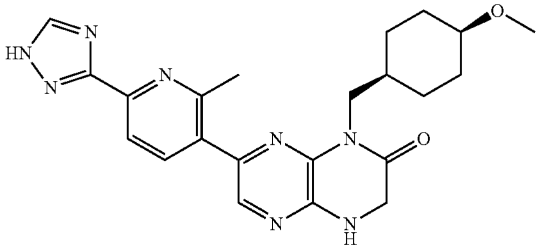 [SMILES: CO[C@H]1CC[C@@H](CN2C(=O)CNc3ncc(-c4ccc(-c5nc[nH]n5)nc4C)nc32)CC1] | 1-((cis-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one | 435.5 $[M + 1]^+$ | D |
| 220 | 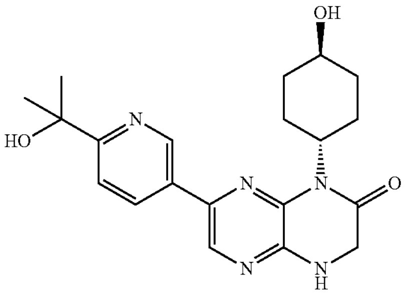 [SMILES: CC(C)(O)c1ccc(-c2cnc3c(n2)N([C@H]2CC[C@H](O)CC2)C(=O)CN3)cn1] | 1-(trans-4-hydroxycyclohexyl)-7-(6-(2-hydroxypropan-2-yl)pyridin-3-yl)-3,4-dihydropyrazino[2,3-b]pyrazin-2(1H)-one | 384.2 $[M + 1]^+$ | D |
| 221 | 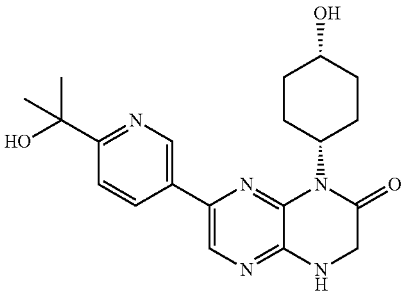 [SMILES: CC(C)(O)c1ccc(-c2cnc3c(n2)N([C@H]2CC[C@@H](O)CC2)C(=O)CN3)cn1] | 1-(cis-4-hydroxycyclohexyl)-7-(6-(2-hydroxypropan-2-yl)pyridin-3-yl)-3,4-dihydropyrazino[2,3-b]pyrazin-2(1H)-one | 384.2 $[M + 1]^+$ | D |
| 222 | 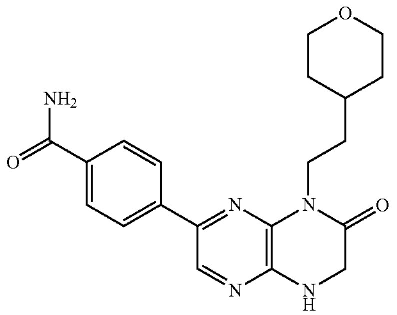 [SMILES: NC(=O)c1ccc(-c2cnc3c(n2)N(CCC2CCOCC2)C(=O)CN3)cc1] | 4-(7-oxo-8-(2-(tetrahydro-2H-pyran-4-yl)ethyl)-5,6,7,8-tetrahydropyrazino[2,3-b]pyrazin-2-yl)benzamide | 382.3 $[M + 1]^+$ | D |

TABLE 1-continued

| Cmpd No. | Cmpd Structure | Cmpd Name | MS (ESI) m/z | Act. Level |
|---|---|---|---|---|
| 223 | 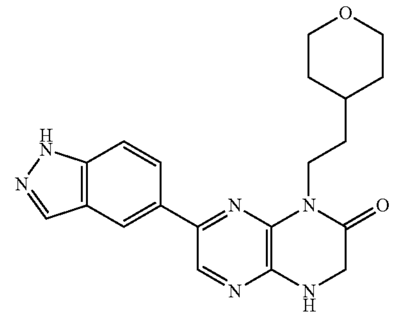 [SMILES: O=C1CNc2ncc(-c3ccc4[nH]ncc4c3)nc2N1CCC1CCOCC1] | 7-(1H-indazol-5-yl)-1-(2-(tetrahydro-2H-pyran-4-yl)ethyl)-3,4-dihydropyrazino[2,3-b]pyrazin-2(1H)-one | 379.2 $[M + 1]^+$ | B |
| 224 | 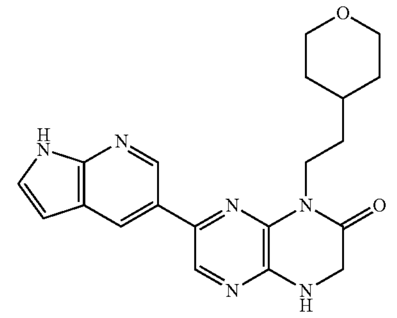 [SMILES: O=C1CNc2ncc(-c3cnc4[nH]ccc4c3)nc2N1CCC1CCOCC1] | 7-(1H-pyrrolo[2,3-b]pyridin-5-yl)-1-(2-(tetrahydro-2H-pyran-4-yl)ethyl)-3,4-dihydropyrazino[2,3-b]pyrazin-2(1H)-one | 379.2 $[M + 1]^+$ | D |
| 225 | 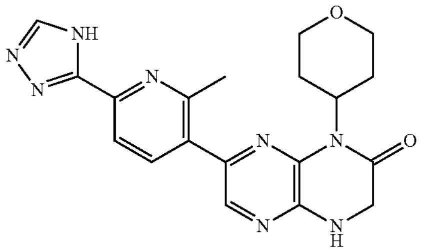 [SMILES: Cc1nc(-c2nnc[nH]2)ccc1-c1cnc2c(n1)N(C1CCOCC1)C(=O)CN2] | 7-(2-methyl-6-(4H-1,2,4-triazol-3-yl)pyridin-3-yl)-1-(tetrahydro-2H-pyran-4-yl)-3,4-dihydropyrazino[2,3-b]pyrazin-2(1H)-one | 393.2 $[M + 1]^+$ | D |
| 226 | 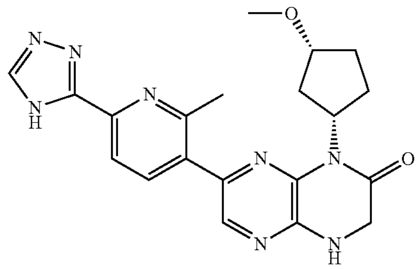 [SMILES: CO[C@@H]1CC[C@H](N2C(=O)CNc3ncc(-c4ccc(-c5nnc[nH]5)nc4C)nc32)C1] | 1-((2S,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one | 407.5 $[M + 1]^+$ | D |
| 227 | 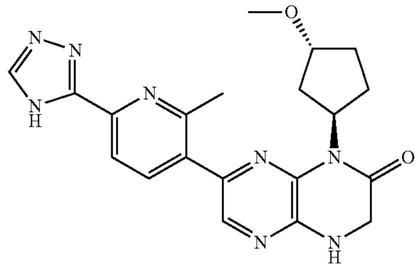 [SMILES: CO[C@@H]1CC[C@@H](N2C(=O)CNc3ncc(-c4ccc(-c5nnc[nH]5)nc4C)nc32)C1] | 1-((1R,3R)-3-methoxycyclopentyl)-7-(2-methyl-6-(4H-1,2,4-triazol-3-yl)pyridin-3-yl)-3,4-dihydropyrazino[2,3-b]pyrazin-2(1H)-one | 407.5 $[M + 1]^+$ | D |

TABLE 1-continued

| Cmpd No. | Cmpd Structure | Cmpd Name | MS (ESI) m/z | Act. Level |
|---|---|---|---|---|
| 228 | 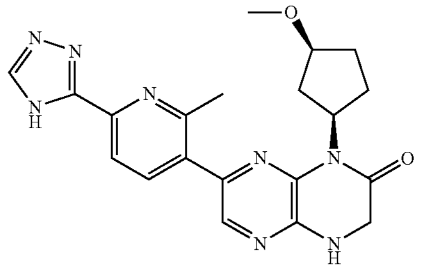 [SMILES: CO[C@H]1CC[C@@H](N2C(=O)CNc3ncc(-c4ccc(-c5nnc[nH]5)nc4C)nc32)C1] | 1-((1R,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one | 407.5 $[M + 1]^+$ | D |
| 229 | 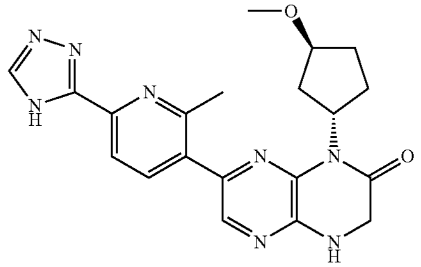 [SMILES: CO[C@H]1CC[C@H](N2C(=O)CNc3ncc(-c4ccc(-c5nnc[nH]5)nc4C)nc32)C1] | 1-((1S,3S)-3-methoxycyclopentyl)-7-(2-methyl-6-(4H-1,2,4-triazol-3-yl)pyridin-3-yl)-3,4-dihydropyrazino[2,3-b]pyrazin-2(1H)-one | 407.5 $[M + 1]^+$ | D |
| 230 | 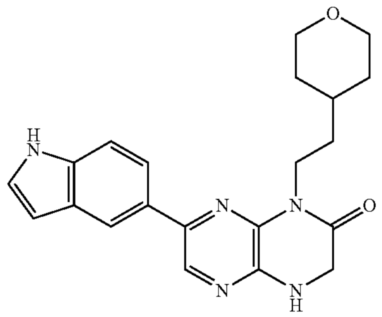 [SMILES: O=C1CNc2ncc(-c3ccc4[nH]ccc4c3)nc2N1CCC1CCOCC1] | 7-(1H-indol-5-yl-1-(2-(tetrahydro-2H-pyran-4-yl)ethyl)-3,4-dihydropyrazino[2,3-b]pyrazin-2(1H)-one | 378.2 $[M + 1]^+$ | D |
| 231 | 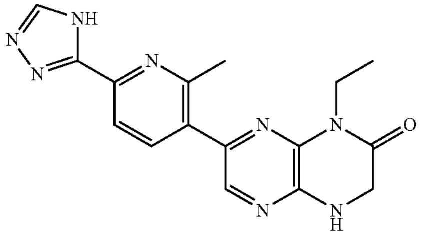 [SMILES: CCN1C(=O)CNc2ncc(-c3ccc(-c4nnc[nH]4)nc3C)nc21] | 1-ethyl-7-(2-methyl-6-(4H-1,2,4-triazol-3-yl)pyridin-3-yl)-3,4-dihydropyrazino[2,3-b]pyrazin-2(1H)-one | 337.6 $[M + 1]^+$ | D |
| 232 | 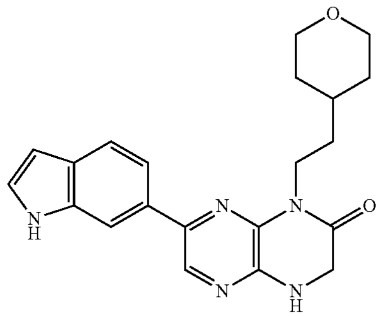 [SMILES: O=C1CNc2ncc(-c3ccc4cc[nH]c4c3)nc2N1CCC1CCOCC1] | 7-(1H-indol-6-yl)-1-(2-(tetrahydro-2H-pyran-4-yl)ethyl)-3,4-dihydropyrazino[2,3-b]pyrazin-2(1H)-one | 378.2 $[M + 1]^+$ | C |

TABLE 1-continued

| Cmpd No. | Cmpd Structure | Cmpd Name | MS (ESI) m/z | Act. Level |
|---|---|---|---|---|
| 233 | 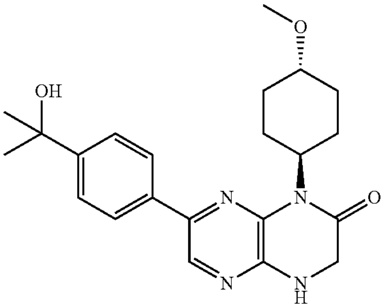 [SMILES: CO[C@H]1CC[C@H](N2C(=O)CNc3ncc(-c4ccc(C(C)(C)O)cc4)nc32)CC1] | 7-(4-(2-hydroxypropan-2-yl)phenyl)-1-(trans-4-methoxycyclohexyl)-3,4-dihydropyrazino[2,3-b]pyrazin-2(1H)-one | 397.2 [M + 1]$^+$ | D |
| 234 | 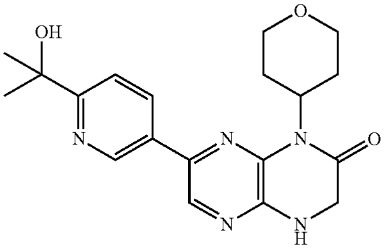 [SMILES: CC(C)(O)c1ccc(-c2cnc3c(n2)N(C2CCOCC2)C(=O)CN3)cn1] | 7-(6-(2-hydroxypropan-2-yl)pyridin-3-yl)-1-(tetrahydro-2H-pyran-4-yl)-3,4-dihydropyrazino[2,3-b]pyrazin-2(1H)-one | 370.2 [M + 1]$^+$ | B |
| 235 | 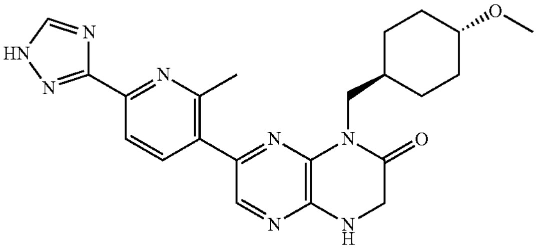 [SMILES: CO[C@H]1CC[C@H](CN2C(=O)CNc3ncc(-c4ccc(-c5nc[nH]n5)nc4C)nc32)CC1] | 1-((trans-4-methoxycyclohexyl)methyl)-7-(2-methyl-6-(1H-1,2,4-triazol-3-yl)pyridin-3-yl)-3,4-dihydropyrazino[2,3-b]pyrazin-2(1H)-one | 435.4 [M + 1]$^+$ | D |
| 236 | 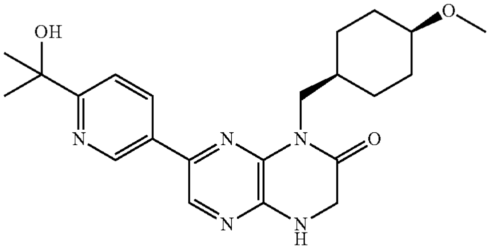 [SMILES: CO[C@H]1CC[C@@H](CN2C(=O)CNc3ncc(-c4ccc(C(C)(C)O)nc4)nc32)CC1] | 7-(6-(2-hydroxypropan-2-yl)pyridin-3-yl)-1-((cis-4-methoxycyclohexyl)methyl)-3,4-dihydropyrazino[2,3-b]pyrazin-2(1H)-one | 412.3 [M + 1]$^+$ | D |
| 237 | 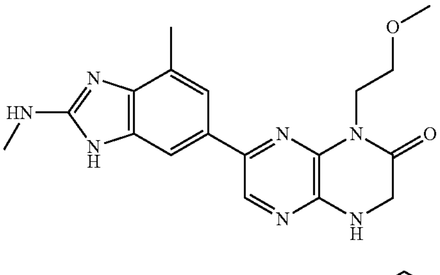 | 1-(2-methoxyethyl)-7-(4-methyl-2-(methylamino)-1H-benzo[d]imidazol-6-yl)-3,4-dihydropyrazino[2,3-b]pyrazin-2(1H)-one | 368.3 [M + 1]$^+$ | D |
| 238 | 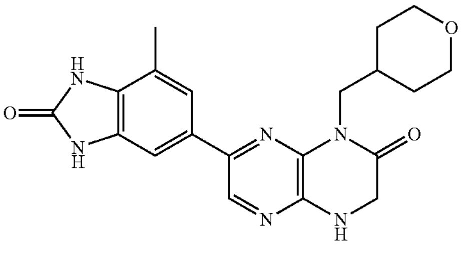 [SMILES: Cc1cc(-c2cnc3c(n2)N(CC2CCOCC2)C(=O)CN3)cc2[nH]c(=O)[nH]c12] | 7-(7-methyl-2-oxo-2,3-dihydro-1H-benzo[d]imidazol-5-yl)-1-((tetrahydro-2H-pyran-4-yl)methyl)-3,4-dihydropyrazino[2,3-b]pyrazin-2(1H)-one | 395.2 [M + 1]$^+$ | B |

TABLE 1-continued

| Cmpd No. | Cmpd Structure | Cmpd Name | MS (ESI) m/z | Act. Level |
|---|---|---|---|---|
| 239 | 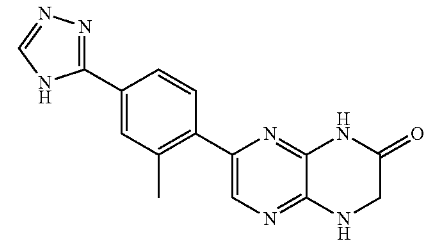 [SMILES: Cc1cc(-c2nnc[nH]2)ccc1-c1cnc2c(n1)NC(=O)CN2] | 7-(2-methyl-4-(4H-1,2,4-triazol-3-yl)phenyl)-3,4-dihydropyrazino[2,3-b]pyrazin-2(1H)-one | 308.3 $[M+1]^+$ | D |
| 240 | 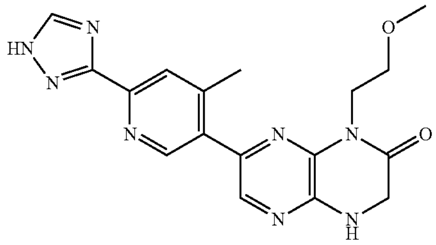 [SMILES: COCCN1C(=O)CNc2ncc(-c3cnc(-c4nc[nH]n4)cc3C)nc21] | 1-(2-methoxyethyl)-7-(4-methyl-6-(1H-1,2,4-triazol-3-yl)pyridin-3-yl)-3,4-dihydropyrazino[2,3-b]pyrazin-2(1H)-one | 367.4 $[M+1]^+$ | D |
| 241 | 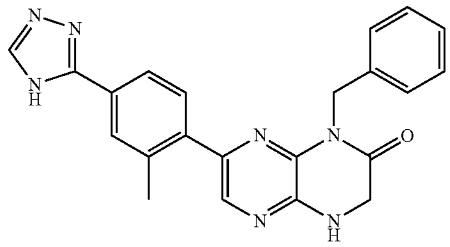 [SMILES: Cc1cc(-c2nnc[nH]2)ccc1-c1cnc2c(n1)N(Cc1ccccc1)C(=O)CN2] | 1-benzyl-7-(2-methyl-4-(4H-1,2,4-triazol-3-yl)phenyl)-3,4-dihydropyrazino[2,3-b]pyrazin-2(1H)-one | 398.3 $[M+1]^+$ | D |
| 242 | 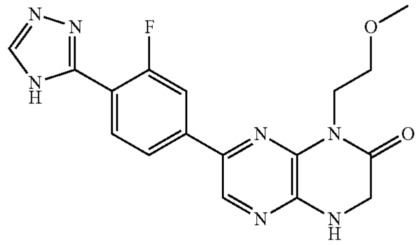 [SMILES: COCCN1C(=O)CNc2ncc(-c3ccc(-c4nnc[nH]4)c(F)c3)nc21] | 7-(3-fluoro-4-(4H-1,2,4-triazol-3-yl)phenyl)-1-(2-methoxyethyl)-3,4-dihydropyrazino[2,3-b]pyrazin-2(1H)-one | 370.3 $[M+1]^+$ | D |
| 243 | 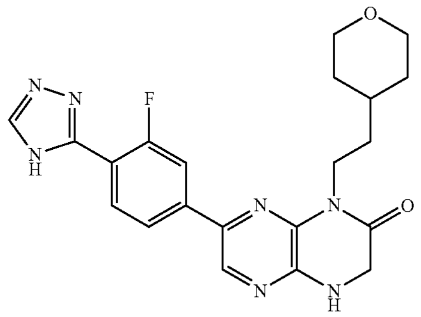 [SMILES: O=C1CNc2ncc(-c3ccc(-c4nnc[nH]4)c(F)c3)nc2N1CCC1CCOCC1] | 7-(3-fluoro-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one | 424.2 $[M+1]^+$ | D |

TABLE 1-continued

| Cmpd No. | Cmpd Structure | Cmpd Name | MS (ESI) m/z | Act. Level |
|---|---|---|---|---|
| 244 | 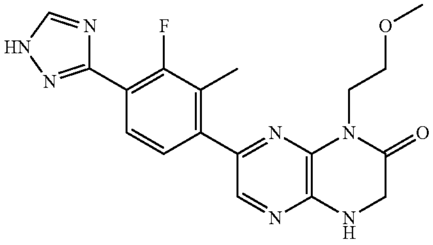 [SMILES: COCCN1C(=O)CNc2ncc(-c3ccc(-c4nc[nH]n4)c(F)c3C)nc21] | 7-(3-fluoro-2-methyl-4-(1H-1,2,4-triazol-3-yl)phenyl)-1-(2-methoxyethyl)-3,4-dihydropyrazino[2,3-b]pyrazin-2(1H)-one | 384.5 [M + 1]$^+$ | D |
| 245 | 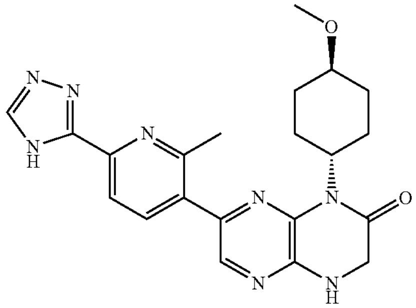 [SMILES: CO[C@H]1CC[C@H](N2C(=O)CNc3ncc(-c4ccc(-c5nnc[nH]5)nc4C)nc32)CC1] | 1-(trans-4-methoxycyclohexyl)-7-(2-methyl-6-(4H-1,2,4-triazol-3-yl)pyridin-3-yl)-3,4-dihydropyrazino[2,3-b]pyrazin-2(1H)-one | 421.2 [M + 1]$^+$ | D |
| 246 | 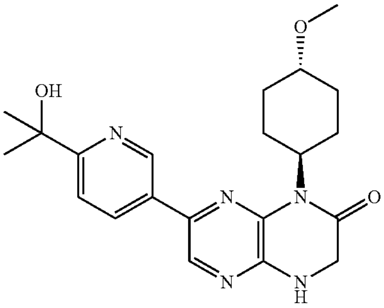 [SMILES: CO[C@H]1CC[C@H](N2C(=O)CNc3ncc(-c4ccc(C(C)(C)O)nc4)nc32)CC1] | 7-(6-(2-hydroxypropan-2-yl)pyridin-3-yl)-1-(trans-4-methoxycyclohexyl)-3,4-dihydropyrazino[2,3-b]pyrazin-2(1H)-one | 398.3 [M + 1]$^+$ | D |
| 247 | 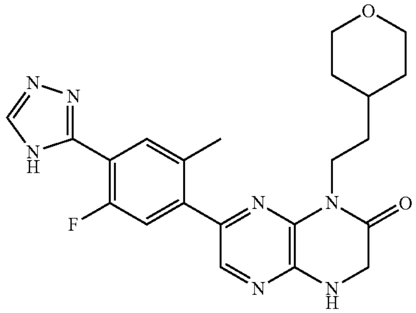 [SMILES: Cc1cc(-c2nnc[nH]2)c(F)cc1-c1cnc2c(n1)N(CCC1CCOCC1)C(=O)CN2] | 7-(5-fluoro-2-methyl-4-(4H-1,2,4-triazol-3-yl)phenyl)-1-(2-(tetrahydro-2H-pyran-4-yl)ethyl)-3,4-dihydropyrazino[2,3-b]pyrazin-2(1H)-one | 438.3 [M + 1]$^+$ | D |
| 248 | 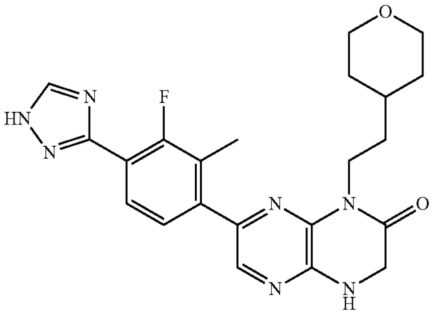 [SMILES: Cc1c(-c2cnc3c(n2)N(CCC2CCOCC2)C(=O)CN3)ccc(-c2nc[nH]n2)c1F] | 7-(3-fluoro-2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one | 438.6 [M + 1]$^+$ | D |

TABLE 1-continued

| Cmpd No. | Cmpd Structure | Cmpd Name | MS (ESI) m/z | Act. Level |
|---|---|---|---|---|
| 249 | 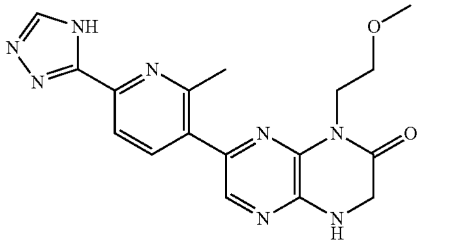 [SMILES: COCCN1C(=O)CNc2ncc(-c3ccc(-c4nnc[nH]4)nc3C)nc21] | 1-(2-methoxyethyl)-7-(2-methyl-6-(4H-1,2,4-triazol-3-yl)pyridin-3-yl)-3,4-dihydropyrazino[2,3-b]pyrazin-2(1H)-one | 367.2 [M + 1]$^+$ | D |
| 250 | 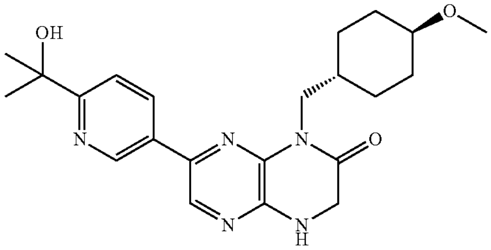 [SMILES: CO[C@H]1CC[C@H](CN2C(=O)CNc3ncc(-c4ccc(C(C)(C)O)nc4)nc32)CC1] | 7-(6-(2-hydroxypropan-2-yl)pyridin-3-yl)-1-((trans-4-methoxycyclohexyl)methyl)-3,4-dihydropyrazino[2,3-b]pyrazin-2(1H)-one | 412.3 [M + 1]$^+$ | D |
| 251 | 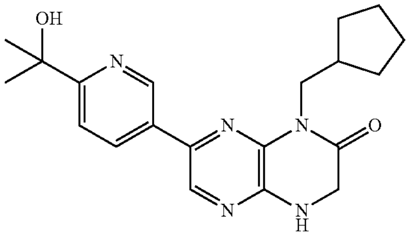 [SMILES: CC(C)(O)c1ccc(-c2cnc3c(n2)N(CC2CCCC2)C(=O)CN3)cn1] | 1-(cyclopentylmethyl)-7-(6-(2-hydroxypropan-2-yl)pyridin-3-yl)-3,4-dihydropyrazino[2,3-b]pyrazin-2(1H)-one | 368.3 [M + 1]$^+$ | B |
| 252 | 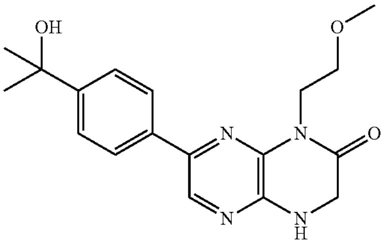 [SMILES: COCCN1C(=O)CNc2ncc(-c3ccc(C(C)(C)O)cc3)nc21] | 7-(4-(2-hydroxypropan-2-yl)phenyl)-1-(2-methoxyethyl)-3,4-dihydropyrazino[2,3-b]pyrazin-2(1H)-one | 343.2 [M + 1]$^+$ | A |
| 253 | 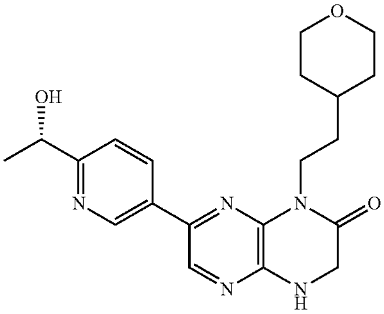 [SMILES: C[C@H](O)c1ccc(-c2cnc3c(n2)N(CCC2CCOCC2)C(=O)CN3)cn1] | (S)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one | 384.3 [M + 1]$^+$ | D |

TABLE 1-continued

| Cmpd No. | Cmpd Structure | Cmpd Name | MS (ESI) m/z | Act. Level |
|---|---|---|---|---|
| 254 | 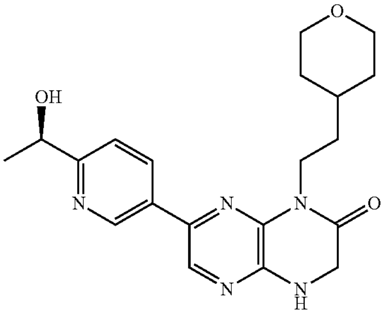 [SMILES: C[C@@H](O)c1ccc(-c2cnc3c(n2)N(CCC2CCOCC2)C(=O)CN3)cn1] | (R)-7-(6-(1-hydroxyethyl)pyridin-3-yl)-1-(2-(tetrahydro-2H-pyran-4-yl)ethyl)-3,4-dihydropyrazino[2,3-b]pyrazin-2(1H)-one | 384.3 [M + 1]+ | D |
| 255 | 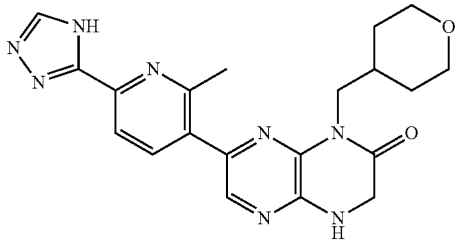 [SMILES: Cc1nc(-c2nnc[nH]2)ccc1-c1cnc2c(n1)N(CC1CCOCC1)C(=O)CN2] | 7-(2-methyl-6-(4H-1,2,4-triazol-3-yl)pyridin-3-yl)-1-((tetrahydro-2H-pyran-4-yl)methyl)-3,4-dihydropyrazino[2,3-b]pyrazin-2(1H)-one | 407.3 [M + 1]+ | D |
| 256 | 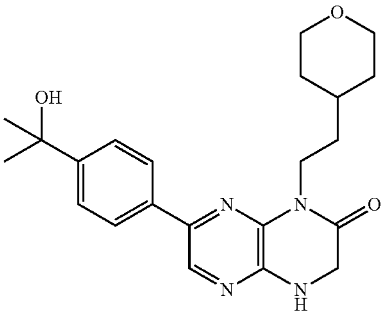 [SMILES: CC(C)(O)c1ccc(-c2cnc3c(n2)N(CCC2CCOCC2)C(=O)CN3)cc1] | 7-(4-(2-hydroxypropan-2-yl)phenyl)-1-(2-(tetrahydro-2H-pyran-4-yl)ethyl)-3,4-dihydropyrazino[2,3-b]pyrazin-2(1H)-one | 397.2 [M + 1]+ | D |
| 257 | 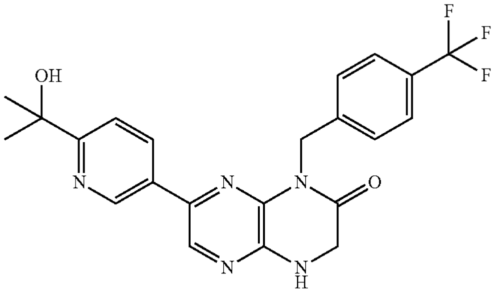 [SMILES: CC(C)(O)c1ccc(-c2cnc3c(n2)N(Cc2ccc(C(F)(F)F)cc2)C(=O)CN3)cn1] | 7-(6-(2-hydroxypropan-2-yl)pyridin-3-yl)-1-(4-(trifluoromethyl)benzyl)-3,4-dihydropyrazino[2,3-b]pyrazin-2(1H)-one | 444.3 [M + 1]+ | D |
| 258 | 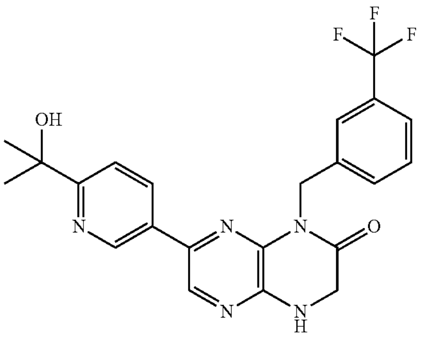 [SMILES: CC(C)(O)c1ccc(-c2cnc3c(n2)N(Cc2cccc(C(F)(F)F)c2)C(=O)CN3)cn1] | 7-(6-(2-hydroxypropan-2-yl)pyridin-3-yl)-1-(3-(trifluoromethyl)benzyl)-3,4-dihydropyrazino[2,3-b]pyrazin-2(1H)-one | 444.2 [M + 1]+ | D |

TABLE 1-continued

| Cmpd No. | Cmpd Structure | Cmpd Name | MS (ESI) m/z | Act. Level |
|---|---|---|---|---|
| 259 | 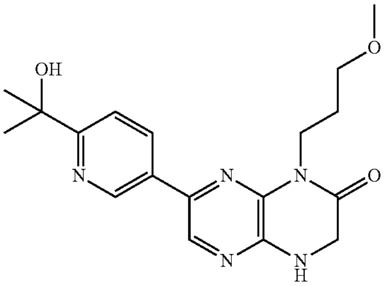 [SMILES: COCCCN1C(=O)CNc2ncc(-c3ccc(C(C)(C)O)nc3)nc21] | 7-(6-(2-hydroxypropan-2-yl)pyridin-3-yl)-1-(3-methoxypropyl)-3,4-dihydropyrazino[2,3-b]pyrazin-2(1H)-one | 358.2 [M + 1]$^+$ | D |
| 260 | 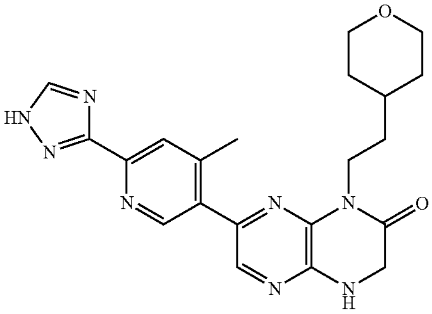 [SMILES: Cc1cc(-c2nc[nH]n2)ncc1-c1cnc2c(n1)N(CCC1CCOCC1)C(=O)CN2] | 7-(4-methyl-6-(1H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one | 421.4 [M + 1]$^+$ | D |
| 261 | 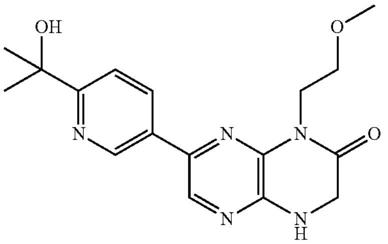 [SMILES: COCCN1C(=O)CNc2ncc(-c3ccc(C(C)(C)O)nc3)nc21] | 7-(6-(2-hydroxypropan-2-yl)pyridin-3-yl)-1-(2-methoxyethyl)-3,4-dihydropyrazino[2,3-b]pyrazin-2(1H)-one | 344.3 [M + 1]$^+$ | A |
| 262 | 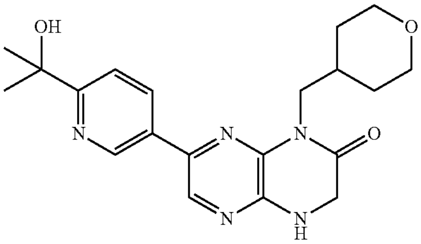 [SMILES: CC(C)(O)c1ccc(-c2cnc3c(n2)N(CC2CCOCC2)C(=O)CN3)cn1] | 7-(6-(2-hydroxypropan-2-yl)pyridin-3-yl)-1-((tetrahydro-2H-pyran-4-yl)methyl)-3,4-dihydropyrazino[2,3-b]pyrazin-2(1H)-one | 384.3 [M + 1]$^+$ | A |
| 263 | 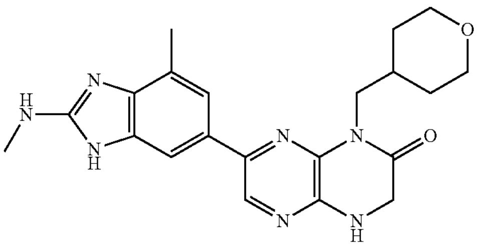 [SMILES: CNc1nc2c(C)cc(-c3cnc4c(n3)N(CC3CCOCC3)C(=O)CN4)cc2[nH]1] | 7-(4-methyl-2-(methylamino)-1H-benzo[d]imidazol-6-yl)-1-((tetrahydro-2H-pyran-4-yl)methyl)-3,4-dihydropyrazino[2,3-b]pyrazin-2(1H)-one | 408.3 [M + 1]$^+$ | D |

TABLE 1-continued

| Cmpd No. | Cmpd Structure | Cmpd Name | MS (ESI) m/z | Act. Level |
|---|---|---|---|---|
| 264 | 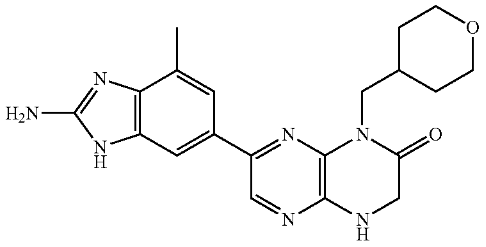 [SMILES: Cc1cc(-c2cnc3c(n2)N(CC2CCOCC2)C(=O)CN3)cc2[nH]c(N)nc12] | 7-(2-amino-4-methyl-1H-benzo[d]imidazol-6-yl)-1-((tetrahydro-2H-pyran-4-yl)methyl)-3,4-dihydropyrazino[2,3-b]pyrazin-2(1H)-one | 394.2 $[M + 1]^+$ | D |
| 265 | 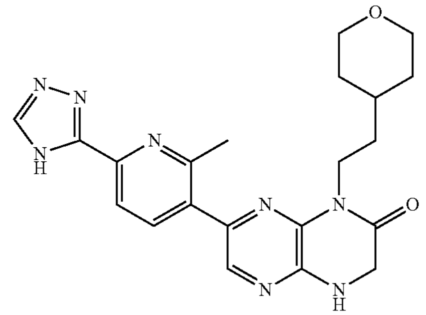 [SMILES: Cc1nc(-c2nnc[nH]2)ccc1-c1cnc2c(n1)N(CCC1CCOCC1)C(=O)CN2] | 7-(2-methyl-6-(4H-1,2,4-triazol-3-yl)pyridin-3-yl)-1-(2-(tetrahydro-2H-pyran-4-yl)ethyl)-3,4-dihydropyrazino[2,3-b]pyrazin-2(1H)-one | 421.1 $[M + 1]^+$ | D |
| 266 | 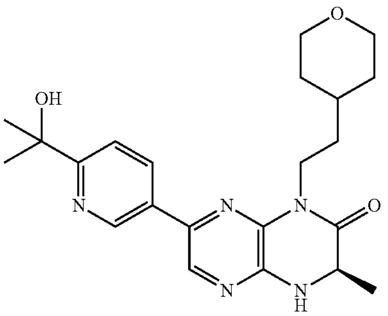 [SMILES: C[C@H]1Nc2ncc(-c3ccc(C(C)(C)O)nc3)nc2N(CCC2CCOCC2)C1=O] | (R)-7-(6-(2-hydroxypropan-2-yl)pyridin-3-yl)-3-methyl-1-(2-(tetrahydro-2H-pyran-4-yl)ethyl)-3,4-dihydropyrazino[2,3-b[pyrazin-2(1H)-one | 412.5 $[M + 1]^+$ | B |
| 267 | 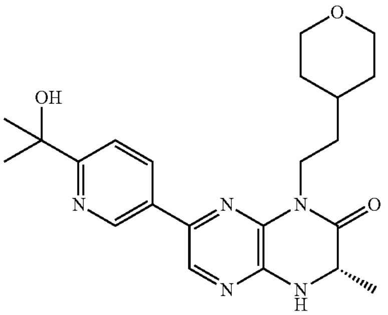 [SMILES: C[C@@H]1Nc2ncc(-c3ccc(C(C)(C)O)nc3)nc2N(CCC2CCOCC2)C1=O] | (S)-7-(6-(2-hydroxypropan-2-yl)pyridin-3-yl)-3-methyl-1-(2-(tetrahydro-2H-pyran-4-yl)ethyl)-3,4-dihydropyrazino[2,3-b]pyrazin-2(1H)-one | 412.5 $[M + 1]^+$ | B |
| 269 | 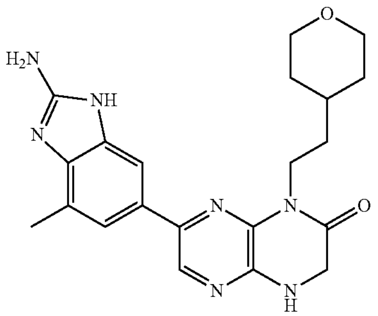 [SMILES: Cc1cc(-c2cnc3c(n2)N(CCC2CCOCC2)C(=O)CN3)cc2[nH]c(N)nc12] | 7-(2-amino-4-methyl-1H-benzo[d]imidazol-6-yl)-1-(2-(tetrahydro-2H-pyran-4-yl)ethyl)-3,4-dihydropyrazino[2,3-b]pyrazin-2(1H)-one | 408.5 $[M + 1]^+$ | D |

TABLE 1-continued

| Cmpd No. | Cmpd Structure | Cmpd Name | MS (ESI) m/z | Act. Level |
|---|---|---|---|---|
| 270 | 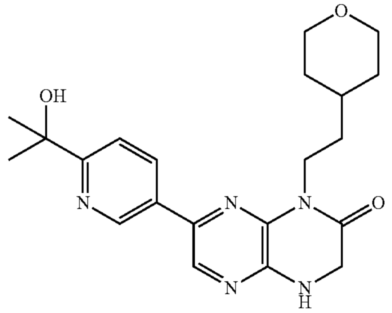 | 7-(6-(2-hydroxypropan-2-yl)pyridin-3-yl)-1-(2-(tetrahydro-2H-pyran-4-yl)ethyl)-3,4-dihydropyrazino[2,3-b]pyrazin-2(1H)-one | 398.4 $[M + 1]^+$ | D |
| 271 | 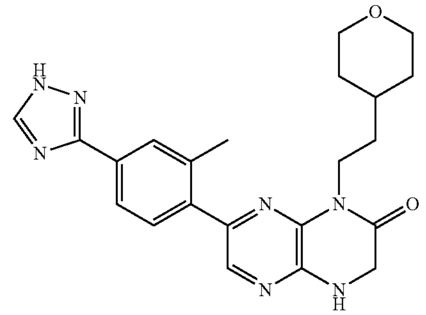 [SMILES: Cc1cc(-c2nc[nH]n2)ccc1-c1cnc2c(n1)N(CCC1CCOCC1)C(=O)CN2] | 7-(2-methyl-4-(1H-1,2,4-triazol-3-yl)phenyl)-1-(2-(tetrahydro-2H-pyran-4-yl)ethyl)-3,4-dihydropyrazino[2,3-b]pyrazin-2(1H)-one | 420.4 $[M + 1]^+$ | D |
| 272 | 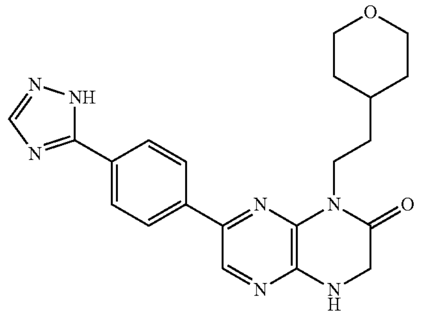 [SMILES: O=C1CNc2ncc(-c3ccc(-c4ncn[nH]4)cc3)nc2N1CCC1CCOCC1] | 7-(4-(1H-1,2,4-triazol-5-yl)phenyl)-1-(2-(tetrahydro-2H-pyran-4-yl)ethyl)-3,4-dihydropyrazino[2,3-b]pyrazin-2(1H)-one | 406.0 $[M + 1]^+$ | D |
| 273 | 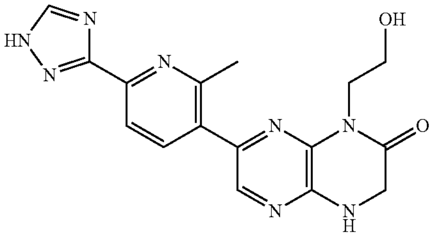 [SMILES: Cc1nc(-c2nc[nH]n2)ccc1-c1cnc2c(n1)N(CCO)C(=O)CN2] | 1-(1-hydroxypropan-2-yl)-7-(2-methyl-6-(1H-1,2,4-triazol-3-yl)pyridin-3-yl)-3,4-dihydropyrazino[2,3-b]pyrazin-2(1H)-one | N/A | D |
| 274 | 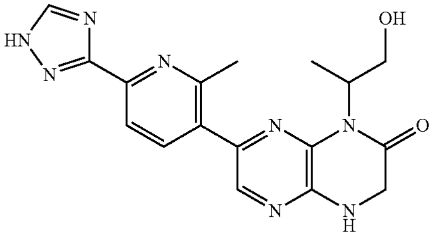 | 1-(2-hydroxyethyl)-7-(2-methyl-6-(1H-1,2,4-triazol-3-yl)pyridin-3-yl)-3,4-dihydropyrazino[2,3-b]pyrazin-2(1H)-one | 353.3 $[M + 1]^+$ | D |

The embodiments disclosed herein are not to be limited in scope by the specific embodiments disclosed in the examples which are intended as illustrations of a few aspects of the disclosed embodiments and any embodiments that are functionally equivalent are encompassed by the present disclosure. Indeed, various modifications of the embodiments disclosed herein are in addition to those shown and described herein will become apparent to those skilled in the art and are intended to fall within the scope of the appended claims.

A number of references have been cited, the disclosures of which are incorporated herein by reference in their entirety.

What is claimed is:

1. A method for preparing a compound of formula (II):

(II)

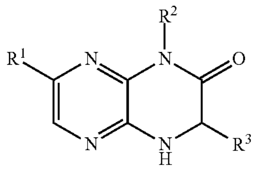

the method comprising contacting a compound of formula (VI):

(VI)

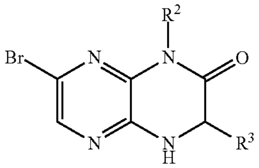

with $R^1$—Y in a solvent, in the presence of a palladium catalyst, wherein said contacting occurs in the presence of a base, wherein Y is $B(OR^+)_2$ or $Sn(R^{++})_3$;

$R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl;

$R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl;

$R^3$ is H, or a substituted or unsubstituted $C_{1-8}$ alkyl; and each $R^+$ is hydrogen, or each $R^+$, together with the boron atom and the atoms to which they are attached, form a cyclic boronate;

each $R^{++}$ is independently $C_{1-3}$ alkyl;

the palladium catalyst is bis(dibenzylideneacetone)palladium(0)/tri-o-tolylphosphine, or palladium (II) acetate/4,5-bis(diphenylphosphino)-9,9-dimethylxanthene; and substituted means substituted with a substituent selected from the group consisting of chloro; iodo; bromo; fluoro; alkyl; hydroxy; alkoxy; alkoxyalkyl; amino; alkylamino; carboxy; nitro; cyano; thiol; thioether; imine; imide; amidine; guanidine; enamine; aminocarbonyl; acylamino; phosphonato; phosphine; thiocarbonyl; alkylsulfonyl; sulfonamide; acyl; ester; urea; urethane; oxime; hydroxylamine; alkoxyamine; aralkoxyamine; N-oxide; hydrazine; hydrazide; hydrazone; azide; isocyanate; isothiocyanate; cyanate; thiocyanate; oxo; $B(OH)_2$, O(alkyl)aminocarbonyl; cycloalkyl, which may be monocyclic or fused or non-fused polycyclic, or a heterocyclyl, which may be monocyclic or fused or non-fused polycyclic; monocyclic or fused or non-fused polycyclic aryl or heteroaryl; aryloxy; aralkyloxy; heterocyclyloxy; and heterocyclylalkoxy.

2. The method of claim 1, wherein each $R^{++}$ is $CH_3$.

3. The method of claim 1, wherein the $B(OR^+)_2$ is $B(OH)_2$ or

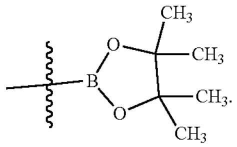

4. The method of claim 1, wherein the solvent is dimethylformamide, isopropanol, dioxane, toluene, dimethylacetamide, tetrahydrofuran, acetonitrile, isopropyl acetate, dimethyl sulfoxide, acetone, methanol, methyl t-butyl ether or a combination thereof, optionally with the presence of water.

5. The method of claim 1, wherein the contacting occurs in the presence of a base and the base is sodium carbonate, triethylamine, diisopropylethylamine, piperidine, pyridine, cesium carbonate, potassium carbonate, potassium phosphate, or sodium hydroxide.

* * * * *